United States Patent
Failli et al.

(10) Patent No.: US 7,678,787 B2
(45) Date of Patent: Mar. 16, 2010

(54) PYRROLOBENZODIAZEPINE PYRIDINE CARBOXAMIDES AND DERIVATIVES AS FOLLICLE-STIMULATING HORMONE RECEPTOR ANTAGONISTS

(75) Inventors: Amedeo A. Failli, Princeton Junction, NJ (US); Gavin D. Heffernan, Florence, NJ (US); Arthur A. Santilli, Havertown, PA (US); Dominick A. Quagliato, Bridgewater, NJ (US); Richard D. Coghlan, Phoenixville, PA (US); Patrick M. Andrae, Jamesburg, NJ (US); Susan C. Croce, Lambertville, NJ (US); Emily S. Shen, West Chester, PA (US); Eugene J. Trybulski, Huntingdon Valley, PA (US)

(73) Assignee: Wyeth, Madison, NJ (US)

( * ) Notice: Subject to any disclaimer, the term of this patent is extended or adjusted under 35 U.S.C. 154(b) by 708 days.

(21) Appl. No.: 11/449,376

(22) Filed: Jun. 8, 2006

(65) Prior Publication Data
US 2006/0287522 A1 Dec. 21, 2006

Related U.S. Application Data

(60) Provisional application No. 60/688,988, filed on Jun. 9, 2005.

(51) Int. Cl.
*A61P 15/18* (2006.01)
*A61K 31/55* (2006.01)
*C07D 487/12* (2006.01)

(52) U.S. Cl. ...................... 514/220; 540/561
(58) Field of Classification Search ................ 514/220; 540/561
See application file for complete search history.

(56) References Cited

U.S. PATENT DOCUMENTS

| 6,200,963 B1 | 3/2001 | Wrobel et al. |
| 6,355,633 B1 | 3/2002 | Wrobel et al. |
| 6,426,357 B1 | 7/2002 | Scheuerman et al. |

FOREIGN PATENT DOCUMENTS

| WO | WO 00/58277 A | 10/2000 |
| WO | WO 01/47875 | 7/2001 |
| WO | WO 00/08015 | 2/2002 |
| WO | WO 02/09705 | 2/2002 |
| WO | WO 02/09706 | 2/2002 |
| WO | WO 02/070493 | 9/2002 |
| WO | WO 02/083678 A | 10/2002 |
| WO | WO 02/083680 | 10/2002 |
| WO | WO 02/083683 | 10/2002 |
| WO | WO 02/083684 | 10/2002 |
| WO | WO 02/085907 A | 10/2002 |
| WO | WO 03/004028 | 1/2003 |
| WO | WO 2004/056779 A | 7/2004 |
| WO | WO 2004/056780 A2 | 7/2004 |

OTHER PUBLICATIONS

Guo, Small Molecule Agonists and Antagonists for the LH and FSH Receptors, Expert Opinion in Therapeutic Patents, vol. 15, No. 11, pp. 1555-1564, Nov. 2005.*
K. Aittomaki et al., "Mutations in the Follicle-Stimulating Hormone Receptor Gene Causes Hereditary Hypergonadotropic Ovarian Failure", Cell, 82: 959-968, 1995.
B.J. Arey et al., "Identification and Characterization of Selective, Non-peptide Follicle-Stimulating Hormone Receptor Antagonist", CL-272219, The Endrocine Society 82$^{nd}$ Annual Meeting, Toronto, Canada Jun. 21-24, 2000 and Endocrinology 143 (10), 3822 (2002).
Badone et al., "Highly Efficient Palladium-Catalyzed Boronic Acid Coupling Reactions in Water: Scope and Limitations", J. Org. Chem., 62: 7170-71731 (1997).
Coffen et al., "2-Benzazepines. 8. Zerovalent nickel mediated biaryl synthesis of an anxiolytic pyrimido[5,4-d][2]benzazepine," *J Org Chem* (1984) 49(2):296-300.
R. Danesi et al., "Clinical and Experimental Evidence of Inhibition of Testosterone Production by Suramin", J. Clin. Endocrinal. Metab., 81: 2238-2246 1996.
R.L. Daugherty et al., "Suramin Inhibits Gonadotropin Action in Rat Tests Implications for Treatment of Advanced Prostate Cancer", J. Urol, 147: 727 (1992).
Farina et al., "On the Nature of the "Copper Effect" in the Stille Cross-Coupling," *J Org Chem* (1994) 59(20):5905.

(Continued)

*Primary Examiner*—Brenda L Coleman
(74) *Attorney, Agent, or Firm*—Pepper Hamilton LLP

(57) ABSTRACT

This invention provides pyrrolobenzodiazepine pyridine carboxamides selected from those of Formula (1), which act as follicle stimulating hormone receptor antagonists. The invention also provides pharmaceutical compositions and methods of treatment utilizing the compounds of Formulae (1) and (2).

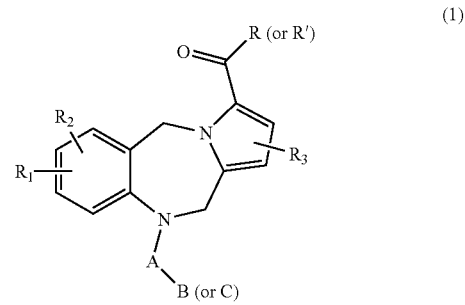

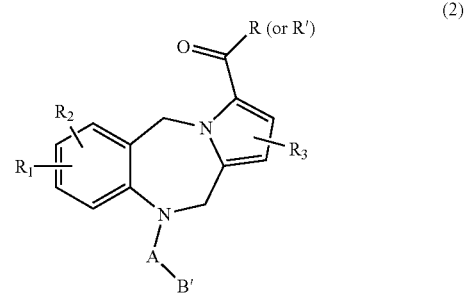

32 Claims, No Drawings

OTHER PUBLICATIONS

George, S.E. et al., "Evaluation of a CRE-directed luciferase reporter gene assay as an alternative to measuring cAMP accumulation", J. Biomol. Screening 2:235-240 1997.

Giroux et al., "One pot biaryl synthesis via in situ boronate formation," *Tetrahedron Lett* (1997) 38(22):3841-3844.

T. Guo et al., "Small molecule biaryl FSH receptor agonists. Part 1: Lead discovery via encoded combinatorial synthesis. Part 2 : Lead Optimization via Parallel synthesis," Bioorg. Med. Chem. Lett., 14: 1713-1716, 1717-1720 (2004).

A.J. Hsueh et al., "Cells as Hormone Targets: The Role of Biologically Active Follicle-Stimulating Hormone in Reproduction", Rec. Prog. Horm. Res., 45: 209-227,1989.

Inanaga et al., "A Rapid Esterification by Means of Mixed Anhydride and Its Application to Large-ring Lactonization," *Bull Chem Soc Jpn* (1979) 52(7):1989-1993.

Ishiyama et al., "Synthesis of arylboronates via the palladium(0)-catalyzed cross-coupling reaction of tetra(alkoxo)diborons with aryl triflates," *Tetrahedron Lett* (1997) 38(19):3447-3450.

Ishiyama et al., "Palladium(0)-Catalyzed Cross-Coupling Reaction of Alkoxydiboron with Haloarenes: A Direct Procedure for Arylboronic Esters," *J Org Chem* (1995) 60(23):7508-7510.

Kelton, C.A. et al., ,"The cloning of the human follicle stimulating hormone receptor and its expression in COS-7, CHO, and Y-1 cells", Mol. Cell. Endocrinol., 89:141-151 1992.

Lindstedt et al., "Follitropin (FSH) deficiency in an infertile male due to FSHbeta gene mutation. A syndrome of normal puberty and virilization but underdeveloped testicles with azoospermia, low FSH but high lutropin and normal serum testosterone concentrations," *Clin Chem Lab Med* (1998) 36(8):663-665.

March, *Advanced Organic Chemistry*, 3$^{rd}$ Edn., p. 647-648, John Wiley & Sons, New York (1985).

March, *Advanced Organic Chemistry*, 3$^{rd}$ Edn., p. 788 John Wiley & Sons, New York, (1985).

Mukherjee et al., "Gonadotropins induce rapid phosphorylation of the 3',5'-cyclic adenosine monophosphate response element binding protein in ovarian granulosa cells", Endocrinology, 137: 3234 (1996).

Quattropani et al., "Discovery and development of a new class of potent, selective, orally active oxytocin receptor antagonists," *J Med Chem* (2005) 48(24):7882-7905.

Schoenberg et al., "Palladium-catalyzed amidation of aryl, heterocyclic, and vinylic halides," *J. Org. Chem.* (1974) 39(23): 3327-3331.

Serradeil-Le Gal et al., "SSR126768A (4-chloro-3-[(3R)-(+)-5-chloro-1-(2,4-dimethoxybenzyl)-3- methyl-2-oxo-2,3-dihydro-1H-indol-3-yl]-N-ethyl-N-(3-pyridylmethyl)-benzamide, hydrochloride): a new selective and orally active oxytocin receptor antagonist for the prevention of preterm labor," *J Pharmacol Exper Ther* (2004) 309(1):414-424.

Shen "Palladium catalyzed coupling of aryl chlorides with arylboronic acids," *Tetrahedron Letters* (1997) 38(32):5575.

Street et al., "Synthesis and serotonergic activity of 5-(oxadiazolyl)tryptamines: potent agonists for 5-HT1D receptors", J. Med. Chem., 36: 1529 (1993).

Suzuki "New synthetic transformations via organoboron compounds," *Pure & Appl Chem* (1994) 66(2):213-222.

Tilly, J.L. et al., "Expression of recombinant human follicle-stimulating hormone receptor: Species-specific ligand binding, signal transduction, and identification of multiple ovarian messenger ribonucleic acid transcripts", Endocrinology, 131:799-806 1992.

Wolfe et al., "Highly Active Palladium Catalysts for Suzuki Coupling Reactions," *J Am Chem Soc* (1999) 121(41):9550-9561.

Wrobel et al., "Synthesis of (bis)sulfonic acid, (bis)benzamides as follicle-stimulating hormone (FSH) antagonists," *Bioorg Med Chem* (2002) 10(3):639-656.

Wyatt et al., "Structure-activity relationship investigations of a potent and selective benzodiazepine oxytocin antagonist," *Bioorg Med Chem Letters* (2001) 11(10):1301-1305.

Wyatt et al., "Identification of potent and selective oxytocin antagonists. Part 1: indole and benzofuran derivatives," *Bioorg Med Chem Letters* (2002) 12(10):1399-1404.

Wyatt et al., "Identification of potent and selective oxytocin antagonists. Part 2: further investigation of benzofuran derivatives," *Bioorg Med Chem Letters* (2002) 12(10):1405-1411.

* cited by examiner

PYRROLOBENZODIAZEPINE PYRIDINE CARBOXAMIDES AND DERIVATIVES AS FOLLICLE-STIMULATING HORMONE RECEPTOR ANTAGONISTS

This applications claims benefit of priority to U.S. provisional application No. 60/688,988 filed Jun. 9, 2005, which is hereby incorporated by reference in its entirety.

BACKGROUND OF INVENTION

This invention concerns novel pyrrolobenzodiazepine pyridine carboxamides, which act as follicle-stimulating hormone receptor antagonists, as well as pharmaceutical compositions and methods of treatment utilizing these compounds.

Reproduction in women depends upon the dynamic interaction of several compartments of the female reproductive system. The hypothalamic-pituitary-gonadal axis orchestrates a series of events affecting the ovaries and the uterine-endometrial compartment that leads to the production of mature ova, ovulation, and ultimately, appropriate conditions necessary for fertilization. Specifically, luteinizing hormone-releasing hormone (LHRH), which is released from the hypothalamus, initiates the release of the gonadotropins, luteinizing hormone (LH) and follicle-stimulating hormone (FSH) from the pituitary. These hormones act directly on the ovary to promote the development of selected follicles by inducing granulosa and theca cell proliferation and differentiation. FSH stimulates aromatization of androgens to estrogens and increases the expression of LH receptors in the theca cells. The follicles, in turn, secrete steroids (estradiol, progesterone) and peptides (inhibin, activin). Estradiol and inhibin levels progressively increase during the follicular phase of the menstrual cycle until ovulation. Inhibin decreases FSH secretion from the pituitary gland, while estradiol acts on the hypothalamus and pituitary to induce the LH surge in mid-cycle, which results in ovulation. Afterwards, the post-ovulation ruptured follicle forms the corpus luteum, which produces progesterone. Ovarian hormones, in turn, regulate the secretion of gonadotropins through a classical long-loop negative feedback mechanism. The elucidation of these control mechanisms has provided opportunities for the development of effective strategies to control fertility, including both enhancement of fertility and contraception. For recent reviews of FSH action see: "FSH Action and Intraovarian Regulation," B. C. J. M. Fauser, ed., Vol. 6 (London: Parthenon Publishing Group), 1997, and A. J. Hsueh et. al., *Rec. Prog. Horm. Res.*, 45, 209-227, 1989.

Current hormonal contraception methods are steroidal in nature (progestins and estrogens) and modulate long-loop feedback inhibition of gonadotropin secretion, as well as affecting peripheral mechanisms such as sperm migration and fertilization. The development of specific antagonists of the receptor for FSH (FSH-R) would provide an alternative strategy for hormonal contraception. Such antagonists would block FSH-mediated follicular development leading to a blockade of ovulation, thereby producing the desired contraceptive effect. Support for the effectiveness of this strategy is provided by the mechanism that causes resistant ovary syndrome, which results in infertility in women. The infertility experienced by these women is the result of non-functional FSH receptors (K. Aittomaki et al., *Cell*, 82, 959-968,1995). This approach to contraception may be applicable to men as well, since idiopathic male infertility seems to be related to a reduction in FSH binding sites. In addition, men with selective FSH deficiency are oligo- or azoospermic with normal testosterone levels and present normal virilization (G. Lindstedt et al., *Clin. Lab. Med.*, 36, 664, 1998). Therefore, low molecular weight FSH antagonists may provide a versatile novel method of contraception. Such an antagonist could be expected to interfere with follicle development and thus, ovulation, while maintaining sufficient estrogen production and beneficial effects on bone mass.

FSH actions are mediated by binding of the hormone to a specific transmembrane G protein-coupled receptor that is exclusively expressed in the ovary, thus, leading to activation of the adenyl cyclase system and elevation of intracellular levels of the second messenger cAMP (A. Mukherjee et al., *Endocrinology*, 137, 3234 1996).

Recently suramin, a sulfonic acid anticancer agent with a wide variety of activities, was shown to inhibit FHS binding to its receptor (R. L. Daugherty et al., *J. Urol.*, 147, 727 (1992). Administration of suramin causes a decrease in testosterone production in rats and humans (R. Danesi et al., *J. Clin. Endocrinol. Metab.* 81, 2238-2246,1996). Recently, other more selective sulfonic acid-based FSH receptor antagonists were reported by B. J. Arey et al. (*The Endocrine Society*, 82nd *Annual Meeting, Toronto, Canada Jun. 21-24, 2000*, and *Endocrinology* 143 (10), 3822, 2002). An additional class of stilbene (bis)sulfonic acid competitive inhibitors of FSH at its receptor has also been reported by J. Wrobel et al. (*Bioorg. Med. Chem.* 10, 639-656, 2002).

Thiazolidinone FSH-R agonists and antagonists have been disclosed by R. Scheuerman et al. in WO 02/09705 and WO 02/09706 (2002) and in U.S. Pat. No. 6,426,357 (2002), respectively. Cyclic and acyclic alpha- and beta-aminocarboxamides as FSH-R agonists are disclosed by El Tayer et al. in WO 00/08015 (2000). Substituted aminoalkylamide derivative FSH-R antagonists have been disclosed by Coats et al. in WO 01/47875 (2001). Aryl sulfonic acids and derivatives FSH-R antagonists have been disclosed by Wrobel et al. in U.S. Pat. Nos. 6,200,963 (2001) and 6,355,633 (2002). Tetrahydroquinoline derivatives have been disclosed as FSH-R modulators to control fertility by Van Straten et al. in WO 03/004028 (2003). Bisaryl derivatives with FSH-R modulatory activity have been disclosed by T. Guo et al. in WO 02/070493A1. T. Guo et al. also have reported encoded combinatorial and parallel synthesis approaches to bisaryl FSH-R agonists; see *Bioorg. Med. Chem. Lett.* 14, 1713-1716, 2004 and 1717-1720, 2004, respectively. Failli et al. in WO 02/083683 (2002) have disclosed a subset of pyrrolobenzodiazepines as tocolytic oxytocin receptor binding antagonists.

It can be seen that there is a great need for FSH receptor binding antagonists that can be used for contraception. This invention is directed to these, as well as other, important ends.

SUMMARY OF THE INVENTION

The present invention relates to pyrrolobenzodiazepine pyridine carboxamides and derivatives having antagonist activity on the FSH receptor, and to their use as contraceptives.

In accordance with this invention are novel compounds represented by the structure of Formula I:

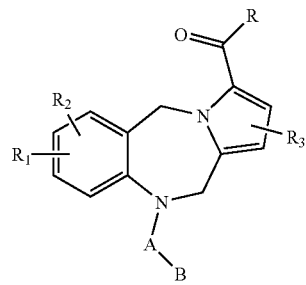

wherein

R$_1$ and R$_2$ are selected independently from hydrogen, (C$_1$-C$_6$)alkyl, halogen, trifluoromethyl, hydroxyl, (C$_1$-C$_6$)alkoxy, OCF$_3$, carboxy, —CONH[(C$_1$-C$_6$)alkyl], or —CON[(C$_1$-C$_6$)alkyl]$_2$, amino, (C$_1$-C$_6$)alkylamino, —NHCO[(C$_1$-C$_6$)alkyl];

R$_3$ is selected from the group consisting of hydrogen, (C$_1$-C$_6$)alkyl, (C$_1$-C$_6$)alkoxy, hydroxyl, amino, (C$_1$-C$_6$)alkylamino, C(O)—(C$_1$-C$_6$)alkyl, and halogen;

A is selected from the group consisting of C=O, CH$_2$, and SO$_2$;

B is

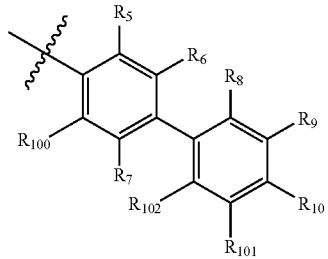

wherein R$_5$, R$_6$, R$_7$, R$_8$, R$_9$, R$_{10}$, R$_{100}$, R$_{101}$, and R$_{102}$ are selected independently from the group consisting of hydrogen, alkyl, alkoxy, trihalomethyl, halogen, —C(O)alkyl, hydroxy, hydroxyalkyl, alkyloxyalkyl, —CH(OH)alkyl, —CH(alkoxy)alkyl, formyl, nitro, thioalkyl, —SO$_2$alkyl, —SO$_2$NHR$_{11}$, —SO$_2$N(R$_{11}$)$_2$, —(CH$_2$)$_p$CN, —(CH$_2$)$_p$COOR$_{12}$, —(CH$_2$)$_p$NR$_{13}$R$_{14}$, —(CH$_2$)$_p$CONR$_{13}$R$_{14}$, —CH=NOH, —CH=NO-alkyl,

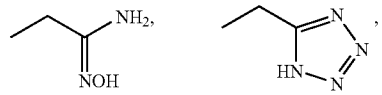

and —C(O)aryl optionally substituted by alkyl;

R$_{11}$ and R$_{12}$ are each independently hydrogen or alkyl;

R$_{13}$ and R$_{14}$ are each independently hydrogen or alkyl; or can be taken together with the nitrogen to which they are attached to form a 4-6 membered saturated ring optionally containing one or more additional O, S or N atoms;

p is 0 or 1;

R is a group consisting of

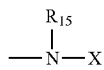

wherein

R$_{15}$ is hydrogen or alkyl;

X is selected independently from the group consisting of

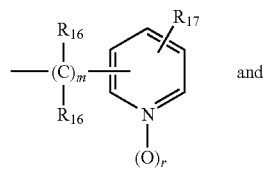 and 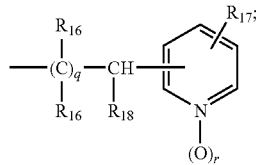

wherein

R$_{16}$ is hydrogen or alkyl;

R$_{17}$ is one to three substituents selected from the group consisting of hydrogen, alkyl, halogen, hydroxy, aryloxy, and hydroxyalkyl;

R$_{18}$ is 5 or 6-membered saturated heterocycle containing one nitrogen atom;

m is an integer from 1 to 4;

q is an integer from 1 to 2; and r is 0 or 1;

provided that:

if A is C=O, m is 1 or 2, r is 0, R$_7$ is methyl or methoxy and R$_5$, R$_6$, R$_8$, R$_9$, R$_{10}$, R$_{17}$, R$_{100}$, and R$_{101}$ are hydrogen, then R$_{102}$ is not methyl or methoxy;

if A is C=O, m is 2, r is 0, R$_6$ is methoxy and R$_5$, R$_7$, R$_9$, R$_{10}$, R$_{17}$, R$_{100}$, R$_{101}$, and R$_{102}$ are hydrogen, then R$_8$ is not methoxy;

if A is C=O, m is 1 or 2, r is 0, R$_6$ is methyl or methoxy, and R$_5$, R$_7$, R$_8$, R$_{10}$, R$_{17}$, R$_{100}$, R$_{101}$, and R$_{102}$ are hydrogen, then R$_9$ is not methoxy;

if A is C=O, m is 2, r is 0, R$_6$ is chlorine, R$_{100}$ is methoxy, then R$_{101}$ is not methoxy wherein R$_5$, R$_7$, R$_8$, R$_9$, R$_{10}$, R$_{17}$, and R$_{102}$ are hydrogen, or R$_{102}$ is not methyl wherein R$_5$, R$_7$, R$_8$, R$_9$, R$_{10}$, R$_{17}$, and R$_{101}$ are hydrogen;

if A is C=O, m is 1 or 2, r is 0 or 1, R$_7$ is methyl, and R$_5$, R$_6$, R$_9$, R$_{10}$, R$_{17}$, R$_{100}$, R$_{101}$, and R$_{102}$ are hydrogen, then R$_8$ is not trifluoromethyl;

if A is C=O, m is 1, r is 0, R$_7$ is methoxy, R$_5$, R$_6$, R$_9$, R$_{10}$, R$_{17}$, R$_{100}$, and R$_{102}$ are hydrogen then R$_8$ is not chlorine wherein R$_{101}$ is hydrogen or R$_{101}$ is not methoxy wherein R$_8$ is hydrogen;

if A is C=O, m is 1, r is 0, R$_5$ is methoxy, R$_7$ is chlorine, and R$_6$, R$_{10}$, R$_{17}$, R$_{100}$, R$_{101}$, and R$_{102}$ are hydrogen, then R$_8$ is not trifluoromethyl, chlorine, or methyl wherein R$_9$ is hydrogen, or R$_9$ is not methoxy wherein R$_8$ is hydrogen;

if A is C=O, m is 2, r is 0, R$_7$ is methyl, and R$_5$, R$_6$, R$_9$, R$_{10}$, R$_{17}$, R$_{100}$, R$_{101}$ and R$_{102}$ are hydrogen, then R$_8$ is not methoxy;

if A is C=O, m is 1 or 2, r is 0 or 1, R$_6$ is chlorine, R$_{100}$ is methoxy, and R$_5$, R$_7$, R$_9$, R$_{10}$, R$_{17}$ are hydrogen, then R$_8$ is not ethoxy wherein R$_{101}$ and R$_{102}$ are hydrogen, or R$_{101}$ is not methyl wherein R$_8$ and R$_{102}$ are hydrogen, or R$_{102}$ is not fluorine, trifluoromethyl, or methyl wherein R$_8$ and R$_{101}$ are hydrogen;

if A is C=O, m is 1 or 2, r is 0, R$_7$ is methyl, and R$_5$, R$_6$, R$_8$, R$_9$, R$_{10}$, R$_{17}$, R$_{100}$, and R$_{102}$ are hydrogen, then R$_{101}$ is not methoxy;

if A is C=O, m is 1, r is 0 or 1, R$_6$ is methoxy, R$_{102}$ is trifluoromethyl, and R$_5$, R$_7$, R$_8$, R$_9$, R$_{10}$, R$_{17}$, and R$_{101}$ are hydrogen, then R$_{100}$ is not hydrogen or methoxy;

if A is C=O, m is 1 or 2, r is 0, R$_8$ is methyl, and R$_5$, R$_7$, R$_9$, R$_{10}$, R$_{17}$, R$_{100}$, R$_{101}$ and R$_{102}$ are hydrogen, then R$_6$ is not hydrogen or methyl; and if A is C=O, m is 1 or 2, r is 0, and R$_5$, R$_6$, R$_7$, R$_9$, R$_{10}$, R$_{17}$, R$_{100}$, R$_{101}$ and R$_{102}$ are hydrogen, then R$_8$ is not methoxy; or a pharmaceutically acceptable salt thereof.

In accordance with this invention, there is also provided a group of compounds represented by the Formula II:

II wherein
- $R_1$ and $R_2$ are as defined hereinbefore;
- $R_3$ is as defined hereinbefore;
- A is as defined hereinbefore;
- C is selected from the group consisting of —Y and Z wherein
- $R_{19}$ and $R_{20}$ are selected independently from the group consisting of hydrogen, alkyl, alkoxy, halogen, trifluoromethyl, trifluoromethoxy, —COO $R_{21}$, dialkylamino, nitro, cyano, aryloxy, aroyl, naphthyl and —CH$_2$NHC(O)O-alkyl; or $R_{19}$ and $R_{20}$ can be taken together with the phenyl moiety to which they are attached to form a structure of the formula —O(—CH$_2$)$_n$—O— wherein n is 1 or 2, e.g.,

- $R_{21}$ is hydrogen or alkyl;
- Y is selected from the group consisting of alkyl, cycloalkyl, naphthyl, -continued and wherein
- $R_{22}$ is selected from the group consisting of hydrogen, alkyl, halogen, aralkyloxy-, alkylamino, hydroxyalkylamino, cycloalkylamino, N-alkyl piperazino, (pyridinoalkyl)amino, (N-alkyl)aralkyl amino and aralkyl amino wherein the aryl is optionally substituted with alkoxy;
- $R_{23}$ and $R_{24}$ are each independently hydrogen or halogen;
- $R_{25}$ and $R_{30}$ are each independently hydrogen or alkyl;
- $R_{26}$, $R_{27}$, $R_{28}$, and $R_{29}$ are selected independently from the group consisting of hydrogen, alkyl and halogen;
- $R_{31}$ is hydrogen, alkyl, halogen or aryl; and
- $R_{32}$ is each independently H, OH or taken together with the carbon to which they are attached form —C=O;

Z consists of the moiety D-E, wherein
- D is an aryl optionally substituted by one or more substituents selected from the group consisting of hydrogen, alkyl, alkoxy, halogen, nitro, —SO$_2$NH$_2$, and trifluoromethyl; and
- E is selected from the group consisting of and wherein $R_{33}$ is hydrogen or alkyl; and
R' is a group consisting of $$—N—X$$

wherein
- $R_{150}$ is hydrogen or alkyl;
- X is selected independently from the group consisting of and wherein
- $R_{160}$ is hydrogen or alkyl;

$R_{170}$ is one to three substituents selected from the group consisting of hydrogen, alkyl, halogen, hydroxy, aryloxy, and hydroxyalkyl;

$R_{180}$ is 5 or 6-membered saturated cycloalkylamine;

m' is an integer from 1 to 4;

q' is an integer from 1 to 2;

r' is 0 or 1; or a pharmaceutically acceptable salt thereof.

In some embodiments, when either $R_{19}$ or $R_{20}$ is naphthyl, then A is not C=O.

The compounds of the present invention are useful for inhibiting the fertility of a mammal. The compounds are useful also for preventing conception and for blocking follicular development that is mediated by follicle-stimulating hormone in a mammal.

The present invention also provides methods of inhibiting the fertility, preventing conception and blocking follicular development mediated by follicle-stimulating hormone in a mammal with a compound having the struction of Formula III:

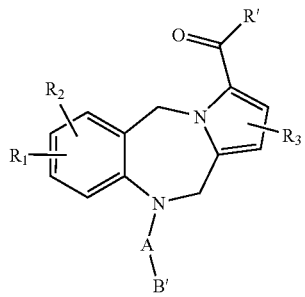

wherein $R_1$, $R_2$, $R_3$, A, and R' are as defined hereinbefore;

B' is selected independently from the group consisting of

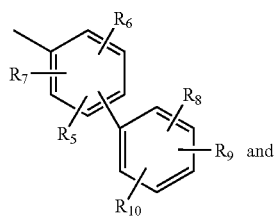

(a)

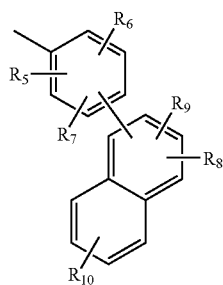

(b)

wherein $R_5$, $R_6$, $R_7$, $R_8$, $R_9$ and $R_{10}$ are as defined hereinbefore; or a pharmaceutically acceptable salt thereof.

DETAILED DESCRIPTION OF THE INVENTION

The present invention discloses novel, non-peptidic, low molecular weight FSH receptor binding antagonists of unique structure. None of the aforementioned compounds are disclosed to be follicle-stimulating hormone receptor (FSH-R) antagonists or contraceptive agents. The compounds of the present invention differ from these previously described compounds in that they contain the optimal substitution in the biphenyl moiety, are active as FSH-R antagonists and useful as contraceptive agents.

In accordance with this invention are novel compounds represented by the structure of Formula I:

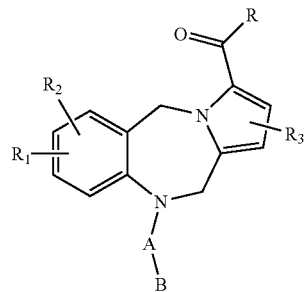

I wherein $R_1$ and $R_2$ are selected independently from hydrogen, ($C_1$-$C_6$)alkyl, halogen, trifluoromethyl, hydroxyl, ($C_1$-$C_6$)alkoxy, $OCF_3$, carboxy, —CONH[($C_1$-$C_6$)alkyl], —CON[($C_1$-$C_6$)alkyl]$_2$, amino, ($C_1$-$C_6$)alkylamino, or -NHCO[($C_1$-$C_6$)alkyl];

$R_3$ is selected from the group consisting of hydrogen, ($C_1$-$C_6$)alkyl, ($C_1$-$C_6$)alkoxy, hydroxyl, amino, ($C_1$-$C_6$)alkylamino, C(O)—($C_1$-$C_6$)alkyl, and halogen;

A is selected from the group consisting of C=O, $CH_2$, and $SO_2$;

B is

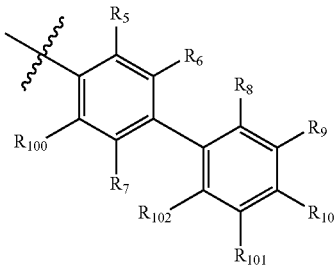

wherein $R_5$, $R_6$, $R_7$, $R_8$, $R_9$, $R_{10}$, $R_{100}$, $R_{101}$, and $R_{102}$ are selected independently from the group consisting of hydrogen, alkyl, alkoxy, trihalomethyl, halogen, —C(O)alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_p$CN, —$(CH_2)_p$COOR$_{12}$, —$(CH_2)_p$NR$_{13}$R$_{14}$, —$(CH_2)_p$CONR$_{13}$R$_{14}$, —CH=NOH, —CH=NO-alkyl,

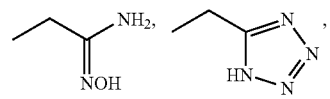

and —C(O)aryl optionally substituted by alkyl;

$R_{11}$ and $R_{12}$ are each independently hydrogen or alkyl;

$R_{13}$ and $R_{14}$ are each independently hydrogen or alkyl; or can be taken together with the nitrogen to which they are attached to form a 4-6 membered saturated ring optionally containing one or more additional O, S or N atoms;

p is 0 or 1;

R is a group consisting of $$-N(R_{15})-X$$

wherein $R_{15}$ is hydrogen or alkyl;

X is selected independently from the group consisting of

[chemical structures showing two pyridine-containing groups with substituents $R_{16}$, $R_{17}$, $R_{18}$, $(C)_m$, $(C)_q$, and $(O)_r$]

wherein $R_{16}$ is hydrogen or alkyl;

$R_{17}$ is one to three substituents selected from the group consisting of hydrogen, alkyl, halogen, hydroxy, aryloxy, and hydroxyalkyl;

$R_{18}$ is 5 or 6-membered saturated heterocycle containing one nitrogen atom;

m is an integer from 1 to 4;

q is an integer from 1 to 2; and r is 0 or 1;

provided that:

if A is C=O, m is 1 or 2, r is 0, $R_7$ is methyl or methoxy and $R_5$, $R_6$, $R_8$, $R_9$, $R_{10}$, $R_{17}$, $R_{100}$, and $R_{101}$ are hydrogen, then $R_{102}$ is not methyl or methoxy;

if A is C=O, m is 2, r is 0, $R_6$ is methoxy and $R_5$, $R_7$, $R_9$, $R_{10}$, $R_{17}$, $R_{100}$, $R_{101}$, and $R_{102}$ are hydrogen, then $R_8$ is not methoxy;

if A is C=O, m is 1 or 2, r is 0, $R_6$ is methyl or methoxy, and $R_5$, $R_7$, $R_8$, $R_{10}$, $R_{17}$, $R_{100}$, $R_{101}$, and $R_{102}$ are hydrogen, then $R_9$ is not methoxy;

if A is C=O, m is 2, r is 0, $R_6$ is chlorine, $R_{100}$ is methoxy, then $R_{101}$ is not methoxy wherein $R_5$, $R_7$, $R_8$, $R_g$, $R_{10}$, $R_{17}$, and $R_{102}$ are hydrogen, or $R_{102}$ is not methyl wherein $R_5$, $R_7$, $R_8$, $R_9$, $R_{10}$, $R_{17}$, and $R_{101}$ are hydrogen;

if A is C=O, m is 1 or 2, r is 0 or 1, $R_7$ is methyl, and $R_5$, $R_6$, $R_9$, $R_{10}$, $R_{17}$, $R_{100}$, $R_{101}$, and $R_{102}$ are hydrogen, then $R_8$ is not trifluoromethyl;

if A is C=O, m is 1, r is 0, $R_7$ is methoxy, $R_5$, $R_6$, $R_9$, $R_{10}$, $R_{17}$, $R_{100}$, and $R_{102}$ are hydrogen then $R_8$ is not chlorine wherein $R_{101}$ is hydrogen or $R_{101}$ is not methoxy wherein $R_8$ is hydrogen;

if A is C=O, m is 1, r is 0, $R_5$ is methoxy, $R_7$ is chlorine, and $R_6$, $R_{10}$, $R_{17}$, $R_{100}$, $R_{101}$, and $R_{102}$ are hydrogen, then $R_8$ is not trifluoromethyl, chlorine, or methyl wherein $R_9$ is hydrogen, or $R_9$ is not methoxy wherein $R_8$ is hydrogen;

if A is C=O, m is 2, r is 0, $R_7$ is methyl, and $R_5$, $R_6$, $R_9$, $R_{10}$, $R_{17}$, $R_{100}$, $R_{101}$, $R_{102}$ are hydrogen, then $R_8$ is not methoxy;

if A is C=O, m is 1 or 2, r is 0 or 1, $R_8$ is chlorine, $R_{100}$ is methoxy, and $R_5$, $R_7$, $R_9$, $R_{10}$, $R_{17}$ are hydrogen, then $R_8$ is not ethoxy wherein $R_{101}$ and $R_{102}$ are hydrogen, or $R_{101}$ is not methyl wherein $R_8$ and $R_{102}$ are hydrogen, or $R_{102}$ is not fluorine, trifluoromethyl, or methyl wherein $R_8$ and $R_{101}$ are hydrogen;

if A is C=O, m is 1 or 2, r is 0, $R_7$ is methyl, and $R_5$, $R_6$, $R_8$, $R_9$, $R_{10}$, $R_{17}$, $R_{100}$, and $R_{102}$ are hydrogen, then $R_{101}$ is not methoxy;

if A is C=O, m is 1, r is 0 or 1, $R_6$ is methoxy, $R_{102}$ is trifluoromethyl, and $R_5$, $R_7$, $R_8$, $R_9$, $R_{10}$, $R_{17}$, and $R_{101}$ are hydrogen, then $R_{100}$ is not hydrogen or methoxy;

if A is C=O, m is 1 or 2, r is 0, $R_8$ is methyl, and $R_5$, $R_7$, $R_9$, $R_{10}$, $R_{17}$, $R_{100}$, $R_{101}$ and $R_{102}$ are hydrogen, then $R_6$ is not hydrogen or methyl; and if A is C=O, m is 1 or 2, r is 0, and $R_5$, $R_6$, $R_7$, $R_9$, $R_{10}$, $R_{17}$, $R_{100}$, $R_{101}$ are hydrogen, then $R_8$ is not methoxy; or a pharmaceutically acceptable salt thereof.

In some embodiments of the invention, $R_1$, $R_2$, and $R_3$ are each hydrogen and $R_{15}$ is hydrogen or methyl. In some such embodiments, $R_{16}$ is hydrogen, m is 1 and r is 0, and $R_{17}$ has at least one substituent that is not hydrogen or none that are hydrogen. In some such embodiments, $R_{16}$ and $R_{17}$ are hydrogen, q is 1 and r is 0, and $R_{18}$ is a 5-membered saturated cycloalkylamine. In some such embodiments, $R_{16}$ and $R_{17}$ are hydrogen, m is 1, r is 0 and $R_6$ is methyl, or $R_7$ is methyl or methoxy, or $R_7$ is methyl and $R_8$ is methyl. In some such embodiments, $R_{16}$ and $R_{17}$ are hydrogen, m is 1, r is 0, and $R_8$ is selected from the group consisting of methyl, chlorine, hydroxy, methoxy, —COCH$_3$, —CHO, —CH(OH)CH$_2$CH$_3$, —CH$_2$OH, —CN, —CH(CH$_3$)$_2$, —CO(phenyl), —CH$_2$OCH$_3$, —CH$_2$COOCH$_3$, —OCH$_2$CH$_3$, —CH$_2$CN, —SCH$_3$, —CH$_2$COOH, —CH(OH)CH$_3$, —COCH(CH$_3$)$_2$, —SO$_2$CH$_3$, —COOCH$_3$, —COOC(CH$_3$)$_3$, —COOH, —CH$_2$CONH$_2$, —CH$_2$CONHCH$_3$, —CH$_2$CON(CH$_3$)$_2$, —CH$_2$CONH(CH$_2$CH$_3$), —CH$_2$CON(CH$_2$CH$_3$)$_2$, —CH(OH)CH(CH$_3$)$_2$, —CON(CH$_3$)$_2$, —CH$_2$N(CH$_3$)$_2$, —CH$_2$NHCH$_3$, —CH$_2$C(NH$_2$)=NOH, —CH$_2$NH$_2$, —SO$_2$NH$_2$, —CONHCH$_3$, and 4-6 membered saturated ring optionally containing one or more O, S or N atoms; or further still, $R_8$ is selected from the group consisting of —CH$_2$OH, —CH$_2$OCH$_3$, —CH$_2$COOCH$_3$, —CH(OH)CH$_3$, —CH$_2$CONH$_2$, and —CH$_2$C(NH$_2$)=NOH.

In some embodiments, A is SO$_2$.

In some embodiments, compounds of the present invention are represented by the structure of Formula I-2:

I-2

[chemical structure of Formula I-2 with substituents $R_{15}$, $R_{500}$, $R_{501}$, $R_{502}$, $(O)_k$, $R_6'$, $R_8'$, $R_9'$, $R_{10}'$, $R_{102}'$]

wherein $R_6'$ is H or (C$_{1-3}$)alkyl;

$R_8'$ is selected from the group consisting of H, (C$_{1-3}$)alkoxy, halogen, (C$_{1-3}$)alkyl, (C$_{1-5}$)hydroxyalkyl, —C(O)R$_{600}$, CN, (C$_{1-3}$)alkoxyalkyl, CH$_2$C(O)R$_{601}$, CH$_2$CN, HC=NOH, OH, S((C$_{1-3}$)alkyl), SO$_2$((C$_{1-3}$)alkyl), CH$_2$N(R$_{602}$)(R$_{603}$), CH$_2$C(NH$_2$)=NOH, and SO$_2$NH$_2$;

R$_9$' is H, halogen or (C$_{1-3}$)alkyl;
R$_{10}$' is H, halogen, (C$_{1-3}$)alkyl, or C(O)(C$_{1-3}$)alkyl;
R$_{102}$' is H or (C$_{1-3}$)alkyl;
R$_{15}$ is as defined hereinbefore;
R$_{500}$ is H, OH, halogen, (C$_{1-3}$)alkyl, or O-phenyl;
R$_{501}$ and R$_{502}$ are each independently H or OH; and
k is 0 or 1;

wherein
R$_{600}$ is H, OH, (C$_{1-3}$)alkyl, phenyl, (C$_{1-6}$)alkoxy, or NR$_{602}$R$_{603}$;
R$_{601}$ is OH, (C$_{1-3}$)alkoxy, or NR$_{602}$R$_{603}$; and
R$_{602}$ and R$_{603}$ are each independently H or (C$_{1-3}$)alkyl, or R$_{602}$ and R$_{603}$ together form a 5-6 membered heterocycle with up to 3 additional N or O atoms;

provided that:
when R$_6$' is methyl, R$_8$' is not methoxy;
when R$_6$' is methyl, and one of R$_8$' or R$_{102}$' is methyl, then either:
(a) the other of R$_8$' or R$_{102}$' is not H; or
(b) k=1; and
if R$_6$', R$_9$', R$_{10}$', R$_{102}$', R$_{500}$, R$_{501}$, and R$_{502}$ are all H, then R$_8$ is not methyl or methoxy.

The present invention also provides the compounds having the structure of Formula II:

II

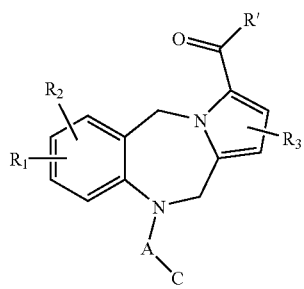

wherein
R$_1$ and R$_2$ are as defined hereinbefore;
R$_3$ is as defined hereinbefore;
A is as defined hereinbefore;
C is selected from the group consisting of

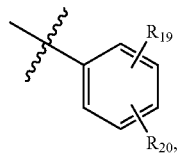

—Y and Z wherein
R$_{19}$ and R$_{20}$ are selected independently from the group consisting of hydrogen, alkyl, alkoxy, halogen, trifluoromethyl, trifluoromethoxy, —COOR$_{21}$, dialkylamino, nitro, cyano, aryloxy, aroyl, naphthyl and —CH$_2$NHC(O)O-alkyl; or R$_{19}$ and R$_{20}$ can be taken together with the phenyl moiety to which they are attached to form a structure of the formula —O(—CH$_2$)$_n$—O— wherein n is 1 or 2, e.g.,

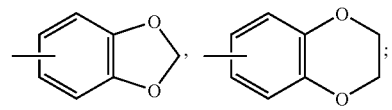

R$_{21}$ is hydrogen or alkyl;
Y is selected from the group consisting of alkyl, cycloalkyl, naphthyl,

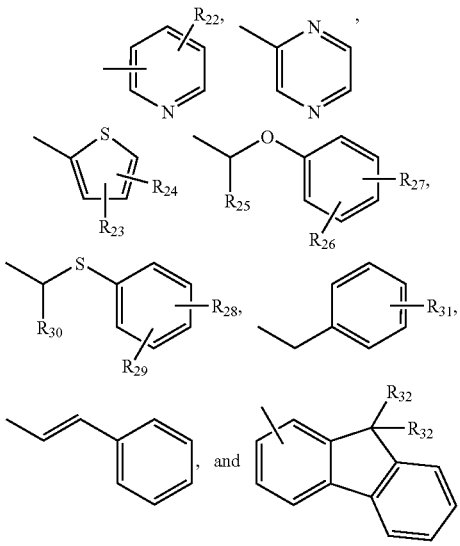

, and wherein
R$_{22}$ is selected from the group consisting of hydrogen, alkyl, halogen, aralkyloxy-, alkylamino, hydroxyalkylamino, cycloalkylamino, N-alkyl piperazino, (pyridinoalkyl)amino, (N-alkyl)aralkyl amino and aralkyl amino wherein the aryl is optionally substituted with alkoxy;
R$_{23}$ and R$_{24}$ are each independently hydrogen or halogen;
R$_{25}$ and R$_{30}$ are each independently hydrogen or alkyl;
R$_{26}$, R$_{27}$, R$_{28}$, and R$_{29}$ are selected independently from the group consisting of hydrogen, alkyl and halogen;
R$_{31}$ is hydrogen, alkyl, halogen or aryl; and
R$_{32}$ is each independently H, OH or taken together with the carbon to which they are attached form —C=O;

Z consists of the moiety D-E, wherein
D is an aryl optionally substituted by one or more substituents selected from the group consisting of hydrogen, alkyl, alkoxy, halogen, nitro, —SO$_2$NH$_2$, and trifluoromethyl; and
E is selected from the group consisting of

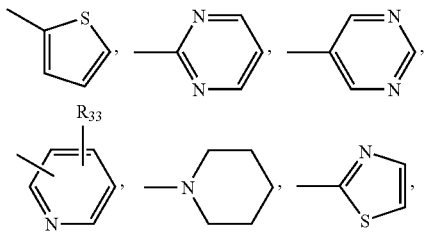

-continued

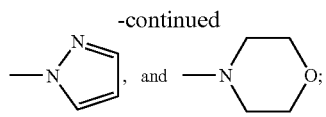

wherein R$_{33}$ is hydrogen or alkyl; and
R' is a group consisting of

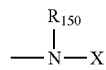

wherein
R$_{150}$ is hydrogen or alkyl;
X is selected independently from the group consisting of

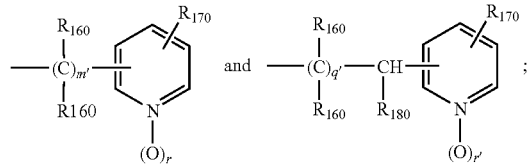

wherein
R$_{160}$ is hydrogen or alkyl;
R$_{170}$ is one to three substituents selected from the group consisting of hydrogen, alkyl, halogen, hydroxy, aryloxy, and hydroxyalkyl;
R$_{180}$ is 5 or 6-membered saturated cycloalkylamine;
m' is an integer from 1 to 4;
q' is an integer from 1 to 2;
r' is 0 or 1.

In some such embodiments, R$_{19}$ and R$_{20}$ are each selected independently from the group consisting of hydrogen, alkyl and halogen; or from the group consisting of hydrogen, methyl, methoxy, fluorine, chlorine, trifluoromethyl, aroyl, —OCF$_3$, —C(CH$_3$)$_3$, —(CH$_2$)$_2$CH$_3$, —COOCH$_3$, —COOH, —CN, —N(CH$_3$)$_2$, —N(O)═O, —N(CH$_2$CH$_3$)$_2$, —CH$_2$NHCOOC(CH$_3$)$_3$, and —O-phenyl.

In some such embodiments, D is an unsubstituted aryl and E is selected from the group consisting of

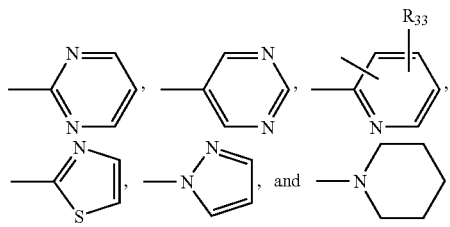

or D is an aryl substituted by methyl or —S(O)$_2$NH$_2$ and E is

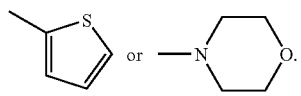

In some such embodiments, Y is

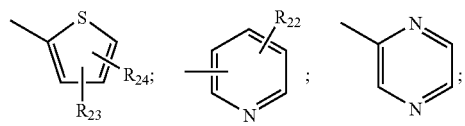

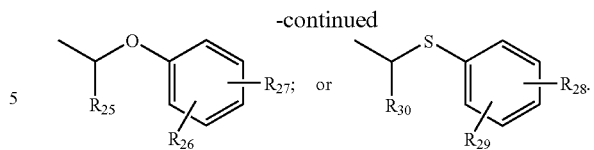

In some such embodiments, Y is selected from the group consisting of

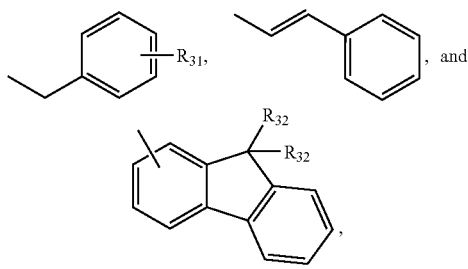

wherein R$_{31}$ is chlorine or phenyl and R$_{32}$ is each independently H; or from the group consisting of 3,3-dimethylbutane, cyclohexyl, isobutane, 1-naphthyl, or 2-naphthyl.

In some embodiments, the present invention provides the compounds 10-{[2'-(1-Hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide; 10-{[2'-(Hydroxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide; 10-{[2'-(Methoxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide; methyl(4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetate; (−)-10-({2'-[1-Hydroxyethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide; 10-{[2'-(2-Amino-2-oxoethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide; and 10-({2'-[2-Amino-2-(hydroxyimino)ethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide.

In further embodiments, the present invention provides the compounds described as Examples 1-150, hereinbelow.

Also provided in accordance with the invention are compositions comprising a pharmaceutically effective amount of a compound according to the invention, and a pharmaceutically acceptable carrier or excipient.

The present invention also provides methods for using the compounds disclosed herein. In some such embodiments, the invention provides methods of inhibiting fertility comprising administering to a mammal, e.g., a human, an effective amount of a compound of the invention. In some such embodiments, the invention provides methods for preventing conception, which comprises administering to a mammal an effective amount of a compound of the invention. In further embodiments, the methods of inhibiting fertility and preventing conception comprises administering a compound of Formula III:

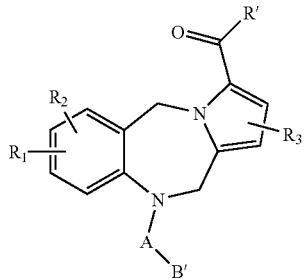

III wherein $R_1$, $R_2$, $R_3$, A, and R' are as defined hereinbefore; B' is selected independently from the group consisting of

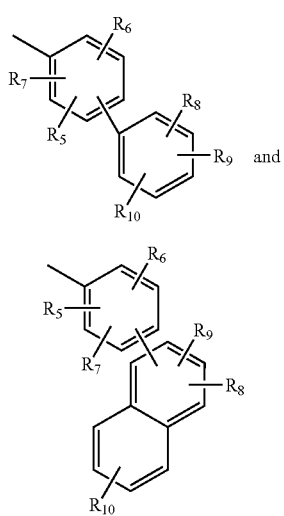

wherein $R_5$, $R_6$, $R_7$, $R_8$, $R_9$ and $R_{10}$ are as defined hereinbefore. In some such embodiments of the methods of the invention, the mammal can be a female; in other embodiments, the mammal is male. When the mammal of such method is female, the onset of pregnancy is prevented in the female mammal, while when the mammal is male, onset of pregnancy is prevented in a second mammal that is female.

In further embodiments of the methods of the invention, FSH-mediated follicular development is blocked by the administration to a mammal of an effective amount of a compound of the invention. In further embodiments, the methods of blocking FSH-mediated follicular development comprises administering a compound of Formula III, as described hereinbefore.

In some embodiments, the present invention provides methods of inhibiting fertility. In some embodiments, the methods include administering to a mammal an effective amount of at least one compound as described herein, or a pharmaceutically acceptable salt thereof. In some embodiments, the methods further comprise identifying a mammal in need of contraception.

In some embodiments, the methods include administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt or free acid forms; i.e., includes the administration of such compounds each in the acid form, or each in the salt form, or one or more in the acid form and one or more in the salt form, in any proportion of the compounds and/or salts.

The invention is to be understood as embracing all simultaneous, sequential or separate use of any combination of the compounds of the invention with any pharmaceutical composition useful in the methods described herein.

As used herein, the term "effective amount" when applied to a compound of the invention, is intended to denote an amount sufficient to cause the intended biological effect. In some embodiments, the methods of the invention provide for administration of combinations of compounds. In such instances, the "effective amount" is the amount of the combination sufficient to cause the intended biological effect.

The term "alkyl", employed alone or as part of a group, is defined herein, unless otherwise stated, as either a straight-chain or branched saturated hydrocarbon of 1 to 10 carbon atoms. In some embodiments, the alkyl moiety contains 1 to 10, 1 to 8, 1 to 6, 1 to 4, 1 to 3 or 1 carbon atoms. Where the term "alkyl" appears herein without a carbon atom range it means a range of $C_1$-$C_{10}$. Examples of saturated hydrocarbon alkyl moieties include, but are not limited to, chemical groups such as methyl, ethyl, n-propyl, isopropyl, n-butyl, tert-butyl, isobutyl, sec-butyl, n-pentyl, n-hexyl, and the like.

The term "alkoxy", employed alone or in combination with other terms, is defined herein, unless otherwise stated, as —O-alkyl. Examples of alkoxy moieties include, but are not limited to, chemical groups such as methoxy, ethoxy, isopropoxy, sec-butoxy, tert-butoxy, and homologs, isomers, and the like.

The term "cycloalkyl," employed alone or in combination with other terms, is defined herein, unless otherwise stated, as a cyclized alkyl group having from 3 to 8 ring carbon atoms.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (bicyclic, up to three rings) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, and the like.

The term "aryloxy" employed alone or in combination with other terms, is defined herein, unless otherwise stated, as a group of formula —O-aryl, where the term "aryl" has the definition as previously described herein.

The term "arylalkyl" or "aralkyl" employed alone or in combination with other terms, is defined herein, unless otherwise stated, as an alkyl, as herein before defined, substituted with an aryl moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "acyl" employed alone or in combination with other terms, is defined herein, unless otherwise stated, as groups of formula —C(O)-alkyl of 2 to 7 carbon atoms.

The term "alkoxyalkyl" employed alone or in combination with other terms, is defined herein, unless otherwise stated, as -alkyl-alkoxy wherein the terms "alkyl" and "alkoxy" have the definitions as previously described herein.

The term "carbalkoxy" employed alone or in combination with other terms, is defined herein, unless otherwise stated, as alkoxycarbonyl, e.g., —COOCH$_3$.

The term "aminoalkyl" employed alone or in combination with other terms, is defined herein, unless otherwise stated, as -alkyl-amino, wherein the term "alkyl" has the definition as previously described herein and the term "amino" is —NH$_2$ or —NH—.

The term "alkylamino" employed alone or in combination with other terms, is defined herein, unless otherwise stated, as —NH-alkyl, wherein the term "alkyl" has the definition as previously described herein.

The terms "inhibit," "inhibiting," "block," or "blocking" as used herein mean to retard, arrest, restrain, impede or obstruct the progress of a system, condition or state.

The terms "prevent" or "preventing" as used herein mean to keep from happening or existing.

The term "administering" as used herein means either directly administering the compounds of the present invention, or administering a prodrug, derivative or analog of the compounds of the present invention that will form an effective amount of the compounds of the present invention within a mammal.

The compositions of the present invention may be adapted to any mode of administration, including intravenous administration such as subcutaneous, intraperitoneal, or intramuscular, bolus and infusion, and oral administration.

The compounds of the present invention can be used in the form of salts derived from non toxic pharmaceutical acceptable acids or bases. These salts include without limitation the following: salts with inorganic acids, e.g., hydrochloric acid, hydrobromic acid, sulfuric acid, nitric acid, phosphoric acid, and organic acids such as acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium or magnesium, or with organic bases, including quaternary ammonium salts.

The compounds of the present invention also can be used in the form of esters, carbamates and other conventional prodrug forms, which generally will be functional derivatives of the compounds of this invention that are readily converted to the active moiety in vivo. Also included are metabolites of the compounds of the present invention defined as active species produced upon introduction of these compounds into a biological system.

When the compounds of this invention are employed as described above, they may be combined with one or more pharmaceutically acceptable excipients or carriers, e.g, solvents, diluents and the like. Such pharmaceutical preparations may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such preparations may contain, for example, from about 25 to about 90% of the active ingredient in combination with the carrier, more usually between about 5% and 60% by weight. The effective dosage of active ingredients employed may vary depending on the particular compound or salt employed, the mode of administration, age, weight, sex and medical condition of the patient, and the severity of the condition being treated. The selection of the appropriate administration and dosage forms for an individual mammal will be apparent to those skilled in the art. Such determinations are routine to a physician, veterinarian or clinician of ordinary skill in the art (see for example, *Harrison's Principles of Internal Medicine* (1998), edited by Anthony Fauci et al., 14$^{th}$ ed., published by McGraw Hill). Further, the dosage regimen may be adjusted to provide the optimal therapeutic response. For example, several divided doses may be administered daily or the dose may be proportionally reduced as indicated by the needs of the therapeutic situation.

These active compounds of the present invention may be administered orally as well as by intravenous, intramuscular, or subcutaneous routes. Solid carriers such as starch, lactose, dicalcium phosphate, microcrystalline cellulose, sucrose and kaolin, liquid carriers such as sterile water, polyethylene glycols, glycerol, non-ionic surfactants, and edible oils such as corn, peanut and sesame oils, may be employed as are appropriate to the nature of the active ingredient and the particular form of administration desired. Adjuvants customarily employed in the preparation of pharmaceutical compositions advantageously may be included, such as flavoring agents, coloring agents, preserving agents, and antioxidants, for example, vitamin E, ascorbic acid, BHT and BHA.

These active compounds also may be administered parenterally or intraperitoneally. Solutions or suspensions of these active compounds as a free base or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations shall contain a preservative to prevent the growth of microorganisms under ordinary conditions of storage and use.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally, for example, by using transdermal skin patches known to those ordinarily skilled in the art. Transdermal administration further includes all administrations across the surface of the body and the inner linings of bodily passages, including epithelial and mucosal tissues, using carrier systems such as lotions, creams, foams, patches, suspensions, solutions, and suppositories (rectal and vaginal). When using a transdermal delivery system, the dosage administration will be continuous rather than in a single or divided daily doses. The compounds of the present invention can also be administered in the form of liposome delivery system wherein the liposomal lipid bilayer are formed from a variety of phospholipids.

Compounds of the present invention may be delivered by the use of carriers such as monoclonal antibodies to which the active compounds are coupled. The compounds of the present invention also may be coupled to soluble polymers as drug carriers or to biodegradable polymers that are useful in achieving controlled release of the active agent.

It is understood by those practicing the art that some of the compounds of this invention depending on the definition of R, R', $R_1$, $R_2$, $R_3$, B, B' and C may contain one or more asymmetric centers, and thus may give rise to enantiomers and diastereomers. The present invention includes all stereoisomers, including individual diastereomers and resolved, enantiomerically pure R and S stereoisomers, as well as racemates, and all other mixtures of R and S stereoisomers, and pharmaceutically acceptable salts thereof, which possess the indicated activity. Optical isomers may be obtained in pure form by standard procedures known to those skilled in the art, and include, but are not limited to, diastereomeric salt formation, kinetic resolution, and asymmetric synthesis. It is also understood that this invention encompasses all possible regioisomers, E-Z isomers, endo-exo isomers, and mixtures thereof that possess the indicated activity. Such isomers can be obtained in pure form by standard procedures known to those skilled in the art, and include, but are not limited to, column chromatography, thin-layer chromatography, and high-performance liquid chromatography. It is understood by those practicing the art that some of the compounds of this invention depending on the definition of B and C may be chiral due to hindered rotation, and give rise to atropisomers, which can be resolved and obtained in pure form by standard procedures known to those skilled in the art. Also included in this invention are all polymorphs and hydrates of the compounds of the present invention.

Also according to the present invention there are provided processes for producing the compounds of the present invention.

Process of the Invention

The compounds of the present invention may be prepared according to one of the general processes outlined below. The compounds of Formula III may be prepared as describe in PCT Application No. WO 2002/083683, filed Apr. 11, 2002, which is incorporated herein in its entirety.

The compounds of general formula (I) where A is —C═O and B is as defined hereinbefore, and compounds of general formula (II) where A is —C═O and C is as defined hereinbefore, can be conveniently prepared as shown in Scheme I.

Scheme I

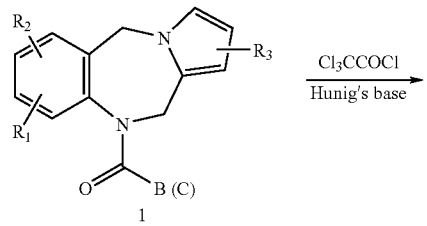

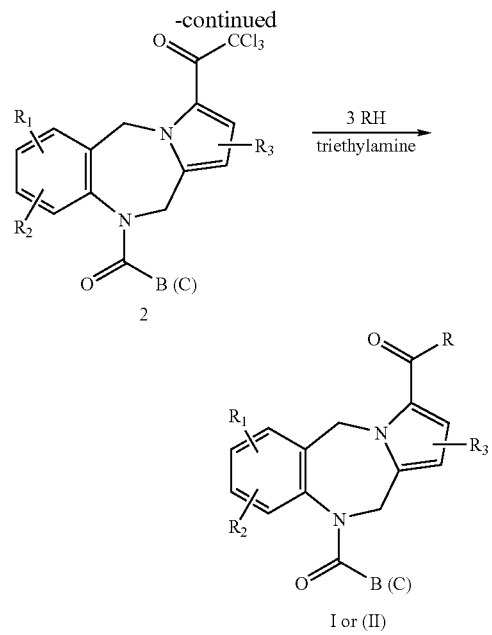

According to the above preferred process, a tricyclic diazepine of formula (1), where $R_1$, $R_2$, $R_3$ and B (or C) are defined hereinbefore, is reacted with a perhaloalkanoyl halide such as trichloroacetyl chloride, in the presence of an organic base such as N,N-diisopropylethyl amine (Hünig's base), in an aprotic organic solvent such as dichloromethane or 1,4-dioxane, at temperatures ranging from −10° C. to ambient, to provide the desired trichloroacetyl intermediate of formula (2). Subsequent reaction of (2) with an appropriately substituted primary or secondary amine of formula (3) in refluxing 1,4-dioxane, or with dimethylsulfoxide optionally in the presence of an organic base such as triethylamine in a solvent such as acetonitrile, at temperatures ranging from ambient to the refluxing temperature of the solvent, yields the desired compounds of formula (I) or (II) where $R_1$, $R_2$, $R_3$, B (or C) are as defined hereinbefore. When the amine (3) is a pyridylamine the compounds of formula (I) or (II) can be further converted to their N-oxides by treatment with an oxidizing agent such as a peracid or other pyridine oxidizing agents known in the literature at temperatures ranging from −40° C. to ambient temperature.

Another preferred process is shown in Scheme II below.

Scheme II

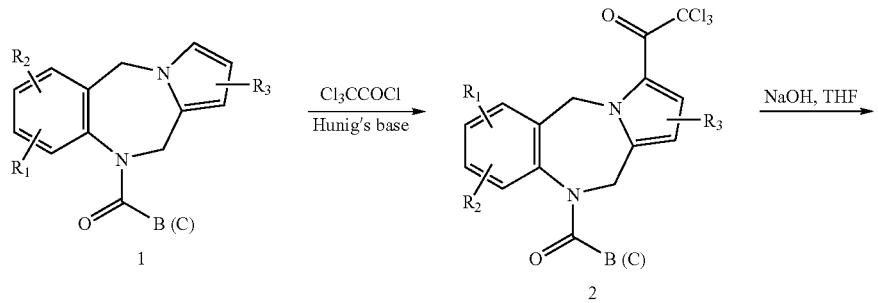

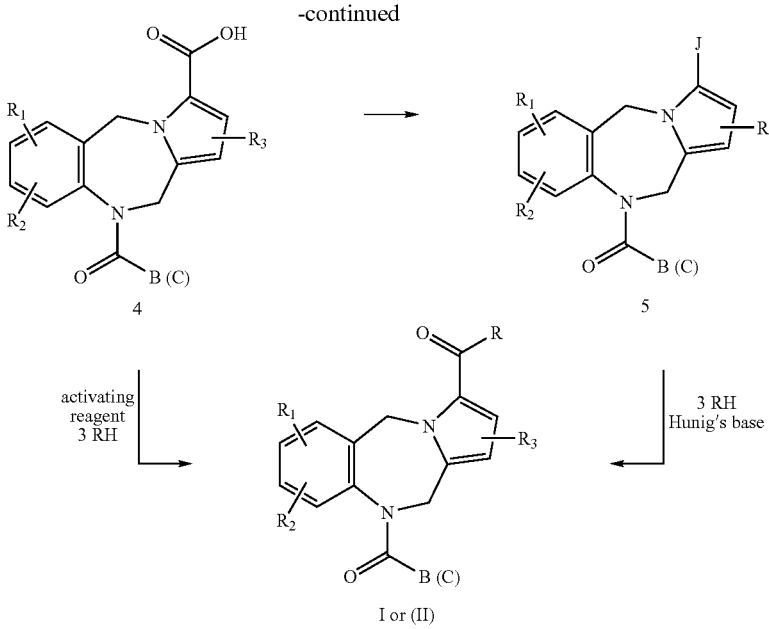

According to the above process the trichloroacetyl intermediate of formula (2) is hydrolyzed with aqueous base such as sodium hydroxide, in an organic solvent such as tetrahydrofuran or acetone, at temperatures ranging from −10° C. to ambient, to yield the intermediate acid of formula (4). The required activation of the carboxylic acid (4) for the subsequent coupling with a primary or secondary amine of formula (3) can be accomplished in several ways. Thus, (4) can be converted to an acyl halide such as a chloride or bromide of formula (5, J=COCl or COBr) by reaction with thionyl chloride (bromide) or oxalyl chloride (bromide) or similar reagents known in the art, either neat or in the presence of an inorganic base such as potassium carbonate, or in the presence of an organic base such as pyridine, 4-(dimethylamino)pyridine, or a tertiary amine such as triethylamine in an aprotic solvent such as dichloromethane, N,N-dimethylformamide or tetrahydrofuran, at temperatures ranging from −5° C. to 50° C., to yield the intermediate acylated derivative (5). Subsequent coupling of the acyl chloride (bromide) (5, J=COCl or COBr) with an appropriately substituted primary or secondary amine of formula (3) in the presence of a stoichiometric amount of Hünig's base, in an aprotic solvent such as dichloromethane, N,N-dimethylformamide or tetrahydrofuran, at temperatures ranging from ambient to the reflux temperature of the solvent, provides the desired compounds of formula (I) or (II) where $R_1$, $R_2$, $R_3$ and B (or C) are as defined hereinbefore.

Alternatively, the acylating species can be a mixed anhydride of the corresponding carboxylic acid, such as that prepared by treating the acid of formula (4) with 2,4,6-trichlorobenzoyl chloride in an aprotic organic solvent such as dichloromethane according to the procedure of Inanaga et al., Bull. Chem. Soc. Jpn. 52, 1989 (1979). Treatment of said mixed anhydride of formula (5) with an appropriately substituted primary or secondary amine of formula (3) in an aprotic solvent such as dichloromethane, at temperatures ranging from ambient to the reflux temperature of the solvent, provides the desired compounds of formula (I) or (II) where $R_1$, $R_2$, $R_3$ and B (or C) are as defined hereinbefore.

Alternatively, amidation of the carboxylic acids of formula (4) can be effectively carried out by treatment of the acid with triphosgene in an aprotic solvent such as dichloromethane, followed by reaction of the activated intermediate with an appropriately substituted primary or secondary amine of formula (3) in the presence of an organic base such as Hünig's base at temperatures ranging from −10° C. to ambient.

Another process for the preparation of the compounds of the present invention of formula (I) or (II), where $R_1$, $R_2$, $R_3$ and B (or C) are as defined hereinbefore, consists of treating the acid of formula (4) with an activating reagent such as N,N-dicyclohexylcarbodiimide or 1-ethyl-3-(3-dimethylamino-propyl)carbodiimide hydrochloride in the presence of 1-hydroxybenzotriazole, followed by reaction of the activated intermediate with an appropriately substituted primary or secondary amine of formula (3), optionally in the presence of an organic base such as Hünig's base and a catalytic amount of 4-(dimethylamino)pyridine, in an aprotic solvent such as dichloromethane, N,N-dimethylformamide or tetrahydrofuran at temperatures ranging from −10° C. to ambient.

In another preferred process, the acid (4) can be activated by treatment with other activating agents such as N,N'-carbonyldiimidazole in an aprotic solvent such as dichloromethane or tetrahydrofuran, at temperatures ranging from −10° C. to the reflux temperature of the solvent. Subsequent reaction of the intermediate activated imidazolide with an appropriately substituted primary or secondary amine of formula (3) provides the desired compounds of formula (I) or (II) where $R_1$, $R_2$, $R_3$ and B (or C) are as defined herein before.

Alternatively, the coupling of the appropriately substituted primary or secondary amine of formula (3) with the acid of formula (4) can be effectively carried out by using hydroxybenzotriazole tetramethyluronium hexafluorophosphate as the coupling reagent in the presence of an organic base such as Hünig's base and in a solvent such as N,N-dimethylformamide, at temperatures ranging from −10° C. to ambient, to provide in good isolated yield and purity the desired compounds of formula (I) or (II) where $R_1$, $R_2$, $R_3$ and B (or C) are as defined hereinbefore.

Related coupling reagents such as diphenylphosphoryl azide, diethyl cyano phosphonate, benzotriazol-1-yl-oxy-tris-(dimethylamino) phosphonium hexafluorophosphate and all other known in the literature that have been used in the formation of amide bonds in peptide synthesis can also be used for the preparation of compounds of formula (I) or (II) where $R_1$, $R_2$, $R_3$ and B (or C) are as defined hereinbefore.

The method of choice for the preparation of compounds of formula (I) or (II) from the intermediate carboxylic acid (4) is ultimately chosen on the basis of its compatibility with the $R_1$, $R_2$, $R_3$ and B (or C) groups and its reactivity with the tricyclic diazepine of formula (1).

Another process for the preparation of compounds of formula (I) or (II) is shown in Scheme III. A tricyclic diazepine of formula (1) is reacted with diphosgene in an aprotic solvent such as dichloromethane, optionally in the presence of an organic base such as triethylamine, followed by reaction of the resulting acylated intermediate with an appropriately substituted primary or secondary amine of formula (3), to provide the desired compounds of formula (I) or (II) where $R_1$, $R_2$, $R_3$ and B (or C) are as defined hereinbefore.

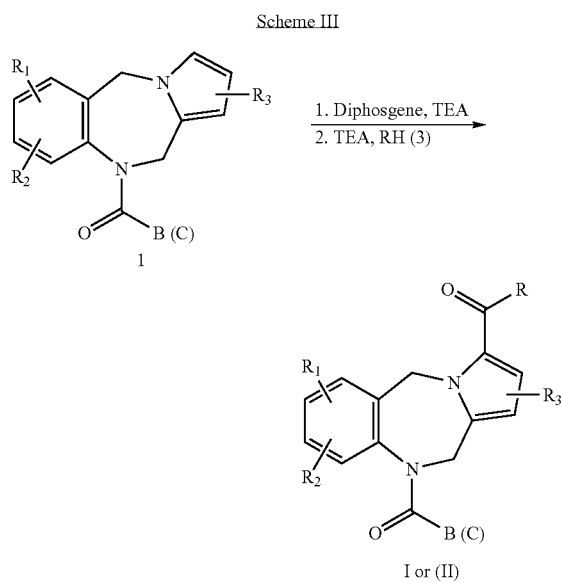

The tricyclic diazepines of formula (1) of Scheme I, wherein A is —C=O and B and C are as defined hereinbefore, can be conveniently prepared as shown in Scheme IV.

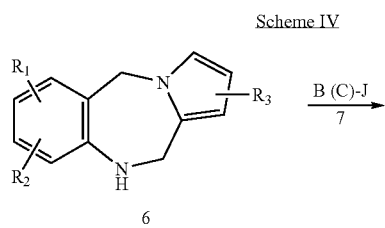

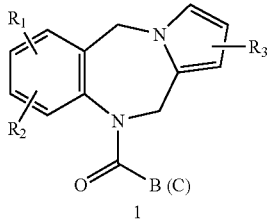

Thus, a tricyclic diazepine of formula (6) is treated with an appropriately substituted acylating agent such as an aroyl halide, such as an appropriately substituted acyl chloride (or bromide) of formula (7, J=COCl or COBr), where B (or C) is ultimately chosen on the basis of its compatibility with the present reaction scheme, in the presence of an inorganic base such as potassium carbonate, or in the presence of an organic base such as pyridine, 4-(dimethylamino)pyridine, or a tertiary amine such as triethylamine, N,N-diisopropylethyl amine or N,N-dimethylaniline, in an aprotic solvent such as dichloromethane, N,N-dimethylformamide, tetrahydrofuran or 1,4-dioxane, at temperatures ranging from −5° C. to 50° C. to provide intermediates of general formula (1).

Alternatively, the acylating species of formula (7) can be a mixed anhydride of the corresponding carboxylic acid, such as that prepared by treating the acid with 2,4,6-trichlorobenzoyl chloride in an aprotic organic solvent such as dichloromethane according to the procedure of Inanaga et al., *Bull. Chem. Soc. Jpn.*, 52, 1989 (1979). Treatment of the mixed anhydride of general formula (7) with a tricyclic diazepine of formula (6) in a solvent such as dichloromethane, and in the presence of an organic base such as 4-(dimethylaminopyridine), at temperatures ranging from 0° C. to the reflux temperature of the solvent yields the intermediate acylated derivative (1) of Scheme IV.

The acylating intermediate of formula (7) is ultimately chosen on the basis of its compatibility with the B (or C) group and its reactivity with the tricyclic diazepine of formula (6).

The intermediates of formula (7) of scheme IV wherein C is Y or Z are either available commercially, or are known in the art, or can be readily prepared by procedures analogous to those in the literature for the known compounds.

The desired intermediates of formula (7) of Scheme IV where B is as defined hereinbefore can be conveniently prepared by a process shown in Scheme V. Thus, an appropriately substituted aryl iodide (bromide, chloride, or trifluoromethane sulfonate) of formula (8, wherein P is a carboxylic acid protecting group, for example, P=alkyl or benzyl, M=I, Br, Cl, OTf; and $R_5$, $R_6$, $R_7$ and $R_{100}$ are defined hereinbefore) is reacted with an aryl tri(alkyl)tin(IV) derivative of formula (9, T=Sn(trialkyl)$_3$, for example, Sn(n-Bu)$_3$), where $R_8$, $R_9$, $R_{10}$, $R_{101}$, and $R_{102}$ are defined hereinbefore, in the presence of a Pd(0) catalyst, and in the presence or absence of inorganic salts (e.g., LiCl or copper(I) salts), to provide the intermediate ester (10). Subsequent unmasking of the carboxylic function by hydrolysis, hydrogenolysis or similar methods known in the art, followed by activation of the intermediate acid (11) provides the desired compounds of formula (7), where $R_5$, $R_6$, $R_7$, $R_8$, $R_9$, $R_{10}$, $R_{100}$, $R_{101}$, and $R_{102}$ are as hereinbefore defined, suitable for coupling with the tricyclic diazepine of formula (6).

Scheme V

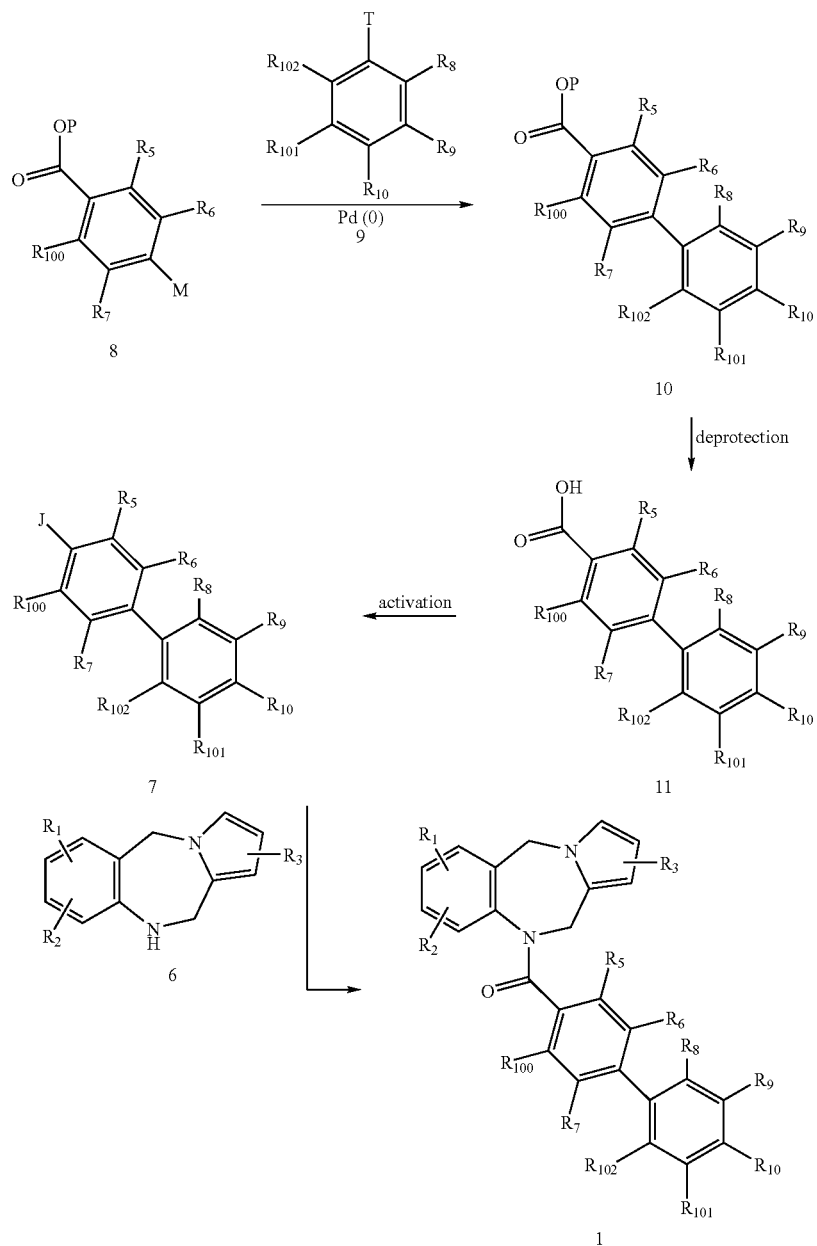

Alternatively, the desired intermediates of formula (10) of Scheme V where B is as defined hereinbefore can be prepared by coupling of the iodide (bromide, chloride, trifluoromethane sulfonate) (8, M=I, Br, Cl or OTf) and an appropriately substituted aryl boron derivative of formula (9, preferably T=B(OH)$_2$), in the presence of a palladium catalyst such as palladium(II)acetate or tetrakis(triphenylphosphine) palladium(0) and an organic base such as triethylamine or an inorganic base such as sodium (potassium or cesium) carbonate, with or without added tetrabutylammonium bromide (iodide), in a mixture of solvents such as toluene-ethanol-water, acetone-water, water or water-acetonitrile, at temperatures ranging from ambient to the reflux temperature of the solvent (Suzuki, *Pure & Appl. Chem.* 66, 213-222 (1994), Badone et al., *J. Org. Chem.* 62, 7170-7173 (1997), Wolfe et al. *J. Am. Chem. Soc.* 121,9559 (1999), Shen, *Tetr. Letters* 38, 5575 (1997)). The exact conditions for the Suzuki coupling of the halide and the boronic acid intermediates are chosen on the basis of the nature of the substrate and the substituents. The desired intermediates of formula (10) of Scheme V can be prepared similarly from the bromide (8, M=Br) and the boronic acid (9) in a solvent such as dioxane in the presence of potassium phosphate and a Pd(0) catalyst.

Alternatively, a palladium-catalyzed cross-coupling reaction of an aryl halide (or trifluoromethane sulfonate) of formula (9, T=Br, I or OTf) with a pinacolato boronate [boronic acid, or trialkyltin(IV)] derivative of formula (8, M=

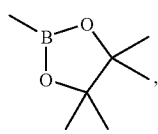

B(OH)$_2$, or SnBu$_3$) yields the desired intermediate of formula (10), which is converted to (1) in the manner of Scheme V.

The required appropriately substituted aryl halides of formula (8, M=Br or I) of Scheme V are either available commercially, or are known in the art, or can be readily accessed in quantitative yields and high purity by diazotization of the corresponding substituted anilines (8, P=H, alkyl or benzyl, M=NH$_2$) followed by reaction of the intermediate diazonium salt with iodine and potassium iodide in aqueous acidic medium essentially according to the procedures of Street et al. *J. Med. Chem.* 36, 1529 (1993) and Coffen et al., *J. Org. Chem.* 49, 296 (1984), respectively, or with copper(I) bromide (March, *Advanced Organic Chemistry*, 3$^{rd}$ ed., p. 647-648, John Wiley & Sons, New York (1985)).

Alternatively, the desired intermediates of formula (11) of Scheme V where B is as defined hereinbefore can be conveniently prepared as shown in Scheme VI by a cross-coupling reaction of an appropriately substituted pinacolato boronate of formula (13), where R$_8$, R$_9$, R$_{10}$, R$_{101}$ and R$_{102}$ are as hereinbefore defined, with an aryl triflate or an aryl halide of formula (14, Q=OTf, Br, I), where R$_5$, R$_6$, R$_7$ and R$_{100}$ are as defined hereinbefore, according to the general procedures of Ishiyama et al., *Tetr. Lett.* 38, 3447-3450 (1997) and Giroux et al. *Tetr. Lett.* 38, 3841-3844 (1997), followed by basic or acidic hydrolysis of the intermediate nitrile of formula (15) (cf. March, *Advanced Organic Chemistry*, 3$^{rd}$ ed., John Wiley & Sons, New York, p. 788 (1985)).

Scheme VI

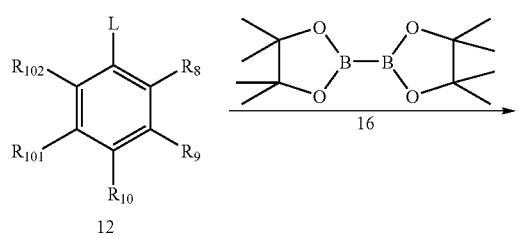

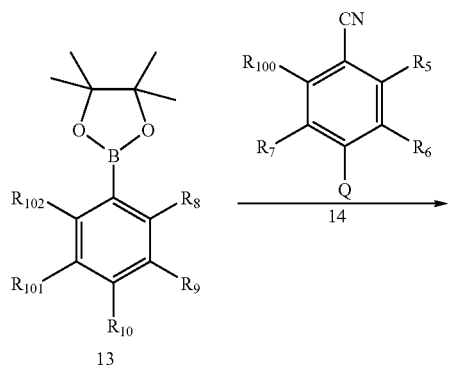

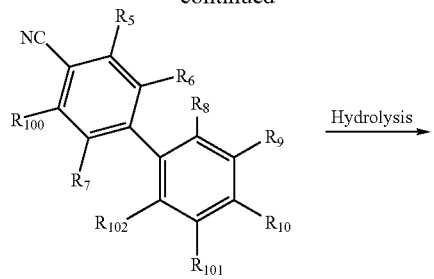

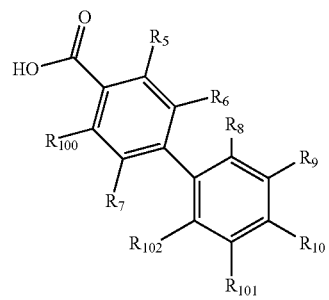

Alternatively, reaction of an iodide (bromide, chloride, or trifluoromethane sulfonate) of formula (12, L=Br, Cl, I, or OTf) with a boronic acid [or trialkyl tin(IV)] derivative of formula (14, Q=B(OH)$_2$, or SnBu$_3$) yields the desired intermediate of formula (15), which is converted to (11) in the manner of Scheme VI.

The desired phenyl boronic esters of formula (13) of Scheme VI can be prepared conveniently by the palladium-catalyzed cross-coupling reaction of bis(pinacolato)diboron (16) with an appropriately substituted aryl halide such as a bromide or iodide (12, L=Br, I) or aryl triflate (12, L=OTf) according to the described procedures of Ishiyama et al., *J. Org. Chem.* 60, 7508-7510 (1995) and Giroux et al., *Tetr. Lett.* 38, 3841-3844 (1997).

The desired compounds of formula (1) of Scheme IV wherein A is —C=O and B is as defined hereinbefore can be alternatively prepared by a process shown in Scheme VII.

Scheme VII

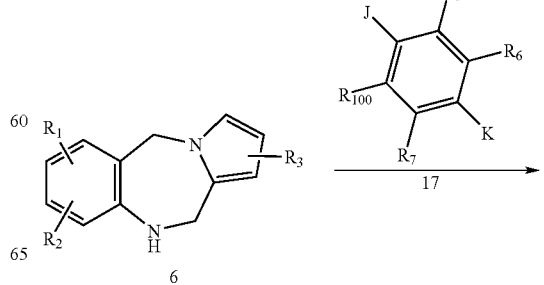

-continued

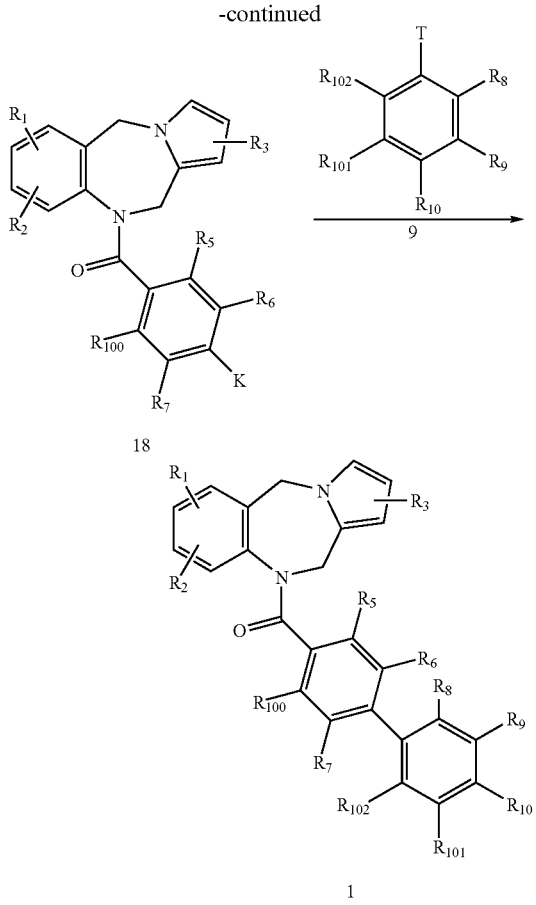

Thus, a tricyclic diazepine of formula (6) is treated with an appropriately substituted acylating agent such as a halo aroyl halide such as an iodo(bromo)aroyl chloride(bromide) of formula (17, J=COCl or COBr; K=I, Br), where $R_5$, $R_6$, $R_7$ and $R_{100}$ are as defined hereinbefore, using any of the procedures hereinbefore described, to provide the acylated intermediate of general formula (18) of Scheme VII.

Alternatively, the acylating species of formula (17) can be a mixed anhydride of the corresponding carboxylic acid. Treatment of said mixed anhydride of general formula (17) with a tricyclic diazepine of formula (6) according to the procedure described hereinbefore yields the intermediate acylated derivative (18).

The acylating intermediate of formula (17) is ultimately chosen on the basis of its compatibility with the $R_5$, $R_6$, $R_7$ and $R_{100}$ groups, and its reactivity with the tricyclic diazepine of formula (6).

A Stille coupling reaction of an halide (18, K=I) with an appropriately substituted organotin reagent such as a trialkyltin(IV) derivative, for example, a tri-n-butyltin(IV) derivative of formula (9, T=SnBu₃), where $R_8$, $R_9$, $R_{10}$, $R_{101}$ and $R_{102}$ are as hereinbefore defined, in the presence of a catalyst such as tetrakis (triphenylphosphine) palladium(0), in an aprotic organic solvent such as toluene and N,N-dimethylformamide, at temperatures ranging from ambient to 150° C. (cf. Farina et al., *J. Org. Chem*, 59, 5905 (1994) and references cited therein), affords the desired compounds of formula (1) wherein $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore.

Alternatively, the reaction of a compound of formula (18, K=Cl, Br or I) with an appropriately substituted aryl boronic acid of formula (9, T=B(OH)₂), where $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore, in a mixture of solvents such as toluene-ethanol-water in the presence of a Pd(0) catalyst and a base such as sodium carbonate, at temperatures ranging from ambient to the reflux temperature of the solvent, yields the desired compounds of formula (1) where $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore.

The preferred substituted aroyl chlorides (bromides) of formula (17) of Scheme VII (K=I, Br; J=COCl or COBr), where $R_5$, $R_6$, $R_7$ and $R_{100}$ are as defined hereinbefore are either available commercially, or are known in the art, or can be readily prepared by procedures analogous to those in the literature for the known compounds.

The intermediates of formula (9, T=Sn(alkyl)₃; for example, alkyl=n-butyl) of Scheme VII are either commercially available, or can be conveniently prepared as shown in Scheme VIII from the corresponding bromo starting materials of formula (19) where $R_8$, $R_9$, $R_{10}$, $R_{101}$ and $R_{102}$ are as hereinbefore defined, by first reacting them with n-butyl lithium followed by reaction of the intermediate lithiated species with a trialkyl (e.g., trimethyl or tri-n-butyl) tin(IV) chloride.

Scheme VIII

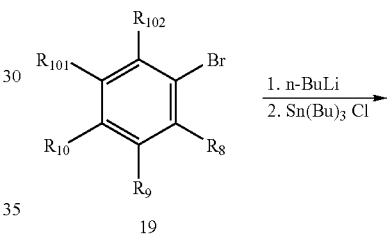

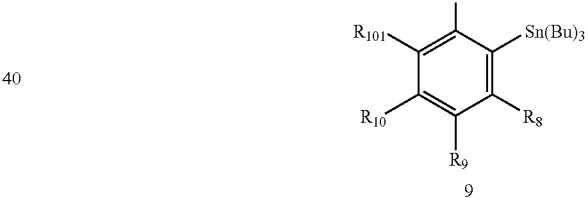

The substituted aryl boronic acids of formula (9, T=B(OH)₂) are either available commercially, or are known in the art, or can be readily prepared by procedures analogous to those in the literature for the known compounds.

Alternatively, as shown in Scheme IX, the appropriately substituted aroyl halides, for example, aroyl chlorides of formula (20, J=COCl), where $R_5$, $R_6$, $R_7$ and $R_{100}$ are as hereinbefore defined, are reacted with a tricyclic diazepine of formula (6) to provide the intermediate bromides of formula (21). Subsequent reaction of (21) with an hexa alkyl-di-tin (e.g., hexa-n-butyl-di-tin(IV)) in the presence of a Pd(0) catalyst such as tetrakis(tri-phenylphosphine)palladium(0) and lithium chloride or copper(I) salts, provides the stannane intermediate of formula (22). Further reaction of the tri-n-butyl tin(IV) derivative (22) with the appropriately substituted aryl halide of formula (23, M=bromo or iodo), where $R_8$, $R_9$, $R_{10}$, $R_{101}$ and $R_{102}$ are hereinbefore defined, in the presence of a Pd(0) catalyst such as tetrakis(triphenylphosphine) palladium(0), yields the desired compounds of formula (1) wherein A is —C═O and B, $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore.

Scheme IX

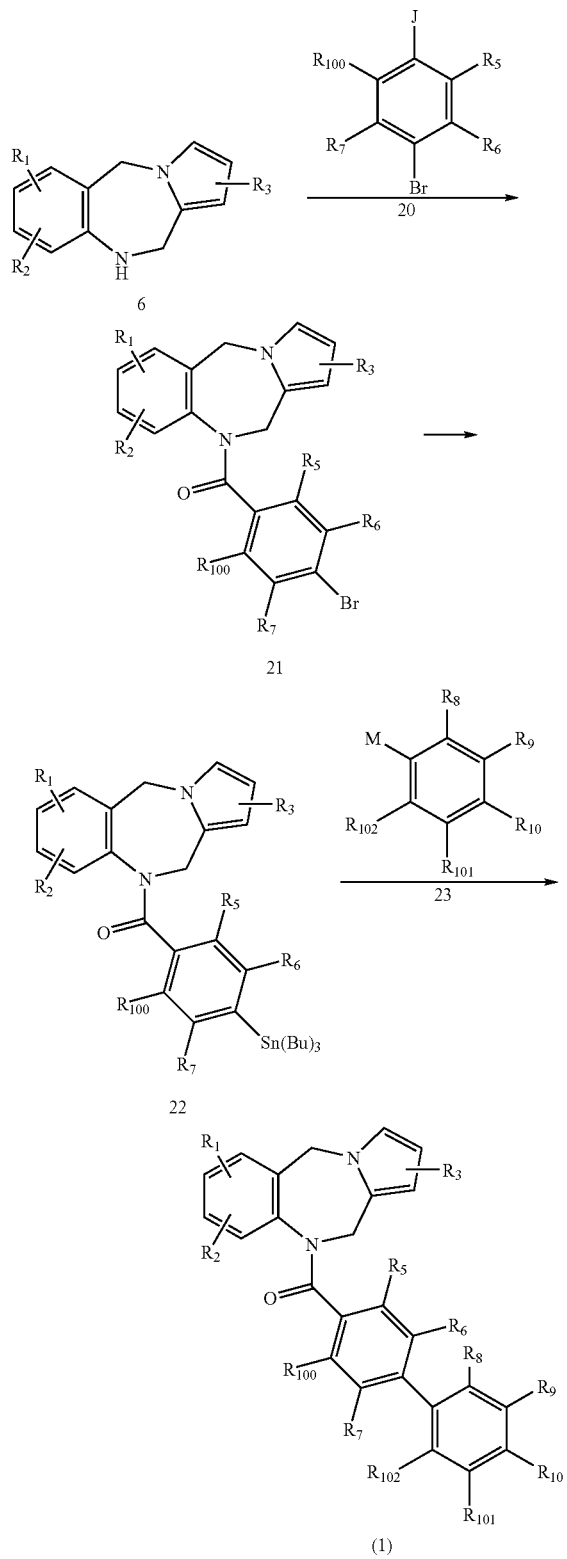

Scheme X

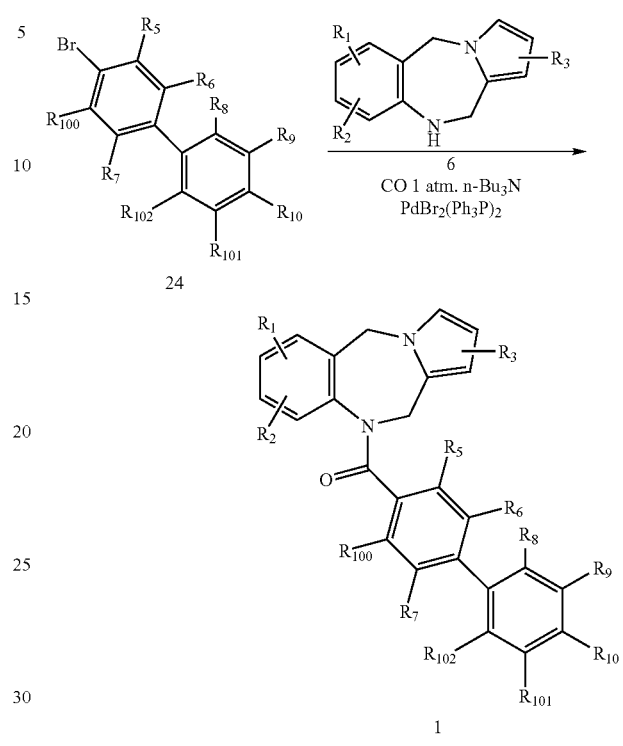

Thus, an appropriately substituted biphenyl of formula (24), wherein $R_5$, $R_6$, $R_7$ and $R_{100}$ are defined hereinbefore, is treated with carbon monoxide in the presence of a tricyclic diazepine of formula (6), a palladium(0) catalyst such as $PdBr_2(Ph_3P)_2$ and a tertiary amine such as n-tributylamine, in a solvent such as anisole or dioxane, at temperatures ranging from ambient to the reflux temperature of the solvent (cf. Schoenberg et al. *J. Org. Chem.* 39, 3327 (1974)) to provide the desired compounds of formula (1) wherein $R_1$, $R_2$, $R_3$, $R_5$, $R_6$, $R_7$, $R_8$, $R_9$, $R_{10}$, $R_{100}$, $R_{101}$ and $R_{102}$ are defined hereinbefore.

Another process for the preparation of the desired compounds of general formula (I) or (II) of Scheme I, wherein A is —C═O and B and C are as defined hereinbefore, is shown in Scheme XI.

Scheme XI

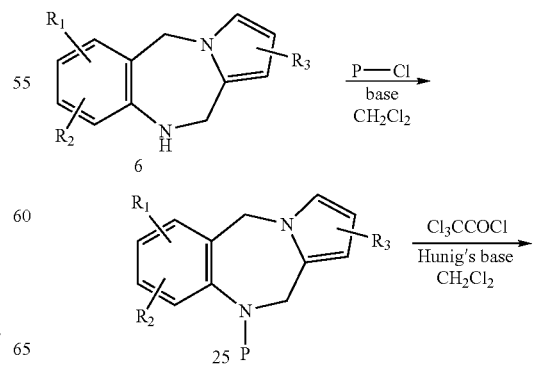

Alternatively, the desired compounds of formula (1) of Scheme IX wherein B is as defined hereinbefore can be prepared as shown in Scheme X.

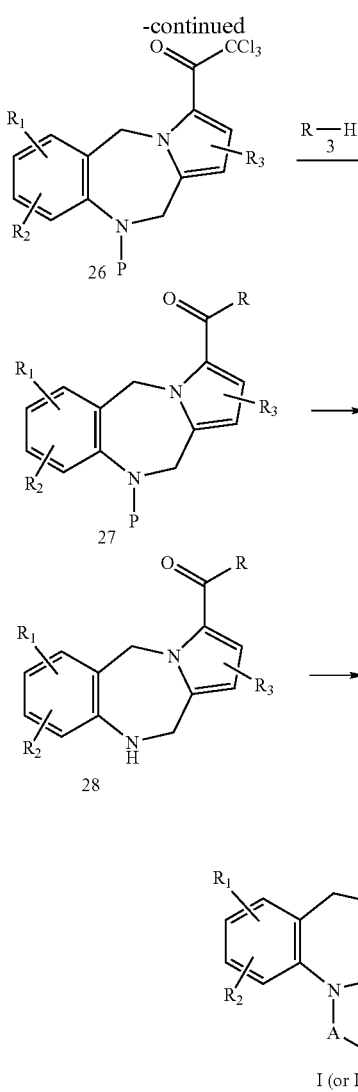

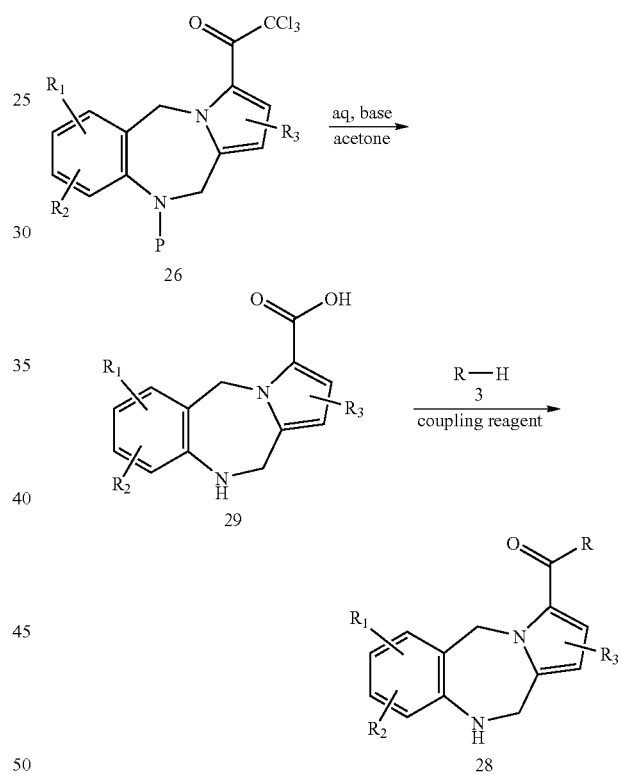

Alternatively, hydrolysis of the trichloroacetate intermediate (26) with aqueous base such as sodium hydroxide in an organic solvent such as acetone, at temperatures ranging from −10° C. to ambient, is accompanied by simultaneous removal of the protecting group (P=Fmoc) and yields the intermediate acid of formula (29), as shown in Scheme XII. The required amidation of the carboxylic acid (29) can be effectively accomplished by treating (29) with an activating reagent such as N,N-dicyclohexylcarbodiimide or 1-ethyl-3-(3-dimethylamino-propyl) carbodiimide hydrochloride in the presence of 1-hydroxybenzotriazole, followed by reaction of the activated intermediate with an appropriately substituted primary or secondary amine of formula (3) optionally in the presence of Hünig's base or a catalytic amount of 4-(dimethylamino) pyridine, in an aprotic solvent such as dichloromethane, N,N-dimethylformamide or tetrahydrofuran at temperatures ranging from −10° C. to ambient. Subsequent acylation of the amide (28) under the conditions of Scheme IV provides the desired compounds of formula (I) or (II).

Thus, a tricyclic diazepine of formula (25), wherein $R_1$, $R_2$ and $R_3$ are defined hereinbefore, carrying a protecting group such a fluorenylalkoxycarbonyl group, such as a fluorenylmethyloxycarbonyl (P=Fmoc) group or an alkoxycarbonyl protecting group such as a tert-butyloxycarbonyl (P=Boc) group is reacted with a perhaloalkanoyl halide such as trichloroacetyl chloride, in the presence of an organic base such as N,N-diisopropylethyl amine (Hünig's base) or a tertiary amine such as triethylamine or N,N-dimethylaniline, optionally in the presence of catalytic amounts of 4-(dimethylamino) pyridine, in an aprotic organic solvent such as dichloromethane at temperatures ranging from −10° C. to ambient to provide the desired trichloroacetyl intermediate of formula (26). Subsequent reaction with a primary or secondary amine of formula (3) under the conditions of Scheme I yields the intermediate amide of formula (27, P=Boc), which is then deprotected (intermediate 28) and acylated to the desired product of formula I (or II). Alternatively, the conversion of (26) to (28) can be carried out in a single step by treatment of (26, P=Fmoc) with a primary amine (3) in the presence of dimethylsulfoxide in an aprotic solvent such as acetonitrile and at the reflux temperature of the solvent.

Other coupling reagents known in the literature that have been used in the formation of amide bonds in peptide synthesis also can be used for the preparation of compounds of formula (28). The method of choice for the preparation of compounds of formula (28) from the intermediate carboxylic acid (20) is ultimately chosen on the basis of its compatibility with the $R_1$, $R_2$, and $R_3$ groups.

Alternatively, the intermediate acids of formula (29) of Scheme XII, wherein $R_1$, $R_2$, and $R_3$ are defined hereinbefore, can be obtained by reacting a tricyclic diazepine of formula (6) with an excess of acylating agent such as trifluoroacetic anhydride or trichloroacetyl chloride, in the presence of an inorganic base such as potassium carbonate or an organic base such as N,N-diisopropylethylamine, in an aprotic solvent such as N,N-dimethylformamide, followed by basic hydrolysis of the intermediate bis-trifluoroacetyl (trichloroacetyl) intermediate of formula (30) optionally with aqueous sodium hydroxide in a protic organic solvent such as ethanol, at temperatures ranging from ambient to the reflux temperature of the solvent as shown in Scheme XIII.

Scheme XIII

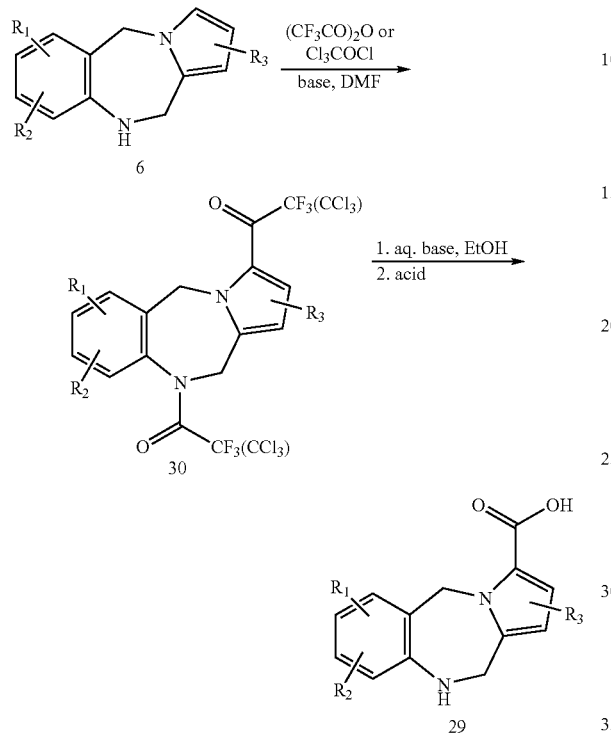

Some processes for the preparation of compounds of formula (I) of Scheme I, wherein A is —C═O and B, $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore, also utilize acylation of the amide intermediate (28) of Scheme XII with an acylating agent of formula (17) of Scheme VII, as shown in Scheme XIV. Subsequent coupling of the intermediate (31, K═Br or I) with an appropriately substituted aryl boronic acid (9, T═B(OH)$_2$) in a mixture of solvents such as dimethoxyethane and water or acetonitrile and water, and in the presence of a Pd(0) catalyst such as tetrakis(triphenylphosphine)palladium(0) or a Pd(II) catalyst such as [1.1'-bis(diphenylphosphino)ferrocene]dichloro palladium(II), and a base such as potassium or sodium carbonate, at temperatures ranging from ambient to reflux, yields the desired compound (I).

Scheme XIV

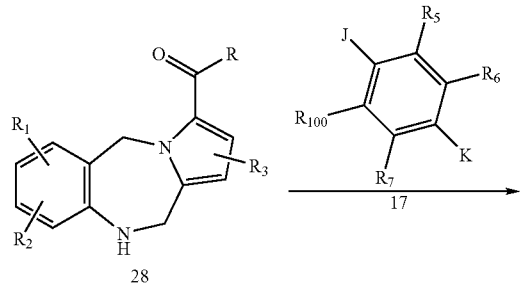

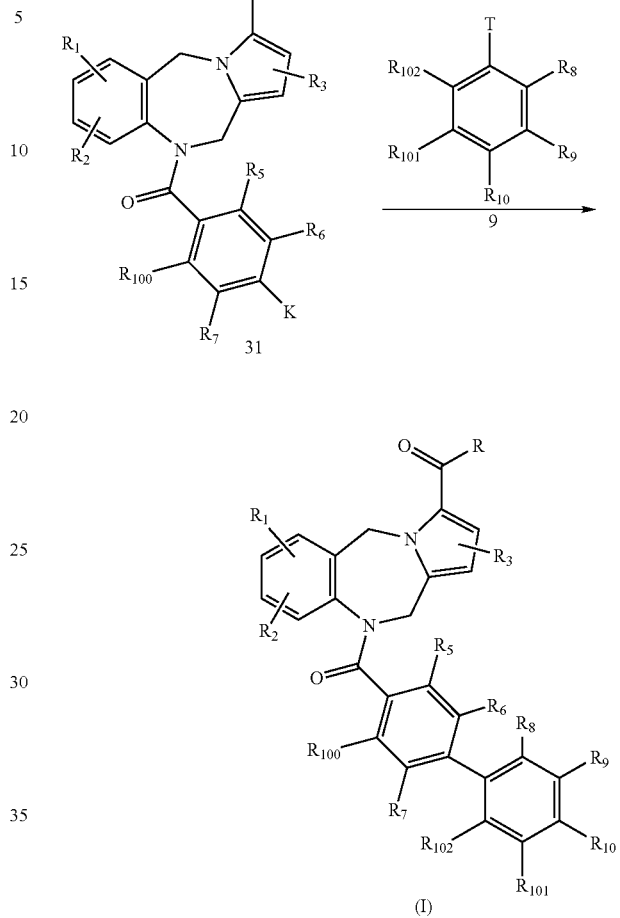

Alternatively, some compounds of formula (I) of Scheme I, wherein A is —C═O and B, $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore, can be prepared, as shown in Scheme XV, by acylation of the amide intermediate (28) of Scheme XII with an acylating agent of formula (20) of Scheme IX.

Scheme XV

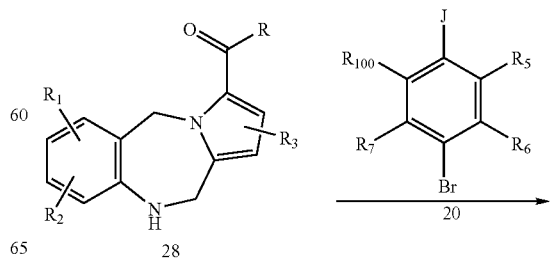

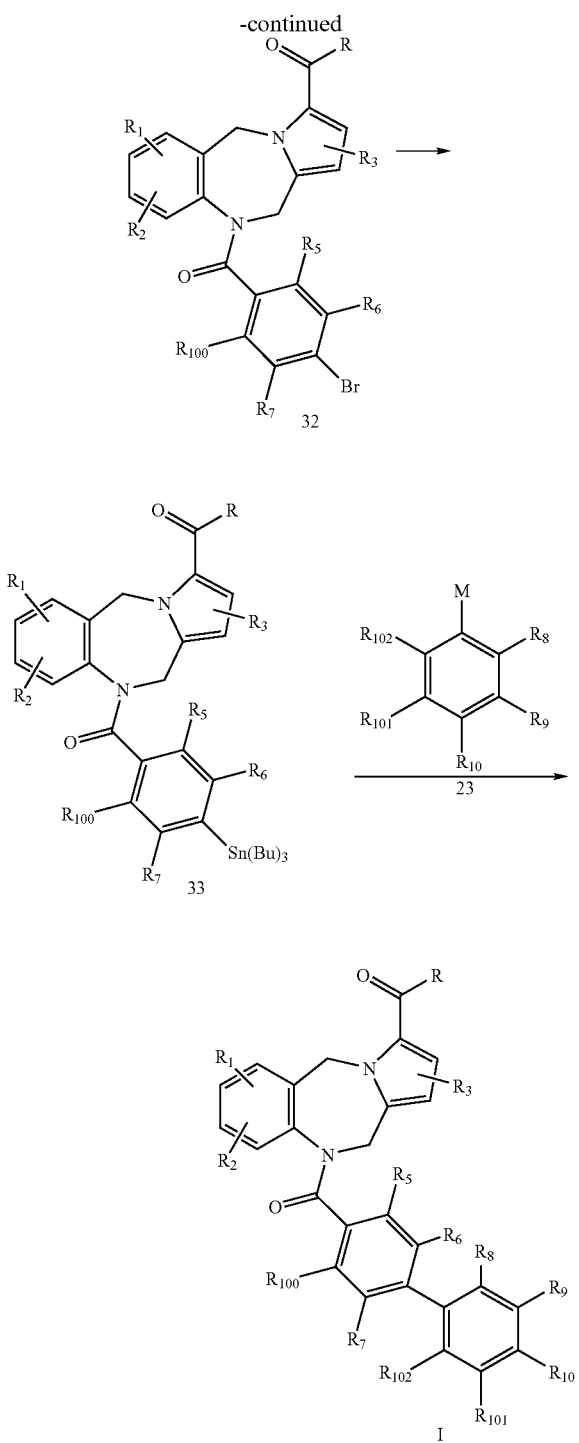

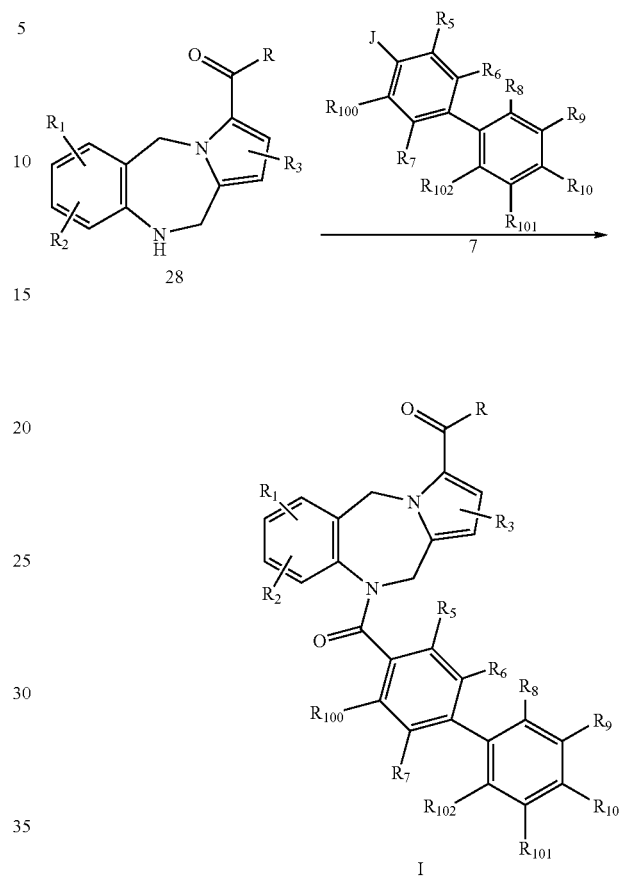

Another process for the preparation of the amide intermediate (31) of Scheme XIV is shown in Scheme XVII. A tricyclic benzodiazepine of formula (6) is acylated with an acylating agent (17, K=Br or I) to provide the intermediate (34), which then is reacted with a perhaloalkanoyl halide (e.g., trichoroacetyl chloride) under the conditions of Scheme I to provide the trichloroacetyl intermediate of formula (35). Subsequent reaction of (35) with an appropriate primary or secondary amine, also under the conditions of Scheme I, provides the desired product (31).

Alternatively, the preferred compounds of formula I of Scheme I, where A is —C=O and B, $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore, can be prepared by acylation of the amide intermediate (28) of Scheme XII with an acylating agent of formula (7) of Scheme V, wherein J is as hereinbefore defined, as shown in Scheme XVI.

Scheme XVII

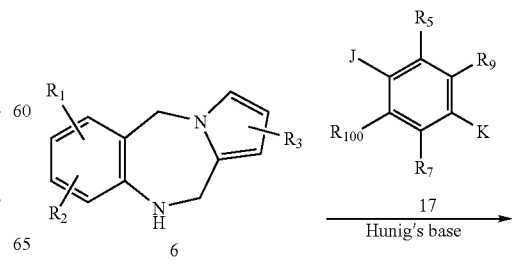

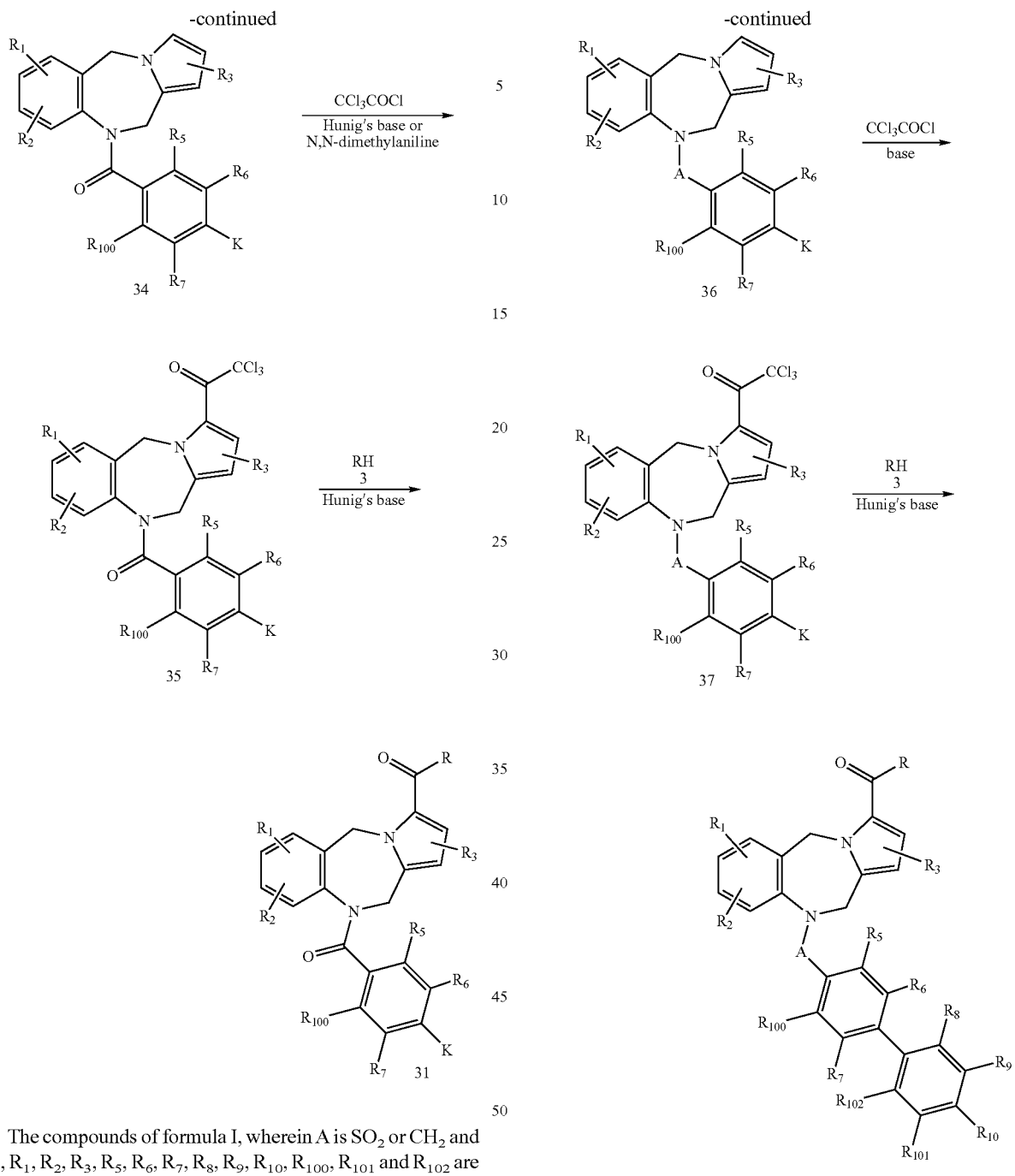

The compounds of formula I, wherein A is $SO_2$ or $CH_2$ and B, $R_1$, $R_2$, $R_3$, $R_5$, $R_6$, $R_7$, $R_8$, $R_9$, $R_{10}$, $R_{100}$, $R_{101}$ and $R_{102}$ are as defined hereinbefore, also can be prepared as shown in Scheme XVIII below Scheme XVIII

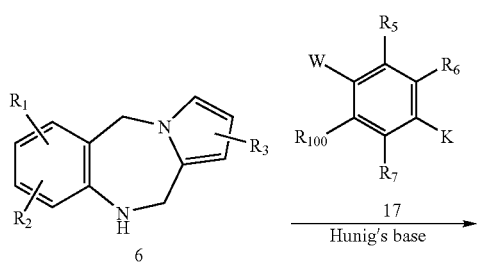

Acylation of (6) with either an aryl sulfonyl halide such as a sulfonyl chloride or bromide (17, W=$SO_2Cl$ or $SO_2Br$) in the presence of Hunig's base in dichloromethane or alkylation of (6) with a benzyl halide, for example, chloride or bromide (17, W=$CH_2Cl$ or $CH_2Br$), in the presence of potassium carbonate in N,N-dimethylformamide provides the intermediates (36, A'=$SO_2$ or $CH_2$), which are converted to

(37) in the manner of Scheme XVII, and then to compounds (I) wherein A' is $SO_2$ or $CH_2$ in the manner of Scheme XIV.

EXAMPLES

Compound Examples

The following examples are presented to illustrate rather than limit the scope of the present invention.

Example 1

10-[(2-METHOXY-2'-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. Methyl 4-bromo-3-hydroxybenzoate

To a solution of 4-bromo-3-hydroxybenzoic acid (30 mmol) in methanol (100 mL) was added concentrated sulfuric acid (2.6 mL). The solution was heated at reflux for 5 hours, cooled to 0° C., and brought to pH 7 by adding saturated. aqueous sodium carbonate. The solution was evaporated to one-third the original volume. Water was added and the product was extracted into ethyl acetate. The organic extracts were washed with water and brine, and dried over anhydrous sodium sulfate. Evaporation gave 6.15 g (89%) of the title compound as a white solid. This was used without further purification.

Step B. Methyl 4-bromo-3-methoxybenzoate

A solution of 4-bromo-3-hydroxybenzoic acid of Step A (27 mmol), potassium carbonate (33 mmol) and dimethyl sulfate (32 mmol), in acetone (40 mL) was stirred at reflux temperature under nitrogen atmosphere for three hours. The mixture was cooled and 5 mL of water was added. The acetone was evaporated and 30 mL of water was added. The product was extracted into dichloromethane. The organic solution was dried over anhydrous magnesium sulfate, and evaporated to provide the title compound (6.5 g; 99%) as a hard, white, crystalline solid.

Step C. 2-Methoxy-2'-methyl-1,1'-biphenyl-4-carboxylic acid methyl ester

A solution consisting of toluene (100 mL), ethanol (50 mL), and water (50 mL), was sparged with dry nitrogen gas for 45 minutes. To the solvent mixture was added 4-bromo-3-methoxybenzoic acid methyl ester of Step B (26.5 mmol), o-tolylboronic acid (29.1 mmol), and sodium carbonate (112.5 mmol). The mixture was sparged with nitrogen gas for an additional ten minutes. Tetrakis(triphenylphosphine)palladium(0) (1 mmol) was added to the mixture which was then heated at 105° C. for 6 hours. The mixture was cooled and the phases separated. The organic phase was washed three times with a sequence of saturated aqueous sodium carbonate, and brine. The organics were dried over anhydrous sodium sulfate, and evaporated to an oil. Chromatography on silica gel using dichloromethane and hexane (3:1) provided the title compound as a clear oil (6.7g, 99%).

Step D. 2-Methoxy-2'-methyl-1,1'-biphenyl-4-carboxylic acid

To the ester of Step C (26 mmol) was added methanol (10 mL), tetrahydrofuran (45 mL), and 1 N sodium hydroxide (33 mL). The solution was refluxed vigorously in an oil bath at 105° C. for one hour. The volatile solvents were evaporated and the solution was chilled in ice. Hydrochloric acid (2.0 N) was added until the pH was −1. The product was extracted into ethyl acetate, dried with anhydrous magnesium sulfate, filtered and evaporated to a white solid. This was recrystallized in ethyl acetate and hexane to afford 5.5 g of the title compound (86%).

Step E. 10-[(2-Methoxy-2'-methyl-1,1'-biphenyl-4-yl)carbonyl]-10,11-dihydro-5H-pyrrolo[2,1-c][1,4]benzodiazepine To a solution of 2-methoxy-2'-methyl-biphenyl-4-carboxylic acid of Step D (23 mmol) in dichloromethane (50 mL) was added a drop of N,N-dimethylformamide. Oxalyl chloride (36 mmol) was then added dropwise to the solution. The solution was then stirred at reflux temperature for 2 hours. The solvents were evaporated and the resulting acid chloride was dissolved in 20 mL dichloromethane. This was added dropwise to a stirred mixture of 10,11-dihydro-5H-pyrrolo[2,1-c][1,4]benzodiazepine (25 mmol), and triethylamine (34 mmol) in dichloromethane (30 mL) at 0° C. under nitrogen atmosphere. After 20 hours the mixture was quenched with water and washed with 0.5 N hydrochloric acid, 1.0 N sodium hydroxide, and brine. The solution was dried over anhydrous sodium sulfate, and evaporated to a solid. The product was purified by column chromatography using ethyl acetate and hexane (1:3) to provide 8.77 g (95%) of the title compound as a white solid.

Step F. 2,2,2-Trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone A solution of 10-[(2-methoxy-2'-methyl-1,1'-biphenyl-4-yl)carbonyl]-10,11-dihydro-5H-pyrrolo[2,1-c][1,4]benzodiazepine of Step E (21 mmol) and triethylamine (43 mmol) in anhydrous dichloromethane (45 mL) was cooled in an ice bath. To the stirred solution was added, dropwise, trichloroacetyl chloride (65 mmol). The mixture was allowed to stir at ambient temperature for 72 hours. The solution was washed with 0.1 N hydrochloric acid and brine and dried over anhydrous sodium sulfate. Evaporation gave a green foam. This was crystallized by heating in ethyl acetate and chloroform to give 10.2 g of the title compound as a white powder (85%), m.p. 221-222° C.

MS [(+)ESI, m/z]: 553 [M+H]$^+$

Step G. 10-[(2-Methoxy-2'-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide A solution of 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3-yl}ethanone of Step F (2 mmol), and 3-aminomethylpyridine (4.2 mmol), in dimethylsulfoxide (7 mmol) and acetonitrile (15 mL) was stirred at 80° C. for 18 hours. The solvents were evaporated and the residue was dissolved in dichloromethane, washed with water, dried over anhydrous sodium sulfate, and evaporated. The product crystallized from ethyl acetate and hexane (0.96g; 89%), m.p. 165-167° C.

MS [(+)ESI, m/z]: 541 [M+H]$^+$

Example 2

N-{[3-HYDROXY-5-(HYDROXYMETHYL)-2-METHYLPYRIDIN-4-YL]METHYL}-10-[(2-METHOXY-2'-METHYL-1,1'-BIPHENYL-4-YL)CARBONYL]-10,11-DIHYDRO-5H-PYRROLO[2,1-C][1,4]BENZODIAZEPINE-3-CARBOXAMIDE

The title compound was prepared from 2,2,2-trichloro-1-{10-[(2-methoxy-2'-methyl-1,1'-biphenyl-4-yl)carbonyl]-10,11-dihydro-5H-pyrrolo[2,1-c][1,4]benzodiazepin-3- yl}ethanone of Example 1, step F and pyridoxamine dihydrochloride hydrate in the manner of Example 1, m.p. 179° C.

MS [(+)ESI, m/z]: 603 [M+H]+

Example 3

10-[(2,2'-DIMETHYL-1,1'-BIPHENYL-4-YL)CAR-BONYL]-N-(PYRIDIN-3-YLMETHYL)-10,11-DIHYDRO-5H-PYRROLO[2,1-C][1,4]BENZODI-AZEPINE-3-CARBOXAMIDE

Step A. Methyl 2,2'-dimethyl-1,1'-biphenyl-4-carboxylate

A mixture of methyl 4-bromo-3-methylbenzoate (25.0 g, 110 mmol), o-tolylboronic acid (16.5 g, 120 mmol) and potassium carbonate (50 g, 360 mmol) in dioxane:water (300 mL: 200 mL) was purged with nitrogen for 1 hour. [1,1'bis(Diphenylphosphino)ferrocene]dichloropalladium[II] (4.5 g, 5.5 mmol) was added and the reaction mixture was heated to 100° C. with vigorous stirring for 3.5 hours. The cooled reaction mixture was filtered through Celite and the cake washed with ethyl acetate (500 mL). The organic phase was separated, washed with 1 M sodium hydroxide (500 mL) and brine (500 mL), dried over anhydrous potassium carbonate and concentrated in vacuo to give the crude product as a dark oil (28.6 g). Purification by flash chromatography using a solvent gradient of 2% ethyl acetate in hexane afforded the title compound (24.7 g, 93%) as a pale yellow oil.

MS [(+)ESI, m/z]: 241 [M+H]+

HRMS [(+)ESI, m/z]: 241.12205 [M+H]+. Calcd for $C_{16}H_{17}O_2$: 241.12231

Anal. Calcd for $C_{16}H_{16}O_2$: C, 79.97; H, 6.71. Found: C, 79.67; H, 6.61.

Step B. 2,2'-Dimethyl-biphenyl-4-carboxylic acid

To a solution of methyl 2,2'-dimethyl-1,1'-biphenyl-4-carboxylate of Step A (24.7 g, 103 mmol) in 5:1 tetrahydrofuran: methanol (200 mL) was added 1 M sodium hydroxide (108 mL, 108 mmol) and the reaction mixture was heated at reflux for 1 hour. The cooled mixture was then concentrated in vacuo to remove organic solvents. The resulting aqueous solution was cooled to 0° C. and 2 M hydrochloric acid (60 mL, 120 mmol) added slowly followed by water (60 mL) to facilitate stirring of the precipitated product. The suspension was stirred for 1 hour at 0° C. then filtered to afford the title compound (22.6 g, 97%) as a white solid, m.p. 140-143° C.

MS [(−)ESI), m/z]: 225 [M-H]−

Step C. (10,11-Dihydro-5H-pyrrolo[2,1-c][1,4]benzodiazepin-10-yl)-(2,2'-dimethyl-biphenyl-4-yl)-methanone To a suspension of 2,2'-dimethyl-biphenyl-4-carboxylic acid of Step B (22.4 g, 99.0 mmol) in dry dichloromethane (500 mL) at room temperature under nitrogen was added dry N,N-dimethylformamide (5 mL) followed by the dropwise addition of a 2.0 M solution of oxalyl chloride in dichloromethane (60 mL, 120 mmol). The reaction mixture was stirred at room temperature for 2 hours then concentrated in vacuo and the residue redissolved in dry dichloromethane (200 mL). The solution was concentrated in vacuo to afford the crude acid chloride as a brown oil. The acid chloride was dissolved in dichloromethane (500 mL), and 10,11-dihydro-5H-pyrrolo[2,1-c][1,4]benzodiazepine (21.9 g, 119 mmol) was added followed by N,N-diisopropylethylamine (87 mL, 500 mmol). The reaction mixture stirred at room temperature under nitrogen for 16 hours. The mixture was then washed with 1 M hydrochloric acid (5×1 L), 10% aqueous sodium hydroxide (1 L) and brine (500 mL), dried over anhydrous magnesium sulfate, and concentrated in vacuo to give a dark foam. Purification by flash chromatography using a solvent gradient of 2.5 to 40% ethyl acetate in hexane gave a tan solid that was recrystallized from ethyl acetate/hexane to afford the title compound (12.4 g, 32%) as a pale orange solid. Purification of the mother liquors by flash chromatography yielded additional title compound (11.5 g, 30%) as a white solid, m.p. 145-148° C.

MS [+)ESI, m/z]: 393 [M+H]+

Step D. 2,2,2-Trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone To a solution of (10,11-dihydro-5H-pyrrolo[2,1-c][1,4]benzodiazepin-10-yl)-(2,2'dimethyl-biphenyl-4-yl)-methanone of Step C (8.38 mmol) and triethylamine (16.76 mmol) in dichloromethane (30 mL) at ~5° C. was added, rapidly dropwise, trichloroacetyl chloride (25 mmol). The mixture was allowed to stir and warm to room temperature overnight. The mixture was washed with 0.1N hydrochloric acid and dilute brine, then dried over anhydrous sodium sulfate and evaporated to leave a light green oil. The title compound was obtained pure as a light yellow crystalline solid by treatment with hot ethyl acetate/hexane (3/1), mp 212-214° C.

MS [(+)ESI, m/z]: 537 [M+H]+

Anal. Calcd for $C_{29}H_{23}Cl_3N_2O_2$: C, 64.76; H, 4.31; N, 5.21. Found: C, 64.70; H, 4.35; N, 4.96.

Step E. 10-[(2,2'-Dimethyl-1,1'-biphenyl-4-yl)carbonyl]-N-(pyridin-3-ylmethyl)-10,11-dihydro-5H-pyrrolo[2,1-c][1,4]benzodiazepine-3-carboxamide To a solution of 2,2,2-trichloro-1-{10-[(2,2'-dimethyl-1,1'-biphenyl-4-yl)carbonyl]-10,11-dihydro-5H-pyrrolo[2,1-c][1,4]benzodiazepin-3-yl}ethanone of Step D (8.0 g, 15 mmol) and dimethyl sulfoxide (5.3 mL, 75 mmol) in dry acetonitrile (90 mL) at room temperature under nitrogen was added 3-(aminomethyl)pyridine (3.1 mL, 30 mmol) and the reaction mixture was heated to reflux for 48 hours. The cooled mixture was concentrated in vacuo, the oily residue redissolved in ethyl acetate (400 mL), washed with 1M sodium hydroxide (100 mL) and brine (100 mL), dried over anhydrous magnesium sulfate, and concentrated in vacuo to give a red foam. Purification by flash chromatography using a solvent gradient of 50 to 100% ethyl acetate in hexane gave a pale yellow foam. Trituration with hot diethyl ether (150 mL) afforded the title compound (5.9 g, 75%) as a pale yellow solid, m.p. 147-149° C. Alternatively, the title compound could be purified by HPLC (normal phase, Luna CN bonded packing) and crystallized from ethyl acetate/hexane, m.p. 148-150° C.

MS [(−)ESI, m/z]: 525 [M-H]−

HRMS [(+)ESI, m/z]: 527.24314 [M+H]+. Calcd for $C_{34}H_{31}N_4O_2$: 527.24415

Anal. Calcd for: C, 77.54; H, 5.74; N, 10.64. Found: C, 77.20; H, 5.81; N, 10.50.

Example 4

10-[(2,2'-DIMETHYL-1,1'-BIPHENYL-4-YL)CAR-BONYL]-N-[(1-OXIDOPYRIDIN-3-YL)ME-THYL]-10,11-DIHYDRO-5H-PYRROLO[2,1-C][1,4]BENZODIAZEPINE-3-CARBOXAMIDE

Prepared in essentially the same manner as Example 56, replacing 10-{[2'-(1-hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide with 10-[(2,2'-dimethyl-1,1'-biphenyl-4-yl)carbonyl]-N-(pyridin-3- ylmethyl)-10,11-dihydro-5H-pyrrolo[2,1-c][1,4]benzodiazepine-3-carboxamide of Example 3. Purification by flash chromatography using a solvent gradient of 3 to 10% methanol in dichloromethane afforded a colorless foam that was crystallized from ethyl acetate/hexane to give the title compound (0.0317 g, 15%) as a white crystalline solid, m.p. 170-173° C.

MS [(+)ESI, m/z]: 543 [M+H]$^+$
MS [(−)ESI, m/z]: 541 [M−H]$^-$
HRMS [[(+)ESI, m/z]: 543.23825 [M+H]+. Calcd for $C_{34}H_{31}N_4O_3$: 543.23907

Example 5

10-{[2-METHYL-2'-TRIFLUOROMETHYL-[1,1'-BIPHENYL]-4-YL]CARBONYL}-N-(3-PYRIDINYLMETHYL)-10,11-DIHYDRO-5H-PYRROLO[2,1-C][1,4]BENZODIAZEPINE-3-CARBOXAMIDE

Prepared in essentially the same manner as Example 58 Step D, replacing phenylboronic acid with 2-trifluoromethylphenylboronic acid. Purification by flash chromatography using a solvent gradient of 1 to 4% methanol in dichloromethane gave a brown glass that was triturated with diethyl ether to afford the title compound (0.289 g, 66%) as a tan solid.

MS [(+)ESI, m/z]: 581 [M+H]$^+$
MS [(−)ESI, m/z]: 579 [M−H]$^-$
Anal. Calcd for $C_{34}H_{27}F_3N_4O_2$: C, 70.34; H, 4.69; N, 9.65. Found: C, 70.04; H, 4.61; N, 9.58.

Example 6

N-[(5-BROMOPYRIDIN-3-YL)METHYLL]-10-[(2'-METHOXY-1,1'-BIPHENYL-4-YL)CARBONYL]-10,11-DIHYDRO-5H-PYRROLO[2,1-C][1,4]BENZODIAZEPINE-3-CARBOXAMIDE

Step A. 5-Bromonicotinic acid ethyl ester
A solution of 5-bromonicotinic acid (5.15 g, 25.5 mmol) in ethanol (100 mL) containing 1 mL of concentrated sulfuric acid was refluxed for 18 hours. The solvent was removed under reduced pressure and the residue basified with saturated aqueous sodium bicarbonate. The solution was then extracted three times with ether. The organics were dried over anhydrous magnesium sulfate, and concentrated under reduced pressure to give the tittle compound (5.29 g) as an off white solid.

Anal. Calcd for $C_8H_8BrNO_2$: C, 41.77; H, 3.5; N, 6.09. Found: C, 41.74; H, 3.2; N, 5.75.

Step B. (5-Bromo-pyridin-3-yl)-methanol
Crushed pellets of sodium borohydride were added over 30 minutes to a solution of 5-bromonicotinic acid ethyl ester of Step A (5.0 g, 21.7 mmol) in ethanol (150 mL). The reaction was stirred at room temperature for five days and then quenched with water. The ethanol was removed under reduced pressure and the aqueous residue was extracted three times with methylene chloride. The combined organics were dried over anhydrous magnesium sulfate, and concentrated under reduced pressure to a yellow oil. The material was purified by flash chromatography over silica gel Marck-60 using 2:1 hexane/ethyl acetate as an eluant to give the title compound (1.41 g) as a light yellow liquid which was used in the next step without further purification.

Step C. (5-Bromopyridin-3-yl) methylamine
A solution of (5-bromo-pyridin-3-yl) methanol of Step B (1.26 g, 6.7 mmol) in dichloromethane (10 mL) was added dropwise at ice bath temperature to 5 mL of thionyl chloride. The resulting mixture was stirred at room temperature for one hour and then cooled in an ice bath before adding ethyl ether (40 mL). The resulting precipitate was collected by filtration, washed with ethyl ether and dried under reduced pressure for 10 minutes. The solid was then added with stirring to an ice cold solution of aqueous ammonia (30 mL) and ethanol (40 mL). The reaction stirred at room temperature for 20 hours, the solvent was removed under reduced pressure and the resulting residue partitioned between 2N sodium hydroxide and dichloromethane. The organic layer was dried over anhydrous magnesium sulfate, and concentrated under reduced pressure to a yellow solid. The solid was purified by flash chromatography over silica gel Merck-60 using a gradient of methanolic ammonia in dichloromethane to give the title compound (0.456 g).

MS [EI, m/z)] 186.0 [M]$^+$

Step D. N-[(5-Bromopyridin-3-yl)methyl]-10-[(2'-methoxy-1,1'-biphenyl-4-yl)carbonyl]-10,11-dihydro-5H-pyrrolo[2,1-c][1,4]benzodiazepine-3-carboxamide A solution of 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone (0.288 g, 0.534 mmol), (5-bromopyridin-3-yl)methylamine of Step C (0.20 g, 1.07 mmol), triethylamine (0.043 g, 0.588 mmol), dimethylsulfoxide (0.190 mL, 2.67 mmol), and acetonitrile (5 mL) was heated for 17 hours at an oil bath temperature of 81° C. The solvent was removed under reduced pressure and the resulting residue taken up in dichloromethane. The organics were washed with water and brine, dried over anhydrous magnesium sulfate, and concentrated under reduced pressure to a yellow solid. The solid was triturated with hexane, diethyl ether, and ethyl acetate, collected by filtration, and dried under reduced pressure to give the title compound (0.145 g) as an off white solid, m.p 180-184° C.

MS [(+)ESI, m/z]: 607 [M+H]$^+$
Anal. Calcd for $C_{33}H_{27}BrN_4O_3$: C, 65.24; H, 4.48; N, 9.22. Found: C, 64.81; H, 4.66; N, 9.02.

Example 7

10-[(2'-METHOXY-1,1'-BIPHENYL-4-YL)CARBONYL]-N-[(2-PHENOXYPYRIDIN-3-YL)METHYL]-10,11-DIHYDRO-5H-PYRROLO[2,1-C][1,4]BENZODIAZEPINE-3-CARBOXAMIDE

The title compound was prepared according to the procedure of Example 6, Step D, from 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone (0.20 g, 0.379 mmol), 2-phenoxy-pyridin-3-ylmethyl-ammonium chloride (0.192 g, 0.78 mmol), triethylamine (0.112 g, 0.8 mmol), dimethylsulfoxide (0.131 mL, 1.85 mmol), and acetonitrile (5 mL). The crude material was purified by hplc using the following conditions: solvent system, 65:35 acetonitrile:water (0.1% trifluoroacetic acid); Primesphere 10 C18, 250 by 50 mm column; flow rate 100 mL/min) to provide the title compound (0.062 g) as a white solid.

MS [(+)ESI, m/z]: 621 [M+H]$^+$
Anal. Calcd for $C_{39}H_{32}N_4O_4$: C, 75.47; H, 5.20; N, 9.03. Found: C, 74.96; H, 4.94; N, 8.80.

Example 8

10-[(2'-METHOXY-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared according to the procedure of Example 6, Step D, from pyridin-3-yl-methylamine (0.515 mL, 5.057 mmol), 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone (1.30 g, 2.41 mmol), triethylamine (0.738 mL, 5.30 mmol), dimethylsulfoxide (0.854 mL, 12.04 mmol) and acetonitrile (15 mL). The crude material was purified by flash column chromatography on silica gel Merck-60 using 4% methanol in dichloromethane as the eluant to give a light yellow solid. The solid was taken up in dichloromethane and precipitated by the addition of diethyl ether and ethyl acetate. The precipitate was collected by filtration and dried under reduced pressure to give the title compound (0.69 g, 54%) of as a white solid, m.p. 123-127° C.

MS [(+)ESI, m/z]: 527 [M–H]$^-$

Example 9

10-[(2'-METHOXY-1,1'-BIPHENYL-4-YL)CARBONYL]-N-(2-PYRIDIN-3-YL-2-PYRROLIDIN-1-YLETHYL)-10,11-DIHYDRO-5H-PYRROLO[2,1-C][1,4]BENZODIAZEPINE-3-CARBOXAMIDE

The title compound was prepared according to the procedure Example 6, Step D, from 2,2,2-trichloro-1-{10-[(2'-methoxy-1,1'-biphenyl-4-yl)carbonyl]-10,11-dihydro-5H-pyrrolo[2,1-c][1,4]benzodiazepin-3-yl}ethanone (1.21 g, 2.25 mmol), 2-(3-pyridyl)-2-pyrrolidinylethyl amine trihydrochloride (0.450 g, 1.5 mmol), triethylamine (5 equivalents), dimethylsulfoxide (0.540 mL) and acetonitrile (28 mL). The crude material was flash chromatographed over silica gel Merck-60 using a gradient of methanol (1-5%) in dichloromethane containing 0.2% ammonium hydroxide, to provide a brown foam. The material was further purified by preparative HPLC (40:60 acetonitrile:water containing 0.1% formic acid; Primesphere 10 C18, 250×50 mm column; flow 90 mL/min). The solution was brought to pH 8 with concentrated ammonium hydroxide prior to concentration to small volume in vacuo. The residue was redissolved in dichloromethane, dried over anhydrous potassium carbonate and evaporated to dryness to provide an off-white foam (0.560 g). This material was sonicated with hexane (containing a few drops of ethyl acetate). The resulting off-white powder was collected and dried (0.442 g).

MS [(+)ESI, m/z]: 612.25 (M+H)$^+$
MS [(–)ESI, m/z]: 610.3 [M–H]$^-$
Anal. Calcd for $C_{38}H_{37}N_5O_3$ 0.35 $CH_2Cl_2$: C, 71.81; H, 5.92; N, 10.92. Found: C, 71.80; H, 6.22; N 10.88.

Example 10

N-(PYRIDIN-3-YLMETHYL)-10-[(2,2',6'-TRIMETHYL-1,1'-BIPHENYL-4-YL)CARBONYL]-10,11-DIHYDRO-5H-PYRROLO[2,1-C][1,4]BENZODIAZEPINE-3-CARBOXAMIDE

Step A. 2,2',6'-Trimethyl-biphenyl-4-carboxylic acid methyl ester 2,6-Dimethyl boronic acid (13.7 g, 91 mmol) and 3-methyl benzoic acid methyl ester (20.9 g, 91 mmol) were dissolved in toluene (425 mL). Then ethanol (250 mL) and water (250 mL) were added followed by sodium carbonate (38.7 g, 365 mmol). The system was purged with nitrogen and then tetrakis triphenylphospine palladium(0) catalyst (10.5 g, 9 mmol) was added. The mixture was heated under nitrogen for 21 hours and filtered through celite. The cake was washed with a large amount of ethyl acetate, the combined filtrate was washed with water and brine, dried over anhydrous magnesium sulfate, and concentrated to give a solid. Flash chromatography of the residue over silica gel Merck-60 using a gradient of 0-20% ethyl acetate in hexane as the eluant, gave the title compound as a white solid (19.2 g, 83%).

Anal. Calcd. for $C_{17}H_{18}O_2$: C, 80.28; H, 7.13. Found: C, 80.37; H, 7.21.

Step B. 2,2',6'-Trimethyl-biphenyl-4-carboxylic acid

A solution of 2,2',6'-trimethyl-biphenyl-4-carboxylic acid methyl ester of Step A (18.5 g, 75.4 mmole) in tetrahydrofuran was treated with 1 N sodium hydroxide (250 mL) and heated at 90° C. for 20 hours. The mixture was acidified to pH ~1 with concentrated hydrochloric acid, extracted with dichloromethane, dried over anhydrous magnesium sulfate, and concentrated to give the title compound as a white powder (15.63 g). Recrystallization from aqueous ethanol provided white plates, m.p. 172-173° C.

MS [(–)ESI, m/z]: 239.1 [M–H]$^-$
Anal. Calcd. For. $C_{16}H_{16}O_2$: C, 79.97; H, 6.71. Found: C, 79.71; H, 6.70.

Step C. (5H, 10)-[(2,2',6'-Trimethyl-1,1'-biphenyl-4-yl)carbonyl]-10,11-dihydro-5H-pyrrolo[2,1-c][1,4]benzodiazepine The 2,2',6'-trimethyl-biphenyl-4-carboxylic acid of Step B (11.4 g, 47.4 mmol) was stirred with 35 mL (479 mmol) of thionyl chloride, and heated to 70° C. for 3 hours. The excess thionyl chloride was removed under vacuum with the aid of toluene. The crude acid chloride was dissolved in dichloromethane (100 mL) and a solution of 10,11-dihydro-5H-pyrrolo[2,1-c][1,4]benzodiazepine (12.23g, 47.4 mmol) in dichloromethane (50 mL) was added dropwise. After stirring overnight at room temperature, the mixture was washed with water, 1N hydrochloric acid, saturated aqueous sodium bicarbonate, and brine, dried over anhydrous magnesium sulfate, and concentrated. Flash chromatography of the residue on silica gel Marck-60 using a gradient of dichloromethane in hexane (from 1:1 to 4:1) gave the pure title compound which was recrystallized from aqueous ethanol as fine translucent plates, m.p. 170-171° C.

MS [(+)ESI, m/z]: 407.2 [M+H]$^+$
Anal. Calcd for $C_{28}H_{26}N_2O$ 0.15 $H_2O$: C, 82.18; H, 6.48; N 6.85. Found: C, 82.28; H, 6.32; N, 6.76.

Step D. 2,2,2-Trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone To a solution of (5H, 10)-[(2,2',6'-trimethyl-1,1'-biphenyl-4-yl)carbonyl]-10,11-dihydro-5H-pyrrolo[2,1-c][1,4]benzodiazepine of Step C (7.934 g, 19.5 mmol) in dichloromethane (160 mL) was added trichloroacetyl chloride (11 g, 60.5 mmol, 3.1 eq.), N,N-diisopropylethyl amine (5.54g, 43 mmol, 2.2 eq.) and 4-dimethylamino pyridine (10 mole %). The mixture was stirred for 16.5 hours at room temperature, then quenched with water (100 mL) and stirred for 1 hour. The organic layer was washed with 0.1N hydrochloric acid and brine, dried over anhydrous magnesium sulfate, and concentrated to a yellow foam.

MS [(+)ESI, m/z]: 551.1 [M+H]$^+$

Anal. Calcd. For. $C_{30}H_{25}C_{13}N_2O_2 \cdot H_2O$: C, 64.97; N, 4.60; H, 5.05. Found: C, 64.79; H, 4.94; H, 4.58.

Step E. N-(Pyridin-3-ylmethyl)-10-[(2,2',6'-trimethyl-1,1'-biphenyl-4-yl)carbonyl]-10,11-dihydro-5H-pyrrolo[2,1-c][1,4]benzodiazepine-3-carboxamide A suspension of 2,2,2-trichloro-1-{10-[(2,2',6'-trimethyl-1,1'-biphenyl-4-yl)carbonyl]-10,11-dihydro-5H-pyrrolo[2,1-c][1,4]benzodiazepin-3-yl}ethanone of Step D (0.610 g, 1.1 mmol) and 3-(aminomethyl)pyridine (0.119 g, 1.0 mmol) in acetonitrile (15 mL), was treated with dimethylsulfoxide (0.432 g, 5.5 mmol) and triethylamine (0.246 g, 2.4 mmol). The mixture was heated under nitrogen at 80° C. overnight, and then concentrated. The residue was taken up in dichloromethane (25 mL), washed with brine and water, dried over anhydrous magnesium sulfate and concentrated. Flash chromatography of the residue on silica gel Merck-60 eluting with 85:10:5 ethylacetate:hexane:dichloromethane provided the title compound (0.275 g).

MS [(+)ESI, m/z]: 541.2 [M+H]$^+$
MS [(−)ESI, m/z]: 539.2 [M−H]$^-$

Example 11

N-(PYRIDIN-3-YLMETHYL)-10,11-DIHYDRO-5H-PYRROLO[2,1C][1,4]BENZODIAZEPINE-3-CARBOXAMIDE

To a stirred solution of 10,11-dihydro-5H-pyrrolo[2,1-c][1,4]benzodiazepine-3-carboxylic acid (0.912 g, 4 mmol) in N,N-dimethylformamide (10 mL) under nitrogen was added N-methyl morpholine (0.440 mL) followed by 1-hydroxybenzotriazole hydrate (1.22 g, 8 mmol) and 1-ethyl-3-(3-dimethylamino-propyl)carbodiimide hydrochloride (0.843 g, 4.4 mmol). After 15 minutes at room temperature 3-(aminoethyl)pyridine was added (0.432 g, 4 mmol). The mixture was stirred overnight at room temperature, evaporated to dryness, and the residue washed with water and dried over anhydrous magnesium sulfate. The crude product was flash chromatographed over silica gel Merck-60 eluting with a gradient from 0.5 to 2.5% of methanol in dichloromethane to provide the title compound as an off white solid (1.09 g).

MS [(+)ESI, m/z]: 319 [M+H]$^+$

Example 12

10-[(2',6'-DIMETHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2',6'-Dimethyl-1,1'-biphenyl-4-carboxylic acid

A solution of 2',6'-dimethyl-1,1'-biphenyl-4-carboxylic acid methyl ester (5 g, 20.8 mmol) in tetrahydrofuran (70 mL) was treated dropwise under nitrogen with 1 N lithium hydroxide (45 mL). The mixture was heated at reflux for 8 hours, filtered warm (Celite) and concentrated in vacuo to remove organic solvents. The aqueous residue was acidified in the cold to pH 3 with 2N hydrochloric acid. The precipitate was collected, washed with water ad dried. The residue was dissolved in ethyl acetate, treated with charcoal (with warming), filtered (Celite) and evaporated to yield the title compound as an off-white crystalline solid.

MS [(−)ESI, m/z]: 225 [M−H]$^-$

Step B. 10-[(2',6'-Dimethyl-1,1'-biphenyl-4-yl)carbonyl]-N-(pyridin-3-ylmethyl)-10,11-dihydro-5H-pyrrolo[2,1-c][1,4]benzodiazepine-3-carboxamide A stirred solution of 2',6'-dimethyl-1,1'-biphenyl-4-carboxylic acid of Step A (0.790 g, 3.5 mmol) in dichloromethane (15 mL) was treated under nitrogen with a catalytic amount of N,N-dimethylformamide followed by dropwise addition of 2N oxalyl chloride in dichloromethane (2.8 mL). After the gas evolution ceased the mixture was refluxed for 4 hours, cooled, and evaporated. The residue was azeotroped twice with benzene and dried in vacuo to provide 2',6'-dimethyl-1,1'-biphenyl-4-carboxylic acid chloride. The crude 2',6'-dimethyl-1,1'-biphenyl-4-carboxylic acid chloride (0.856 g, 3.5 mmol) was dissolved in dichloromethane (7 mL) and added dropwise to a suspension of N-(pyridin-3-ylmethyl)-10,11-dihydro-5H-pyrrolo[2,1-c][1,4]benzodiazepine-3-carboxamide of Example 12 (0.450 g, 1.41 mmol) in anhydrous tetrahydrofuran 10 mL) containing N,N-diisopropylethyl amine (0.860 mL). The mixture was stirred for 18 hours at room temperature and evaporated to dryness. The residue was dissolved in dichloromethane, the solution washed with saturated aqueous sodium bicarbonate and brine, dried over anhydrous potassium carbonate and evaporated. The residue was chromatographed over silica gel Merck-60 eluting with a gradient from 0 to 4% methanol in 1:1 hexane-ethyl acetate to provide the title compound (0.452 g) as a white solid after trituration with hexane, m.p. 216-218° C. (dec).

MS [(+)ESI, m/z]: 527[M+H]$^+$
MS [(−)ESI, m/z] 525 [M−H]$^-$

Anal. Calcd for $C_{34}H_{30}N_4O_2 \cdot C_4H_8O$: C, 77.17; H, 5.80; N, 10.46. Found: C, 76.91; H, 5.64, N, 10.46.

Example 13

10-(1,1'-BIPHENYL-4-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

Step A. 10-(1,1'-Biphenyl-4-ylcarbonyl)-10,11-dihydro-5H-pyrrolo[2,1-c][1,4]benzodiazepine To a solution of 5.53 g (0.03 mol) of 10,11-dihydro-5H-pyrrolo[2,1-c][1,4]benzodiazepine in 50 mL of 1,4-dioxane was added 3.64 g (0.03 mol) of N,N-dimethylaniline followed by 6.50 g. of 4-biphenylcarbonyl chloride. The reaction solution was allowed to stand at room temperature for 2 hours and then slowly poured into 2 L of water. On cooling the mixture a crystalline white solid was formed which was collected and dried to provide the title compound (9.5 g). The product was used directly in the next step.

MS [(+)ESI,m/z]: 365 [M+H]$^+$

Step B. 1-[10-(1,1'-Biphenyl-4-ylcarbonyl)-10,11-dihydro-5H-pyrrolo[2,1-c][1,4]benzodiazepin-3-yl]-2,2,2-trichloroethanone 10-(1,1'-Biphenyl-4-ylcarbonyl)-10,11-dihydro-5H-pyrrolo[2,1-c][1,4]benzodiazepine of Step A (1.822 g; 0.005 mol) was dissolved in 50 mL of 1,4-dioxane to which was then added 0.946 g (0.0052 mol) of trichloroacetyl chloride. The reaction solution was heated under reflux with stirring over night, cooled to room temperature and then poured into 250 mL of water. Recrystallization of the crude material from ethanol provided a solid, m.p. 197-198° C.

MS [(+) ESI, m/z]: 509 [M+H]$^+$.

Anal. Calcd for $C_{27}H_{19}Cl_3N_2O_2$: C, 63.61; H, 3.76; N, 5.49; Found: C, 63.49; H, 3.79; N, 5.47.

Step C. 10-(1,1'-biphenyl-4-ylcarbonyl)-N-(pyridin-3-ylmethyl)-10,11-dihydro-5H-pyrrolo[2,1-c][1,4]benzodiazepine-3-carboxamide A solution of 0.216 g (0.002 mol) of 3-aminomethylpyridine and 0.508 g (0.001 mol) of 1-[10-(1,1'-biphenyl-4-ylcarbonyl)-10,11-dihydro-5H-pyrrolo[2,1-c][1,4]benzodiazepin-3-yl]-2,2,2-trichloroethanone of Step B in 25 mL of 1,4-dioxane was heated overnight under reflux with stirring. The cooled reaction mixture was poured into 200 mL of water. The solid was collected and dried to provide the title compound (0.053 g).

MS [(+)ESI, m/z]: 499 [M+H]$^+$.

Anal. Calcd. For $C_{32}H_{26}N_4O_2$ $H_2O$. C, 74.40; H, 5.46; N, 10.85. Found: C, 74.82; H, 5.21; N, 11.00.

Example 14

10-{[2'-(METHYLTHIO)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE 0.67 HYDRATE

Step A. 2'-(Methylthio)-1,1'-biphenyl-4-carboxylic acid

A stirred mixture containing 4.15 g (0.025 mole) of 2-bromothioanisole, 5.08 g. (0.0025 mole) of 4-carboxybenzeneboronic acid, 10.36 g (0.075 mol) of potassium carbonate and 0.45 g (0.00063 mol) of dichlorobis(triphenylphosphine)palladium(II) in 40 mL of water and 20 mL of 1,4-dioxane was heated under reflux for two hours under nitrogen. The reacton mixture was allowed to cool to room temperature and filtered. The dioxane was removed in vacuo, the residue was diluted with 100 mL of water and then acidified with 20% hydrochloric acid. The crude product (6.1 g) was recrystallized from ethanol to yield the title compound, m.p. 220-222° C.

MS [(+)ESI, m/z]: 245 [M+H]$^+$

Anal. Calcd. for $C_{14}H_{12}O_2S$: C, 68.83; H, 4.95. Found: C, 68.66; H, 4.76.

Step B. 10-{[2'-(Methylthio)-1,1'-biphenyl-4-yl]carbonyl}-N-(pyridin-3-ylmethyl)-10,11-dihydro-5H-pyrrolo[2,1-c][1,4]benzodiazepine-3-carboxamide To 20 mL of thionyl chloride was added 0.244 g (0.001 mol) of 2'-(methylthio)-1,1'-biphenyl-4-carboxylic acid of Step A. The solution was heated under reflux for 1 hour. The excess thionyl chloride was removed in a vacuo. To the residue was added 25 mL of dry pyridine and 0.318 g (0.001 mol) of N-(pyridyl-3-ylmethyl)-10,11-dihydro-5H-pyrrolo[2,1-c][1,4]benzodiazepine-3-carboxamide of Example 12. The reaction was allowed to stand at room temperature for 1 hour and the pyridine was removed in vacuo. The residue was collected and washed with water giving a tan solid (0.62 g), m.p. 172-175° C.

MS [(+)ESI, m/z]: 545 [M+H]$^+$.

Anal. Calcd. for $C_{33}H_{28}N_4O_2S$ 0.67 $H_2O$: C, 71.19; H, 5.31; N, 10.06. Found: C, 71.46; H, 5.21; N, 9.68.

Example 15

10-{[2'-(METHYLSULFONYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

Step A. 2'-(Methylsulfonyl)-1,1'-biphenyl-4-carboxylic acid

To a solution of 0.977 g (0.004 mole) of 2'-(methylthio)-1,1'-biphenyl-4-carboxylic acid of Example 14, Step A, in 25 mL of water and 75 mL of acetone was added 10 g. (0.163 mole) of oxone. The mixture was stirred overnight at room temperature. The acetone was removed in vacuo, and the residue was collected (0.80 g) and washed with water to provide a solid, m.p. 273-275° C.

MS [(−)ESI, m/z]: 275 [M−H]$^−$.

Anal. Calcd. For $C_{14}H_{12}O_4S$: C, 60.86; H, 4.38. Found: C, 60.67; H, 4.22.

Step B. 10-{[2'-(Methylsulfonyl)-1,1'-biphenyl-4-yl]carbonyl}-N-(pyridin-3-ylmethyl)-10,11-dihydro-5H-pyrrolo[2,1-c][1,4]benzodiazepine-3-carboxamide The title compound (0.23 g) was obtained starting with the conversion of 0.74 g (0.0027 mol) of 2'-methylsulfonyl)-1,1'-biphenyl-4-carboxylic acid of step A to the acid chloride and its subsequent reaction with 0.863 g (0.0027 mol) of N-(pyridin-3-ylmethyl)-10,11-dihydro-5H-pyrrolo[2,1-c][1,4]benzodiazepine-3-carboxamide of Example 12, in 30 mL of dry pyridine according to the procedure of Example 15 Step B, m.p. 153-156° C.

MS [(+)ESI, m/z]: 577 [M+H]$^+$.

Anal. Calcd. for $C_{33}H_{28}N_4O_4S$ 0.1 $H_2O$: C, 68.52; H, 4.91; N, 9.69. Found: C, 68.27; H, 4.91; N, 9.59.

Example 16

10-{[2'-(AMINOSULFONYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound (0.08 g) was obtained starting with the conversion of 0.555 g (0.002 mol) of 2'-(aminosulfonyl)-1,1'-biphenyl-4-carboxylic acid to the acid chloride and its subsequent reaction with 0.637 g (0.002 mol) of N-(pyridin-3-ylmethyl)-10,11-dihydro-5H-pyrrolo[2,1-c][1,4]benzodiazepine-3-carboxamide of Example 11, in 30 mL of dry pyridine according to the procedure of Example 15 Step B, m.p. 153-156° C.

MS [(+)ESI, m/z]: 578 [M+H]$^+$.

Anal. Calcd. for $C_{32}H_{27}N_5O_4S$ $H_2O$: C, 64.52; H, 4.91; N, 11.76. Found: C, 64.78; H 4.63; N, 11.6.

Example 17

10-{[2'-(CYANOMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

Step A. 2'-(Cyanomethyl)-1,1'-biphenyl-4-carboxylic acid

A stirred mixture containing 5.88 g (0.03 mol) of (2-bromo-phenyl)-acetonitrile, 4.978 g. (0.03 mol) of 4-carboxyphenylboronic acid, 8.29 g (0.06 mol) of potassium carbonate and 0.52 g of dichlorobis(triphenylphosphine)palladium(II) in 46 mL of water and 25 mL of 1,4-dioxane was heated under reflux for two hours in an atmosphere of nitrogen. The reaction mixture was allowed to cool to room temperature and filtered. The dioxane was removed in vacuo and the residue diluted with 100 mL of water and then acidified with 20% hydrochloric acid. The crude product (1.2g) was recrystallized from ethanol to give a solid, m.p. 218-220° C.

MS [(−)ESI, m/z]: 236 [M−H]$^−$

Anal. Calcd. for $C_{15}H_{11}NO_2$ 0.33 $H_2O$: C, 74.08; H, 4.83; N, 5.76. Found: C, 74.01; H, 4.45; N, 5.39.

Step B. 10-{[2'-(Cyanomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide A mixture of 20 mL of thionyl chloride and 0.243 g (0.001 mol) of 2'-(cyanomethyl)-1,1'-biphenyl-4-carboxylic acid of Step A was heated under reflux for 1 hour. The excess thionyl chloride was removed in vacuo. To the residue was added 35 mL of dry 1,4-dioxane, 0.318 g (0.001 mol) of N-(pyridin-3-ylmethyl)-10,11-dihydro-5H-pyrrolo[2,1-c][1,4]benzodiazepine-3-carboxamide and 0.122 g (0.001 mol) of N,N-dimethylformamide. The reaction was heated under reflux for three hours, cooled and evaporated to dryness. The residue was collected, washed with water and triturated with ether to give 0.62 g. of a tan solid, m.p. 105-108° C.

MS: [(+)ESI, m/z]: 538 [M+H]$^+$. Calcd. for $C_{34}H_{27}N_5O_2$ $0.67H_2O$: C, 74.29; H, 5.20; N, 12.74. Found: C, 74.57; H, 4.96; N, 11.92.

Example 18

10-({2'-[2-AMINO-2-(HYDROXYIMINO) ETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

A mixture of 0.806 g (0015 mol) of 10-{[2'-(cyanomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Example 17, 0.52 g (0.0075 mol) of hydroxylamine hydrochloride and 1.03 g (0.0075 mol) of potassium carbonate in 100 mL of ethanol and 25 mL of water was heated under reflux for 2 hours. An additional 1.04 g (0.015 mol) of hydroxylamine hydrochloride and 2.06 g (0.015 mol) of potassium carbonate was added to the and refluxing was allowed to continue until LC/MS indicated that all the starting nitrile was consumed. The solvents were removed in vacuo and the residue was washed with water and purified by chromatography to provide the title compound (0.191 g), m.p. 131-134° C.

MS [(+)ESI, m/z]: 571 [M+H]$^+$

Anal. Calcd. for $C_{34}H_{30}N_6O_3$ 1 $H_2O$: C, 69.37; H, 5.48; N, 14.28. Found: C, 69.11; H, 5.66; N, 13.83.

Example 19

N-(PYRIDIN-3-YLMETHYL)-10-{[2'-(1H-TETRAZOL-5-YLMETHYL)-1,1'-BIPHENYL-4-YL]CARBONYL}-10,11-DIHYDRO-5H-PYRROLO[2,1-C][1,4]BENZODIAZEPINE-3-CARBOXAMIDE

A mixture of 0.537 g (0.001 mol) of 10-{[2'-(cyanomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Example 17, 0.32 g (0.005 mole) of sodium azide and 0.26 g (0.005 mole) of ammonium chloride in 20 mL of dimethyl sulfoxide was heated with stirring at 50° C. for three hours. The reaction mixure was poured into 100 mL of water, and the precipitated crude product was subjected to chromatographic purification giving 0.46 g of title compound, m.p. 164-167° C.

MS [(+)ESI, m/z]: 581 [M+H]$^+$.

Anal. Calcd for $C_{34}H_{28}N_8O_2$ $1.5H_2O$: C, 67.20; H, 5.14; N, 18.44. Found: C, 67.14; H, 5.13; N, 18.29.

Example 20

10-[(2'-FLUORO-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 2-fluorophenylboronic acid. Purification by flash chromatography using a solvent gradient of 2.5 to 5% methanol in dichloromethane gave the title compound (0.288 g, 72%) as a tan foam.

MS ([(+)ESI, m/z]: 531 [M+H]$^+$
MS [(−)ESI, m/z]: 529 [M−H]$^-$
HRMS [(−)ESI, m/z]: 529.2035 [M−H]$^-$. Calcd for $C_{33}H_{26}FN_4O_2$: 529.20398.

Example 21

10-[(2'-CHLORO-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 2-chlorophenylboronic acid. Purification by flash chromatography using a solvent gradient of 1 to 4% methanol in dichloromethane gave the title compound (0.276 g, 67%) as a tan foam.

MS [(+)ESI, m/z]: 547/549 [M+H]$^+$
MS [(−)ESI, m/z]: 545/547 [M−H]$^-$
HRMS [(−)ESI, m/z]: 545.17433 [M−H]$^-$. Calcd for $C_{33}H_{26}ClN_4O_2$: 545.17443

Example 22

10-[(2,4'-DIMETHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with p-tolylboronic acid. Purification by flash chromatography using a solvent gradient of 1 to 4% methanol in dichloromethane gave the title compound (0.268 g, 68%) as a tan foam.

MS [(+)ESI, m/z]: 527 [M+H]$^+$
MS [(−)ESI, m/z]: 525 [M−H]$^-$
HRMS [(−)ESI, m/z]: 525.2286 [M−H]$^-$. Calcd for $C_{34}H_{29}N_4O_2$: H, 525.22905

Example 23

10-[(3'-CHLORO-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 3-chlorophenylboronic acid. Purification by flash chromatography using a solvent gradient of 1 to 4% methanol in dichloromethane gave the title compound (0.353 g, 86%) as a tan foam.

MS [(+)ESI, m/z]: 547/549 [M+H]+
MS [(−)ESI, m/z]: 545/547 [M−H]−
HRMS [(+)ESI, m/z]: 547.18868. Calcd for $C_{33}H_{28}ClN_4O_2$: 547.19008

Example 24

10-[(4'-CHLORO-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 4-chlorophenylboronic acid. Purification by flash chromatography using a solvent gradient of 1 to 4% methanol in dichloromethane gave the title compound (0.359 g, 88%) as a tan foam.
MS [+)ESI, m/z]: 547/549 [M+H]+
MS [(−)ESI, m/z]: 545/547 [M−H]−
HRMS [(+)ESI, m/z}; 547.18916 [M+H]+: Calcd for $C_{33}H_{28}ClN_4O_2$: 547.19008

Example 25

10-[(3',4'-DICHLORO-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 3,4-dichlorophenylboronic acid. Purification by flash chromatography using a solvent gradient of 1 to 4% methanol in dichloromethane gave the title compound (0.294 g, 67%) as an off-white foam.
MS [(+)ESI, m/z]: 581/583 [M+H]+
MS [(−)ESI. m/z]: 579/581 [M−H]−
HRMS [(+)ESI, m/z]: 581.14997 [M+H]+. Calcd for $C_{33}H_{27}Cl_2N_4O_2$ 581.15111

Example 26

10-[(4'-ACETYL-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 57, replacing phenylboronic acid with 4-acetylphenylboronic acid. Purification by flash chromatography using a solvent gradient of 1 to 4% methanol in dichloromethane gave the title compound (0.262 g, 63%) as an off-white foam.
MS [+)ESI, m/z]: 555 [M+H]+
MS [(−)ESI, m/z]: 553 [M−H]−
HRMS [(+)ESI, m/z]: 555.23803 [M+H]+. Calcd for $C_{35}H_{10}N_4O_3$: 555.23962

Example 27

10-[(2'-METHYL-1,1'-BIPHENYL-3-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 10-(3-Bromobenzoyl)-10,11-dihydro-5H-pyrrolo[2,1-c][1,4]benzodiazepine
To a solution of 10,11-dihydro-5H-pyrrolo[2,1-c][1,4]benzodiazepine (5.0 g, 27 mmol) and N,N-diisopropylethylamine (7.5 mL, 43 mmol) in dry dichloromethane (135 mL) was added 3-bromobenzoyl chloride (2.9 mL, 22 mmol) and the reaction mixture was stirred at room temperature under nitrogen for 16 hours. The reaction mixture was then washed with 1 M hydrochloric acid (5×200 mL), 1 M sodium hydroxide (200 mL), and brine (200 mL), dried over anhydrous magnesium sulfate, and concentrated in vacuo to give a yellow solid (7.2 g). Recrystallization from ethyl acetate gave the title compound (5.8 g, 72%) as a white crystalline solid.
MS [(+) ESI, m/z]: 367 [M+H]+
HRMS [(+)ESI, m/z]: 367.04375 [M+H]+. Calcd for $C_{19}H_{16}BrN_2O$: 367.04405

Step B. 10-[(2'-Methyl-1,1'-biphenyl-3-yl)carbonyl]-10,11-dihydro-5H-pyrrolo[2,1-c][1,4]benzodiazepine
A mixture of 10-(3-bromobenzoyl)-10,11-dihydro-5H-pyrrolo[2,1-c][1,4]benzodiazepine of Step A (2.0 g, 5.4 mmol), o-tolylboronic acid (0.8 g, 5.9 mmol) and potassium carbonate (2.4 g, 17.7 mmol) in ethylene glycol dimethyl ether: water (20 mL: 5 mL) was purged with nitrogen for 1 hour. [1,1'-Bis(diphenylphosphino)ferrocene]dichloropalladium [II] (0.22 g, 0.26 mmol) was added and the reaction mixture heated to 75° C. with vigorous stirring for 16 hours. The cooled reaction mixture was then filtered through Celite and the cake washed with dichloromethane (100 mL). The organic phase was separated, washed with 1 M sodium hydroxide (100 mL) and brine (100 mL), dried over anhydrous potassium carbonate and concentrated in vacuo to give the crude product (2.3 g) as a dark brown solid. Purification by flash chromatography using a solvent gradient of 40% to 100% dichloromethane in hexane afforded the title compound (1.7 g, 85%) as a white solid.
MS [(+)ESI, m/z]: 379 [M+H]+
HRMS [(+)ESI, m/z]: 379.18052 [M+H]+. Calcd for $C_{26}H_{23}N_2O$: 379.18049

Step C. 2,2,2-Trichloro-1-{10-[(2'-methyl-1,1'-biphenyl-3-yl)carbonyl]-10,11-dihydro-5H-pyrrolo[2,1-c][1,4]benzodiazepin-3-yl}ethanone
To a mixture of 10-[(2'-methyl-1,1'-biphenyl-3-yl)carbonyl]-10,11-dihydro-5H-pyrrolo[2,1-c][1,4]benzodiazepine of Step B (1.7 g, 4.5 mmol) and sodium carbonate (0.95 g, 9.0 mmol) in dry tetrahydrofuran (40 mL) was added dropwise trichloroacetyl chloride (0.75 mL, 6.7 mmol) and the reaction mixture stirred at room temperature under nitrogen for 18 hours. The reaction mixture was then diluted with ethyl acetate (150 mL), washed with 1 M hydrochloric acid (150 mL), water (150 mL) and brine (150 mL), dried over anhydrous magnesium sulfate, and concentrated in vacuo to give a dark foam. Purification by flash chromatography using a solvent gradient of 60% to 80% dichloromethane in hexane afforded a white solid that was recrystallized from hot ethyl acetate to give the title compound (1.2 g, 50%) as a white needles.
MS [(+)ESI, m/z]: 523 [M+H]+
Anal. Calcd for $C_{28}H_{21}Cl_3N_2O_2$: C, 64.20; H, 4.04; N, 5.35. Found: C, 64.01; H, 4.10; N, 5.22.

Step D. 10-[(2'-Methyl-1,1'-biphenyl-3-yl)carbonyl]-N-(pyridin-3-ylmethyl)-10,11-dihydro-5H-pyrrolo[2,1-c][1,4]benzodiazepine-3-carboxamide
To a solution of 2,2,2-trichloro-1-{10-[(2'-methyl-1,1'-biphenyl-3-yl)carbonyl]-10,11-dihydro-5H-pyrrolo[2,1-c][1,4]benzodiazepin-3-yl}ethanone of Step C (0.600 g, 1.1 mmol) and dimethyl sulfoxide (0.41 mL, 5.8 mmol) in dry acetonitrile (5.5 mL) at room temperature under nitrogen was added 3-(aminomethyl)pyridine (0.23 mL, 2.2 mmol) and the reaction mixture heated to reflux for 45 hours. The cooled reaction mixture was concentrated in vacuo, the oily residue redissolved in ethyl acetate (25 mL), washed with 1 M sodium hydroxide (25 mL), water (25 mL) and brine (25 mL), dried over anhydrous magnesium sulfate, and concentrated in vacuo to give a pale orange foam. Purification by flash chromatography using ethyl acetate as solvent afforded a pale yellow foam that was recrystallized from ethyl acetate/diethyl ether/hexane to give the title compound (0.435 g, 74%) as an off-white crystalline solid.

MS [(+)ESI, m/z]: 513 [M+H]$^+$
MS [(−)ESI, m/z]: 511 [M−H]$^-$
HRMS [(+)ESI, m/z]: 513.22694 [M+H]$^+$. Calcd for $C_{33}H_{29}N_4O_2$: 513.22850

Example 28

10-[(2'-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

A solution of 2,2,2-trichloro-1-{10-[(2'-methyl-1,1'-biphenyl-4-yl)carbonyl]-10,11-dihydro-5H-pyrrolo[2,1-c][1,4]benzodiazepine-3-yl}ethanone (1.72 mmol), and 3-aminomethylpyridine (3.44 mmol) in dimethylsulfoxide (8.6 mmol) and acetonitrile (15 mL) was stirred at 80° C. for 18 hours. The solvent was evaporated and the residue dissolved in dichloromethane, washed with water, dried over anhydrous sodium sulfate, and evaporated. The material was purified by HPLC (Normal phase, Luna CN bonded packing) and crystallized from ethyl acetate/hexane. (0.68 g; 77%), m.p. 176-177° C.

MS [(+)ESI, m/z]: 511 [M+H]$^+$
Anal. Calcd for $C_{33}H_{28}N_4O_2$: C, 77.32; H, 5.51; N, 10.93. Found: C, 77.28; H, 5.45; N, 10.93.

Example 29

10-[(2'-ACETYL-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 47, replacing 2-methoxyphenylboronic acid with 2-acetylphenylboronic acid. Purification by flash chromatography using a solvent gradient of 1 to 5% methanol in dichloromethane gave a yellow syrup that was crystallized from ethyl acetate/hexane to afford the title compound (0.276 g, 58%) as a white solid, m.p. 171-172° C.

MS [(+)ESI, m/z]: 555 [M+H]$^+$
MS [(−)ESI, m/z]: 553 [M−H]$^-$
HRMS [(+)ESI, m/z]: 555.23866 [M+H]$^+$. Calcd for $C_{35}H_{31}N_4O_3$: 555.23907

Example 30

10-[(2'-CYANO-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Cyano-1,1'-biphenyl-4-carboxylic acid
The title compound was prepared in essentially the same manner as Example 51, Step A, replacing 1-(2-bromo-phenyl)-ethanone with 2-bromobenzonitrile. The title compound (3.3 g, 92%) was obtained as a tan solid.

MS [(−)ESI, m/z]: 222 [M−H]$^-$
HRMS [(−)ESI, m/z]: 222.05607 [M−H]$^-$. Calcd for $C_{14}H_8NO_2$: 222.05605

Step B. 10-[(2'-Cyano-1,1'-biphenyl-4-yl)carbonyl]-N-(pyridin-3-ylmethyl)-10,11-dihydro-5H-pyrrolo[2,1-c][1,4]benzodiazepine-3-carboxamide The title compound was prepared in essentially the same manner as Example 51, Step B, replacing 2'-acetyl-biphenyl-4-carboxylic acid with 2'-cyano-1,1'-biphenyl-4-carboxylic acid of Step A. Purification by flash chromatography using a solvent gradient of 1 to 3% methanol in dichloromethane gave the title compound (0.322 g, 62%) as a tan solid.

MS (+)ESI, m/z]: 524 [M+H]$^+$
HRMS [(+)ESI, m/z]: 524.20802 [M+H]$^+$. Calcd for $C_{33}H_{26}N_5O_2$: 524.20810

Example 31

10-[(2'-ISOPROPYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Isopropyl-1,1'-biphenyl-4-carboxylic acid
The title compound was prepared in essentially the same manner as Example 51, Step A, replacing 1-(2-bromo-phenyl)-ethanone with 2-bromoisopropylbenzene. The title compound (1.5 g, 41%) was obtained as a tan solid.

MS [(−)ESI, m/z]: 239 [M−H]$^-$
HRMS [(+)ESI, m/z]: 241.12173 [M+H]$^+$. Calcd for $C_{16}H_{17}O_2$: 241.12231
Anal. Calcd for $C_{16}H_{16}O_2$: C, 79.97; H, 6.71. Found: C, 79.63; H, 6.71.

Step B. 10-[(2'-Isopropyl-1,1'-biphenyl-4-yl)carbonyl]-N-(pyridin-3-ylmethyl)-10,11-dihydro-5H-pyrrolo[2,1-c][1,4]benzodiazepine-3-carboxamide The title compound was prepared in essentially the same manner as Example 51, Step B, replacing 2'-acetyl-biphenyl-4-carboxylic acid with 2'-isopropyl-1,1'-biphenyl-4-carboxylic acid of Step A. Purification by flash chromatography using a solvent gradient of 1 to 3% methanol in dichloromethane gave the title compound (0.298 g, 55%) as a white solid.

MS [(+)ESI, m/z]: 541 [M+H]$^+$
HRMS [(+)ESI, m/z]: 541.26016 [M+H]$^+$. Calcd for $C_{35}H_{33}N_4O_2$: 541.25980
Anal. Calcd for $C_{35}H_{32}N_4O_2$: C, 77.75; H, 5.97; N, 10.36. Found: C, 77.51; H, 5.92; N, 10.13.

Example 32

METHYL(4'-{[3-{[(PYRIDIN-3-YLMETHYL)AMINO]CARBONYL}-5H-PYRROLO[2,1-C][1,4]BENZODIAZEPIN-10(11H)-YL]CARBONYL}-1,1'-BIPHENYL-2-YL)ACETATE

Step A. Methyl(2-bromophenyl)acetate
A solution of 2-bromophenylacetic acid (10 g, 46 mmol) and 12 M hydrochloric acid (1 mL, 12 mmol) in methanol (100 mL) was heated to reflux for 16 hours. The cooled solution was then quenched with saturated aqueous sodium hydrogen carbonate (50 mL) and concentrated in vacuo to remove methanol. The aqueous phase (ca. 50 mL) was extracted with ethyl acetate (150 mL), and the organic phase washed with water (75 mL) and brine (75 mL), dried over anhydrous magnesium sulfate, and concentrated in vacuo to give the title compound (10.1 g, 96 %) as a clear, colorless oil.

MS [(+)ESI, m/z]: 229/231 [M+H]+

Anal. Calcd for $C_9H_9BrO_2$: C, 47.19; H, 3.96. Found: C, 47.24; H, 3.88.

Step B. 2'-(2-Methoxy-2-oxoethyl)-1,1'-biphenyl-4-carboxylic acid

A mixture of methyl (2-bromophenyl)acetate of Step A (20.0 g, 87.3 mmol), 4-carboxybenzeneboronic acid (14.5 g, 87.4 mmol), [1,1'-bis(diphenylphosphino) ferrocene]dichloropalladium [II] (3.6 g, 4.4 mmol) and potassium phosphate (55.6 g, 262 mmol) in dry 4-dioxane (ca. 400 mL) was heated at 100° C. with vigorous stirring for 17 hours. The cooled mixture was then filtered through Celite and washed with 1,4-dioxane (ca. 200 mL). The filtrate was concentrated in vacuo to give a tacky brown solid (28.0 g). Purification by flash chromatography using a solvent gradient of 320:1:1 to 80:1:1 dichloromethane/acetic acid/methanol afforded an impure tacky orange solid (11.9 g). The solid product was dissolved in ethyl acetate (300 mL), filtered from insoluble material, and the filtrate washed with water (2×150 mL) and brine (150 mL), dried over anhydrous magnesium sulfate, and concentrated in vacuo to give a light orange solid (7.3 g). Recrystallization from diethyl ether provided the title compound (5.2 g, 22%) as pale orange needles.

MS [(−)ESI, m/z]: 269 [M−H]−

HRMS [(+)ESI, m/z]: 293.07804 [M+Na]+. Calcd for $C_{16}H_{14}O_4Na$: 293.07843

Anal. Calcd for $C_{16}H_{14}O_4$: C, 71.10; H, 5.22. Found: C, 71.30; H, 5.19.

Step C. Methyl (4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetate The title compound was prepared in essentially the same manner as Example 51, Step B, replacing 2'-acetyl-biphenyl-4-carboxylic acid with 2'-(2-methoxy-2-oxoethyl)-1,1'-biphenyl-4-carboxylic acid of Step B. Purification by flash chromatography using a solvent gradient of 0.5 to 4% methanol in dichloromethane gave a brown foam that was crystallized from hot methanol to afford the title compound (0.730 g, 53%) as a tan crystalline solid.

MS [(+)ESI, m/z]: 571 [M+H]+

MS [(−)ESI, m/z]: 569 [M−H]−

HRMS [(+)ESI, m/z]: 571.23261 [M+H]+. Calcd for $C_{35}H_{32}N_4O_4$: 571.23398

Example 33

10-[(2'-ETHOXY-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Ethoxy-1,1'-biphenyl-4-carboxylic acid

The title compound was prepared in essentially the same manner as Example 61, Step A, replacing 2-methoxymethylphenylboronic acid with 2-ethoxybenzeneboronic acid. The title compound (1.26 g, 88%) was obtained as a white solid.

MS [(+)ESI, m/z]: 243 [M+H]+

MS [(−)ESI, m/z]: 241 [M−H]−

HRMS [(+)ESI, m/z]: 243.10112 [M+H]+. Calcd for $C_{15}H_{15}O_3$: 243.10157

Step B. 10-[(2'-Ethoxy-1,1'-biphenyl-4-yl)carbonyl]-N-(pyridin-3-ylmethyl)-10,11-dihydro-5H-pyrrolo[2,1-c][1,4]benzodiazepine-3-carboxamide The title compound was prepared in essentially the same manner as Example 61, Step B, replacing 2'-acetyl-biphenyl-4-carboxylic acid with 2'-ethoxy-1,1'-biphenyl-4-carboxylic acid of Step A. Purification by flash chromatography using a solvent gradient of 1 to 4% methanol in dichloromethane gave a brown foam that was crystallized from methanol to afford the title compound (0.56 g, 51%) as a pale yellow solid.

MS [(+)ESI, m/z]: 543 [M+H]+

HRMS [(+)ESI, m/z]: 543.23874 [M+H]+. Calcd for $C_{34}H_{31}N_4O_3$: 543.23907

Example 34

10-[(2'-HYDROXY-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

To a suspension of 10-[(2'-ethoxy-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 33 (0.281 g, 0.518 mmol) in dry dichloromethane (2.6 mL) at 0° C. under nitrogen was added dropwise a 1.0 M solution of boron tribromide in dichloromethane (2.6 mL, 2.6 mmol) over ca. 5 minutes. The reaction mixture was allowed to warm to room temperature and then stirred for 5 hours. The reaction was quenched by the addition of saturated aqueous sodium bicarbonate solution (50 mL) and extracted with ethyl acetate (2×50 mL). The combined organic extracts were washed with brine (50 mL), dried over anhydrous magnesium sulfate, and concentrated in vacuo to give a tan solid (0.210 g). Purification by flash chromatography using a solvent gradient of 1 to 4% methanol in dichloromethane gave the title compound (0.042 g, 16%) as a white solid.

MS [(+)ESI, m/z]: 515 [M+H]+

MS [(−)ESI, m/z]: 513 [M−H]−

HRMS [(+)ESI, m/z]: 515.20677 [M+H]+. Calcd for $C_{32}H_{27}N_4O_3$: H, 515.20777

Example 35

(4'-{[3-{[(PYRIDIN-3-YLMETHYL)AMINO]CARBONYL}-5H-PYRROLO[2,1-C][1,4]BENZODIAZEPIN-10(11H)-YL]CARBONYL}-1,1'-BIPHENYL-2-YL)ACETIC ACID

To a suspension of methyl (4'-{[3-{[(pyridin-3-ylmethyl)amino]carbonyl}-5H-pyrrolo[2,1-c][1,4]benzodiazepin-10 (11H)-yl]carbonyl}-1,1'-biphenyl-2-yl)acetate of Example 32 (0.585 g, 1.03 mmol) in 2:1 v/v methanol:water (12 mL) was added lithium hydroxide monohydrate (87 mg, 2.07 mmol) and the mixture heated to reflux for 90 minutes. The cooled reaction mixture was concentrated in vacuo to remove methanol and then diluted with water (10 mL). The aqueous phase was washed with ethyl acetate (2×10 mL) then slowly added to a mixture of 1 M aqueous hydrochloric acid (2.2 mL) in water (20 mL) and the resulting suspension cooled to 0° C. for 1 hour. Filtration afforded the title compound (0.381 g, 66%) as a tan solid.

MS [(+)ESI, m/z]: 557 [M+H]+

MS [(−)ESI, m/z]: 555 [M−H]−

HRMS [(+)ESI, m/z]: 557.21794 [M+H]+. Calcd for $C_{34}H_{29}N_4O_4$: 557.21833

Example 36

10-[(2'-ISOBUTYRYL-1,1'-BIPHENYL-4-YL) CARBONYL]-N-(PYRIDIN-3-YLMETHYL)-10, 11-DIHYDRO-5H-PYRROLO[2,1-C][1,4]BENZO-DIAZEPINE-3-CARBOXAMIDE

Step A. 1-(2-Bromophenyl)-2-methylpropan-1-ol

To a solution of 2-bromobenzoyl chloride (1.3 mL, 9.9 mmol) in dry tetrahydrofuran (38 mL) at 0° C. under nitrogen was added dropwise a 2.0 M solution of isopropylmagnesium bromide in tetrahydrofuran (12.4 mL, 24.8 mmol) over ca. 5 minutes. The reaction mixture was stirred at 0° C. for 30 minutes then at room temperature for 27 hours. The reaction was quenched by the addition of 1 M aqueous hydrochloric acid (30 mL) and concentrated in vacuo to remove tetrahydrofuran. The aqueous phase was diluted to ca. 50 mL with water and extracted with ethyl acetate (2×50 mL). The combined organic extracts were washed with water (50 mL) and brine (50 mL), dried over anhydrous magnesium sulfate, filtered and concentrated in vacuo to give the crude product as an orange oil (2.1 g). Purification by flash chromatography using a solvent gradient of 1 to 4% ethyl acetate in hexane gave the title compound (0.77 g, 33%) as a clear, pale yellow oil.

MS [(+)ESI, m/z]: 211/213 [M+H—$H_2O$]$^+$

Step B. 1-(2-Bromophenyl)-2-methylpropan-1-one

To a suspension of [1,1,1-tris(acetyloxy)-1,1-dihydro-1,2-benziodoxol-3-(1H)-one] (2.2 g, 5.19 mmol) in dichloromethane (18 mL) at room temperature under nitrogen was added dropwise a solution of 1-(2-bromophenyl)-2-methylpropan-1-ol of Step A (1.00 g, 4.36 mmol) in dichloromethane (18 mL) over ca. 5 minutes. After 2 hours, additional [1,1,1-tris(acetyloxy)-1,1-dihydro-1,2-benziodoxol-3-(1H)-one] (0.20 g, 0.47 mmol) was added and the reaction mixture stirred at room temperature for 4 days. The reaction mixture was then diluted with diethyl ether (100 mL) and the resulting suspension added to 1.3 M aqueous sodium hydroxide solution (40 mL) with stirring. After 10 minutes the organic phase was separated, washed with 1.3 M sodium hydroxide (40 mL) and water (50 mL), dried over anhydrous magnesium sulfate, and concentrated in vacuo to give the title compound (0.89 g, 90%) as a clear, pale yellow oil.

MS [(+)ESI, m/z]: 227/229 [M+H]$^+$

HRMS [(+)ESI, m/z]: 227.00596 [M+H]$^+$. Calcd for $C_{10}H_{12}BrO$: 227.00660

Step C. 2'-Isobutyryl-biphenyl-4-carboxylic acid

The title compound was prepared in essentially the same manner as Example 51, Step A, replacing 1-(2-bromo-phenyl)-ethanone with 1-(2-bromophenyl)-2-methylpropan-1-one of Step B. The title compound (0.59 g, 60%) was obtained as a white solid.

MS [(−)ESI, m/z]: 267 [M−H]$^-$

Step D. 10-[(2'-Isobutyryl-1,1'-biphenyl-4-yl)carbonyl]-N-(pyridin-3-ylmethyl)-10,11-dihydro-5H-pyrrolo[2,1-c][1,4] benzodiazepine-3-carboxamide The title compound was prepared in essentially the same manner as Example 51, Step B, replacing 2'-acetyl-biphenyl-4-carboxylic acid with 2'-isobutyryl-biphenyl-4-carboxylic acid of Step C. Purification by flash chromatography using a solvent gradient of 0.5 to 4% methanol in dichloromethane gave a brown oil that was crystallized from methanol/diethyl ether to afford the title compound (0.463 g, 62%) as white needles.

MS [(+)ESI, m/z]: 569 [M+H]$^+$

MS [(−)ESI, m/z]: 567 [M−H]$^-$

HRMS [(+)ESI, m/z]: 569.253 [M+H]$^+$. Calcd for $C_{36}H_{33}N_4O_3$: 569.25472

Example 37

10-{[2'-(1-HYDROXY-2-METHYLPROPYL)-1,1'-BIPHENYL-4-YL]CARBONYL}-N-(PYRIDIN-3-YLMETHYL)-10,11-DIHYDRO-5H-PYRROLO[2, 1-C][1,4]BENZODIAZEPINE-3-CARBOXAMIDE

The title compound was prepared in essentially the same manner as Example 50, replacing 10-[(2'-acetyl-2-methyl-1, 1'-biphenyl-4-yl)carbonyl]-N-(pyridin-3-ylmethyl)-10,11-dihydro-5H-pyrrolo[2,1-c][1,4]benzodiazepine-3-carboxamide with 10-[(2'-isobutyryl-1,1'-biphenyl-4-yl)carbonyl]-N-(pyridin-3-ylmethyl)-10,11-dihydro-5H-pyrrolo[2,1-c][1, 4]benzodiazepine-3-carboxamide of Example 37. Purification by flash chromatography using a solvent gradient of 2 to 8% methanol in dichloromethane gave title compound (0.212 g, 64%) as a yellow solid.

MS [(−)ESI, m/z]: 569 [M−H]$^-$

HRMS [(+)ESI, m/z]: 571.26906 [M+H]$^+$. Calcd for $C_{36}H_{35}N_4O_3$: 571.27037

Example 38

10-{[2'-(2-AMINO-2-OXOETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 68, replacing 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid with (4'-{[3-{[(pyridin-3-ylmethyl)amino]carbonyl}-5H-pyrrolo[2,1-c][1,4]benzodiazepin-10(11H)-yl]carbonyl}-1, 1'-biphenyl-2-yl)acetic acid of Example 36, and dimethylamine with ammonia. Purification by flash chromatography using a solvent gradient of 2 to 8% methanol in dichloromethane gave the title compound (0.138 g, 58%) as a white solid.

MS [(+)ESI, m/z]: 556 [M+H]$^+$

MS ([(−)ESI, m/z]: 554 [M−H]$^-$

HRMS [(+)ESI, m/z]: 556.23307 [M+H]$^+$. Calcd for $C_{34}H_{30}N_5O_3$: 556.23432

Example 39

10-({2'-[2-(METHYLAMINO)-2-OXOETHYL]-1, 1'-BIPHENYL-4-YL}CARBONYL)-N-(PYRIDIN-3-YLMETHYL)-10,11-DIHYDRO-5H-PYRROLO [2,1-C][1,4]BENZODIAZEPINE-3-CARBOXAMIDE

The title compound was prepared in essentially the same manner as Example 68, replacing 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid with (4'-{[3-{[(pyridin-3-ylmethyl)amino]carbonyl}-5H-pyrrolo[2,1-c][1,4]benzodiazepin-10(11H)-yl]carbonyl}-1, 1'-biphenyl-2-yl)acetic acid, Example 36, and dimethylamine with methylamine. Purification by flash chromatography using a solvent gradient of 2 to 8% methanol in dichloromethane gave the title compound (0.149 g, 61%) as an off-white solid.

MS [(+)ESI, m/z]: 570 [M+H]+
MS [(−)ESI, m/z]: 568 [M−H]−
HRMS [(+)ESI, m/z]: 570.24846 [M+H]+. Calcd for $C_{35}H_{32}N_5O_3$: 570.24997

Example 40

10-({2'-[2-(DIMETHYLAMINO)-2-OXOETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 68, replacing 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid with (4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetic acid of Example 36. Purification by flash chromatography using a solvent gradient of 2 to 8% methanol in dichloromethane gave the title compound (0.180 g, 72%) as a white solid.

MS [(+)ESI, m/z]: 584 [M+H]+
MS [(−)ESI, m/z]: 582 [M−H]−
HRMS [(+)ESI, m/z]: 584.26446 [M+H]+. Calcd for $C_{36}H_{34}N_5O_3$: 584.26562

Example 41

N-(PYRIDIN-3-YLMETHYL)-10-{[2'-(PYRROLIDIN-1-YLMETHYL)-1,1'-BIPHENYL-4-YL]CARBONYL}-10,11-DIHYDRO-5H-PYRROLO[2,1-C][1,4]BENZODIAZEPINE-3-CARBOXAMIDE

To a solution of 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56, Step B (0.38 mmol), and pyrrolidine (0.80 mmol) in methanol (5 mL) was added a methanolic solution of sodium cyanoborohydride (0.2 M) and zinc chloride (0.1 M). The mixture was stirred at ambient temperature for 20 hours. The methanol was evaporated and the residue was taken up in chloroform and washed with 1.0 N sodium hydroxide, dried over anhydrous sodium sulfate, and evaporated. The solid was crystallized from ethyl acetate and hexane, m.p. 210-212° C.

MS [(+)ESI, m/z]: 582.2 [M+H]+

EXAMPLE 42

10-({2'-[(METHYLAMINO)METHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared from 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56, Step B, and methylamine (8 M solution in ethanol) in the manner of Example 42, m.p. 149-150° C.

MS [(+)ESI, m/z]: 540.3 [M+H]+

Example 43

10-{[2'-(MORPHOLIN-4-YLMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared from 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56, Step B, and morpholine in the manner of Example 42, m.p. 191-194° C.

MS [(+)ESI, m/z]: 596.3 [M+H]+

Example 44

10-{[2'-(PIPERIDIN-1-YLMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared from 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56, Step B, and piperidine, in the manner of Example 42, m.p. 199-202° C.

MS [(+)ESI, m/z]: 596.2 [M+H]+

Example 45

10-({2'-[(DIMETHYLAMINO)METHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared from 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56, Step B, and dimethylamine (2.0 M solution in methanol) in the manner of Example 42, m.p. 95-104° C.

MS [(+)ESI, m/z]: 554.3 [M+H]+

Example 46

10-{[2'-(AMINOMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

Step A. 10-{[2'-(Hydroxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide A solution of 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 567, Step B (0.75 mmole), in ethanol (5 mL) at 5° C. was treated with sodium borohydride (4.5 mmole). The mixture was stirred and allowed to warm to room temperature over 6 hours. To the reaction mixture was added 2N hydrochloric acid until a pH of 8.0 was reached. The ethanol was evaporated and the residue extracted with dichloromethane. The organic solutions were combined, dried over anhydrous sodium sulfate, and evaporated. The residue was purified by passing it through a short column of silica gel to give the title compound, m.p. 119-121° C.

MS [(+)ESI, m/z]: 529 [M+H]+
MS [(−)ESI, m/z]: 527 [M−H]−
HRMS [(+)ESI, m/z]: 529.22249 [M+H]+. Calcd for $C_{33}H_{29}N_4O_3$: 529.22342

Step B. 10-{[2'-(Azidomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide The 10-{[2'-(hydroxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Step A (0.495 mmole) was dissolved in tetrahydrofuran (4 mL) and cooled to 5° C. The soludiuon was treated with 1,8-diazabicyclo[5.4.0]undec-7-ene (0.692 mmole) and diphenylphosphorylazide (0.692 mmole). After warming to room temperature and stirring for 16 hours, the tetrahydrofuran was removed by evaporation and the desired material was purified by flash chromatography on silica gel eluting with ethyl acetate and used as such in the next step.

Step C. 10-{[2'-(Aminomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide To a solution of 10-{[2'-(azidomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide (0.49 mmole) of Step B in tetrahydrofuran (3 mL) was added solid triphenylphosphine (0.55 mmole). The mixture was stirred at room temperature for 16 hours. Water (0.3 mL) was then added and the reaction mixture was heated to 45° C. for 3 hours. The solvent was removed by evaporation and the residue was extracted with dichloromethane. The organic solution was dried over anhydrous sodium sulfate, and evaporated. The residue was purified by HPLC (normal phase, 20-70% gradient of [20% methanol in dichloromethane] and hexane, Luna CN bonded packing) and crystallized upon solvent evaporation, m.p. 115-120° C.
MS [(+)ESI, m/z]: 528.4 [M+H]+

Example 47

10-[(2'-METHOXY-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

To a solution of 10-(4-iodo-3-methylbenzoyl)-N-(pyridin-3-ylmethyl)-10,11-dihydro-5H-pyrrolo[2,1-c][1,4]benzodiazepine-3-carboxamide of Example 74, Step C (0.200 g, 0.356 mmol), and 2-methoxyphenylboronic acid (0.081 g, 0.533 mmol) in acetonitrile (3 mL) was added a 0.4 M aqueous sodium carbonate solution (3 mL) and the mixture purged with nitrogen for 10 minutes. Tetrakis(triphenylphosphine)palladium(0) (0.021 g, 0.018 mmol) was then added and the reaction mixture heated to 90° C. for 4 hours. The cooled reaction mixture was partitioned between ethyl acetate (50 mL) and 2 M sodium hydroxide (50 mL). The organic phase was separated, washed with 2 M sodium hydroxide (50 mL), water (50 mL) and brine (50 mL), dried over amnhydrous magnesium sulfate, and concentrated in vacuo to give a yellow syrup (0.23 g). Purification by flash chromatography using a solvent gradient of 1 to 5% methanol in dichloromethane gave a colorless glass that was recrystallized from dichloromethane/hexane to afford the title compound (0.181 g, 94%) as a white solid, m.p. 119-124° C.
MS [(+)ESI, m/z]: 543 [M+H]+
Anal. Calcd for $C_{34}H_{30}N_4O_3$: C, 75.26; H, 5.57; N, 10.32. Found: C, 75.11; H, 5.58; N, 10.30.

Example 48

10-[(2'-ETHOXY-2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 47, replacing 2-methoxy phenylboronic acid with 2-ethoxyphenylboronic acid. Purification by flash chromatography using a solvent gradient of 1 to 5% methanol in dichloromethane gave a colorless glass that was recrystallized from diethyl ether/hexane to afford the title compound (0.182 g, 92%) as white solid, m.p. 139-143° C.
MS [(+)ESI, m/z]: 557 [M+H]+
MS [(−)ESI, m/z]: 555 [M−H]−
Anal. Calcd for $C_{35}H_{32}N_4O_3$: C, 75.52; H, 5.79; N, 10.06. Found: C, 75.21; H, 5.74; N, 9.83.

Example 49

10-{[2'-(METHOXYMETHYL)-2-METHYL-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 47, replacing 2-methoxyphenylboronic acid with 2-methoxymethylphenylboronic acid. Purification by flash chromatography using a solvent gradient of 1 to 4% methanol in dichloromethane gave a white foam that was crystallized from diethyl ether to afford the title compound (0.147 g, 74%) as white solid, m.p. 163-164° C.
MS [(+)ESI, m/z]: 557 [M+H]+
MS [(−)ESI, m/z]: 555 [M−H]−
Anal. Calcd for $C_{35}H_{32}N_4O_3$: C, 75.52; H, 5.79; N, 10.06. Found: C, 75.27; H, 5.91; N, 10.10.

Example 50

10-{[2'-(1-HYDROXYETHYL)-2-METHYL-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

To a solution of 10-[(2'-acetyl-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 29 (0.122 g, 0.220 mmol) in 2-propanol (5 mL) and water (1 mL) was added sodium borohydride (0.0092 mg, 0.242 mmol) and the reaction mixture stirred at room temperature under nitrogen for 24 hours. The reaction was quenched by the addition of 2 M hydrochloric acid (10 mL) and then washed with diethyl ether (20 mL). The aqueous phase was basified by the addition of 2 M sodium hydroxide and the resulting milky suspension extracted with ethyl acetate ( 2×30 mL). The combined organic extracts were washed with water (50 mL) and brine (50 mL), dried over anhydrous magnesium sulfate, and concentrated in vacuo to afford a colorless syrup. Purification by flash chromatography using a solvent gradient of 1 to 5% methanol in dichloromethane gave a colorless glass that was recrystallized from diethyl ether/hexane to afford the title compound (0.061 g, 50%) as white solid.
MS [(+)ESI, m/z]: 557 [M+H]+
MS [(−)ESI, m/z]: 555 [M−H]−

HRMS [(+)ESI, m/z]: 557.25391 [M+H]⁺. Calcd for C₃₅H₃₃N₄O₃: 557.25472

Example 51

10-[(2'-ACETYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Acetyl-biphenyl-4-carboxylic acid

To a suspension of 4-carboxybenzeneboronic acid (2.0 g, 12.1 mmol) and 1-(2-bromo-phenyl)-ethanone (1.63 mL, 12.1 mmol) in dry acetonitrile (60 mL) was added a 0.4 M aqueous sodium carbonate solution (60 mL) and the reaction mixture purged with nitrogen for 10 minutes. Tetrakis(triphenylphosphine)palladium(0) (0.5 g, 0.433 mmol) was then added and the reaction mixture heated to 90° C. for 22 hours. The hot reaction mixture was filtered through celite and then concentrated in vacuo to remove acetonitrile. The resulting aqueous suspension was diluted with water to 75 mL then washed with diethyl ether (75 mL). The aqueous phase was acidified to pH 1 by the addition of concentrated hydrochloric acid and the resulting white suspension cooled to 4° C. for 1 hour. The solid product was filtered, washed with water and then dried in vacuo at 50° C. overnight to afford the title compound (2.62 g, 91%) as a white solid, m.p. 199-201° C.

MS [(+)ESI, m/z]: 241 [M+H]⁺

Step B. 10-[(2'-Acetyl-1,1'-biphenyl-4-yl)carbonyl]-N-(pyridin-3-ylmethyl)-10,11-dihydro-5H-pyrrolo[2,1-c][1,4]benzodiazepine-3-carboxamide To a solution of 2'-acetyl-biphenyl-4-carboxylic acid of Step A (0.340 g, 1.41 mmol) in dry tetrahydrofuran (30 mL) at room temperature under nitrogen was added dry N,N-dimethylformamide (1 drop) followed by the dropwise addition of a 2.0 M solution of oxalyl chloride in dichloromethane (1.17 mL, 2.34 mmol). The reaction mixture was stirred at room temperature for 2 hours then concentrated in vacuo and the residue redissolved in dry dichloromethane (30 mL). The solution was concentrated in vacuo to afford the crude acid chloride as a cream solid. The acid chloride was dissolved in tetrahydrofuran (30 mL); N-(pyridin-3-ylmethyl)-10,11-dihydro-5H-pyrrolo[2,1-c][1,4]benzodiazepine-3-carboxamide of Example 11 (0.300 g, 0.942 mmol) was added, followed by N,N-diisopropylethylamine (0.49 mL, 2.83 mmol) and the reaction mixture stirred at room temperature under nitrogen for 19 hours. The reaction was quenched by the addition of 2 M sodium hydroxide (20 mL), the mixture stirred vigorously for 5 minutes and then partitioned between ethyl acetate (100 mL) and 2 M sodium hydroxide (100 mL). The organic phase was separated, washed with 2 M sodium hydroxide (100 mL), water (100 mL) and brine (100 mL), dried over anhydrous magnesium sulfate, and concentrated in vacuo to give a yellow foam. Purification by flash chromatography using a solvent gradient of 1 to 3.5% methanol in dichloromethane gave a cream foam that was crystallized from ethyl acetate/hexane to afford the title compound (0.45 g, 88%) as a white solid, m.p. 149-150° C.

MS [(+)ESI, m/z]: 541 [M+H]⁺

MS [(−)ESI, m/z]: 539 [M−H]⁻

HRMS [(+)ESI, m/z]: 541.22378 [M+H]⁺. Calcd for C₃₄H₂₉N₄O₃: 541.22342

Anal. Calcd for C₃₄H₂₈N₄O₃: C, 75.54; H, 5.22; N, 10.36. Found: C, 75.31; H, 5.29; N, 10.26.

Example 52

10-{[2'-(1-HYDROXYETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 50, replacing 10-[(2'-acetyl-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide with 10-[(2'-acetyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 51. Purification by flash chromatography using a solvent gradient of 1 to 5% methanol in dichloromethane gave a white foam that was crystallized from ethyl acetate/hexane to afford the title compound (0.076 g, 58%) as white solid, m.p. 122° C. (foaming).

MS [(+)ESI, m/z]: 543 [M+H]⁺

MS [(−)ESI, m/z]: 541 [M−H]⁻

HRMS [(−)ESI, m/z]: 541.22394 [M−H]⁻. Calcd for C₃₄H₂₉N₄O₃: 541.22451

Example 53

(−)-10-({2'-[1-HYDROXYETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

Racemic 10-{[2'-(1-hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Example 52 was passed through a chiral chromatography column using 75:25 hexane:ethyl acetate containing 0.1% diethylamine as the eluant to afford the title compound as a white solid, m.p. 122-126° C., $[\alpha]^{21.4}_D = -6.0°$ (c=1.04, CHCl₃)

MS [(+)ESI, m/z]: 543 [M+H]⁺

MS [(−)ESI, m/z]: 541 [M−H]⁻

Example 54

(+)-10-({2'-[1-HYDROXYETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

Racemic 10-{[2'-(1-hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Example 52 was passed through a chiral chromatography column using 75:25 hexane:ethyl acetate containing 0.1% diethylamine as the eluant to afford the title compound as a white solid, m.p. 118° C. (shrinking), $[\alpha]^{21.4}_D = +6.7°$ (c=1.04, CHCl₃)

MS [(+)ESI, m/z]: 543 [M+H]⁺

MS [(−)ESI, m/z]: 541 [M−H]⁻

Example 55

10-{[2'-(1-HYDROXYETHYL)-1,1'-BIPHENYL-4-YL]CARBONYL}-N-[(1-OXIDOPYRIDIN-3-YL)METHYL]-10,11-DIHYDRO-5H-PYRROLO[2,1-C][1,4]BENZODIAZEPINE-3-CARBOXAMIDE

To a solution of 10-{[2'-(1-hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide of Example 52 (0.500 g, 0.92 mmol) in dichloromethane (20 mL) was added saturated aqueous sodium hydrogencarbonate solution (20 mL) followed by 70% 3-chloroperoxybenzoic acid (909 mg, 3.69 mmol) and the biphasic mixture was stirred vigorously for 1 hour. The reaction was quenched by the addition of 5% aqueous sodium metabisulfite solution (20 mL), the mixture stirred vigorously for 5 minutes, then partitioned between ethyl acetate (100 mL) and 2 M sodium hydroxide (100 mL). The organic layer was separated, washed with 2 M sodium hydroxide (2×100 mL), water (100 mL) and brine (100 mL), dried over anhydrous magnesium sulfate, and concentrated in vacuo to afford a white solid. Purification by flash chromatography using a solvent gradient of 3 to 10% methanol in dichloromethane gave the title compound (31.1 mg, 6%) as a white solid, m.p. 213-215° C.

MS [(+)ESI, m/z]: 559 [M+H]$^+$

MS [(−)ESI, m/z]: 557 [M−H]$^-$

HRMS [(+)ESI, m/z]: 559.23356 [M+H]$^+$. Calcd for $C_{34}H_{31}N_4O_4$: 559.23398

Example 56

10-[(2'-FORMYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Formyl-1,1'-biphenyl-4-carboxylic acid

The title compound was prepared in essentially the same manner as Example 51, Step A, replacing 1-(2-bromo-phenyl)-ethanone with 2-bromobenzaldehyde. The title compound (2.26 g, 83%) was obtained as a white solid, m.p. 215-219° C.

MS [(+)ESI, m/z]: 227 [M+H]$^+$

MS [(−)ESI, m/z]: 225 [M−H]$^-$

Step B. 10-[(2'-Formyl-1,1'-biphenyl-4-yl)carbonyl]-N-(pyridin-3-ylmethyl)-10,11-dihydro-5H-pyrrolo[2,1-c][1,4]benzodiazepine-3-carboxamide The title compound was prepared in essentially the same manner as Example 51, Step B, replacing 2'-acetyl-biphenyl-4-carboxylic acid with 2'-formyl-1,1'-biphenyl-4-carboxylic acid of Step A. Purification by flash chromatography using a solvent gradient of 1 to 5% methanol in dichloromethane gave a white foam that was crystallized from ethyl acetate/hexane to afford the title compound (0.57 g, 92%) as a white solid, m.p. 162-163° C.

MS [(+)ESI, m/z]: 527 [M+H]$^+$

MS [(−)ESI, m/z]: 525 [M−H]$^-$

HRMS [(+)ESI, m/z]: 527.20591 [M+H]$^+$. Calcd for $C_{33}H_{27}N_4O_3$: 527.20777

Example 57

10-[(2-METHYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

A mixture of 10-(4-iodo-3-methylbenzoyl)-N-(pyridin-3-ylmethyl)-10,11-dihydro-5H-pyrrolo[2,1-c][1,4]benzodiazepine-3-carboxamide of Example 74 (0.300 g, 0.53 mmol), phenylboronic acid (0.098 g, 0.80 mmol) and potassium carbonate (0.221 g, 1.60 mmol) in dimethoxyethane:water (8 mL:2 mL) was purged with nitrogen for 10 minutes. [1,1'-bis(Diphenylphosphino)ferrocene]dichloropalladium[II] (0.022 g, 0.0266 mmol) was then added and the reaction mixture heated to 100° C. for 4 hours. The cooled reaction mixture was then partitioned between ethyl acetate (100 mL) and 1 M sodium hydroxide (100 mL). The organic phase was separated, washed with water (100 mL) and brine (100 mL), dried over anhydrous magnesium sulfate, filtered and concentrated in vacuo to give an olive syrup (0.32 g). Purification by flash chromatography using ethyl acetate as solvent afforded the title compound (0.260 g, 95%) as a white foam, m.p. 108-112° C.

MS [(+)ESI, m/]: 513 [M+H]$^+$

HRMS [(+)ESI, m/z]: 513.227 [M+H]$^+$. Calcd for $C_{33}H_{29}N_4O_2$: 513.22905

Example 58

10-{[2'-(1-HYDROXYPROPYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

To a solution of 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56 (0.132 g, 0.251 mmol) in dry tetrahydrofuran (15 mL) was added 3.0 Methylmagnesium bromide in diethyl ether (0.68 mL, 2.04 mmol) and the reaction mixture stirred at room temperature under nitrogen for 17 hours. The reaction was quenched by the addition of saturated aqueous ammonium chloride solution (20 mL) and then the mixture partitioned between ethyl acetate (100 mL) and half saturated aqueous ammonium chloride solution (100 mL). The organic phase was separated, washed with brine (100 ml), dried over anhydrous magnesium sulfate, and concentrated in vacuo to afford a cream foam. Purification by flash chromatography using a solvent gradient of 1 to 6% methanol in dichloromethane gave a colorless glass that was triturated with diethyl ether to afford the title compound (0.039 g, 28%) as a white solid, m.p. 111-115° C.

MS [(+)ESI, m/z]: 557 [M+H]$^+$

MS [(−)ESI, m/z]: 555 [M−H]$^-$

HRMS [(+)ESI, m/z]: 557.25449 [M+H]$^+$. Calcd for $C_{35}H_{33}N_4O_3$: 557.25472

Example 59

10-{[2'-(HYDROXYMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 50, replacing 10-[(2'-acetyl-2-methyl-1, 1'-biphenyl-4-yl)carbonyl]-N-(pyridin-3-ylmethyl)-10,11-dihydro-5H-pyrrolo[2,1-c][1,4]benzodiazepine-3-carboxamide with 10-[(2'-formyl-1,1'-biphenyl-4-yl)carbonyl]-N-(pyridin-3-ylmethyl)-10,11-dihydro-5H-pyrrolo[2,1-c][1,4] benzodiazepine-3-carboxamide of Example 56. Purification by flash chromatography using a solvent gradient of 1 to 6% methanol in dichloromethane gave a white foam that was crystallized from ethyl acetate/hexane to afford the title compound (0.133 g, 84%) as white solid, m.p. 119-121° C.

MS [(+)ESI, m/z]: 529 [M+H]$^+$
MS [(−)ESI, m/z]: 527 [M−H]$^−$
HRMS [(+)ESI, m/z]: 529.22249 [M+H]$^+$. Calcd for $C_{33}H_{29}N_4O_3$: 529.22342

Example 60

10-[(2'-BENZOYL-1,1'-BIPHENYL-4-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

Step A. 2'-Benzoyl-biphenyl-4-carboxylic acid

The title compound was prepared in essentially the same manner as Example 51, Step A, replacing 1-(2-bromo-phenyl)-ethanone with 2-bromobenzophenone. The title compound (3.12 g, 86%) was obtained as a white solid, m.p. 211-215° C.

MS [(+)ESI, m/z]: 303 [M+H]$^+$
MS [(−)ESI, m/z]: 301 [M−H]$^−$

Step B. 10-[(2'-Benzoyl-1,1'-biphenyl-4-yl)carbonyl]-N-(pyridin-3-ylmethyl)-10,11-dihydro-5H-pyrrolo[2,1-c][1,4]benzodiazepine-3-carboxamide The title compound was prepared in essentially the same manner as Example 51, Step B, replacing 2'-acetyl-biphenyl-4-carboxylic acid with 2'-benzoyl-biphenyl-4-carboxylic acid of Step A. Purification by flash chromatography using a solvent gradient of 1 to 5% methanol in dichloromethane gave a yellow glass that crystallized from ethyl acetate/hexane to afford the title compound (0.546 g, 72%) as a white solid, m.p. 198-199° C.

MS [(+)ESI, m/z]: 603 [M+H]$^+$
MS [(−)ESI, m/z]: 601 [M−H]$^−$
Anal. Calcd for $C_{39}H_{30}N_4O_3$: C, 77.72; H, 5.02; N, 9.30. Found: C, 77.43; H, 4.94; N, 9.16.

Example 61

10-{[2'-(METHOXYMETHYL)-1,1'-BIPHENYL-4-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

Step A. 2'-Methoxymethyl-biphenyl-4-carboxylic acid

To a suspension of 4-iodobenzoic acid (0.82 g, 3.31 mmol) and 2-methoxymethylphenylboronic acid (0.55 g, 3.31 mmol) in dry acetonitrile (30 mL) was added a 0.4 M aqueous sodium carbonate solution (30 mL) and the reaction mixture purged with nitrogen for 10 minutes. Tetrakis(triphenylphosphine)palladium(0) (90 mg, 0.078 mmol) was then added and the reaction mixture heated to 90° C. for 19 hours. The hot reaction mixture was filtered through celite, concentrated in vacuo to remove acetonitrile and the resulting aqueous suspension washed with ethyl acetate (2×30 mL). The aqueous phase was acidified to pH 1 by the addition of concentrated hydrochloric acid, the resulting white suspension cooled to 4° C. for 1 hour and the solid product filtered. Recrystallization from dichloroethane gave the title compound (0.469 g, 59%) as a white solid, m.p. 164.5-165.5° C.

MS [(−)ESI, m/z]: 241 [M−H]$^−$

Step B. 10-{[2'-(Methoxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide The title compound was prepared in essentially the same manner as Example 51, Step B, replacing 2'-acetyl-biphenyl-4-carboxylic acid with 2'-methoxymethyl-biphenyl-4-carboxylic acid of Step A. Purification by flash chromatography using a solvent gradient of 1 to 5% methanol in dichloromethane gave a yellow syrup that crystallized from ethyl acetate/hexane to afford the title compound (0.338 g, 66%) as a white solid, m.p. 156-157° C.

MS [(+)ESI, m/z]: 543 [M+H]$^+$
MS [(−)ESI, m/z]: 541 [M−H]$^−$
Anal. Calcd for $C_{34}H_{30}N_4O_3$: C, 75.26; H, 5.57; N, 10.32. Found: C, 74.87; H, 5.27; N, 10.14.

Example 62

10-({2'-[(E)-(HYDROXYIMINO)METHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

To a solution of 10-[(2'-formyl-1,1'-biphenyl-4-yl)carbonyl]-N-(pyridin-3-ylmethyl)-10,11-dihydro-5H-pyrrolo[2,1-c][1,4]benzodiazepine-3-carboxamide of Example 56 (0.500 g, 0.95 mmol) and hydroxylamine hydrochloride (0.132 g, 1.90 mmol) in methanol (15 mL) was added pyridine (0.155 mL, 1.90 mmol) and the reaction mixture heated to reflux under nitrogen for 1 hour. The cooled reaction mixture was then poured into 5% w/v aqueous sodium carbonate solution (100 mL) and extracted with ethyl acetate (100 mL). The organic extract was washed with water (100 mL) and brine (100 mL), dried over anhydrous magnesium sulfate, and concentrated in vacuo to afford a white foam. Crystallization of the crude product from dichloromethane gave the title compound (0.458 g, 89%) as a white crystalline solid, m.p. 165-167° C.

MS [(+)ESI, m/z]: 542 [M+H]$^+$
MS [(−)ESI, m/z]: 540 [M−H]$^−$
Anal. Calcd for $C_{33}H_{27}N_5O_3$: C, 73.18; H, 5.02; N, 12.93. Found: C, 73.01; H, 4.76; N, 12.81.

Example 63

METHYL-4'-{[3-{[(PYRIDIN-3-YLMETHYL)AMINO]CARBONYL}-5H-PYRROLO[2,1-C][1,4]BENZODIAZEPIN-10(11H)-YL]CARBONYL}-1,1'-BIPHENYL-2-CARBOXYLATE

Step A. 2'-(Methoxycarbonyl)-1,1'-biphenyl-4-carboxylic acid

The title compound was prepared in essentially the same manner as Example 51, Step A, replacing 1-(2-bromo-phenyl)-ethanone with methyl 2-bromobenzoate. Purification by flash chromatography using a solvent gradient of 5 to 20% ethyl acetate in dichloromethane (containing 1% acetic acid) gave a white solid that was recrystallized from dichloroethane/hexane to afford the title compound (0.26 g, 9%) as a white solid, m.p. 151-152° C.

MS [(+)ESI, m/z]: 255 [M−H]$^−$

Step B. Methyl 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylate The title compound was prepared in essentially the same manner as Example 51, Step B, replacing 2'-acetyl-biphenyl-4-carboxylic acid with 2'-(methoxycarbonyl)-1,1'-biphenyl-4-carboxylic acid of Step A. Purification by flash chromatography using a solvent gradient of 1 to 5% methanol in dichloromethane gave a colorless glass that crystallized from ethyl acetate/hexane to afford the title compound (0.257 g, 77%) as a white solid, m.p. 179.5-180.5° C.

MS [(+)ESI, m/z]: 557 [M+H]$^+$

HRMS [(+)ESI, m/z]: 557.21758 [M+H]$^+$. Calcd for $C_{34}H_{29}N_4O_4$: 557.21758

Example 64

TERT-BUTYL-4'-{[3-{[(PYRIDIN-3-YLMETHYL)AMINO]CARBONYL}-5H-PYRROLO[2,1-C][1,4]BENZODIAZEPIN-10(11H)-YL]CARBONYL}-1,1'-BIPHENYL-2-CARBOXYLATE

Step A. 2-Bromobenzoic acid tert-butyl ester

To a solution of 2-bromobenzoyl chloride 2.0 g, 9.11 mmol) in dry diethyl ether (40 mL) was added 2-methyl-2-propanol (0.96 mL, 10.02 mmol) followed by 4-(dimethylamino)pyridine (111 mg, 0.911 mmol) and the reaction mixture stirred at room temperature under nitrogen for 48 hours. The resulting white suspension was then partitioned between ethyl acetate (100 mL) and 1 M hydrochloric acid (100 mL). The organic phase was separated, washed with 1 M hydrochloric acid (100 mL), 2 M sodium hydroxide (2×100 mL), water (100 mL) and brine (100 mL), dried over anhydrous magnesium sulfate, and concentrated in vacuo to give a yellow oil. Purification by flash chromatography using ethyl acetate/hexane as eluant gave the title compound (1.22 g, 52%) as a colorless oil.

Step B. 2'-(tert-Butoxycarbonyl)-1,1'-biphenyl-4-carboxylic acid

The title compound was prepared in essentially the same manner as Example 51, Step A, replacing 1-(2-bromo-phenyl)-ethanone with 2-bromobenzoic acid tert-butyl ester of Step A. The title compound (1.28 g, 91%) was obtained as a white solid, m.p. 180-182° C.

MS [(−)ESI, m/z]: 297 [M−H]$^-$

Anal. Calcd for $C_{18}H_{18}O_4$: C, 72.47; H, 6.08. Found: C, 72.12; H, 5.69.

Step C. tert-Butyl 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylate The title compound was prepared in essentially the same manner as Example 51, Step B, replacing 2'-acetyl-biphenyl-4-carboxylic acid with 2'-(tert-butoxycarbonyl)-1,1'-biphenyl-4-carboxylic acid of Step B. Purification by flash chromatography using a solvent gradient of 1 to 5% methanol in dichloromethane gave a cream foam that was crystallized from ethyl acetate/hexane to afford the title compound (956 mg, 66%) as a white crystalline solid, m.p. 163-165° C.

MS [(+)ESI, m/z]: 599 [M+H]$^+$

MS [(−)ESI, m/z]: 597 [M−H]$^-$

HRMS [(+)ESI, m/z]: 599.26473 [M+H]$^+$. Calcd for $C_{37}H_{35}N_4O_4$: 599.26528

Example 65

4'-{[3-{[(PYRIDIN-3-YLMETHYL)AMINO]CARBONYL}-5H-PYRROLO[2,1-C][1,4]BENZODIAZEPIN-10(11H)-YL]CARBONYL}-1,1'-BIPHENYL-2-CARBOXYLIC ACID

To a solution of tert-butyl 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylate of Example 64 (0.710 g, 1.186 mmol) in dry dichloromethane (10 mL) was added trifluoroacetic acid (10 mL) and the reaction mixture stirred at room temperature under nitrogen for 1.75 hours. The reaction mixture was then concentrated in vacuo and the resulting solid dissolved in ethyl acetate (50 mL). The organic phase was extracted with 2 M sodium hydroxide (2×50 mL) and the combined aqueous extracts acidified to pH 1 by the addition of concentrated hydrochloric acid. The resulting white suspension was cooled to 4° C. for 1 hour, the solid product filtered, washed with water and then dried in vacuo at 50° C. overnight to afford the title compound (0.345 g, 54%) as a white solid, m.p. 189-191° C.

MS [(+)ESI, m/z]: 543 [M+H]$^+$

MS [(−)ESI, m/z]: 541 [M−H]$^-$

HRMS [(+)ESI, m/z]: 543.20133 [M+H]$^+$. Calcd for $C_{33}H_{27}N_4O_4$: 543.20268

Example 66

10-({2'-[2-(ETHYLAMINO)-2-OXOETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 68, replacing 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid with (4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetic acid of Example 35, and dimethylamine with ethylamine. Purification by flash chromatography using a solvent gradient of 1 to 4% methanol in dichloromethane gave the title compound (0.152 g, 61%) as a white solid.

MS [(+)ESI, m/z]: 584 [M+H]$^+$

MS [(−)ESI, m/z]: 582 [M−H]$^-$

HRMS [(+)ESI, m/z]: 584.26482 [M+H]$^+$. Calcd for $C_{36}H_{34}N_5O_3$: 584.26562

Example 67

10-({2'-[2-(DIETHYLAMINO)-2-OXOETHYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 68, replacing 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid with (4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetic acid of Example 35, and dimethylamine with diethylamine. Purification by flash chromatography using a solvent gradient of 1 to 4% methanol in dichloromethane gave the title compound (0.158 g, 60%) as an off-white solid.

MS [(+)ESI, m/z]: 612 [M+H]+
MS [(−)ESI, m/z]: 610 [M−H]−
HRMS [(+)ESI, m/z]: 612.29644 [M+H]+. Calcd for $C_{38}H_{38}N_5O_3$: 612.29692

Example 68

10-({2'-[(DIMETHYLAMINO)CARBONYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

To a solution of 4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-carboxylic acid of Example 65 (92 mg, 0.17 mmol) in 1-methyl-2-pyrrolidinone (4.5 mL) was added a 2.0 M solution of dimethylamine in tetrahydrofuran (0.42 mL, 0.848 mmol) followed by O-(7-azabenzotriazol-1-yl)-N,N,N',N',tetramethyluronium hexafluorophosphate (71 mg, 0.187 mmol) and the reaction mixture stirred at room temperature under nitrogen for 2 hours. The reaction mixture was then partitioned between ethyl acetate (50 mL) and 2 M sodium hydroxide (50 mL). The organic phase was separated, washed with 2 M sodium hydroxide (50 mL), water (50 mL) and brine (50 mL), dried over anhydrous magnesium sulfate, and concentrated in vacuo to afford a white foam. Purification by flash chromatography using a solvent gradient of 1 to 7% methanol in dichloromethane gave a colorless glass that was crystallized from ethyl acetate/hexane to afford the title compound 0.082 g, 85%) as a white solid, m.p. 206-207° C.

MS [(+)ESI, m/z]: 570 [M+H]+
MS [(−)ESI, m/z]: 568 [M−H]−
Anal. Calcd for $C_{35}H_{31}N_5O_3$: C, 73.80; H, 5.49; N, 12.29. Found: C, 73.44; H, 5.22; N, 12.10.

Example 69

10-({2'-[(METHYLAMINO)CARBONYL]-1,1'-BIPHENYL-4-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 68, replacing dimethylamine with methylamine. Purification by flash chromatography using a solvent gradient of 1 to 7% methanol in dichloromethane gave a colorless glass that was crystallized from ethyl acetate to afford the title compound (0.078 g, 45%) as a white solid, m.p. 221-224° C.

MS [(+)ESI, m/z]: 556 [M+H]+
MS [(−)ESI, m/z]: 554 [M−H]−
HRMS [(+)ESI, m/z]: 556.23397 [M+H]+. Calcd for $C_{34}H_{30}N_5O_3$: 556.23432

Example 70

10-[(3'-METHOXY-2-METHYL-[1,1'-BIPHENYL]-4-YL)CARBONYL]-N-(3-PYRIDINYLMETHYL)-10,11-DIHYDRO-5H-PYRROLO[2,1-C][1,4]BENZODIAZEPINE-3-CARBOXAMIDE

The title compound was prepared in essentially the same manner as Example 47, replacing 2-methoxyphenylboronic acid with 3-methoxyphenylboronic acid. Purification by flash chromatography using a solvent gradient of 1 to 5% methanol in dichloromethane gave a white foam that was crystallized from dichloromethane/hexane to afford the title compound (0.142 g, 74%) as white solid, m.p. 176-177° C.

MS [(+)ESI, m/z]: 543 [M+H]+
MS [(−)ESI, m/z]: 541 [M−H]−
HRMS [(+)ESI, m/z]: 543.23862 [M+H]+. Calcd for $C34H_{31}N_4O_3$: 543.23907

Example 71

10-[(2'-METHOXY-1,1'-BIPHENYL-4-YL)SULFONYL]-N-(PYRIDIN-3-YLMETHYL)-10,11-DIHYDRO-5H-PYRROLO[2,1-C][1,4]BENZODIAZEPINE-3-CARBOXAMIDE

Step A. 10-[(4-Bromophenyl)sulfonyl]-10,11-dihydro-5H-pyrrolo[2,1-c][1,4]benzodiazepine To a solution of 10,11-dihydro-5H-pyrrolo[2,1-c][1,4]benzodiazepine (10 g, 0.0543 mol) and N,N-diisopropylethylamine (14.2 mL, 0.0814 mol) in dry dichloromethane (200 mL) at 0° C. under nitrogen was added dropwise a solution of 4-bromobenzenesulfonyl chloride (10.4 g, 0.0407 mol) in dry dichloromethane (80 mL) over 10 minutes. The ice bath was removed and the reaction mixture stirred at room temperature for 18 hours. The reaction mixture was then washed with 1 M hydrochloric acid (2×250 mL), 0.5 M sodium hydroxide (250 mL) and water (250 mL), dried over anhydrous magnesium sulfate, and concentrated in vacuo to afford a purple syrup (17.91 g). Purification by flash chromatography using a solvent gradient of 5 to 10% ethyl acetate in hexane afforded a tan solid (3.21 g) that was recrystallized from ethyl acetate/hexane to afford the title compound (2.55 g, 16%) as a tan crystalline solid, m.p. 128-129° C.

MS [(+)ESI, m/z]: 403 [M+H]+
Anal. Calcd for $C_{18}H_{15}BrN_2O_2S$: C, 53.61; H, 3.75; N, 6.95. Found: C, 53.74; H, 3.75; N, 6.82.

Step B. 1-{10-[(4-Bromophenyl)sulfonyl]-10,11-dihydro-5H-pyrrolo[2,1-c][1,4]benzodiazepin-3-yl}-2,2,2-trichloroethanone To a solution of 10-[(4-bromophenyl)sulfonyl]-10,11-dihydro-5H-pyrrolo[2,1-c][1,4]benzodiazepine of Step A (2.32 g, 5.753 mmol) and N,N-dimethylaniline (1.17 mL, 9.204 mmol) in dry dichloromethane (20 mL) at 0° C. under nitrogen was added dropwise trichloroacetyl chloride (0.96 mL, 8.629 mmol). The ice bath was removed and the reaction mixture stirred at room temperature for 21 hours. The reaction mixture was then washed with 2 M hydrochloric acid (2×100 mL) and water (100 mL), dried over anhydrous magnesium sulfate, and concentrated in vacuo to give an olive foam. Purification by flash chromatography using a solvent gradient of 5-15% ethyl acetate in hexane afforded a cream solid that was recrystallized from diethyl ether/hexane to afford the title compound (1.986 g, 63%) as an off-white crystalline solid, m.p. 182-183 ° C.

Step C. 10-[(4-Bromophenyl)sulfonyl]-N-(pyridin-3-ylmethyl)-10,11-dihydro-5H-pyrrolo[2,1-c][1,4]benzodiazepine-3-carboxamide To a solution of 1-{10-[(4-bromophenyl)sulfonyl]-10,11-dihydro-5H-pyrrolo[2,1-c][1,4]benzodiazepin-3-yl}-2,2,2-trichloroethanone of Step B (1.80 g, 3.297 mmol) and dimethyl sulfoxide (1.17 mL, 16.487 mmol) in dry acetonitrile (30 mL) at room temperature under nitrogen was added 3-(aminomethyl)pyridine (0.67 mL, 6.595 mmol) and the reaction mixture heated to reflux for 20 hours. The cooled reaction mixture was concentrated in vacuo, the oily residue dissolved in ethyl acetate (100 mL), washed with 1M sodium hydroxide (2×100 mL), water (100 mL) and brine (100 mL), dried over anhydrous magnesium sulfate, filtered and concentrated in vacuo to give a yellow foam. Purification by flash chromatography using a solvent gradient of 0 to 3% methanol in dichloromethane gave the title compound (1.61 g, 91%) as a yellow foam.

MS [(+)ESI, m/z]: 537 [M+H]$^+$

Anal. Calcd for $C_{25}H_{21}BrN_4O_3S$: C, 55.87; H, 3.94; N, 10.42. Found: C, 55.53; H, 3.80; N, 10.23.

Step D. 10-[(2'-Methoxy-1,1'-biphenyl-4-yl)sulfonyl]-N-(pyridin-3-ylmethyl)-10,11-dihydro-5H-pyrrolo[2,1-c][1,4] benzodiazepine-3-carboxamide A mixture of 10-[(4-bromophenyl)sulfonyl]-N-(pyridin-3-ylmethyl)-10,11-dihydro-5H-pyrrolo[2,1-c][1,4]benzodiazepine-3-carboxamide of Step C (0.500 g, 0.93 mmol), 2-methoxyphenylboronic acid (0.212 g, 1.40 mmol) and potassium carbonate (0.386 g, 2.79 mmol) in dimethoxyethane:water (8 mL:2 mL) was purged with nitrogen for 10 minutes. [1,1'-Bis(diphenylphosphino)ferrocene]dichloropalladium[II] (38 mg, 0.0465 mmol) was then added and the reaction mixture heated to 90° C. for 21 hours. The cooled reaction mixture was partitioned between ethyl acetate (100 mL) and 1 M sodium hydroxide (100 mL). The separated organic phase was washed with water (100 mL) and brine (100 mL), dried over anhydrous magnesium sulfate, and concentrated in vacuo to give a brown syrup (0.60 g). Purification by flash chromatography using a solvent gradient of 0 to 3% methanol in dichloromethane gave the title compound (0.520 g, 99%) as a yellow foam.

MS [(−)ESI, m/z]: 563 [M−H]$^-$.

Example 72

10-[(2'-CHLORO-1,1'-BIPHENYL-4-YL)SULFONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 71, Step D, replacing 2-methoxyphenylboronic acid with 2-chlorophenylboronic acid, as a white foam (0.100 g, 32%)

Anal. Calcd for $C_{31}H_{25}ClN_4O_3S$: C, 65.43; H, 4.43; N, 9.85. Found: C, 65.47; H, 4.35; N, 9.54.

Example 73

10-(1,1'-BIPHENYL-4-YLMETHYL)-N-(PYRIDIN-3-YLMETHYL)-10,11-DIHYDRO-5H-PYRROLO[2,1-C][1,4]BENZODIAZEPINE-3-CARBOXAMIDE

Step A. 10-(1,1'-Biphenyl-4-ylmethyl)-10,11-dihydro-5H-pyrrolo[2,1-c][1,4]benzodiazepine A mixture of 10,11-dihydro-5H-pyrrolo[2,1-c][1,4]benzodiazepine (0.200 g, 1.09 mmol), 4-bromomethyl-biphenyl (0.322 g, 1.303 mmol) and potassium carbonate (0.300 g, 2.17 mol) in dry N,N-dimethyl formamide (6 mL) was stirred at room temperature under nitrogen for 24 hours. The reaction mixture was then partitioned between ethyl acetate (50 mL) and 2 M sodium hydroxide (50 mL). The separated organic phase was washed with 2 M sodium hydroxide (50 mL), water (50 mL) and brine (50 mL), dried over anhydrous magnesium sulfate, and concentrated in vacuo to afford a colorless syrup (0.42 g). Purification by flash chromatography using a solvent gradient of 0 to 5% ethyl acetate in hexane afforded a white foam that was crystallized from ethyl acetate/hexane to afford the title compound (0.261 g, 68%) as a white crystalline solid, m.p. 135-137° C.

MS [(−)ESI, m/z]: 349 [M−H]$^-$.

Anal. Calcd for $C_{25}H_{22}N_2$: C, 85.68; H, 6.33; N, 7.99. Found: C, 85.89; H, 6.24; N, 7.83.

Step B. 10-(1,1'-Biphenyl-4-ylmethyl)-N-(pyridin-3-ylmethyl)-10,11-dihydro-5H-pyrrolo[2,1-c][1,4]benzodiazepine-3-carboxamide To a solution of 10-(1,1'-biphenyl-4-ylmethyl)-10,11-dihydro-5H-pyrrolo[2,1-c][1,4]benzodiazepine of Step A (0.93 g, 2.65 mmol) and N,N-dimethylaniline (0.51 mL, 3.98 mmol) in dry dichloromethane (30 mL) at 0° C. under nitrogen was added dropwise trichloroacetyl chloride (0.33 mL, 2.92 mmol). The ice bath was removed and the reaction mixture stirred at room temperature for 19 hours. The reaction mixture was then quenched by the addition of 2 M sodium hydroxide (30 mL) then partitioned between additional dichloromethane (75 mL) and 2 M sodium hydroxide (75 mL). The separated organic phase was washed with 2 M sodium hydroxide (75 mL) and water (75 mL), dried over anhydrous magnesium sulfate, and concentrated in vacuo to give a yellow syrup (2.12 g). Purification by flash chromatography using a solvent gradient of 1-5% ethyl acetate in hexane afforded 1-{10-[(1,1'-biphenyl)-4-ylmethyl]-10,11-dihydro-5H-pyrrolo[2,1-c][1,4]benzodiazepine-3-yl}-2,2,2-trichloroethanone (0.88 g, 67%) as a cream foam. To a solution of 1-{10-[(1,1'-biphenyl)-4-ylmethyl]-10,11-dihydro-5H-pyrrolo[2,1-c][1,4]benzodiazepine-3-yl}-2,2,2-trichloroethanone (0.4 g, 0.807 mmol) and dimethyl sulfoxide (0.29 mL, 4.034 mmol) in dry acetonitrile (5 mL) at room temperature under nitrogen was added 3-(aminomethyl)pyridine (0.17 mL, 1.613 mmol) and the reaction mixture was heated to reflux for 2 days. The cooled mixture was concentrated in vacuo, the semi-solid residue dissolved in ethyl acetate (50 mL), filtered and concentrated in vacuo to afford a dark brown syrup. Purification by flash chromatography using a solvent gradient of 0.5 to 3% methanol in dichloromethane afforded an orange semi-solid that was crystallized from dichloromethane/hexane to give the title compound (0.047 g, 12%) as a cream solid, m.p. 161-165° C. (dec.).

MS [(+)ESI, m/z]: 485 [M+H]$^+$

Example 74

10-(4-IODO-3-METHYLBENZOYL)-N-(PYRIDIN-3-YLMETHYL)-10,11-DIHYDRO-5H-PYRROLO[2,1-C][1,4]BENZODIAZEPINE-3-CARBOXAMIDE

Step A. 10-(4-Iodo-3-methylbenzoyl)-10,11-dihydro-5H-pyrrolo[2,1-c][1,4]benzodiazepine To a solution of 10,11-dihydro-5H-pyrrolo[2,1-c][1,4] benzodiazepine (9.38 g, 0.0509 mol) and N,N-diisopropylethylamine (13.31 mL, 0.0764 mol) in dry dichloromethane (250 mL) at 0° C. under nitrogen was added dropwise a solution of 4-iodo-3-methyl-benzoyl chloride (10.71 g, 0.0382 mol) in dry dichloromethane (30 mL) over ca. 10 minutes. The reaction mixture was allowed to warm slowly to room temperature with stirring over 3 hours then quenched by the addition of water (100 mL). The organic phase was separated, washed with 1 M hydrochloric acid (2×200 mL) and 5% wt/v aqueous sodium carbonate solution (200 mL), dried over anhydrous magnesium sulfate, and concentrated in vacuo to afford a cream solid. Diethyl ether (150 mL) was added and the resulting suspension stirred vigorously for 3 hours then filtered to afford the title compound (14.73 g, 90%) as a white solid, m.p. 152-153° C.

MS [(+)ESI, m/z]: 429 [M+H]$^+$

Anal. Calcd for $C_{20}H_{17}IN_2O$: C, 56.09; H, 4.00; N, 6.54. Found: C, 55.90; H, 3.86; N, 6.38.

Step B. 2,2,2-Trichloro-1-[10-(4-iodo-3-methylbenzoyl)-10,11-dihydro-5H-pyrrolo[2,1-c][1,4]benzodiazepin-3-yl]ethanone To a solution of 10-(4-iodo-3-methylbenzoyl)-10,11-dihydro-5H-pyrrolo[2,1-c][1,4]benzodiazepine of Step A (5.0 g, 0.0117 mmol) and N,N-diisopropylethylamine (3.25 mL, 0.0187 mol) in dry dichloromethane (50 mL) at room temperature under nitrogen was added dropwise trichloroacetyl chloride (1.95 mL, 0.0175 mol) and the reaction mixture was stirred at room temperature for 23 hours. Additional N,N-diisopropylethylamine (1.02 mL, 0.00583 mol) and trichloroacetyl chloride (0.65 mL, 0.00583 mol) were added and stirring continued at room temperature for 4 hours. The reaction mixture was then partitioned between dichloromethane (200 mL) and 2 M hydrochloric acid (200 mL). The organic phase was separated, washed with 2 M hydrochloric acid (200 mL) and water (200 mL), dried over anhydrous magnesium sulfate, and concentrated in vacuo to afford a black syrup. Purification by flash chromatography using a solvent gradient of 10 to 15% ethyl acetate in hexane gave an orange foam. Diethyl ether (100 mL) was added and the resulting suspension stirred vigorously for 4 hours then filtered to afford the title compound (5.21 g, 78%) as an off-white solid, m.p. 163° C.

Anal. Calcd for $C_{22}H_{16}Cl_3IN_2O_2$: C, 46.06; H, 2.81; N, 4.88. Found: C, 45.91; H, 2.72; N, 4.81.

Step C. 10-(4-Iodo-3-methylbenzoyl)-N-(pyridin-3-ylmethyl)-10,11-dihydro-5H-pyrrolo[2,1-c][1,4]benzodiazepine-3-carboxamide To a solution of 2,2,2-trichloro-1-[10-(4-iodo-3-methylbenzoyl)-10,11-dihydro-5H-pyrrolo[2,1-c][1,4]benzodiazepin-3-yl]ethanone of Step B (1 g, 1.74 mmol) in dry acetonitrile (30 mL) at room temperature under nitrogen was added dimethyl sulfoxide (0.62 mL, 8.72 mmol) followed by 3-(aminomethyl)pyridine (0.36 mL, 3.49 mmol) and the reaction mixture heated to reflux for 36 hours. The cooled reaction mixture was concentrated in vacuo to a small volume then partitioned between ethyl acetate (50 mL) and 1 M sodium hydroxide (50 mL). The organic layer was separated, washed with water (50 mL) and brine (50 mL), dried over anhydrous magnesium sulfate, and concentrated in vacuo to afford a yellow foam. Purification by flash chromatography using ethyl acetate as solvent afforded a white foam (0.94 g). Recrystallization from ethyl acetate/hexane gave the title compound (0.77 g, 79%) as white solid, m.p. 176-177° C.

MS [(+)ESI, m/z]: 563 [M+H]$^+$

MS [(−)ESI, m/z]: 561 [M−H]$^−$

Anal. Calcd for $C_{27}H_{23}IN_4O_2$: C, 57.66; H, 4.12; N, 9.96. Found: C, 57.83; H, 4.04; N, 9.75.

Example 75

10-(4-BENZOYLBENZOYL)-N-(PYRIDIN-3-YL-METHYL)-10,11-DIHYDRO-5H-PYRROLO[2,1-C][1,4]BENZODIAZEPINE-3-CARBOXAMIDE

Step A. Phenyl[4-(5H-pyrrolo[2,1-c][1,4]benzodiazepin-10(11H)-ylcarbonyl)phenyl]methanone To solution of 10,11-dihydro-5H-pyrrolo[2,1-c][1,4]benzodiazepine (0.807 g, 4.38 mmol) in dry dichloromethane (20 mL) cooled in an ice bath was added N,N-diisopropylethyl amine (1.14 mL). The solution was treated dropwise with a suspension of 4-benzoylbenzoyl chloride (prepared from 3 mmol of 4-benzoylbenzoic acid and oxalyl chloride) in 8 mL of dichloromethane. The solution was stirred overnight at room temperature, diluted with dichloromethane, washed with water, 1 N hydrochloric acid, saturated aqueous sodium bicarbonate and brine, dried over anhydrous magnesium sulfate and evaporated to dryness. The residue was flash chromatographed over silica gel Merck-60 with a solvent gradient of 5 to 20% of ethyl acetate in hexane to provide the title compound (1.2 g) as a crystalline solid.

MS [(+)ESI, m/z]: 393.12 [M+H]$^+$

Step B. 2,2,2-Trichloro-1-{[10-(4-benzoyl)-benzoyl]-10,11-dihydro-5H-pyrrolo[2,1-c][1,4]benzodiazepin-3-yl}ethanone To a solution of phenyl[4-(5H-pyrrolo[2,1-c][1,4]benzodiazepin-10(11H)-ylcarbonyl)phenyl]methanone of Step A (1 g, 2.55 mmol) and N,N-diisopropylethyl amine (0.9 mL) in dry dichloromethane (20 mL) kept under nitrogen and cooled in an ice bath was added dropwise trichloroacetyl chloride (0.88 mL). The solution was stired overnight at room temperature, and then quenched with water. The organic layer was washed with water, dried over anhydrous magnesium sulfate and evaporated to dryness. The residue was flash chromatographed over silica gel Merck-60 using a solvent gradient of 0 to 2% of ethyl acetate in dichloromethane to provide the title compound as an off white, amorphous solid (1.43 g).

MS [(+)ESI, m/z]: 539.04 [M+H]$^+$

Step C. 10-(4-Benzoylbenzoyl)-N-(pyridin-3-ylmethyl)-10,11-dihydro-5H-pyrrolo[2,1-c][1,4]benzodiazepine-3-carboxamide To a suspension of 2,2,2-trichloro-1-{[10-(4-benzoyl)-benzoyl]-10,11-dihydro-5H-pyrrolo[2,1-c][1,4]benzodiazepin-3-yl}ethanone of Step B (1.2 g, 2.23 mmol) in dry acetonitrile (30 mL) kept under nitrogen was added triethylamine (0.680 mL), and dimethylsulfoxide (0.8 mL) followed by 3-(aminomethyl)pyridine (0.478 mL). The mixture was stirred overnight at room temperature, and then evaporated to dryness. The residue was dissolved in dichloromethane and the solution washed with brine, dried over anhydrous sodium sulfate and evaporated to dryness. The residue was flash chromatographed over silica gel Merck-60 using a solvent gradient of 0 to 50% of ethyl acetate in dichloromethane to provide the title compound as a white solid, m.p. 211-213° C. dec.

MS [(−)ESI, m/z]: 525.25 [M−H]$^−$

Anal. Calcd for $C_{33}H_{26}N_4O_3$ 0.40 $C_4H_8O_2$: C, 73.97; H, 5.24; N, 9.97. Found: C, 73.62; H, 5.08; N, 10.05.

Example 76

10-BENZOYL-N-(PYRIDIN-3-YLMETHYL)-10,11-DIHYDRO-5H-PYRROLO[2,1-C][1,4]BENZO-DIAZEPINE-3-CARBOXAMIDE

Step A. 10,11-Dihydro-5H-pyrrolo[2,1-c][1,4]benzodiazepine-10-carboxylic acid 9H-fluoren-9-ylmethyl ester To a solution of 10,11-dihydro-5H-pyrrolo[2,1-c][1,4]benzodiazepine (19.23 g, 0.104 mol) and N,N-diisopropylethylamine (27.3 mL, 0.157 mol) in dichloromethane (500 mL) was added 9-fluorenylmethyl chloroformate (27 g, 0.104 mol). The reaction mixture was stirred at room temperature under nitrogen for 4 hours, and then washed with 1 M hydrochloric acid (3×300 mL), water (300 mL) and brine (300 mL), dried over anhydrous magnesium sulfate, and concentrated in vacuo to give a pale yellow solid. The solid was slurried in dichloromethane (75 mL), the slurry was diluted with diethyl ether (300 mL) and the resulting white suspension stirred overnight. Filtration afforded the title compound (34.64 g, 82%) as a white solid, m.p. 141-142° C.

MS [APCI, m/z]: 407 [M+H]$^+$

Anal. Calcd for $C_{27}H_{22}N_2O_2$: C, 79.78; H, 5.46; N, 6.89. Found: C, 79.44; H, 5.72; N, 6.67.

Step B. 2,2,2-Trichloro-1-[10-(fluorenylmethoxycarbonyl)-10,11-dihydro-5H-pyrrolo[2,1-c][1,4]benzodizepin-3-yl]ethanone To a solution of 10,11-dihydro-5H-pyrrolo[2,1-c][1,4]benzodiazepine-10-carboxylic acid9H-fluoren-9-ylmethyl ester of Step A (13.9 g, 34.2 mmol) and N,N-dimethylaniline (6.9 mL, 54 mmol) in dichloromethane (100 mL) at 0° C. under nitrogen was added dropwise trichloroacetyl chloride (5.7 mL, 51 mmol) over ca. 5 minutes. The cooling bath was then removed and the reaction mixture stirred at room temperature for 16 hours then quenched by the addition of water. The organic phase was washed with 2 M hydrochloric acid (3×100 mL), water (100 mL) and brine (100 mL), dried over anhydrous magnesium sulfate, and concentrated in vacuo to give the crude product as a gray foam (19.1 g). Purification by filtration through a plug of silica gel (90 g) eluting with diethyl ether afforded the title compound (18.3 g, 97%) as a pink foam.

Anal. Calcd for $C_{29}H_{21}Cl_3N_2O_3$: C, 63.12; H, 3.84; N, 5.08. Found: C, 62.98; H, 3.61; N, 5.01.

Step C. N-(Pyridin-3-ylmethyl)-10,11-dihydro-5H-pyrrolo[2,1-c][1,4]benzodiazepine-3-carboxamide To a solution of 2,2,2-trichloro-1-[10-(fluorenylmethoxycarbonyl)-10,11-dihydro-5H-pyrrolo[2,1-c][1,4]benzodizepin-3-yl]ethanone of Step B (19.04 g, 34.5 mmol) in dry acetonitrile (11 mL) was added dry dimethylsulfoxide (12.25 mL, 172.5 mmol) followed by 3-(aminomethyl)pyridine (10.54 mL, 103.5 mmol) and the reaction mixture was heated to reflux under nitrogen for 19.5 hours. The reaction mixture was slowly cooled to 4° C. and the resulting suspension filtered to afford the title compound (8.45 g, 77%) as an off-white solid, identical to the product of Example 12.

MS [(+)ESI, m/z]: 319 [M+H]$^+$

Anal. Calcd for $C_{19}H_{18}N_4O$: C, 71.68; H, 5.70; N, 17.60. Found: C, 71.63; H, 5.53; N, 17.61.

Step D. 10-Benzoyl-N-(pyridin-3-ylmethyl)-10,11-dihydro-5H-pyrrolo[2,1-c][1,4]benzodiazepine-3-carboxamide To a suspension of N-(pyridin-3-ylmethyl)-10,11-dihydro-5H-pyrrolo[2,1-c][1,4]benzodiazepine-3-carboxamide of Step C (300 mg, 0.942 mmol) in dry tetrahydrofuran (15 mL) at room temperature under nitrogen was added N,N-diisopropylethylamine (0.26 mL, 1.508 mmol) followed by benzoyl chloride (0.165 mL, 1.41 mmol) and the reaction mixture stirred at room temperature for 21 hours. The reaction was quenched by the addition of 2 M sodium hydroxide (5 mL) and then the mixture partitioned between ethyl acetate (50 mL) and 2 M sodium hydroxide (50 mL). The organic phase was washed with 2 M sodium hydroxide (50 mL), water (50 mL) and brine (50 mL), dried over anhydrous magnesium sulfate and concentrated in vacuo to afford a yellow syrup. Purification by flash chromatography using a solvent gradient of 0 to 4% methanol in dichloromethane gave a white foam that was crystallized from diethyl ether/hexane to give the title compound (0.319 g, 80%) as a white crystalline solid, m.p. 197° C.

MS [(+)ESI, m/z]: 423 [M+H]$^+$

MS [(−)ESI, m/z]: 421 [M−H]$^-$

Anal. Calcd for $C_{26}H_{22}N_4O_2$: C, 73.92; H, 5.25; N, 13.26. Found: C, 73.61; H, 5.41; N, 13.14.

Example 77

10-(4-METHYLBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with p-toluoyl chloride. Purification by flash chromatography using a solvent gradient of 0 to 4% methanol in dichloromethane gave the title compound (0.410 g, 99%) as a white foam.

MS [(+)ESI, m/z]: 437 [M+H]$^+$

MS [(−)ESI, m/z]: 435 [M−H]$^-$

HRMS [(+)ESI, m/z]: 437.19607 [M+H]$^+$. Calcd for $C_{27}H_{25}N_4O_2$: 437.19775

Example 78

10-(3-FLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 3-fluorobenzoyl chloride. Purification by flash chromatography using a solvent gradient of 0 to 4% methanol in dichloromethane gave the title compound (0.390 g, 94%) as a white solid, m.p. 101° C.

MS [(+)ESI, m/z]: 441 [M+H]$^+$

MS [(−)ESI, m/z]: 439 [M−H]$^-$

HRMS [(+)ESI, m/z]: 441.17103 [M+H]$^+$. Calcd for $C_{26}H_{22}FN_4O_2$: 441.17268

Example 79

N-(PYRIDIN-3-YLMETHYL)-10-[4-(TRIFLUOROMETHYL)BENZOYL]-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-(trifluoromethyl)benzoyl chloride. Purification by flash chromatography using a solvent gradient of 0 to 4% methanol in dichloromethane gave the title compound (0.430 g, 93%) as a white foam.

MS [(−)ESI, m/z]: 489 [M−H]$^-$

Anal. Calcd for $C_{27}H_{21}F_3N_4O_2$: C, 66.12; H, 4.32; N, 11.42. Found: C, 65.81; H, 4.38; N, 11.21.

Example 80

10-(4-TERT-BUTYLBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-tert-butylbenzoyl chloride. Purification by flash chromatography using a solvent gradient of 0 to 4% methanol in dichloromethane gave the title compound (0.450 g, 99%) as a white foam.

MS [(+)ESI, m/z]: 479 [M+H]$^+$

MS [(−)ESI, m/z]: 477 [M−H]⁻

Anal. Calcd for $C_{30}H_{30}N_4O_2$: C, 75.29; H, 6.32; N, 11.71. Found: C, 74.93; H, 6.16; N, 11.32.

Example 81

10-(3,4-DICHLOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 3,4-dichlorobenzoyl chloride. Purification by flash chromatography using a solvent gradient of 0 to 4% methanol in dichloromethane gave a yellow solid that was recrystallized from dichloromethane/diethyl ether to afford the title compound (0.376 g, 81%) as a white crystalline solid, m.p. 192° C.

MS [(+)ESI, m/z]: 491 [M+H]⁺

MS [(−)ESI, m/z]: 489 [M−H]⁻

HRMS [(+)ESI, m/z]: 491.10219][M+H]⁺. Calcd for $C_{26}H_{21}Cl_2N_4O_2$: 491.10415

Example 82

N-(PYRIDIN-3-YLMETHYL)-10-[2-(TRIFLUOROMETHYL)BENZOYL]-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 2-(trifluoromethyl)benzoyl chloride. Purification by flash chromatography using a solvent gradient of 0 to 4% methanol in dichloromethane gave a yellow solid that was recrystallized from diethyl ether/hexane to afford the title compound (0.395 g, 85%) as a white solid, m.p. 157-158° C.

MS [(+)ESI, m/z]: 491 [M+H]⁺

MS [(−)ESI, m/z]: 489 [M−H]⁻

Anal. Calcd for $C_{27}H_{21}F_3N_4O_2$: C, 66.12; H, 4.32; N, 11.42. Found: C, 66.05; H, 4.48; N, 11.22.

Example 83

10-(3-METHYLBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with m-toluoyl chloride. Purification by recrystallization from diethyl ether/ethanol gave the title compound (0.298 g, 45%) as light orange needles.

MS [(+)ESI, m/z]: 437 [M+H]⁺

MS [(−)ESI, m/z]: 435 [M−H]⁻

HRMS [(+)ESI, m/z]: 437.19614 [M+H]⁺. Calcd for $C_{27}H_{25}N_4O_2$: 437.19775

Example 84

10-[4-(DIMETHYLAMINO)BENZOYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-(dimethylamino)benzoyl chloride. Purification by flash chromatography using ethyl acetate as solvent gave an orange solid that was recrystallized from ethanol/ethyl acetate to afford the title compound (0.280 g, 40%) as an orange crystalline solid.

MS [(+)ESI, m/z]: 466 [M+H]⁺

HRMS [(+)ESI, m/z]: 466.22317 [M+H]⁺. Calcd for $C_{28}H_{28}N_5O_2$: 466.22430

Example 85

N-(PYRIDIN-3-YLMETHYL)-10-[4-(TRIFLUOROMETHOXY)BENZOYL]-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-(trifluoromethoxy)benzoyl chloride. Purification by flash chromatography using ethyl acetate as solvent gave a white foam that was recrystallized from diethyl ether to afford the title compound (0.499 g, 66%) as pale yellow needles.

MS [(+)ESI, m/z]: 507 [M+H]⁺

MS [(−)ESI, m/z]: 505 [M−H]⁻

Anal. Calcd for $C_{27}H_{21}F_3N_4O_3$: C, 64.03; H, 4.18; N, 11.06. Found: C, 63.85; H, 4.20; N, 11.01.

Example 86

10-(2,6-DIFLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 2,6-difluorobenzoyl chloride. Purification by flash chromatography using a solvent gradient of 0 to 4% methanol in dichloromethane gave the title compound (0.210 g, 49%) as a white solid, m.p. 103-109° C.

MS [(+)ESI, m/z]: 459 [M+H]⁺

MS [(−)ESI, m/z]: 457 [M−H]⁻

HRMS [(+)ESI, m/z]: 459.16143 [M+H]⁺. Calcd for $C_{26}H_{21}F_2N_4O_2$: 459.16326

Example 87

METHYL 4-{[3-{[(PYRIDIN-3-YLMETHYL)AMINO]CARBONYL}-5H-PYRROLO[2,1-C][1,4]BENZODIAZEPIN-10(11H)-YL]CARBONYL}BENZOATE

The title compound was prepared in essentially the same manner as Example 76, Step D, replacing benzoyl chloride with 4-chlorocarbonyl-benzoic acid methyl ester. Purification by flash chromatography using a solvent gradient of 0 to 4% methanol in dichloromethane gave a colorless syrup that was crystallized from diethyl ether/dichloromethane to afford the title compound (3.06 g, 99%) as a white crystalline solid, m.p. 170-172° C.

MS [(+)ESI, m/z]: 481 [M+H]⁺

MS [(−)ESI, m/z]: 479 [M−H]⁻

HRMS [(+)ESI, m/z]: 481.18613 [M+H]⁺. Calcd for $C_{28}H_{25}N_4O_4$: 481.18758

Example 88

4-{[3-{[(PYRIDIN-3-YLMETHYL)AMINO]CARBONYL}-5H-PYRROLO[2,1-C][1,4]BENZODIAZEPIN-10(11H)-YL]CARBONYL}BENZOIC ACID

To a solution of methyl 4-{[3-{[(pyridin-3-ylmethyl)amino]carbonyl}-5H-pyrrolo[2,1-c][1,4]benzodiazepin-10(11H)-yl]carbonyl}benzoate of Example 87 (0.315 g, 0.656 mmol) in methanol (4 mL) and water (2 mL) was added lithium hydroxide (31.4 mg, 1.31 mmol) and the reaction mixture heated to reflux for 1 hour. The cooled reaction mixture was diluted with water (20 mL) and washed with ethyl acetate (2×20 mL). The aqueous phase was then acidified to pH 4.5 by the addition of 2 M hydrochloric acid and the resulting milky suspension allowed to stand at 4° C. for 16 hours. The solid product was filtered, washed with water, and dried at 50° C. in vacuo overnight to afford the title compound (0.271 g, 89%) as a white solid.

MS [(+)ESI, m/z]: 467 [M+H]$^+$
MS [(−)ESI, m/z]: 465 [M−H]$^−$

Example 89

10-(4-METHOXYBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with p-anisoyl chloride. Purification by flash chromatography using a solvent gradient of 0 to 4% methanol in dichloromethane gave the title compound (0.425 g, 99%) as a white solid, m.p. 110-112° C.

MS [(+)ESI, m/z]: 453 [M+H]$^+$
Anal. Calcd for $C_{27}H_{24}N_4O_3$: C, 71.67; H, 5.35; N, 12.38. Found: C, 71.29; H, 5.51; N, 12.00

Example 90

10-(4-CYANOBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-cyanobenzoyl chloride. Purification by flash chromatography using a solvent gradient of 0 to 4% methanol in dichloromethane gave a pale yellow foam that was crystallized from ethanol to afford the title compound (0.417 g, 62%) as a white crystalline solid.

MS [(+)ESI, m/z]: 448 [M+H]$^+$
MS [(−)ESI, m/z]: 446 [M−H]$^−$
HRMS [(+)ESI, m/z]: 448.17627 [M+H]$^+$. Calcd for $C_{27}H_{22}N_5O_2$: 448.17735
Anal. Calcd for $C_{27}H_{21}N_5O_2$: C, 72.47; H, 4.73; N, 15.65. Found: C, 72.22; H, 4.60; N, 15.66.

Example 91

10-(4-CHLOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-chlorobenzoyl chloride. Purification by flash chromatography using a solvent gradient of 0 to 4% methanol in dichloromethane gave a light tan foam that was crystallized from ethyl acetate/diethyl ether to afford the title compound (0.485 g, 71%) as light orange needles.

MS [(+)ESI, m/z]: 457 [M+H]$^+$
MS [(−)ESI, m/z]: 455 [M−H]$^−$
HRMS [(+)ESI, m/z]: 457.14179 [M+H]$^+$. Calcd for $C_{26}H_{22}ClN_4O_2$: 457.14313

Example 92

N-(PYRIDIN-3-YLMETHYL)-10-[3-(TRIFLUOROMETHYL)BENZOYL]-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 3-(trifluoromethyl)benzoyl chloride. Purification by flash chromatography using a solvent gradient of 0 to 4% methanol in dichloromethane gave a tan foam that was crystallized from dichloromethane/diethyl ether to afford the title compound (0.375 g, 51%) as a white solid.

MS [(+)ESI, m/z]: 491 [M+H]$^+$
MS [(−)ESI, m/z]: 489 [M−H]$^−$
HRMS [(+)ESI, m/z]: 491.16856 [M+H]$^+$. Calcd for $C_{27}H_{22}F_3N_4O_2$: 491.16949
Anal. Calcd for $C_{27}H_{21}F_3N_4O_2$: C, 66.12; H, 4.32; N, 11.42. Found: C, 66.23; H, 4.40; N, 11.46.

Example 93

10-(4-FLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-fluorobenzoyl chloride. Purification by flash chromatography using a solvent gradient of 0 to 4% methanol in dichloromethane gave a yellow syrup that was crystallized from dichloromethane/diethyl ether/hexane to afford the title compound (0.330 g, 80%) as a cream solid, m.p. 171-173° C.

MS [(+)ESI, m/z]: 441 [M+H]$^+$
MS [(−)ESI, m/z]: 439 [M−H]$^−$
HRMS [(+)ESI, m/z]: 441.17104 [M+H]$^+$. Calcd for $C_{26}H_{22}FN_4O_2$: 441.17268

Example 94

10-(2-METHYLBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with o-toluoyl chloride. Purification by flash chromatography using a solvent gradient of 0 to 4% methanol in dichloromethane gave a tan foam that was crystallized from diethyl ether to afford the title compound (0.258 g, 39%) as a pale yellow solid.

MS [(+)ESI, m/z]: 437 [M+H]$^+$
HRMS [(+)ESI, m/z]: 437.19625 [M+H]$^+$. Calcd for $C_{27}H_{25}N_4O_2$: 437.19775

Example 95

10-(3,5-DIFLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 3,5-difluorobenzoyl chloride. Purification by flash chromatography using a solvent gradient of 0 to 4% methanol in dichloromethane gave a colorless syrup that was crystallized from dichloromethane/diethyl ether/hexane to afford the title compound (280 mg, 65%) as a white solid, m.p. 138-140° C.
MS [(+)ESI, m/z]: 459 [M+H]$^+$
MS [(−)ESI, m/z]: 457 [M−H]$^−$
HRMS [(+)ESI, m/z]: 459.16185 [M+H]$^+$. Calcd for $C_{26}H_{21}F_2N_4O_2$: 459.16326

Example 96

10-(1,3-BENZODIOXOL-5-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with benzo[1,3]dioxole-5-carbonyl chloride. Purification by flash chromatography using a solvent gradient of 0 to 4% methanol in dichloromethane gave a colorless syrup that was crystallized from diethyl ether to afford the title compound (0.390 g, 89%) as a white crystalline solid, m.p. 169-171° C.
MS [(+)ESI, m/z]: 467 [M+H]$^+$
Anal. Calcd for $C_{27}H_{22}N_4O_4$: C, 69.52; H, 4.75; N, 12.01. Found: C, 69.25; H, 4.72; N, 11.76.

Example 97

10-(2-FLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 2-fluorobenzoyl chloride. Purification by flash chromatography using a solvent gradient of 0 to 4% methanol in dichloromethane gave a yellow syrup that was crystallized from diethyl ether/hexane to afford the title compound (0.280 g, 67%) as a white solid, m.p. 142-143° C.
MS [(+)ESI, m/z]: 441 [M+H]$^+$
Anal. Calcd for $C_{26}H_{21}FN_4O_2$: C, 70.90; H, 4.81; N, 12.72. Found: C, 70.66; H, 4.76; N, 12.57.

Example 98

10-(4-PROPYLBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-propylbenzoyl chloride. Purification by flash chromatography using a solvent gradient of 0 to 4% methanol in dichloromethane gave a yellow syrup that was crystallized from diethyl ether to afford the title compound (0.343 g, 78%) as a white solid.
MS [(+)ESI, m/z]: 465 [M+H]$^+$
HRMS [(+)ESI, m/z]: 465.22876 [M+H]$^+$. Calcd for $C_{29}H_{29}N_4O_2$: 465.22905

Example 99

10-(4-NITROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-nitrobenzoyl chloride. Purification by flash chromatography using a solvent gradient of 0 to 4% methanol in dichloromethane gave a yellow syrup that was crystallized from diethyl ether to afford the title compound (0.292 g, 66%) as a yellow solid.
MS [(+)ESI, m/z]: 468 [M+H]$^+$
MS [(−)ESI, m/z]: 466 [M−H]$^−$
HRMS [(+)ESI, m/z]: 468.16613 [M+H]$^+$. Calcd for $C_{26}H_{22}N_5O_4$: 468.16718

Example 100

10-(3,4-DIFLUOROBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 3,4-difluorobenzoyl chloride. Purification by flash chromatography using a solvent gradient of 0 to 4% methanol in dichloromethane gave a yellow syrup that was crystallized from diethyl ether to afford the title compound (0.190 g, 44%) as a pale yellow solid.
MS [(+)ESI, m/z]: 459 [M+H]$^+$
HRMS [(+)ESI, m/z]: 459.16255 [M+H]$^+$. Calcd for $C_{26}H_{21}F_2N_4O$: 459.16326
Anal. Calcd for $C_{26}H_{20}F_2N_4O_2$: C, 68.12; H, 4.40; N, 12.22. Found: C, 67.82; H, 4.57; N, 11.95.

Example 101

10-(4-PHENOXYBENZOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-phenoxybenzoyl chloride. Purification by flash chromatography using a solvent gradient of 0 to 4% methanol in dichloromethane gave a white foam that was crystallized from diethyl ether to afford the title compound (0.307 g, 63%) as a white solid.
MS [(+)ESI, m/z]: 515 [M+H]$^+$
HRMS [(+)ESI, m/z]: 515.20868 [M+H]$^+$. Calcd for $C_{32}H_{27}N_4O_3$: 515.20832
Anal. Calcd for $C_{32}H_{26}N_4O_3$: C, 74.69; H, 5.09; N, 10.89. Found: C, 74.38; H, 5.05; N, 10.70.

Example 102

10-[4-(DIETHYLAMINO)BENZOYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 76, Step D, replacing benzoyl chloride with 4-diethylaminobenzoyl chloride. Purification by flash chromatography using a solvent gradient of 0 to 4% methanol in dichloromethane gave a white foam that was crystallized from diethyl ether to afford the title compound (0.254 g, 55%) as a white solid.

MS [(+)ESI, m/z]: 494 [M+H]+

HRMS [(+)ESI, m/z]: 494.25473 [M+H]+. Calcd for $C_{30}H_{32}N_5O_2$: 494.25560

Example 103

TERT-BUTYL(4-{[3-{[(PYRIDIN-3-YLMETHYL) AMINO]CARBONYL}-5H-PYRROLO[2,1-C][1,4] BENZODIAZEPIN-10(11H)-YL] CARBONYL}BENZYL)CARBAMATE

Step A. 4-{[(tert-Butoxycarbonyl)amino]methyl}benzoic acid

To a solution of 4-(aminomethyl)benzoic acid (5.00 g, 0.0331 mol) in dioxane (60 mL), water (30 mL), and 1 M sodium hydroxide (34 mL, 0.034 mol) at 0° C. was added di-tert-butylpyrocarbonate (7.94 g, 0.0364 mol) and the reaction mixture stirred at 0° C. for 1 hour. The reaction mixture was concentrated in vacuo to 30 mL, ethyl acetate (80 mL) added and the mixture acidified to pH 4 by the addition of 1 M aqueous potassium hydrogen sulfate solution with vigorous stirring. The organic phase was separated, washed with water (80 mL), dried over anhydrous sodium sulfate, and concentrated in vacuo to afford a white solid. Recrystallization from ethyl acetate (60 mL) gave the title compound (3.94 g, 47%) as a white crystalline solid, m.p. 165° C.

MS [(−)ESI, m/z]: 250 [M−H]−

Anal. Calcd for C13H17NO4: C, 62.14; H, 6.82; N, 5.57. Found: C, 61.74; H, 6.51; N, 5.42.

Step B. tert-Butyl(4-{[3-{[(pyridin-3-ylmethyl)amino]carbonyl}-5H-pyrrolo[2,1-c][1,4]benzodiazepin-10(11H)-yl] carbonyl}benzyl)carbamate To a suspension of 4-{[(tert-butoxycarbonyl)amino] methyl}benzoic acid of Step A (3.55 g, 0.0141 mmol) in dry dichloromethane (40 mL) at room temperature under nitrogen was added dry N,N-dimethylformamide (2 drops, cat.) followed by a 2.0 M solution of oxalyl chloride in dichloromethane (14.1 mL, 0.0283 mol) and the reaction mixture stirred at room temperature for 4.5 hours. The reaction mixture was then concentrated in vacuo to afford (4-chlorocarbonyl-benzyl)carbamic acid tert-butyl ester as a white solid. The crude acid chloride was dissolved in dry tetrahydrofuran (20 mL), added to a suspension of N-(pyridin-3-ylmethyl)-10,11-dihydro-5H-pyrrolo[2,1-c][1,4]benzodiazepine-3-carboxamide of Example 76, Step C (3 g, 9.42 mmol), and N,N-diisopropylethylamine (4.92 mL, 28.27 mmol) in dry tetrahydrofuran (20 mL), and the reaction mixture stirred at room temperature for 19 hours. The reaction was quenched by the addition of 2 M sodium hydroxide (20 mL) and then partitioned between ethyl acetate (200 mL) and 2 M sodium hydroxide (200 mL). The separated organic phase was washed with 2 M sodium hydroxide (200 mL), water (200 mL) and brine (200 mL), dried over magnesium sulfate, and concentrated in vacuo to afford an orange solid (3.95 g). Purification by flash chromatography using a solvent gradient of 1 to 5% methanol in dichloromethane gave a colorless glass that was recrystallized from ethyl acetate/hexane to afford the title compound (1.29 g, 25%) as a cream crystalline solid, m.p. 171° C.

MS [(+)ESI, m/z]: 552 [M+H]+

HRMS [(+)ESI, m/z]: 552.26037 [M+H]+. Calcd for $C_{32}H_{34}N_5O_4$: 552.26108

Example 104

10-(3-METHYL-4-THIEN-2-YLBENZOYL)-N-(PYRIDIN-3-YLMETHYL)-10,11-DIHYDRO-5H-PYRROLO[2,1-C][1,4]BENZODIAZEPINE-3-CARBOXAMIDE

A mixture of 10-(4-iodo-3-methylbenzoyl)-N-(pyridin-3-ylmethyl)-10,11-dihydro-5H-pyrrolo[2,1-c][1,4]benzodiazepine-3-carboxamide of Example 74 (0.300 g, 0.53 mmol), 2-thiopheneboronic acid (0.102 g, 0.80 mmol) and potassium carbonate (0.221 g, 1.60 mmol) in dimethoxyethane:water (8 mL:2 mL) was purged with nitrogen for 10 minutes. [1,1'-bis (Diphenylphosphino)ferrocene]dichloropalladium [II] (0.022 g, 0.0266 mmol) was then added and the reaction mixture heated to 90° C. for 4 hours. The cooled reaction mixture was partitioned between ethyl acetate (100 mL) and 1 M sodium hydroxide (100 mL). The organic phase was separated, washed with water (100 mL) and brine (100 mL), dried over anhydrous magnesium sulfate, and concentrated in vacuo to give a brown syrup (0.34 g). Purification by flash chromatography using 280:8:1 dichloromethane:ethanol: aqueous ammonia as solvent gave an orange foam that was crystallized from diethyl ether/hexane to afford the title compound (0.168 g, 61%) as a tan solid.

MS [(+)ESI, m/z]: 519 [M+H]+
MS [(−)ESI, m/z]: 517 [M−H]−

Example 105

N-(PYRIDIN-3-YLMETHYL)-10-(4-PYRIMIDIN-2-YLBENZOYL)-10,11-DIHYDRO-5H-PYRROLO [2,1-C][1,4]BENZODIAZEPINE-3-CARBOXAMIDE

Step A. 4-Pyrimidin-2-ylbenzoic acid

To a suspension of 4-carboxybenzeneboronic acid (0.660 g, 3.98 mmol) and 2-bromopyrimidine (0.630 g, 3.98 mmol) in dry acetonitrile (20 mL) was added 0.4 M aqueous sodium carbonate (20 mL) and the mixture was purged with nitrogen for 10 minutes. Tetrakis(triphenylphosphine)palladium(0) (240 mg) was then added and the reaction mixture heated to 90° C. for 17 hours. The hot reaction mixture was filtered through celite and concentrated in vacuo to remove the acetonitrile. The resulting aqueous suspension was washed with dichloromethane (2×30 mL) and then acidified to pH 1 by the addition of concentrated hydrochloric acid. The resulting white suspension was diluted with water (20 mL), filtered and the solid product dried in vacuo at 50° C. overnight to give the title compound (0.709 g, 89%) as a white solid, m.p. 237° C.

MS [(+)ESI, m/z]: 201 [M+H]+
MS [(−)ESI, m/z]: 199 [M−H]−

Anal. Calcd for $C_{11}H_8N_2O_2$: C, 66.00; H, 4.03; N, 13.99. Found: C, 65.72; H, 3.87; N, 14.01.

Step B. N-(Pyridin-3-ylmethyl)-10-(4-pyrimidin-2-ylbenzoyl)-10,11-dihydro-5H-pyrrolo[2,1-c][1,4]benzodiazepine-3-carboxamide To a solution of 4-pyrimidin-2-ylbenzoic acid of Step A (0.283 g, 1.41 mmol) in dry tetrahydrofuran (20 mL) at room temperature under nitrogen was added N,N-dimethylformamide (1 drop, cat) followed by a 2.0 M solution of oxalyl chloride in dichloromethane (1.41 mmol, 2.82 mmol) and the reaction mixture was stirred at room temperature for 3 hours. The mixture was then concentrated in vacuo to afford 4-pyrimidin-2-yl-benzoyl chloride as a yellow syrup. The crude acid chloride was dissolved in dry tetrahydrof-uran (5 mL), added to a suspension of N-(pyridin-3-ylmethyl)-10,11-dihydro-5Hpyrrolo[2,1-c][1,4]benzodiazepine-3-carboxamide of Example 76, Step C (0.300 g, 0.942 mmol), and N,N-diisopropylethylamine (0.49 mL, 2.83 mmol) in dry tetrahydrofuran (5 mL), and the reaction mixture stirred at room temperature under nitrogen for 20 hours. The reaction was then quenched by the addition of 2 M sodium hydroxide (10 mL) and the mixture partitioned between ethyl acetate (50 mL) and 2 M sodium hydroxide (50 mL). The organic phase was separated, washed with 2 M sodium hydroxide (2×50 mL), water (50 mL) and brine (50 mL), dried over anhydrous magnesium sulfate, filtered and concentrated in vacuo to afford a yellow foam. Purification by flash chromatography using a solvent gradient of 1 to 5% methanol in dichloromethane gave an cream foam that was crystallized from diethyl ether/hexane to afford the title compound (0.395 g, 84%) as white solid, m.p. 234-236° C.

MS [(+)ESI, m/z]: 501 [M+H]$^+$

Anal. Calcd for $C_{30}H_{24}N_6O_2$: C, 71.99; H, 4.83; N, 16.79. Found: C, 71.65; H, 4.91; N, 16.56.

Example 106

N-(PYRIDIN-3-YLMETHYL)-10-(4-PYRIMIDIN-5-YLBENZOYL)-10,11-DIHYDRO-5H-PYRROLO[2,1-C][1,4]BENZODIAZEPINE-3-CARBOXAMIDE

Step A. 4-Pyrimidin-5-ylbenzoic acid

The title compound was prepared in essentially the same manner as Example 105, Step A, replacing 2-bromopyrimidine with 5-bromopyrimidine to give the title compound (0.687 g, 86%) as a white solid, m.p. >275° C.

MS [(-)ESI, m/z]: 199 [M-H]$^-$

Step B. N-(Pyridin-3-ylmethyl)-10-(4-pyrimidin-5-ylbenzoyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-pyrimidin-5-ylbenzoic acid of Step A. Purification by flash chromatography using a solvent gradient of 0 to 4% methanol in dichloromethane gave a white foam that was crystallized from dichloromethane/diethyl ether to afford the title compound (0.318 g, 67%) as a white solid, m.p. 172-175° C.

MS [(+)ESI, m/z]: 501 [M+H]$^+$
MS [(-)ESI, m/z]: 499 [M-H]$^-$

Anal. Calcd for $C_{30}H_{24}N_6O_2$: C, 71.99; H, 4.83; N, 16.79. Found: C, 71.68; H, 4.85; N, 16.72.

Example 107

10-(4-PYRIDIN-2-YLBENZOYL)-N-(PYRIDIN-3-YLMETHYL)-10,11-DIHYDRO-5H-PYRROLO[2,1-C][1,4]BENZODIAZEPINE-3-CARBOXAMIDE

Step A. 4-Pyridin-2-ylbenzoic acid

To a suspension of 4-carboxybenzeneboronic acid (0.660 g, 3.98 mmol) and 2-bromopyridine (0.38 mL, 3.98 mmol) in dry acetonitrile (20 mL) was added 0.4 M aqueous sodium carbonate (20 mL) and mixture purged with nitrogen for 10 minutes. Tetrakis(triphenylphosphine)palladium(0) (0.240 g) was then added and the reaction mixture heated to 90° C. for 20 hours. The hot mixture was filtered through celite and concentrated in vacuo to remove acetonitrile. The resulting aqueous suspension was diluted with water (20 mL), washed with dichloromethane (2×40 mL), and then acidified to pH 6 by the addition of concentrated hydrochloric acid. The resulting white suspension was diluted with water (20 mL), filtered and the solid product dried in vacuo at 50° C. overnight to give the title compound (0.662 g, 84%) as a white solid, m.p. 232-234° C.

MS [(+)ESI, m/z]: 200 [M+H]$^+$
MS [(-)ESI, m/z]: 198 [M-H]$^-$

Anal. Calcd for $C_{12}H_9NO_2$: C, 72.35; H, 4.55; N, 7.03. Found: C, 72.04; H, 4.38; N, 6.89.

Step B. 10-(4-Pyridin-2-ylbenzoyl)-N-(pyridin-3-ylmethyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-pyridin-2-ylbenzoic acid of Step A. Purification by flash chromatography using a solvent gradient of 1 to 5% methanol in dichloromethane gave a colorless syrup that was crystallized from dichloromethane/diethyl ether/hexane to afford the title compound (0.323 g, 69%) as a white solid, m.p. 159-161° C.

MS [(+)ESI, m/z]: 500 [M+H]$^+$
HRMS [(+)ESI, m/z]: 500.20754 [M+H]$^+$. Calcd for $C_{31}H_{26}N_5O_2$: 500.20810

Example 108

10-(4-PYRIDIN-3-YLBENZOYL)-N-(PYRIDIN-3-YLMETHYL)-10,11-DIHYDRO-5H-PYRROLO[2,1-C][1,4]BENZODIAZEPINE-3-CARBOXAMIDE

Step A. 4-Pyridin-3-ylbenzoic acid

The title compound was prepared in essentially the same manner as Example 107, Step A, replacing 2-bromopyridine with 3-bromopyridine to give the title compound (0.648 g, 82%) as a white solid, m.p. >275° C.

MS [(+)ESI, m/z]: 200 [M+H]$^+$
MS [(-)ESI, m/z]: 198 [M-H]$^-$

Step B. 10-(4-Pyridin-3-ylbenzoyl)-N-(pyridin-3-ylmethyl)-10,11-dihydro-5H-pyrrolo[2,1-c][1,4]benzodiazepine-3-carboxamide The title compound was prepared in essentially the same manner as Example 105, step B, replacing 4-pyrimidin-2-ylbenzoic acid with 4-pyridin-3-ylbenzoic acid of Step A. Purification by flash chromatography using a solvent gradient of 1 to 5% methanol in dichloromethane gave a colorless syrup that was crystallized from dichloromethane/diethyl ether/hexane to afford the title compound (0.282 g, 60%) as a white solid, m.p. 120-125° C.

MS [(+)ESI, m/z]: 500 [M+H]$^+$
MS [(-)ESI, m/z]: 498 [M-H]$^-$
HRMS [(+)ESI, m/z]: 500.20748 [M+H]$^+$. Calcd for $C_{31}H_{26}N_5O_2$: 500.20810

Example 109

10-[4-(3-METHYLPYRIDIN-2-YL)BENZOYL]-N-(PYRIDIN-3-YLMETHYL)-10,11-DIHYDRO-5H-PYRROLO[2,1-C][1,4]BENZODIAZEPINE-3-CARBOXAMIDE

Step A. 4-(3-Methylpyridin-2-yl)benzoic acid

The title compound was prepared in essentially the same manner as Example 107, Step A, replacing 2-bromopyridine with 2-bromo-3-methylpyridine to give the title compound (0.556 g, 41%) as a white solid, m.p. 178° C.
MS [(+)ESI, m/z]: 214 [M+H]$^+$
MS [(−)ESI, m/z]: 212 [M−H]$^−$ Step B. 10-[4-(3-Methylpyridin-2-yl)benzoyl]-N-(pyridin-3-ylmethyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-(3-methylpyridin-2-yl)benzoic acid of Step A. Purification by flash chromatography using a solvent gradient of 1 to 5% methanol in dichloromethane gave a colorless syrup that was crystallized from dichloromethane/hexane to afford the title compound (0.348 g, 72%) as a white solid, m.p. 150-151° C.
MS [(+)ESI, m/z]: 514 [M+H]$^+$
HRMS [(+)ESI, m/z]: 514.22362 [M+H]$^+$. Calcd for $C_{32}H_{28}N_5O_2$: 514.22375

Example 110

10-(4-PYRIDIN-4-YLBENZOYL)-N-(PYRIDIN-3-YLMETHYL)-10,11-DIHYDRO-5H-PYRROLO[2,1-C][1,4]BENZODIAZEPINE-3-CARBOXAMIDE

Step A. Sodium 4-pyridin-4-yl-benzoate

To a suspension of 4-carboxybenzeneboronic acid (0.660 g, 3.98 mmol) and 4-bromopyridine hydrochloride (0.770 g, 3.98 mmol) in dry acetonitrile (20 mL) was added 0.4 M aqueous sodium carbonate (20 mL) and the mixture was purged with nitrogen for 10 minutes. Tetrakis(triphenylphosphine)palladium(0) (0.240 g) was then added and the reaction mixture heated to 90° C. for 22 hours. The precipitated sodium salt was filtered, washed with acetonitrile and then dried in vacuo at 50° C. overnight to give the title compound (0.162 g, 18%) as a grey solid.
MS [(+)ESI, m/z]: 200 [M+2H−Na]$^+$
MS [(−)ESI, m/z]: 198 [M−Na]$^−$ Step B. 10-(4-Pyridin-4-ylbenzoyl)-N-(pyridin-3-ylmethyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with sodium 4-pyridin-4-yl-benzoate of Step A. Purification by flash chromatography using a solvent gradient of 1 to 5% methanol in dichloromethane gave a colorless glass that was crystallized from dichloromethane/hexane to afford the title compound (0.055 g, 27%) as a white solid, m.p. 119-124° C.
MS [(+)ESI, m/z]: 500 [M+H]$^+$
MS [(−)ESI, m/z]: 498 [M−H]$^−$
HRMS [(+)ESI, m/z]: 500.20788 [M+H]$^+$. Calcd for $C_{31}H_{26}N_5O_2$: 500.20810

Example 111

N-(PYRIDIN-3-YLMETHYL)-10-[4-(1,3-THIAZOL-2-YL)BENZOYL]-10,11-DIHYDRO-5H-PYRROLO[2,1-C][1,4]BENZODIAZEPINE-3-CARBOXAMIDE

Step A. 4-(1,3-Thiazol-2-yl)benzoic acid

The title compound was prepared in essentially the same manner as Example 107, Step A, replacing 2-bromopyridine with 2-bromothiazole to give the title compound (0.674 g, 83%) as a white solid, m.p. 235-237° C.
MS [(+)ESI, m/z]: 206 [M+H]$^+$
MS [(−)ESI, m/z]: 204 [M−H]$^−$ Step B. N-(Pyridin-3-ylmethyl)-10-[4-(1,3-thiazol-2-yl)benzoyl]-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-(1,3-thiazol-2-yl)benzoic acid of Step A. Purification by flash chromatography using a solvent gradient of 1 to 5% methanol in dichloromethane gave a yellow glass that was recrystallized from diethyl ether/hexane to afford the title compound (0.449 g, 94%) as a cream solid, m.p. 178-179° C.
MS [(+)ESI, m/z]: 506 [M+H]$^+$
Anal. Calcd for $C_{29}H_{23}N_5O_2S$: C, 68.89; H, 4.59; N, 13.85. Found: C, 68.89; H, 4.51; N, 13.75.

Example 112

10-[4-(1H-PYRAZOL-1-YL)BENZOYL]-N-(PYRIDIN-3-YLMETHYL)-10,11-DIHYDRO-5H-PYRROLO[2,1-C][1,4]BENZODIAZEPINE-3-CARBOXAMIDE

Step A. Methyl 4-(1H-pyrazol-1-yl)benzoate

A mixture of methyl 4-fluorobenzoate (2 g, 0.0130 mol), pyrazole (1.33 g, 0.0195 mmol) and potassium carbonate (3.59 g, 0.0260 mol) in dry 1-methyl-1-pyrrolidinone (20 mL) was heated to 130° C. for 44 hours. The cooled reaction mixture was then partitioned between ethyl acetate (200 mL) and 2 M sodium hydroxide (200 mL). The organic phase was separated, washed with 2 M sodium hydroxide (200 mL), 2 M hydrochloric acid (2×200 mL), water (200 mL), and brine (200 mL), dried over anhydrous magnesium sulfate, and concentrated in vacuo to afford a white solid (0.71 g). Recrystallization from hexane (40 mL) gave the title compound (0.533 g, 20%) as a white crystalline solid, m.p. 115° C.
MS [(+)ESI, m/z]: 203 [M+H]$^+$
Anal. Calcd for $C_{11}H_{10}N_2O_2$: C, 65.34; H, 4.98; N, 13.85. Found: C, 65.28; H, 4.99; N, 13.61.

Step B. 4-Pyrazol-1-yl-benzoic acid

To a solution of methyl 4-(1H-pyrazol-1-yl)benzoate of Step A (0.529 g, 2.62 mmol) in methanol (20 mL) and water (4 mL) was added lithium hydroxide monohydrate (0.220 g, 5.23 mmol) and the reaction mixture heated to reflux for 2 hours. The cooled reaction mixture was concentrated in vacuo to remove methanol and then diluted with water (40 mL). The resulting aqueous solution was washed with diethyl ether (40 mL), then acidified to pH 3 by the addition of concentrated hydrochloric acid. The solid product was filtered and dried in vacuo at 50° C. overnight to afford the title compound (0.479 g, 97%) as a white solid, m.p. 270-272° C.
MS [(+)ESI, m/z]: 189 [M+H]$^+$
MS [(−)ESI, m/z]: 187 [M−H]$^−$
Anal. Calcd for $C_{10}H_8N_2O_2$: C, 63.83; H, 4.28; N, 14.89. Found: C, 63.56; H, 4.23; N, 14.89.

Step C. 10-[4-(1H-Pyrazol-1-yl)benzoyl]-N-(pyridin-3-ylmethyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-pyrazol-1-yl-benzoic acid of Step B. Purification by flash chromatography using a solvent gradient of 1 to 5% methanol in dichloromethane gave a yellow syrup that was crystallized from dichloromethane/hexane to afford the title compound (0.372 g, 81%) as a white solid, m.p. 107° C. (shrinking).

MS [(+)ESI, m/z]: 489 [M+H]+
MS [(−)ESI, m/z]: 487 [M−H]−
HRMS [(+)ESI, m/z]: 489.20286 [M+H]+. Calcd for $C_{29}H_{25}N_6O_2$: 489.20335

Example 113

10-(4-PIPERIDIN-1-YLBENZOYL)-N-(PYRIDIN-3-YLMETHYL)-10,11-DIHYDRO-5H-PYRROLO[2,1-C][1,4]BENZODIAZEPINE-3-CARBOXAMIDE

Step A. 4-Piperidin-1-ylbenzonitrile

A mixture of 4-fluorobenzonitrile (1 g, 8.26 mmol), piperidine (0.90 mL, 9.08 mmol) and potassium carbonate (2.28 g, 16.51 mmol) in dry 1-methyl-2-pyrrolidinone (10 mL) was stirred at 120° C. under nitrogen for 20 hours. The cooled reaction mixture was then diluted with water (100 mL) and extracted with ethyl acetate (100 mL). The organic extract was washed with water (100 mL) and brine (100 mL), dried over anhydrous magnesium sulfate, and concentrated in vacuo to afford an orange oil. Purification by flash chromatography using a solvent gradient of 1 to 7% ethyl acetate in hexane gave an orange oil that was crystallized from hexane to afford the title compound (1.41 g, 92%) as an orange crystalline solid, m.p. 54° C.

MS [(+)ESI, m/z]: 187 [M+H]+
Anal. Calcd for $C_{12}H_{14}N_2$: C, 77.38; H, 7.58; N, 15.04. Found: C, 77.30; H, 7.41; N, 15.06.

Step B. 4-Piperidin-1-yl-benzoic acid

A suspension of 4-piperidin-1-ylbenzonitrile of Step A (1.13 g, 6.07 mmol) in acetic acid (30 mL) and concentrated hydrochloric acid (30 mL) was stirred at 100° C. for 18 hours. The cooled reaction mixture was then poured over crushed ice, the pH adjusted to 3 by the addition of 2 M sodium hydroxide, and the resulting suspension allowed to stand overnight. The solid product was filtered and dried at 50° C. in vacuo overnight to afford the title compound (1.09 g, 88%) as a white solid, m.p. 225-230° C. (dec).

MS [(+)ESI, m/z]: 206 [M+H]+
Anal. Calcd for $C_{12}H_{15}NO_2$: C, 70.22; H, 7.37; N, 6.82. Found: C, 70.06; H, 7.34; N, 6.69.

Step C. 10-(4-Piperidin-1-ylbenzoyl)-N-(pyridin-3-ylmethyl)-10,11-dihydro-5H-pyrrolo[2,1-c][1,4]benzodiazepine-3-carboxamide The title compound was prepared in essentially the same manner as Example 105, Step B, replacing 4-pyrimidin-2-ylbenzoic acid with 4-piperidin-1-yl-benzoic acid of Step B. Purification by flash chromatography using a solvent gradient of 1 to 5% methanol in dichloromethane gave a cream solid that was recrystallized from dichloromethane/hexane to afford the title compound (0.322 g, 68%) as off-white crystals, m.p. 196-197° C. (dec).

HRMS [(+)ESI, m/z]: 506.25531 [M+H]+. Calcd for $C_{31}H_{32}N_5O_2$: 506.25505

Example 114

10-[3-(AMINOSULFONYL)-4-MORPHOLIN-4-YLBENZOYL]-N-(PYRIDIN-3-YLMETHYL)-10,11-DIHYDRO-5H-PYRROLO[2,1-C][1,4]BENZODIAZEPINE-3-CARBOXAMIDE HEMIHYDRATE

Step A. 2-Chloro-5-(5H-pyrrolo[2,1-c][1,4]benzodiazepin-10(11H)-ylcarbonyl)benzenesulfonamide A solution containing 1.02 g (0.004 mol) of 4-chloro-3-sulfamoylbenzoyl chloride, 0.74 g (0.004 mol) of 10,11-dihydro-5H-pyrolo[2,1-c][1,4]benzodiazepine and 0.48 g (0.004 mol) of N,N-dimethylaniline in 50 ml of 1,4-dioxane was allowed to stand at room temperature for 2 hours. The reaction mixture was then poured into 500 mL of water with stirring. The precipitate was collected, washed and dried to provide the title compound (0.7 g), m.p. 137° C. dec.

MS [(+)ESI, m/z]: 402 [M+H]+.
MS [(−)ESI, m/z]: 400 [M−H]−

Step B. 2-Morpholin-4-yl-5-(5H-pyrrolo[2,1-c][1,4]benzodiazepin-10(11H)-ylcarbonyl)benzenesulfonamide A solution of 1 g of 2-chloro-5-(5H-pyrrolo[2,1-c][1,4]benzodiazepin-10(11H)-ylcarbonyl)benzenesulfonamide of Step A in 20 mL of morpholine was heated for 20 hours under reflux. The reaction solution was allowed to cool to room temperature and poured into 50 mL of water with stirring. The precipitate was collected and washed with an additional 50 mL of water and dried to provide the title compound (0.8 g), m.p. 242-245° C. dec MS [(+)ESI, m/z]: 453 [M+H]+
MS [(−)ESI, m/z]: 451 [M−H]−
Anal. Calcd for $C_{23}H_{24}N_4O_4S \cdot 0.30\ H_2O$: C 60.33, H 5.41, N 12.23. Found: C 59.92, H 5.14, N, 12.05.

Step C. 2-Morpholin-4-yl-5-{[3-(trichloroacetyl)-5H-pyrrolo[2,1-c][1,4]benzodiazepin-10(11H)-yl]carbonyl}benzenesulfonamide A solution containing 0.77 g (0.0017 mol) of 2-morpholin-4-yl-5-(5H-pyrrolo[2,1-c][1,4]benzodiazepin-10(11H)-ylcarbonyl)benzenesulfonamide of Step B and 0.62 g (0.0034 mol) of trichloroacetyl chloride in 50 mL of 1,4-dioxane was heated under reflux for 3 hrours. The solution was allowed to cool to room temperature and then poured into 750 mL of water with stirring. The solid was collected, washed and dries to provide the title compound (0.88 g), m.p. 165-167° C. dec.

MS [(+)ESI, m/z]: 597 [M+H]+
MS [(−)ESI, m/z]: 595 [M−H]−
Anal. Calcd for $C_{25}H_{23}Cl_3N_4O_5S$: C 50.22, H 3.88, N 9.37. Found: C 49.88, H 3.84, N 9.12.

Step D. 10-[3-(Aminosulfonyl)-4-morpholin-4-ylbenzoyl]-N-(pyridin-3-ylmethyl)-10,11-dihydro-5H-pyrrolo[2,1-c][1,4]benzodiazepine-3-carboxamide hemihydrate A solution containing 0.83 g (0.0014 mol) of 2-morpholin-4-yl-5-{[3-(trichloroacetyl)-5H-pyrrolo[2,1-c][1,4]benzodiazepin-10(11H)-yl]carbonyl}benzenesulfonamide of Step C and 0.30 g (0.0028 mol) of 3-aminomethylpyridine in 25 mL of 1,4-dioxane was stirred under reflux overnight. The reaction mixture was allowed to cool to room temperature and poured into 200 mL of water. The beige solid that precipitated was collected and washed with water to provide the title compound (0.35 g), m.p. 159-161° C.

MS [(+)ESI, m/z]: 587 [M+H]+.
MS [(−)ESI, m/z]: 585 [M−H]−
Anal. Calcd for $C_{30}H_{30}N_6O_5S \cdot 0.5\ H_2O$: C 60.49, H 5.25, N 14.11. Found: C 60.21, H 5.48, N 13.92.

Example 115

N-(PYRIDIN-3-YLMETHYL)-10-(THIEN-2-YLCARBONYL)-10,11-DIHYDRO-5H-PYRROLO[2,1-C][1,4]BENZODIAZEPINE-3-CARBOXAMIDE

To a suspension of N-(pyridin-3-ylmethyl)-10,11-dihydro-5H-pyrrolo[2,1-c][1,4]benzodiazepine-3-carboxamide of Example 76, Step C (0.478 g, 1.5 mmol), and N,N-diisopropylethylamine (0.52 mL, 3.0 mmol) in dry tetrahydrofuran (15 mL) was added dropwise 2-(thiophene)carbonyl chloride (0.24 mL, 2.2 mmol) and the reaction mixture stirred at room temperature under nitrogen for 21 hours. The reaction was then quenched by the addition of 2 M sodium hydroxide (10 mL) and the mixture partitioned between ethyl acetate (50 mL) and 2 M sodium hydroxide (50 mL). The organic phase was separated, washed with 2 M sodium hydroxide (50 mL), water (50 mL) and brine (50 mL), dried over anhydrous magnesium sulfate, and concentrated in vacuo to afford a tan solid. The crude product was recrystallized from ethanol to give the title compound (0.250 g, 39%) as rust colored prisms.

MS [(+)ESI, m/z]: 429 [M+H]$^+$

HRMS [(+)ESI, m/z]: 429.13738 [M+H]$^+$. Calcd for $C_{24}H_{21}N_4O_2S$: 429.13797

Example 116

10-(PYRIDIN-2-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with picolinoylchloride hydrochloride. Recrystallization from ethanol/ethyl acetate gave the title compound (0.409 g, 64%) as brown needles.

MS [(+)ESI, m/z]: 424 [M+H]$^+$

HRMS [(+)ESI, m/z]: 424.17653 [M+H]$^+$. Calcd for $C_{25}H_{22}N_5O_2$: 424.17680

Example 117

10-[(6-CHLOROPYRIDIN-3-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with 6-chloronicotinoyl chloride. Recrystallization from dichloromethane gave the title compound (0.871 g, 61%) as a cream solid.

MS [(+)ESI, m/z]: 458 [M+H]$^+$

HRMS [(+)ESI, m/z]: 458.13754 [M+H]$^+$. Calcd for $C_{25}H_{21}ClN_5O_2$: 458.13783

Example 118

10-[(2,5-DICHLOROTHIEN-3-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with 2,5-dichlorothiophene-3-carbonyl chloride. Purification by flash chromatography using a solvent gradient of 0 to 4% methanol in dichloromethane gave a tan foam that was triturated with diethyl ether to afford the title compound (0.483 g, 77%) as a white solid.

MS [(+)ESI, m/z]: 497 [M+H]$^+$

HRMS [(+)ESI, m/z]: 497.05937 [M+H]$^+$. Calcd for $C_{24}H_{19}Cl_2N_4O_2S$: : 497.06003

Example 119

10-{[6-(BENZYLAMINO)PYRIDIN-3-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

A mixture of 10-[(6-chloropyridin-3-yl)carbonyl]-N-(pyridin-3-ylmethyl)-10,11-dihydro-5H-pyrrolo[2,1-c][1,4]benzodiazepine-3-carboxamide of Example 117 (0.100 g, 0.219 mmol) and benzylamine (0.12 mL, 1.094 mmol) was heated to 100° C. in a sealed tube for 17 hours. The cooled reaction mixture was then diluted with dichloromethane (10 mL), washed with saturated aqueous sodium bicarbonate solution (10 mL), dried over anhydrous magnesium sulfate, and concentrated in vacuo to afford a yellow semi-solid. Purification by flash chromatography using a solvent gradient of 1 to 5% methanol in dichloromethane gave a white solid that was triturated with diethyl ether to afford the title compound (0.054 g, 47%) as a white solid.

MS [(+)ESI, m/z]: 529 [M+H]$^+$

HRMS [(+)ESI, m/z]: 529.23385 [M+H]$^+$. Calcd for $C_{32}H_{29}N_6O_2$: 529.23465

Example 120

10-({6-[(2-METHOXYBENZYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with 2-methoxybenzylamine. Purification by flash chromatography using a solvent gradient of 1 to 7% methanol in dichloromethane gave a white foam that was triturated with diethyl ether to afford the title compound (0.071 g, 58%) as a white solid.

MS [(+)ESI, m/z]: 559 [M+H]$^+$

HRMS [(+)ESI, m/z]: 559.24504 [M+H]$^+$. Calcd for $C_{33}H_{31}N_6O_3$: 559.24522

Anal. Calcd for $C_{33}H_{30}N_6O_3$: C, 70.95; H, 5.41; N, 15.04. Found: C, 70.61; H, 5.36; N, 14.93.

Example 121

10-ISONICOTINOYL-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with isonicotinoyl chloride hydrochloride. Purification by flash chromatography using a solvent gradient of 1 to 5% methanol in dichloromethane gave a yellow oil that was triturated with diethyl ether to afford the title compound (0.193 g, 49%) as a cream solid.

MS [(+)ESI, m/z]: 424 [M+H]$^+$

MS [(−)ESI, m/z]: 422 [M−H]$^-$

HRMS [(+)ESI, m/z]: 424.17682 [M+H]$^+$. Calcd for $C_{25}H_{22}N_5O_2$: 424.17680

Example 122

10-({6-[(4-METHOXYBENZYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with 4-methoxybenzylamine. Purification by flash chromatography using a solvent gradient of 1 to 8% methanol in dichloromethane gave a yellow oil that was triturated with diethyl ether to afford the title compound (0.054 g, 44%) as a pale yellow solid.

MS [(+)ESI, m/z]: 559 [M+H]$^+$

HRMS [(+)ESI, m/z]: 559.24438 [M+H]$^+$. Calcd for $C_{33}H_{31}N_6O_3$: 559.24522

Example 123

10-(PYRAZIN-2-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with 2-pyrazinecarbonyl chloride. Purification by flash chromatography using a solvent gradient of 1 to 4% methanol in dichloromethane gave a white foam that was triturated with diethyl ether to afford the title compound (0.213 g, 53%) as a yellow solid.
MS [(+)ESI, m/z]: 425 [M+H]$^+$
HRMS [(+)ESI, m/z]: 425.17128 [M+H]$^+$. Calcd for $C_{24}H_{21}N_6O_2$: 425.17205
Anal. Calcd for $C_{24}H_{20}N_6O_2$: C, 67.91; H, 4.75; N, 19.80. Found: C, 67.62; H, 4.84; N, 19.48.

Example 124

10-(PYRIDIN-3-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 115, replacing 2-(thiophene)carbonyl chloride with nicotinoyl chloride. Purification by flash chromatography using a solvent gradient of 0 to 4% methanol in dichloromethane gave a cream foam that was triturated with diethyl ether to afford the title compound (0.211 g, 53%) as a yellow solid.
MS [(+)ESI, m/z]: 424 [M+H]$^+$
MS [(−)ESI, m/z]: 422 [M−H]$^-$
HRMS [(+)ESI, m/z]: 424.17615 [M+H]$^+$. Calcd for $C_{25}H_{22}N_5O_2$: 424.17680

Example 125

10-[(6-PIPERIDIN-1-YLPYRIDIN-3-YL)CARBONYL]-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with piperidine. Purification by flash chromatography using a solvent gradient of 1 to 4% methanol in dichloromethane gave a yellow oil that was triturated with diethyl ether to afford the title compound (0.076 g, 69%) as a white solid.
MS [(+)ESI, m/z]: 507 [M+H]$^+$
MS [(−)ESI, m/z]: 505 [M−H]$^-$
HRMS [(+)ESI, m/z]: 507.2506 [M+H]$^+$. Calcd for $C_{30}H_{31}N_6O_2$: 507.25030
Anal. Calcd for $C_{30}H_{30}N_6O_2$: C, 71.13; H, 5.97; N, 16.59. Found: C, 70.79; H, 5.87; N, 16.30.

Example 126

10-({6-[(2-PHENYLETHYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with phenethylamine. Purification by flash chromatography using a solvent gradient of 0 to 4% methanol in dichloromethane gave a yellow oil that was triturated with diethyl ether to afford the title compound (0.054 g, 46%) as a white solid.
MS [(+)ESI, m/z]: 543 [M+H]$^+$
HRMS [(+)ESI, m/z]: 543.25071 [M+H]$^+$. Calcd for $C_{33}H_{31}N_6O_2$: 543.25030

Example 127

10-({6-[(3-PHENYLPROPYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with 3-phenyl-1-propylamine. Purification by flash chromatography using a solvent gradient of 0 to 4% methanol in dichloromethane gave a yellow foam that was triturated with diethyl ether to afford the title compound (0.062 g, 51%) as a white solid.
MS [(+)ESI, m/z]: 557 [M+H]$^+$
HRMS [(+)ESI, m/z]: 557.26568 [M+H]$^+$. Calcd for $C_{34}H_{33}N_6O_2$ 557.26595
Anal. Calcd for $C_{34}H_{32}N_6O_2$: C, 73.36; H, 5.79; N, 15.10. Found: C, 73.57; H, 5.76; N, 15.06.

Example 128

10-{[6-(4-METHYLPIPERAZIN-1-YL)PYRIDIN-3-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119 replacing benzylamine with 1-methylpiperazine. Purification by flash chromatography using a solvent gradient of 0 to 16% methanol in dichloromethane gave a clear oil that was triturated with diethyl ether to afford the title compound (0.092 g, 81%) as a white solid.
MS [(+)ESI, m/z]: 522 [M+H]$^+$
HRMS [(+)ESI, m/z]: 522.26064 [M+H]$^+$. Calcd for $C_{30}H_{32}N_7O_2$: 522.26120

Example 129

10-({6-[(3-METHOXYBENZYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with 3-methoxybenzylamine. Purification by flash chromatography using a solvent gradient of 0 to 4% methanol in dichloromethane gave a clear oil that was triturated with diethyl ether to afford the title compound (0.048 g, 39%) as a white solid.
MS [(+)ESI, m/z]: 559 [M+H]$^+$
HRMS [(+)ESI, m/z]: 559.24487 [M+H]$^+$. Calcd for $C_{33}H_{31}N_6O_3$: 559.24522

Example 130

10-({6-[BENZYL(METHYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with N-benzylmethylamine. Purification by flash chromatography using a solvent gradient of 0 to 4% methanol in dichloromethane gave a clear oil that was triturated with diethyl ether to afford the title compound (0.090 g, 76%) as a white solid.
MS [(+)ESI, m/z]: 543 [M+H]$^+$
HRMS [(+)ESI, m/z]: 543.24937 [M+H]$^+$. Calcd for $C_{33}H_{31}N_6O_2$: 543.25030

Example 131

N-(PYRIDIN-3-YLMETHYL)-10-({6-[(PYRIDIN-3-YLMETHYL)AMINO]PYRIDIN-3-YL}CARBONYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with 3-(aminomethyl)pyridine. Purification by flash chromatography using a solvent gradient of 0 to 16% methanol in dichloromethane gave a clear oil that was triturated with diethyl ether to afford the title compound (0.084 g, 73%) as a white solid.
MS [(+)ESI, m/z]: 530 [M+H]$^+$
HRMS [(+)ESI, m/z]: 530.22996 [M+H]$^+$. Calcd for $C_{31}H_{28}N_7O_2$: 530.22990

Example 132

10-({6-[(2-HYDROXYETHYL)AMINO]PYRIDIN-3-YL}CARBONYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with ethanolamine. Recrystallization from diethyl ether gave the title compound (0.067 g, 64%) as a white solid.
MS [(+)ESI, m/z]: 483 [M+H]$^+$
HRMS: [(+)ESI, m/z]: 483.21328 [M+H]$^+$. Calcd for $C_{27}H_{27}N_6O_3$: 483.21391

Example 133

10-{[6-(BUTYLAMINO)PYRIDIN-3-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 119, replacing benzylamine with butylamine. Purification by flash chromatography using a solvent gradient of 0 to 4% methanol in dichloromethane gave a clear oil that was triturated with diethyl ether to afford the title compound (0.032 g, 30%) as a white solid.
MS [(+)ESI, m/z]: 495 [M+H]$^+$
HRMS [(+)ESI, m/z]: 495.25015 [M+H]$^+$. Calcd for $C_{29}H_{31}N_6O_2$: 495.25030

Example 134

10-{[6-(BENZYLOXY)PYRIDIN-3-YL]CARBONYL}-N-(PYRIDIN-3-YLMETHYL)-10,11-DIHYDRO-5H-PYRROLO[2,1-C][1,4]BENZODIAZEPINE-3-CARBOXAMIDE

To a solution of benzylalcohol (0.025 mL, 0.241 mmol) in dry tetrahydrofuran (5 mL) at 0° C. under nitrogen was added a 1.0 M solution of sodium bis(trimethylsilyl)amide in tetrahydrofuran (0.26 mL, 0.26 mmol) and the reaction mixture stirred at 0° C. for 20 minutes. A solution of 10-[(6-chloropyridin-3-yl)carbonyl]-N-(pyridin-3-ylmethyl)-10,11-dihydro-5H-pyrrolo[2,1-c][1,4]benzodiazepine-3-carboxamide of Example 117 (0.100 g, 0.219 mmol) in dry tetrahydrofuran (5 mL) was added and the reaction mixture was stirred at room temperature for 72 hours. The reaction was quenched by the addition of saturated aqueous ammonium chloride solution (10 mL) and then diluted with ethyl acetate (10 mL). The organic phase was separated, washed with water (10 mL) and brine (10 mL), dried over anhydrous magnesium sulfate, and concentrated in vacuo to afford a yellow oil. Purification by flash chromatography using a solvent gradient of 0 to 4% methanol in dichloromethane gave a white foam that was triturated with diethyl ether to afford the title compound (0.034 g, 30%) as a white solid.
MS [(+)ESI, m/z]: 530 [M+H]$^+$
HRMS [(+)ESI, m/z]: 530.21883 {M+H]$^+$. Calcd for $C_{32}H_{28}N_5O_3$: 530.21867

Example 135

10-[(4-TERT-BUTYLPHENOXY)ACETYL]-N-(PYRIDIN-3-YLMETHYL)-10,11-DIHYDRO-5H-PYRROLO[2,1-C][1,4]BENZODIAZEPINE-3-CARBOXAMIDE

To a suspension of N-(pyridin-3-ylmethyl)-10,11-dihydro-5H-pyrrolo[2,1-c][1,4]benzodiazepine-3-carboxamide of Example 76, Step C (0.300 g, 0.942 mmol), and N,N-diisopropylethylamine (0.26 mL, 1.508 mmol) in dry tetrahydrofuran (10 mL) was added dropwise 4-tert-butylphenoxyacetyl chloride (0.32 g, 1.41 mmol) and the reaction mixture was stirred at room temperature under nitrogen for 21 hours. The reaction was then quenched by the addition of 2 M sodium hydroxide (5 mL) and the mixture partitioned between ethyl acetate (50 mL) and 2 M sodium hydroxide (50 mL). The organic phase was separated, washed with 2 M sodium hydroxide (50 mL), water (50 mL) and brine (50 mL), dried over anhydrous magnesium sulfate, and concentrated in vacuo to afford a yellow foam. Purification by flash chromatography using a solvent gradient of 0 to 4% methanol in dichloromethane gave a colorless syrup that was triturated with diethyl ether to afford the title compound (0.280 g, 58%) as a white solid, m.p. 85° C.
MS [(+)ESI, m/z]: 509 [M+H]$^+$
MS [(−)ESI, m/z]: 507 [M−H]$^−$
HRMS [(+)ESI, m/z]: 509.25353 [M+H]$^+$. Calcd for $C_{31}H_{33}N_4O_3$: 509.25472

Example 136

10-(PHENOXYACETYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 135, replacing 4-tert-butylphenoxyacetyl chloride with phenoxyacetyl chloride. Purification by flash chromatography using a solvent gradient of 0 to 4% methanol in dichloromethane gave a colorless syrup that was triturated with diethyl ether to afford the title compound (0.280 g, 66%) as a white solid.
MS [(+)ESI, m/]: 453 [M+H]$^+$
MS [(−)ESI, m/z]: 451 [M−H]$^−$
HRMS [(+)ESI, m/z]: 453.19084 [M+H]$^+$. Calcd for $C_{27}H_{25}N_4O_3$: 453.19212

Example 137

10-(2-PHENOXYPROPANOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 135, replacing 4-tert-butylphenoxyacetyl chloride with 2-phenoxypropionyl chloride. Purification by flash chromatography using a solvent gradient of 0 to 4% methanol in dichloromethane gave a white foam that was triturated with diethyl ether to afford the title compound (0.420 g, 96%) as a white solid, m.p. 83° C.

MS [(+)ESI, m/z]: 465 [M–H]⁻

HRMS [(+)ESI, m/z]: 467.20621 [M+H]⁺. Calcd for $C_{28}H_{27}N_4O_3$: 467.20777

Example 138

10-[(4-CHLOROPHENOXY)ACETYL]-N-(PYRIDIN-3-YLMETHYL)-10,11-DIHYDRO-5H-PYRROLO[2,1-C][1,4]BENZODIAZEPINE-3-CARBOXAMIDE

Step A. 10-[(4-Chlorophenoxy)acetyl]-10,11-dihydro-5H-pyrrolo[2,1-c][1,4]benzodiazepine This compound was prepared from 10,11-dihydro-5H-pyrrolo[2,1-c][1,4]benzodiazepine and 4-chlorophenoxyacetyl chloride in the same manner as the preparation of 10-[(4-chloro-2-methylphenoxy)acetyl]-10,11-dihydro-5H-pyrrolo[2,1-c][1,4]benzodiazepine of Example 139, Step B, m.p. 120-122° C.

MS [(+)ESI, m/z]: 353 [M+H]⁺

Anal. Calcd for $C_{20}H_{17}ClN_2O_2$: C, 68.09; H, 4.86; N, 7.94. Found: C, 67.82; H, 4.87; N, 7.87

Step B. 2,2,2-Trichloro-1-{10-[(4-chlorophenoxy)acetyl]-10,11-dihydro-5H-pyrrolo[2,1-c][1,4]benzodiazepin-3-yl}ethanone The title compound was prepared from 10-[(4-chlorophenoxy)acetyl]-10,11-dihydro-5H-pyrrolo[2,1-c][1,4]benzodiazepine of Step A in the same manner as the preparation of 2,2,2-trichloro-1-{10-[(4-chloro-2-methylphenoxy)acetyl]-10,11-dihydro-5H-pyrrolo[2,1-c][1,4]benzodiazepin-3-yl}ethanone of Example 139, Step C, m.p. 165-167° C.

MS [(+)ESI, m/z]: 497 [M+H]⁺

Anal. Calcd for $C_{22}H_{16}Cl_4N_2O_3$: C, 53.04; H, 3.24; N, 5.62. Found: C, 53.10; H, 3.39; N, 5.36.

Step C. 10-[(4-Chlorophenoxy)acetyl]-N-(pyridin-3-ylmethyl)-10,11-dihydro-5H-pyrrolo[2,1-c][1,4]benzodiazepine-3-carboxamide A solution of 2,2,2-trichloro-1-{10-[(4-chlorophenoxy)acetyl]-10,11-dihydro-5H-pyrrolo[2,1-c][1,4]benzodiazepin-3-yl}ethanone of Step B (0.28 mmol), and 3-aminomethylpyridine (0.59 mmol), in dimethylsulfoxide (1.5 mmol) and acetonitrile (2.5 mL) was stirred at 80° C. for 18 hours. The solvent was evaporated and the residue dissolved in dichloromethane, washed with water, dried over anhydrous sodium sulfate, and evaporated. The material was purified by HPLC (Normal phase, Luna CN bonded packing) and crystallized from ethyl acetate/hexane. (0.103 g; 75%), m.p. 169-171° C.

MS [(+)ESI, m/z]: 487 [M+H]⁺

Anal. Calcd for $C_{27}H_{23}ClN_4O_3$: C, 66.60; H, 4.76; N, 11.51. Found: C, 66.66; H, 4.86; N, 11.53.

Example 139

10-[(4-CHLORO-2-METHYLPHENOXY)ACETYL]-N-(PYRIDIN-3-YLMETHYL)-10,11-DIHYDRO-5H-PYRROLO[2,1-C][1,4]BENZODIAZEPINE-3-CARBOXAMIDE

Step A. 4-Chloro-o-tolyloxyacetic acid chloride

To a cold suspension of 4-chloro-o-tolyloxyacetic acid (17.4 mmol) in 40 mL of dry dichloromethane was added oxalyl chloride (39.15 mmol) followed by one drop of N,N-dimethylformamide. Bubbling began immediately. After 30 minutes the reaction mixture was warmed in a 45° C. oil bath for 1.5 hours. The solution was cooled to room temperature and all volatiles were removed by evaporation. Dry nitrogen gas was introduced into the evaporator and more dry dichloromethane was added. This was again evaporated in vacuo. Finally, dry toluene was added to the residue and this was evaporated at reduced pressure. The crude acid chloride was used without further purification in the following step.

Step B. 10-[(4-Chloro-2-methylphenoxy)acetyl]-10,11-dihydro-5H-pyrrolo[2,1-c][1,4]benzodiazepine To a solution of the acid chloride of Step B (17.4 mmol) in dichloromethane (25 mL) was added a solution of 10,11-dihydro-5H-pyrrolo[2,1-c][1,4]benzodiazepine (17.4 mmol) and triethylamine (19.14 mmol) in dichloromethane (25 mL) in a rapid dropwise fashion. The mixture was stirred for one hour at room temperature, then washed with 0.1 N hydrochloric acid (2×) and water (1×), dried over anhydrous sodium sulfate and evaporated. The product was isolated by crystallization from hot ethyl acetate/t-butyl methyl ether (2/1), m.p. 166-167° C.

MS [(+)ESI, m/z]: 367 [M+H]+

Anal. Calcd for $C_{21}H_{19}ClN_2O_2$: C, 68.76; H, 5.22; N, 7.64. Found: C, 68.53; H, 5.18; N, 7.53.

Step C. 2,2,2-Trichloro-1-[10-[(4-chloro-2-methylphenoxy)acetyl]-10,11-dihydro-5H-pyrrolo[2,1-c][1,4]benzodiazepin-3-yl}ethanone To a cold (0° C.) solution of 10-[(4-chloro-2-methylphenoxy)acetyl]-10,11-dihydro-5H-pyrrolo[2,1-c][1,4]benzodiazepine (2.70 mmol) and triethylamine (0.76 mL) in dichloromethane (15 mL) was added trichloroacetyl chloride (0.90 mL). This was stirred and allowed to warm to room temperature overnight. The reaction mixture was washed with water (2×), 0.1N hydrochloric acid (2×), dilute aqueous sodium bicarbonate (2×) and finally with water (1×). The organic phase was dried over anhydrous sodium sulfate and evaporated. The product was purified by crystallization from warm ethyl acetate/hexane (3/1), m.p. 156-158° C.

MS [(+)ESI, m/z]: 511 [M+H]⁺

Anal. Calcd for $C_{23}H_{18}Cl_4N_2O_3$: C, 53.93; H, 3.54; N, 5.47. Found: C, 53.90; H, 3.45; N, 5.40.

Step D. 10-[(4-Chloro-2-methylphenoxy)acetyl]-N-(pyridin-3-ylmethyl)-10,11-dihydro-5H-pyrrolo[2,1-c][1,4]benzodiazepine-3-carboxamide The title compound was synthesized from 2,2,2-trichloro-1-{10-[(4-chloro-2-methylphenoxy)acetyl]-10,11-dihydro-5H-pyrrolo[2,1-c][1,4]benzodiazepin-3-yl}ethanone of Step C (0.34 mmol), and 3-aminomethylpyridine (0.71 mmol), in a manner similar to the synthesis of 10-[(4-chlorophenoxy)acetyl]-N-(pyridin-3-ylmethyl)-10,11-dihydro-5H-pyrrolo[2,1-c][1,4]benzodiazepine-3-carboxamide of Example 179 (0.126 g; 74%), m.p. 168° C.

MS [(+)ESI, m/z]: 501 [M+H]⁺

Anal. Calcd for C$_{28}$H$_{25}$ClN$_4$O$_3$: C, 67.13; H, 5.03; N, 11.18. Found: C, 66.79; H, 5.06; N, 11.06.

Example 140

10-{[(4-BROMOPHENYL)THIO]ACETYL}-N-{[5-HYDROXY-4-(HYDROXYMETHYL)-6-METHYLPYRIDIN-3-YL]METHYL}-10,11-DIHYDRO-5H-PYRROLO[2,1-C][1,4]BENZODIAZEPINE-3-CARBOXAMIDE

Step A. 10-{[2-(4-Bromophenyl)thio]acetyl}-10,11-dihydro-5H-pyrrolo[2,1-c][1,4]benzodiazepine The title compound was synthesized from (4-bromo-phenylsulfanyl)-acetic acid and 10,11-dihydro-5H-pyrrolo[2,1-c][1,4]benzodiazepine in the manner of Example 1, Step E.

Step B. 2,2,2-Trichloro-1-[10{[(4-bromophenyl)thio]acetyl}-10,11-dihydro-5H-pyrrolo[2,1-c][1,4]benzodiazepine-3-yl]-ethanone The title compound was synthesized from 10-{[2-(4-bromophenyl)thio]acetyl}-10,11-dihydro-5H-pyrrolo[2,1-c][1,4]benzodiazepine of Step A in the manner of Example 1, Step F.

Step C. 10-{[(4-Bromophenyl)thio]acetyl}-N-{[5-hydroxy-4-(hydroxymethyl)-6-methylpyridin-3-yl]methyl}-10,11-dihydro-5H-pyrrolo[2,1-c][1,4]benzodiazepine-3-carboxamide The title compound was synthesized from 2,2,2-trichloro-1-[10{[(4-bromophenyl)thio]acetyl}-10,11-dihydro-5H-pyrrolo[2,1-c][1,4]benzodiazepine-3-yl]-ethanone of Step B and 3-aminomethylpyridine in the manner of Example 1, m.p. 199-200° C.

MS [(+)ESI, m/z]: 607 [M+H]$^+$

Example 141

10-{[(4-BROMOPHENYL)THIO]ACETYL}-N-(PYRIDIN-3-YLMETHYL)-10,11-DIHYDRO-5H-PYRROLO[2,1-C][1,4]BENZODIAZEPINE-3-CARBOXAMIDE

The title compound was synthesized from 2,2,2-trichloro-1-[10{[(4-bromophenyl)thio]acetyl}-10,11-dihydro-5H-pyrrolo[2,1-c][1,4]benzodiazepine-3-yl]-ethanone of Example 140, Step B, and pyridoxamine dihydrochloride hydrate in the manner of Example 1, m.p. 136-7° C.

MS [(+)ESI, m/z]: 547 [M+H]$^+$

Anal. Calcd for C$_{27}$H$_{23}$BrN$_4$O$_2$S: C, 59.24; H, 4.23; N, 10.23. Found: C, 59.03; H, 4.28; N, 10.01.

Example 142

10-[(4-CHLOROPHENYL)ACETYL]-N-(PYRIDIN-3-YLMETHYL)-10,11-DIHYDRO-5H-PYRROLO[2,1-C][1,4]BENZODIAZEPINE-3-CARBOXAMIDE

To a suspension of N-(pyridin-3-ylmethyl)-10,11-dihydro-5H-pyrrolo[2,1-c][1,4]benzodiazepine-3-carboxamide of Example 76, Step C (0.300 g, 0.942 mmol), and N,N-diisopropylethylamine (0.26 mL, 1.508 mmol) in dry tetrahydrofuran (10 mL) was added 4-chlorophenylacetyl chloride (267 mg, 1.41 mmol) and the reaction mixture stirred at room temperature under nitrogen for 21 hours. The reaction was then quenched by the addition of 2 M sodium hydroxide (5 mL) and the mixture partitioned between ethyl acetate (50 mL) and 2 M sodium hydroxide (50 mL). The organic phase was separated, washed with 2 M sodium hydroxide (50 mL), water (50 mL) and brine (50 mL), dried over anhydrous magnesium sulfate, filtered and concentrated in vacuo to afford a orange foam. Purification by flash chromatography using a solvent gradient of 0 to 4% methanol in dichloromethane gave a yellow syrup that was triturated with diethyl ether to afford the title compound 0.230 g, 52%) as a yellow solid, m.p. 83° C.

MS [(+)ESI, m/z]: 471 [M+H]$^+$

MS [(−)ESI, m/]: 469 [M−H]$^−$

HRMS [(+)ESI, m/z]: 471.15711 [M+H]$^+$. Calcd for C$_{27}$H$_{24}$ClN$_4$O$_2$: 471.15823

Example 143

10-(1,1'-BIPHENYL-4-YLACETYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 142, replacing 4-chlorophenylacetyl chloride with biphenyl-4-ylacetyl chloride. Purification by flash chromatography using a solvent gradient of 1 to 4% methanol in dichloromethane gave a yellow syrup that was crystallized from diethyl ether to afford the title compound (0.136 g, 28%) as a cream crystalline solid, m.p. 153-155° C.

MS [(+)ESI, m/z]: 513 [M+H]$^+$

MS [(−)ESI, m/z]: 511 [M−H]$^−$

Anal. Calcd for C$_{33}$H$_{28}$N$_4$O$_2$: C, 77.32; H, 5.51; N, 10.93. Found: C, 77.07; H, 5.51; N, 10.69.

Example 144

10-[(2E)-3-PHENYLPROP-2-ENOYL]-N-(PYRIDIN-3-YLMETHYL)-10,11-DIHYDRO-5H-PYRROLO[2,1-C][1,4]BENZODIAZEPINE-3-CARBOXAMIDE

To a suspension of N-(pyridin-3-ylmethyl)-10,11-dihydro-5H-pyrrolo[2,1-c][1,4]benzodiazepine-3-carboxamide of Example 76, Step C (0.300 g, 0.942 mmol) and N,N-diisopropylethylamine (0.26 mL, 1.508 mmol) in dry tetrahydrofuran (10 mL) was added trans-cinnamoyl chloride (0.235 g, 1.41 mmol) and the reaction mixture was stirred at room temperature under nitrogen for 21 hours. The reaction was then quenched by the addition of 2 M sodium hydroxide (5 mL) and the mixture partitioned between ethyl acetate (50 mL) and 2 M sodium hydroxide (50 mL). The organic phase was separated, washed with 2 M sodium hydroxide (50 mL), water (50 mL) and brine (50 mL), dried over anhydrous magnesium sulfate, and concentrated in vacuo to afford a yellow foam. Purification by flash chromatography using a solvent gradient of 1 to 4% methanol in dichloromethane gave a yellow syrup that was crystallized from diethyl ether/ethyl acetate/hexane to afford the title compound (0.360 g, 85%) as an off-white solid, m.p. 175° C.

MS [(+)ESI, m/z]: 449 [M+H]$^+$

Anal. Calcd for C$_{28}$H$_{24}$N$_4$O$_2$: C, 74.98; H, 5.39; N, 12.49. Found: C, 74.76; H, 5.37; N, 12.33.

Example 145

10-(1-NAPHTHOYL)-N-(PYRIDIN-3-YLM-ETHYL)-10,11-DIHYDRO-5H-PYRROLO[2,1-C][1,4]BENZODIAZEPINE-3-CARBOXAMIDE

The title compound was prepared in essentially the same manner as Example 144, replacing trans-cinnamoyl chloride with 1-naphthoyl chloride. Purification by flash chromatography using a solvent gradient of 1 to 4% methanol in dichloromethane gave a yellow syrup that was crystallized from diethyl ether/hexane to afford the title compound (0.410 g, 92%) as a white solid, m.p. 188° C.

MS [(+)ESI, m/z]: 473 [M+H]$^+$

HRMS [(+)ESI, m/z]: 473.19776 [M+H]$^+$. Calcd for $C_{30}H_{25}N_4O_2$: 473.19720

Example 146

10-(2-NAPHTHOYL)-N-(PYRIDIN-3-YLM-ETHYL)-10,11-DIHYDRO-5H-PYRROLO[2,1-C][1,4]BENZODIAZEPINE-3-CARBOXAMIDE

The title compound was prepared in essentially the same manner as Example 144, replacing trans-cinnamoyl chloride with 2-naphthoyl chloride. Purification by flash chromatography using a solvent gradient of 0 to 4% methanol in dichloromethane gave a yellow syrup that was triturated with diethyl ether to afford the title compound (0.223 g, 50%) as a white solid.

MS [(+)ESI, m/z]: 473 [M+H]$^+$

HRMS [+}ESI, m/z]: 473.19659 [M+H]$^+$. Calcd for $C_{30}H_{25}N_4O_2$: 473.19720

Example 147

10-(9H-FLUOREN-2-YLCARBONYL)-N-(PYRIDIN-3-YLMETHYL)-10,11-DIHYDRO-5H-PYRROLO[2,1-C][1,4]BENZODIAZEPINE-3-CARBOXAMIDE

Step A. 10-(9H-Fluoren-2-ylcarbonyl)-10,11-dihydro-5H-pyrrolo[2,1-c][1,4]benzodiazepine A solution containing 1.84 g (0.01 mol) of 10,11-dihydro-5H-pyrrolo[2,1-c][1,4]benzodiazepine, 2.28 g (0.01 mol) of 9H-fluoren-2-carbonyl chloride (generated via the reaction of 9H-fluorene-2-carboxylic acid and thionyl chloride) and 1.21 g (0.01 mol) of N,N-dimethylaniline in 125 mL of 1,4-dioxane was allowed to stand at room temperature for two hours. The reaction mixture was poured into 1 L of water, the precipitate was collected, washed with water and dried to provide the title compound (3.59 g). The material was recrystallized from acetone, m.p. 202-204° C.

MS [(+)ESI, m/z]: 377 [M+H]$^+$.

Anal. Calcd for $C_{26}H_{20}N_2O.0.25 H_2O$: C 81.97, H 5.42, N 7.35. Found: C 82.00, H 5.24, N 7.35.

Step B. 2,2,2-Trichloro-1-[10-(9H-fluorene-2-carbonyl)-10,11-dihydro-5H-pyrrolo[2,1-c][1,4]benzodiazepin-3-yl]-ethanone To 25 mL of 1,4-dioxane was added 0.59 g (0.0016 mol) of 10-(9H-fluoren-2-ylcarbonyl)-10,11-dihydro-5H-pyrrolo[2,1-c][1,4]benzodiazepine opf Step A followed by the addition of 0.31 g (0.0017 mol) of trichloroacetyl chloride. The solution was heated under reflux for 10 minutes, cooled to room temperature and poured into ice water with stirring The precipitate was collected, washed with water and dried yielding 0.74 g of title compound which was used directly in the next step.

MS [(+)ESI, m/z]: 521 [M+H]$^+$.

Step C. 10-(9H-Fluoren-2-ylcarbonyl)-N-(pyridin-3-ylm-ethyl)-10,11-dihydro-5H-pyrrolo[2,1-c][1,4]benzodiazepine-3-carboxamide A solution of 0.7 g (0.0014 mol) of 2,2,2-trichloro-1-[10-(9H-fluorene-2-carbonyl)-10,11-dihydro-5H-pyrrolo[2,1-c][1,4]benzodiazepin-3-yl]-ethanone of Step B and 0.30 g (0.0028 mol) of 3-aminomethylpyridine in 25 mL of 1,4-dioxane was heated under reflux for 1 hour. The reaction mixture was cooled to room temperature and poured into 75 mL of water with stirring. The precipitate was collected, washed with water, and recrystallized from ethanol to provide the title compound, m.p. 116-119° C.

MS [(+)ESI, m/z]: 511 [M+H]$^+$

MS [(-)ESI, m/z]: 509 [M-H]$^-$

Calcd for $C_{33}H_{26}N_4O_2.0.67H_2O$: C 75.84, H 5.27, N 10.72. Found: C 75.53, H 5.15, N 11.01.

Example 148

10-(3,3-DIMETHYLBUTANOYL)-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 144, replacing trans-cinnamoyl chloride with tert-butylacetyl chloride. Purification by flash chromatography using a solvent gradient of 1 to 4% methanol in dichloromethane gave a colorless syrup that was triturated with diethyl ether to afford the title compound (0.390 g, 99%) as a white solid, m.p. 103-107° C.

MS [(+)ESI, m/z]: 417 [M+H]$^+$

MS [(-)ESI, m/z]: 415 [M-H]$^-$

Anal. Calcd for $C_{25}H_{28}N_4O_2$: C, 72.09; H, 6.78; N, 13.45. Found: C, 71.97; H, 6.72; N, 13.45.

Example 149

10-(CYCLOHEXYLCARBONYL)-N-(PYRIDIN-3-YLMETHYL)-10,11-DIHYDRO-5H-PYRROLO[2,1-C][1,4] BENZODIAZEPINE-3-CARBOXAMIDE

The title compound was prepared in essentially the same manner as 144, replacing trans-cinnamoyl chloride with cyclohexanecarbonyl chloride. Purification by flash chromatography using a solvent gradient of 1 to 4% methanol in dichloromethane gave a colorless syrup that was azeotroped with diethyl ether to afford the title compound (0.370 g, 92%) as a white foam.

MS [(+)ESI, m/z]: 429 [M+H]$^+$

HRMS [(+)ESI, m/z]: 429.22758 [M+H]$^+$. Calcd for $C_{26}H_{29}N_4O_2$: 429.22850

Example 150

10-ISOBUTYRYL-N-(PYRIDIN-3-YLMETHYL)-10,11-DIHYDRO-5H-PYRROLO[2,1-C][1,4]BENZODIAZEPINE-3-CARBOXAMIDE

The title compound was prepared in essentially the same manner as Example 144, replacing trans-cinnamoyl chloride with isobutyryl chloride. Purification by flash chromatography using a solvent gradient of 1 to 4% methanol in dichloromethane gave a colorless syrup that was triturated with diethyl ether to afford the title compound (0.310 g, 85%) as a white solid.

MS [(+)ESI, m/z]: 389 [M+H]$^+$

HRMS [(+)ESI, m/z]: 389.19631 [M+H]$^+$. Calcd for $C_{23}H_{25}N_4O_2$: 389.19720

Biological Activity Examples

The subject compounds of the present invention were tested for biological activity according to the following procedures.

Pharmacology

The FSH antagonist activities of the compounds of this invention were demonstrated by evaluating representative compounds of this invention in the following test procedures.

Example 151

FOLLICLE-STIMULATING HORMONE RECEPTOR-DEPENDENT CRE-LUCIFERASE REPORTER GENE ASSAY FOR THE IDENTIFICATION OF FOLLICLE-STIMULATING HORMONE (FSH) ANTAGONISTS

A Chinese hamster ovarian cell line that stably produces the human FSH receptor and a luciferase reporter gene regulated by cAMP response elements was used to identify and determine the relative potencies of human FSH receptor antagonists. See for example, Kelton, C. A., et al. *Mol. Cell. Endocrinol.* 89:141-151 (1992), Tilly, J. L., et al. *Endocrinology* 131:799-806(1992), and George, S. E., et al. *J. Biomol. Screening* 2:235-240 (1997).

Materials and Methods: Reagents

Compound Vehicle: Stock compounds were solubilized in an appropriate vehicle, e.g., phosphate buffered saline (PBS) or dimethyl sulfoxide (DMSO), at 30 mM. The compounds subsequently were diluted in DMSO to working dilutions of 1 and 20 or 30 mM for 2-dose testing format and 1 µM-10 mM for dose-response format. The DMSO dilutions were diluted 500-fold in sterile growth medium [D-MEM/F-12 (GIBCO/BRL; Grand Island, N.Y.) containing 15 mM HEPES, 2 mM l-glutamine, pyridoxine hydrochloride, phenol red and 5% FETALCLONE® II (HyClone Laboratories, Inc; Logan, Utah), 0.2% DMSO, 100 units penicillin G/ml, and 100 µg streptomycin sulfate/ml (GIBCO/BRL)]. The concentration of the vehicle in each of the compound dilutions was the same.

Positive Controls: Purified human FSH (>98%) was purchased from Cortex Biochem, Inc. (San Leandro, Calif.) and 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-benzamide (an FSH-R thiazolidinone antagonist) was prepared by processes described by R. A. Scheuerman et al. in U.S. Pat. No. 6,426,357 (Affymax).

Preparation of Cells

The CHO FSH-R 6CRE-Luc cells (1D7 cells) were obtained from Affymax (Palo Alto, Calif.). These Chinese hamster ovary cells (CHO-K1) were engineered genetically to stably express the recombinant human FSH receptor gene and a luciferase reporter gene under the regulation of 6 copies of a cAMP response element. The cells were plated one day prior to treatment into 96-well white opaque plates at a density of 50,000 cells/100 µl/well in growth medium. On the day of treatment, the growth medium was removed from the wells by aspiration and 50 µl of fresh growth medium was added to each well. The cells were incubated at 37° C. in a humidified incubator with 5% $CO_2$/95% air.

Assay

Test compounds diluted to 2× final concentration in growth medium containing 2× EC50 purified human FSH (0.8 ng/ml) were added to the wells to achieve a final volume of 100 µl of medium containing 0.25% (v/v) vehicle. The treated cells were incubated for 4 hours at 37° C. in a humidified incubator with 5% $CO_2$/95% air. At the end of the incubation period, luciferase activity was measured by chemiluminescence using a commercially available kit (LucScreen, Tropix, Inc., Bedford, Mass.) according to the manufacturer's specifications, except that Buffer 1 and Buffer 2 were mixed together in equal proportion prior to the addition of 100 µl of the combined reagents to each well. Chemiluminescence was detected using a luminometer (EG & G Berthold Microlumat LB 96 P, Wallac, Gaithersburg, Md.) with chemiluminescence measured for 1 sec/well. Background luminescence was measured for each well prior to the addition of the LucScreen reagent.

Experimental Groups

In the 96-well 2-dose format, each compound was tested in duplicate at each dose. The controls were also tested in duplicate on each plate and consisted of vehicle control and 3 positive controls ($EC_{50}$ of phFSH (0.4 ng/ml), $EC_{100}$ of phFSH (1000 ng/ml), and $IC_{50}$ of 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-benzamide (2 µM) in the presence of $EC_{50}$ of purified human FSH). One plate was used to test a maximum of 22 compounds.

In the 96-well dose-response format, each compound was tested in triplicate at each of 6 doses in the presence of the $EC_{50}$ of purified human FSH. The $EC_{50}$ of purified human FSH alone was tested in triplicate with each test compound. The doses chosen to test each compound were extrapolated from the initial 2-dose screening process. Along with the test compounds, purified human FSH also was tested in a dose response (0.03, 0.1, 0.3, 1, 3, 10, and 30 ng/ml) for a positive control and quality control. One plate was used for 3 test compounds and the FSH positive control.

Analysis of the Results

Luciferase activity is expressed as relative light units/sec/well. Luciferase activity in antagonist was compared to the appropriate negative and positive controls. For 2-dose testing, results are reported as luciferase activity and are expressed as percent inhibition of the response obtained from the $EC_{50}$ of FSH. For dose-response testing, results are reported as $IC_{50}$ values. Data were analyzed statistically by one-way analysis of variance with appropriate weighting and transformation and relevant paired test as determined by Biometrics (Wyeth Research, Princeton, N.J.). $IC_{50}$ values were calculated using statistical software from SAS (SAS Institute, Inc., Cary, N.C.)

Reference Compounds

Test compounds were compared to the effect of purified human FSH and 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-benzamide in 2-dose format and $EC_{50}$ concentration of purified human FSH in dose-response format.

Example 152

IN VITRO BIO-ASSAY OF AGONISTS AND ANTAGONISTS TO THE FSH RECEPTOR. SELECTIVITY AND DEPENDENCY OF AGONISTS AND ANTAGONISTS TO THE FSH RECEPTOR

This assay was used to verify in vitro potency, efficacy, selectivity and receptor dependency of hits found to inhibit an FSH-R-CRE-luciferase driven reporter.

Methods: Reagents

Compound Vehicle: Stock compounds were solubilized in 100% DMSO (Sigma-Aldrich Chemical Co., St. Louis, Mo.) at a concentration of 30 mM. The compounds subsequently were diluted in sterile assay medium consisting of Opti-MEM® I (Invitrogen/Life Technologies, Carlsbad, Calif.) with 0.1% (w/v) BSA (Sigma-Aldrich) prior to use in the bio-assay. The final concentration of DMSO in the assay was 0.1%.

Preparation of CHO-3D2 Cells

The day prior to the experiment, CHO-3D2 cells (hFSH-R)(1) were plated into 96-well tissue culture plates (Falcon®, BD Biosciences, San Jose, Calif.) at a density of 30,000 cells/well in DMEM/F12 medium (Invitrogen/Life Technologies) supplemented with 5% FETALCLONE® II (Hyclone), 2 mM L-glutamine (Invitrogen/Life Technologies) and penicillin/streptomycin (100 U/ml, Invitrogen/Life Technologies). Plated cells are then incubated at 37° C. in a humidified 5% $CO_2$/95% air atmosphere.

Assay: On the day of the assay, cells were washed three times with 100 µl/well of assay medium consisting of Opti-MEM® I (Invitrogen/Life Technologies) with 0.1% (w/v) BSA (Sigma-Aldrich). Medium was removed and 100 µl of assay medium was added to each well. Plates were incubated for an additional 30 minutes at 37° C. Medium was then removed and cells were challenged for 30 minutes at 37° C. in 50 µl of assay media containing vehicle, purified hFSH (>95% pure; Cortex Biochem, Inc., San Leandro, Calif.) in the presence or absence of test compounds. Reactions were terminated by the addition of 50 µl of 0.2N hydrochloric acid to each well and cAMP-accumulation was measured by radioimmunoassay (RIA) using a commercially available kit (Amersham Biosciences, Piscataway, N.J.).

Experimental Groups

All test compounds were evaluated in a dose-response paradigm ranging from 0.01 to 30 µM. Controls and test compounds were evaluated in quadruplicate in a 96-well format. Cells were treated with vehicle, hFSH at $EC_{20}$ (1.85 ng/mL=53 pM), or the compounds in the presence or absence of hFSH at its $EC_{20}$ dose. The ability of the compounds to inhibit the cAMP-accumulation induced by hFSH was evaluated by RIA.

In every assay the $EC_{20}$ concentration was calculated and only those experiments in which the $EC_{20}$ concentrations were equal to 1.85±0.4 ng/mL were accepted as valid. In the 96-well format, the first column contained the negative control (assay media +0.1% DMSO), the second column contained the positive control, hFSH at its $EC_{20}$+0.1% DMSO (1.85 ng/ml or 53 pM), followed by six concentrations of the compound ranging from 0.03-30 µM in the presence of the hFSH at its $EC_{20}$ concentration (1.85 ng/ml or 53 pM).

Along with the test compounds, FSH was run also as a postive control in the agonist mode using concentrations ranging from 0.1-1000 ng/ml.

Selectivity studies:

cAMP accumulation assays using CHO-25 (hTSH-R) cells were performed as described above for the CHO-3D2 cells with the following exceptions: CHO-25 cells were plated at a density of 50,000 cells/well (2). All test compounds were evaluated in a dose-response paradigm ranging from 0.01 to 30 µM. Controls and test compounds were evaluated in quadruplicate. Cells were treated with vehicle, hTSH at $EC_{20}$ (5 nM; hTSH>98% pure, Cortex Biochem, Inc.), or the compounds in the presence or absence of the hTSH at its $EC_{20}$ concentration. The ability of the compounds to inhibit cAMP-accumulation induced by hTSH was evaluated by RIA.

Along with the test compounds, hTSH was also run as a positive control in the agonist mode using concentrations ranging from 0.01 µM-1000 µM.

Non-Receptor Mediated Responses:

cAMP-accumulation assays using CHO-K1 cells (parental cell line) were performed as described above for the CHO-3D2 cells. All test compounds were evaluated in a dose-response paradigm ranging from 0.01 to 30 µM. Controls and test compounds were evaluated in quadruplicate. Cells were treated with vehicle, 5 µM forskolin that induces the equivalent fmol/ml concentration of cAMP-accumulation induced by the hFSH at its $EC_{20}$ (5 µM forskolin, Sigma-Aldrich Chemical Co, St. Louis, Mo.; previously calculated during characterization of the bio-assays), or the compounds in the presence or absence of the 5 µM forskolin. The ability of the compounds to inhibit the cAMP-accumulation induced by forskolin was evaluated by RIA.

Along with the test compounds, forskolin was also run as a positive control in agonist mode using concentrations ranging from 0.01 µM to 1000 µM.

Analysis of Results cAMP accumulation is expressed as fmol/ml. cAMP accumulation in the agonist mode, or the ability of the compound to inhibit hFSH-, hTSH-, or forskolin-induced cAMP-accumulation in the antagonist mode, was compared to the appropriate negative and positive controls. Data were analyzed by one-way analysis of variance and significant differences between treatments and control determined by Least Significant Difference test.

Reference Compounds

Test compounds were compared to the effect of purified human FSH. In the paradigm, hFSH induced a concentration-dependent increase in cAMP accumulation, with apparent $EC_{80}$=22.5 ng/ml, $EC_{50}$=6.03 ng/ml and $EC_{20}$=1.85 ng/ml, calculated using a four-parameter logistic equation. The same comparison was performed with hTSH and forskolin.

Biological Activity

Based on the results obtained in the standard pharmacological test procedures, the compounds of this invention were shown to block cellular function of FSH, in vitro, including the production of second messenger cAMP and estradiol in rat ovarian granulosa cells. Representative compounds of this invention were found to selectively interact with the FSH receptor, but not to antagonize binding of FSH to its receptor (Table 1). As such, the compounds of this invention can be useful as female contraceptive agents.

TABLE 1

| Example | CRE % inhibition (μM) | CRE IC50 (μM) | cAMP IC50 (μM) | Efficacy |
|---|---|---|---|---|
| 3 |  | 0.92* | 0.08* | 96 |
| 1 |  | 1 | 0.2 | 99 |
| 8 |  | 0.54 | 0.5 | 99 |
| 28 |  | 2.0** | 0.8 | 94 |
| 20 |  | 3.7 | 1.3 | 98 |
| 5 |  | 13.8 | 1.5 | 91 |
| 21 |  | 2.9 | 1 | 100 |
| 22 |  | 15 |  |  |
| 7 |  | 5.4 | 0.7 | 85 |
| 23 | 36(30) |  |  |  |
| 24 |  | 10.7 | 1.6 | 96 |
| 25 | 11(30) |  |  |  |
| 26 |  | >30 |  |  |
| 6 |  | 8.9 | 5.4 | 58 |
| 27 |  | 22.7 |  |  |
| 13 |  | 2.8 | 0.7 | 99 |
| 9 |  | 17 |  |  |
| 47 |  | 0.65 | 0.2 | 97 |
| 70 |  | 5.6 | 2.4 | 91 |
| 10 | 25(30) |  |  |  |
| 48 |  | 1.6 | 0.3 | 97 |
| 49 |  | 0.6 | 0.1 | 100 |
| 29 |  | 0.9 | 0.4 | 100 |
| 50 |  | 1 | 0.3 |  |
| 4 |  | 0.95 | 0.8 |  |
| 51 |  | 0.29 | 0.1 | 100 |
| 52 |  | 0.116 | 0.1 | 100 |
| 56 |  | 1.04 | 0.9 | 100 |
| 57 |  | 2.12** | 0.7 | 100 |
| 58 |  | 0.4 | 0.2 | 100 |
| 59 |  | 0.1 | 0.06 | 100 |
| 60 | 29(30) |  |  |  |
| 30 |  | 1.10** | 0.27 | 100 |
| 31 |  | 0.94** | 0.33 | 99 |
| 61 |  | 0.1 | 0.05 | 100 |
| 32 |  | 0.156** | 0.02 | 100 |
| 33 |  | 1.45** | 0.9 | 98 |
| 17 |  | 0.29** | 0.13 | 100 |
| 14 |  | 1.61** | 0.77 | 98 |
| 62 |  | 1.06** | 0.55 | 100 |
| 34 |  | 1.547** | 0.59 | 97 |
| 35 |  | 31 |  |  |
| 53 |  | 0.159** | 0.12 | 100 |
| 54 |  | 0.317** | 0.15 | 100 |
| 55 |  | 1.048 | 0.62 | 99 |
| 36 |  | 1.86** | 0.43 | 98 |
| 12 |  | 16.4 |  |  |
| 15 |  | 1.1** | 0.37 | 100 |
| 63 |  | 1.18** | 0.38 | 100 |
| 64 |  | >30 |  |  |
| 65 |  | >30 |  |  |
| 37 |  | 1.64** | 0.49 | 100 |
| 38 |  | 0.078** | 0.09 | 100 |
| 39 |  | 0.414** | 0.25 | 99 |
| 40 |  | 0.921** | 0.32 | 100 |
| 66 |  | 3.67** | 0.81 | 99 |
| 67 |  | 29.14 |  |  |
| 42 |  | 7.09 | 2 | 100 |
| 41 |  | 25.1 |  |  |
| 43 |  | 0.257* | 0.14 | 100 |
| 44 |  | 2.94** | 1.71 | 100 |
| 45 |  | 3.58** | 0.78 | 100 |
| 46 |  | 2.19** | 0.37 | 100 |
| 18 |  | 0.041* | 0.07 | 100 |
| 16 |  | 0.994 |  |  |
| 69 |  | 14.55 |  |  |
| 19 |  | 2.4 |  |  |
| 71 | 17.3(30) |  |  |  |
| 72 | 6.61(30) |  |  |  |
| 73 |  | 2 |  |  |
| 74 |  | 10.54 | 3.1 | 100 |
| 75 |  | >30 | 21 | 71 |
| 76 |  | 30 |  |  |
| 77 |  | 18.8 |  |  |
| 78 |  | 18.1 |  |  |
| 79 |  | 17.8 |  |  |
| 80 |  | 4.96** | 1.1 | 98 |
| 81 |  | 18.4 |  |  |
| 82 | 2.4(30) |  |  |  |
| 83 |  | 16.6 |  |  |
| 84 |  | 5.82 | 1.2 | 98 |
| 85 |  | 6.44 | 1.1 |  |
| 86 | 40(30) |  |  |  |
| 87 | 38(30) |  |  |  |
| 89 |  | 12.17 |  |  |
| 90 | 13(30) |  |  |  |
| 91 | 37(30) |  |  |  |
| 92 |  | 9.9 |  |  |
| 93 |  | >30 |  |  |
| 94 | 17(30) |  |  |  |
| 95 | 45(30) |  |  |  |
| 96 |  | 30 |  |  |
| 97 | 18(30) |  |  |  |
| 98 |  | 4.96** | 0.4 | 100 |
| 99 | 35(30) |  |  |  |
| 100 |  | 31.5** |  |  |
| 101 |  | 12 |  |  |
| 102 |  | 5.82 | 0.8 | 99 |
| 103 |  | >30 |  |  |
| 104 |  | 3.0** | 0.4 | 98 |
| 105 |  | 2.48** | 0.2 | 99 |
| 106 | 21(30) |  |  |  |
| 107 |  | 3.12** | 0.2 | 99 |
| 108 |  | 9.53** | 1.8 | 99 |
| 113 |  | 8.84** | 0.8 | 100 |
| 109 |  | 2.92** | 0.3 | 99 |
| 110 |  | 7.65 |  |  |
| 111 |  | 5.48 |  |  |
| 112 |  | 7.99 | 1.3 | 99 |
| 114 |  | >30 |  |  |
| 115 | 34(30) |  |  |  |
| 116 |  | >30 |  |  |
| 117 | 24(30) |  |  |  |
| 118 |  | 27.7 |  |  |
| 119 |  | 10.45** | 6.7 | 75 |
| 120 |  | 49.6 |  |  |
| 122 |  | 36.47 | >30 |  |
| 123 | 41(30) |  |  |  |
| 124 | 7(30) |  |  |  |
| 125 | 31(30) |  |  |  |
| 126 |  | 18.7** |  |  |
| 127 | 9(30) |  |  |  |
| 129 | 16(30) |  |  |  |
| 130 | 26(30) |  |  |  |
| 131 |  | 15.8 |  |  |
| 132 | 26(30) |  |  |  |
| 133 |  | 14.46 |  |  |
| 134 | 4(30) |  |  |  |
| 139 |  | 9.86 |  |  |
| 135 | 34(30) |  |  |  |
| 136 | 41(30) |  |  |  |
| 137 | 16(30) |  |  |  |
| 138 |  | 15.8 |  |  |
| 141 | 32(30) |  |  |  |
| 142 |  | 18.5 |  |  |
| 143 | 48(30) |  |  |  |
| 144 | 35(30) |  |  |  |
| 145 | 40(30) |  |  |  |
| 146 |  | 11.34** |  |  |
| 148 | 35(30) |  |  |  |
| 149 | 8(30) |  |  |  |
| 150 | 20(30) |  |  |  |

*n = 3;
**n = 2;
wherein n = number of samples tested from which the average value is reported.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention. Each reference cited in the present application, including literature references, books, patents and patent applications, is incorporated herein by reference in its entirety.

What is claimed is:

1. A compound having the Formula I:

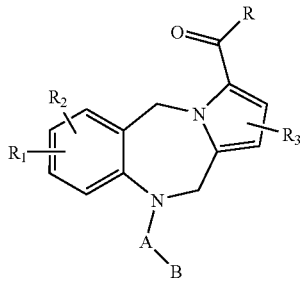

I wherein
$R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —$CONH[(C_1$-$C_6)$ alkyl], or —$CON[(C_1$-$C_6)$ alkyl]$_2$, amino, ($C_1$-$C_6$) alkylamino, —$NHCO[(C_1$-$C_6)$ alkyl];

$R_3$ is selected from the group consisting of hydrogen, ($C_1$-$C_6$) alkyl, ($C_1$-$C_6$) alkoxy, hydroxyl, amino, ($C_1$-$C_6$) alkylamino, $C(O)$—($C_1$-$C_6$) alkyl, and halogen;

A is selected from the group consisting of C=O, $CH_2$, $SO_2$; and $SO_2$;

B is

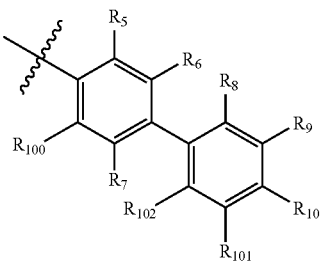

wherein $R_6$, $R_7$, $R_8$, $R_9$, $R_{10}$, $R_{101}$, and $R_{102}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, —$(CH_2)_pCONR_{13}R_{14}$, —CH=NOH, —CH=NO-alkyl,

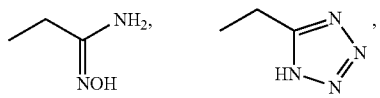

and —C(O)aryl optionally substituted by alkyl;
wherein $R_5$ and $R_{100}$ are selected independently from the group consisting of hydrogen, alkyl, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, —$(CH_2)_pCONR_{13}R_{14}$, —CH=NOH, —CH=NO-alkyl,

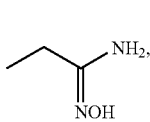 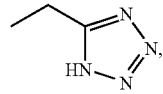

and —C(O)aryl optionally substituted by alkyl;
$R_{11}$ and $R_{12}$ are each independently hydrogen or alkyl;
$R_{13}$ and $R_{14}$ are each independently hydrogen or alkyl; or can be taken together with the nitrogen to which they are attached to form a 4-6 membered saturated ring optionally containing one or more additional O, S or N atoms;
p is 0 or 1;
R is a group consisting of

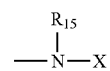

wherein
$R_{15}$ is hydrogen or alkyl;
X is selected independently from the group consisting of

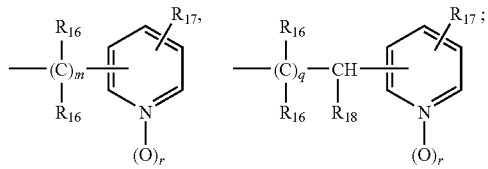

wherein
$R_{16}$ at each occurrence is independently selected from hydrogen or alkyl;
$R_{17}$ is one to three substituents independently selected from the group consisting of hydrogen, alkyl, halogen, hydroxy, aryloxy, or hydroxyalkyl;
$R_{18}$ is 5 or 6-membered saturated heterocycle containing one nitrogen atom;
m is an integer from 1 to 4;
q is an integer from 1 to 2; and
r is 0 or 1;
provided that:
if A is C=O, m is 1 or 2, r is 0, $R_7$ is methyl or methoxy and $R_5$, $R_6$, $R_8$, $R_9$, $R_{10}$, $R_{17}$, $R_{100}$, and $R_{101}$ are hydrogen, then $R_{102}$ is not methyl or methoxy;
if A is C=O, m is 2, r is 0, $R_6$ is methoxy and $R_5$, $R_7$, $R_9$, $R_{10}$, $R_{17}$, $R_{100}$, $R_{101}$, and $R_{102}$ are hydrogen, then $R_8$ is not methoxy;
if A is C=O, m is 1 or 2, r is 0, $R_6$ is methyl or methoxy, and $R_5$, $R_7$, $R_8$, $R_{10}$, $R_{17}$, $R_{100}$, $R_{101}$, and $R_{102}$ are hydrogen, then $R_9$ is not methoxy;
if A is C=O, m is 1 or 2, r is 0 or 1, $R_7$ is methyl, and $R_5$, $R_6$, $R_9$, $R_{10}$, $R_{17}$, $R_{100}$, $R_{101}$, and $R_{102}$ are hydrogen, then $R_8$ is not trifluoromethyl;
if A is C=O, m is 1, r is 0, $R_7$ is methoxy, $R_5$, $R_6$, $R_9$, $R_{10}$, $R_{17}$, $R_{100}$, and $R_{102}$ are hydrogen then $R_8$ is not chlorine wherein $R_{101}$ is hydrogen or $R_{101}$ is not methoxy wherein $R_8$ is hydrogen;
if A is C=O, m is 2, r is 0, $R_7$ is methyl, and $R_5$, $R_6$, $R_9$, $R_{10}$, $R_{17}$, $R_{100}$, $R_{101}$, and $R_{102}$ are hydrogen, then $R_8$ is not methoxy;
if A is C=O, m is 1 or 2, r is 0, $R_7$ is methyl, and $R_5$, $R_6$, $R_8$, $R_9$, $R_{10}$, $R_{17}$, $R_{100}$ and $R_{102}$ are hydrogen, then $R_{101}$ is not methoxy;

if A is C=O, m is 1, r is 0 or 1, $R_6$ is methoxy, $R_{102}$ is trifluoromethyl, and $R_5$, $R_7$, $R_8$, $R_9$, $R_{10}$, $R_{17}$, and $R_{101}$ are hydrogen, then $R_{100}$ is not hydrogen;

if A is C=O, m is 1 or 2, r is 0, $R_8$ is methyl, and $R_5$, $R_7$, $R_9$, $R_{10}$, $R_{17}$, $R_{100}$, $R_{101}$ and $R_{102}$ are hydrogen, then $R_6$ is not hydrogen or methyl; and if A is C=O, m is 1 or 2, r is 0, and $R_5$, $R_6$, $R_7$, $R_9$, $R_{10}$, $R_{17}$, $R_{100}$, $R_{101}$ and $R_{102}$ are hydrogen, then $R_8$ is not methoxy; or a pharmaceutically acceptable salt thereof.

2. A compound of claim 1 wherein $R_1$, $R_2$ and $R_3$ are each hydrogen and $R_{15}$ is hydrogen or methyl.

3. A compound of 1 claim wherein each $R_{16}$ is hydrogen, m is 1 and r is 0, and at least one $R_{17}$ is not hydrogen.

4. A compound of 1 claim wherein $R_{16}$ is hydrogen, m is 1, r is 0, and no $R_{17}$ is hydrogen.

5. A compound of 1 claim wherein each $R_{16}$ and $R_{17}$ are hydrogen, q is 1 and r is 0, and $R_{18}$ is a 5-membered saturated cycloalkylamine.

6. A compound having the Formula I:

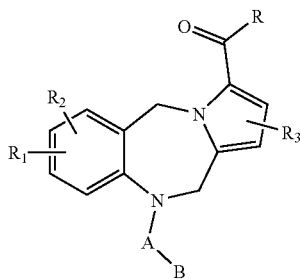

I wherein $R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —CONH[($C_1$-$C_6$) alkyl], or —CON [($C_1$-$C_6$) alkyl]$_2$, amino, ($C_1$-$C_6$) alkylamino, —NHCO[($C_1$-$C_6$) alkyl];

$R_3$ is selected from the group consisting of hydrogen, ($C_1$-$C_6$) alkyl, ($C_1$-$C_6$) alkoxy, hydroxyl, amino, ($C_1$-$C_6$) alkylamino, C(O)—($C_1$-$C_6$) alkyl, and halogen;

A is $SO_2$;

B is

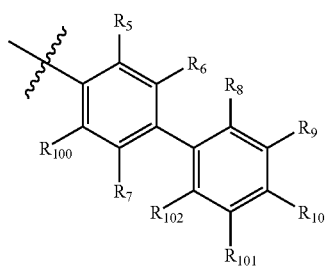

wherein $R_5$, $R_6$, $R_7$, $R_8$, $R_9$, $R_{10}$, $R_{100}$, $R_{101}$, and $R_{102}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, —$(CH_2)_pCONR_{13}R_{14}$, —CH=NOH, —CH=NO-alkyl,

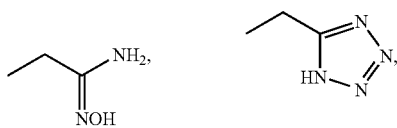

and —C(O)aryl optionally substituted by alkyl;

$R_{11}$ and $R_{12}$ are each independently hydrogen or alkyl;

$R_{13}$ and $R_{14}$ are each independently hydrogen or alkyl; or can be taken together with the nitrogen to which they are attached to form a 4-6 membered saturated ring optionally containing one or more additional O, S or N atoms;

is 0 or 1;

R is a group consisting of

wherein $R_{15}$ is hydrogen or alkyl;

X is selected independently from the group consisting of

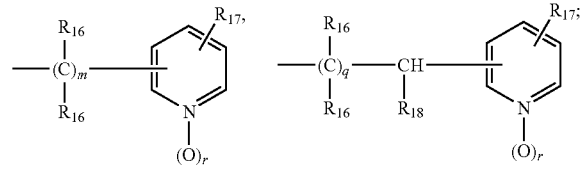

wherein $R_{16}$ at each occurrence is independently selected from hydrogen or alkyl;

$R_{17}$ is one to three substituents independently selected from the group consisting of hydrogen, alkyl, halogen, hydroxy, aryloxy, or hydroxyalkyl;

$R_{18}$ is 5 or 6-membered saturated heterocycle containing one nitrogen atom;

m is an integer from 1 to 4;

q is an integer from 1 to 2; and r is 0 or 1;

or a pharmaceutically acceptable salt thereof.

7. A compound of 1 claim wherein $R_{16}$ and $R_{17}$ are hydrogen, m is 1, r is 0 and $R_6$ is methyl.

8. A compound having the Formula I:

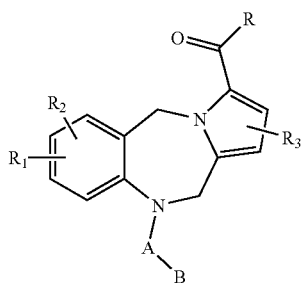

I wherein $R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —CONH[($C_1$-$C_6$) alkyl], or —CON[($C_1$-$C_6$) alkyl]$_2$, amino, ($C_1$-$C_6$) alkylamino, —NHCO[($C_1$-$C_6$) alkyl];

$R_3$ is selected from the group consisting of hydrogen, ($C_1$-$C_6$) alkyl, ($C_1$-$C_6$) alkoxy, hydroxyl, amino, ($C_1$-$C_6$) alkylamino, C(O)—($C_1$-$C_6$) alkyl, and halogen;

A is selected from the group consisting of C=O, $CH_2$, and $SO_2$;

B is

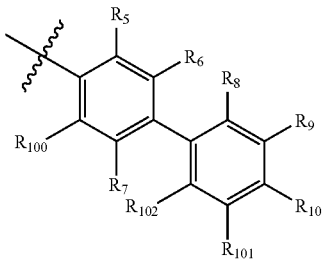

wherein $R_5$, $R_6$, $R_8$, $R_9$, $R_{10}$, $R_{100}$, $R_{101}$, and $R_{102}$ are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, —$(CH_2)_pCONR_{13}R_{14}$, —CH=NOH, —CH=NO-alkyl,

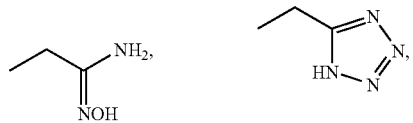

and —C(O)aryl optionally substituted by alkyl;

$R_{11}$ and $R_{12}$ are each independently hydrogen or alkyl;

$R_{13}$ and $R_{14}$ are each independently hydrogen or alkyl; or can be taken together with the nitrogen to which they are attached to form a 4-6 membered saturated ring optionally containing one or more additional 0, S or N atoms;

p is 0 or 1;

$R_7$ is methyl or methoxy;

R is a group consisting of

wherein $R_{15}$ is hydrogen or alkyl;

X is selected independently from the group consisting of

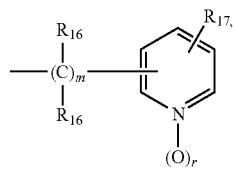 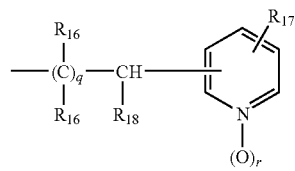

wherein $R_{16}$ and $R_{17}$ are hydrogen;

$R_{18}$ is 5 or 6-membered saturated heterocycle containing one nitrogen atom;

m is 1;

q is an integer from 1 to 2; and r is 0;

provided that:

if A is C=O, m is 1, r is 0, $R_7$ is methyl or methoxy and $R_5$, $R_6$, $R_8$, $R_9$, $R_{10}$, $R_{17}$, $R_{100}$, and $R_{101}$ are hydrogen, then $R_{102}$ is not methyl or methoxy;

if A is C=O, m is 1, r is 0, $R_7$ is methyl, and $R_5$, $R_6$, $R_9$, $R_{10}$, $R_{17}$, $R_{100}$, $R_{101}$, and $R_{102}$ are hydrogen, then $R_8$ is not trifluoromethyl;

if A is C=O, m is 1, r is 0, $R_7$ is methoxy, $R_5$, $R_6$, $R_9$, $R_{10}$, $R_{17}$, $R_{100}$, and $R_{102}$ are hydrogen then $R_8$ is not chlorine wherein $R_{101}$ is hydrogen or $R_{101}$ is not methoxy wherein $R_8$ is hydrogen;

if A is C=O, m is 1, r is 0, $R_7$ is methyl, and $R_5$, $R_6$, $R_8$, $R_9$, $R_{10}$, $R_{17}$, $R_{100}$ and $R_{102}$ are hydrogen, then $R_{101}$ is not methoxy; or a pharmaceutically acceptable salt thereof.

9. A compound of 1 claim wherein $R_{16}$ and $R_{17}$ are hydrogen, m is 1, r is 0, and $R_8$ is selected from the group consisting of methyl, chlorine, hydroxy, methoxy, —$COCH_3$, —CHO, —CH(OH)$CH_2CH_3$, —$CH_2OH$, —CN, —CH($CH_3$)$_2$, —CO(phenyl), —$CH_2OCH_3$, —$CH_2COOCH_3$, —$OCH_2CH_3$, —$CH_2CN$, —$SCH_3$, —$CH_2COOH$, —CH(OH)$CH_3$, —COCH($CH_3$)$_2$, —$SO_2CH_3$, —$COOCH_3$, —COOC($CH_3$)$_3$, —COOH, —$CH_2CONH_2$, —$CH_2CONHCH_3$, —$CH_2CON(CH_3)_2$, —$CH_2CONH(CH_2CH_3)$, —$CH_2CON(CH_2CH_3)_2$, —CH(OH)CH($CH_3$)$_2$, —CON($CH_3$)$_2$, —$CH_2N(CH_3)_2$, —$CH_2NHCH_3$, —$CH_2C(NH_2)$=NOH, —$CH_2NH_2$, —$SO_2NH_2$, and —$CONHCH_3$.

10. A compound of claim 8 wherein $R_8$ is selected from the group consisting of —$CH_2OH$, —$CH_2OCH_3$, —$CH_2COOH_3$, —CH(OH)$CH_3$, —$CH_2CONH_2$, and —$CH_2C(NH_2)$=NOH.

11. A compound of claim 1 wherein $R_{16}$ and $R_{17}$ are hydrogen, m is 1, r is 1, $R_7$ is methyl and $R_8$ is methyl.

12. A compound having the Formula 1-2:

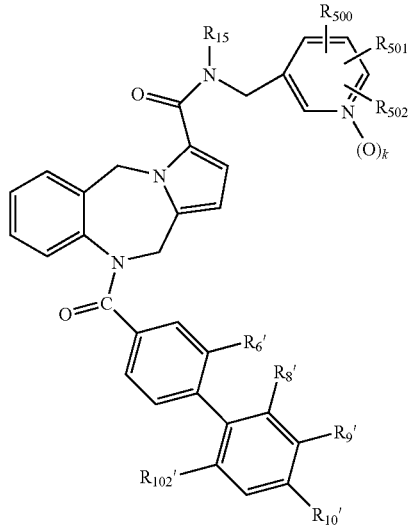

I-2 wherein $R_6'$ is H or ($C_{1-3}$)alkyl;

$R_8'$ is selected from the group consisting of H, ($C_{1-3}$) alkoxy, halogen, ($C_{1-3}$)alkyl, ($C_{1-5}$) hydroxyalkyl, —C(O)$R_{600}$, CN, ($C_{1-3}$)alkoxyalkyl, $CH_2C(O)R_{601}$, $CH_2CN$, HC=NOH, OH, S(($C_{1-3}$) alkyl), $SO_2$(($C_{1-3}$) alkyl), $CH_2N(R_{602})(R_{603})$, $CH_2C(NH_2)$=NOH, and $SO_2NH_2$;

$R_9'$ is H, halogen or ($C_{1-3}$)alkyl;

$R_{10}'$ is H, halogen, ($C_{1-3}$)alkyl, or C(O)($C_{1-3}$)alkyl;

$R_{102}'$ is H or ($C_{1-3}$)alkyl;

$R_{15}$ is hydrogen or alkyl;
$R_{500}$ is H, OH, halogen, ($C_{1-3}$)alkyl, or O-phenyl;
$R_{501}$ and $R_{502}$ are each independently H or OH; and
k is 0 or 1;
wherein
$R_{600}$ is H, OH, ($C_{1-3}$)alkyl, phenyl, ($C_{1-6}$)alkoxy, or $NR_{602}R_{603}$;
$R_{601}$ is OH, ($C_{1-3}$)alkoxy, or $NR_{602}R_{603}$; and
$R_{602}$ and $R_{603}$ are each independently H or ($C_{1-3}$)alkyl, or
$R_{602}$ and $R_{603}$ together form a 5-6 membered heterocycle with up to 3 additional N or $_0$ atoms;
provided that:
when $R_6'$ is methyl, $R_8'$ is not methoxy;
when $R_6'$ is methyl, and one of $R_8'$ or $R_{102}'$ is methyl, then either:
(a) the other of $R_8'$ or $R_{102}'$ is not H; or
(b) k=1; and
if $R_6'$, $R_9'$, $R_{10}'$, $R_{102}'$, $R_{500}$, $R_{501}$, and $R_{502}$ are all H, then $R_8$ is not methyl or methoxy.

13. A compound having the structure of Formula II:

II

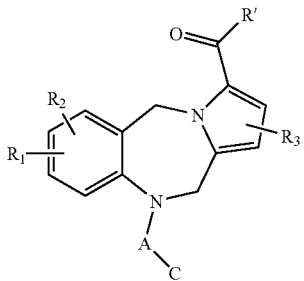

wherein
$R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —CONH[($C_1$-$C_6$) alkyl], or —CON[($C_1$-$C_6$) alkyl]$_2$, amino, ($C_1$-$C_6$) alkylamino, —NHCO[($C_1$-$C_6$) alkyl];
$R_3$ is a substituent selected from the group consisting of hydrogen, ($C_1$-$C_6$) alkyl, ($C_1$-$C_6$) alkoxy, hydroxyl, amino, ($C_1$-$C_6$) alkylamino, C(O)—($C_1$-$C_6$) alkyl, and halogen;
A is selected from the group consisting of C=O, $CH_2$, and $SO_2$;
C is selected from the group consisting of

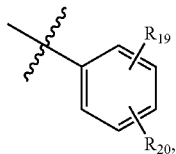

—Y and Z
wherein
$R_{19}$ and $R_{20}$ are selected independently from the group consisting of hydrogen, alkyl, alkoxy, halogen, trifluoromethyl, trifluoromethoxy, —$COOR_{21}$, dialkylamino, nitro, cyano, aryloxy, aroyl, and —$CH_2NHC(O)O$-alkyl; or $R_{19}$ and $R_{20}$ can be taken together with the phenyl moiety to which they are attached to form a structure of the formula —O(—$CH_2$)$_n$—O— wherein n is 1 or 2;
$R_{21}$ is hydrogen or alkyl;
Y is selected from the group consisting of alkyl, cycloalkyl, naphthyl,

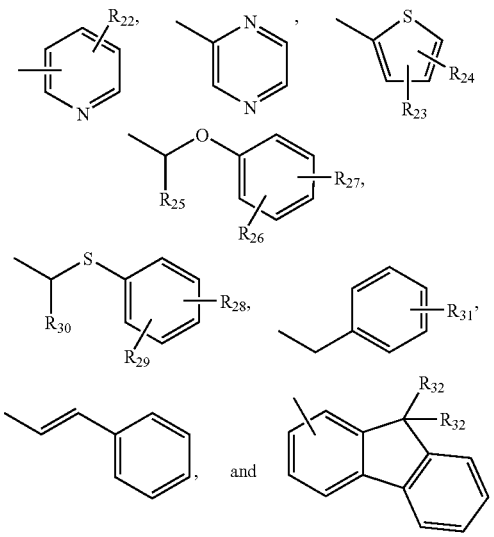

wherein
$R_{22}$ is selected from the group consisting of hydrogen, alkyl, halogen, aralkyloxy-, alkylamino, hydroxyalkylamino, cycloalkylamino, N-alkyl piperazino, (pyridinoalkyl) amino, (N-alkyl) aralkyl amino and aralkyl amino wherein the aryl is optionally substituted with alkoxy;
$R_{23}$ and $R_{24}$ are each independently hydrogen or halogen;
$R_{25}$ and $R_{30}$ are each independently hydrogen or alkyl;
$R_{26}$, $R_{27}$, $R_{28}$, and $R_{29}$ are selected independently from the group consisting of hydrogen, alkyl and halogen;
$R_{31}$ is hydrogen, alkyl, halogen or aryl; and
$R_{32}$ is each independently H, OH or taken together with the carbon to which they are attached form —C=O;
Z consists of the moiety D-E, wherein
D is an aryl optionally substituted by one or more substituents selected from the group consisting of hydrogen, alkyl, alkoxy, halogen, nitro, —$SO_2NH_2$, and trifluoromethyl; and
E is selected from the group consisting of

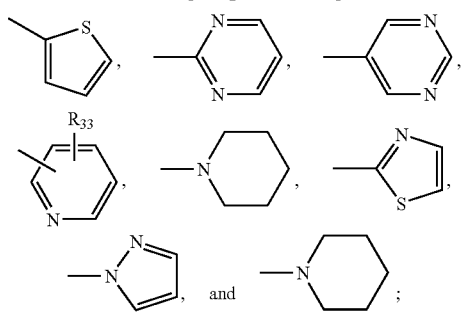

wherein $R_{33}$ is hydrogen or alkyl; and
R' is a group consisting of

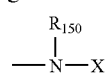

wherein
$R_{150}$ is hydrogen or alkyl;
X is selected independently from the group consisting of

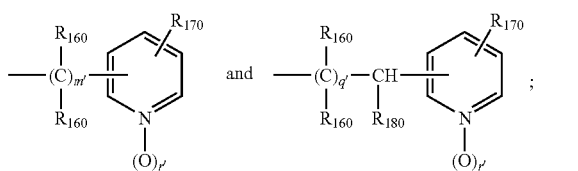

wherein
R₁₆₀ is hydrogen or alkyl;
R₁₇₀ is one to three substituents selected from the group consisting of hydrogen, alkyl, halogen, hydroxy, aryloxy, and hydroxyalkyl;
R₁₈₀ is ₅ or ₆-membered saturated cycloalkylamine;
m' is an integer from 1 to 4;
q' is an integer from 1 to 2;
r' is 0 or 1;
or a pharmaceutically acceptable salt thereof.

14. A compound of claim 13 wherein
C is selected from the group consisting of

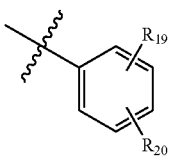

and $R_{19}$ and $R_{20}$ are each selected independently from the group consisting of hydrogen, alkyl and halogen.

15. A compound of claim 13 wherein $R_{19}$ and $R_{20}$ are each selected independently from the group consisting of hydrogen, methyl, methoxy, fluorine, chlorine, trifluoromethyl, aroyl, —OCF₃, —C(CH₃)₃, —(CH₂)₂CH₃, —COOCH₃, —COOH, —CN, —N(CH₃)₂, —N(O)═O, —N(CH₂CH₃)₂, —CH₂NHCOOC(CH₃)₃, and —O-phenyl.

16. A compound of claim 13 wherein D is an unsubstituted aryl and E is selected from the group consisting of

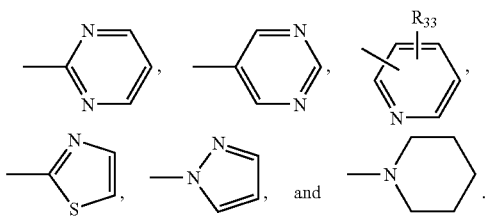

17. A compound of claim 13 where D is an aryl substituted by methyl or —S(O)₂NH₂ and E is

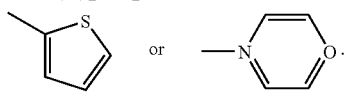

18. A compound of claim 13 where Y is

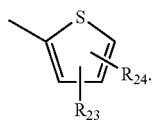

19. A compound of claim 13 where Y is

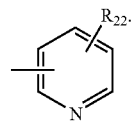

20. A compound of claim 13 where Y is

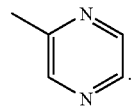

21. A compound of claim 13 where Y is

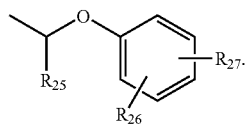

22. A compound of claim 13 where Y is

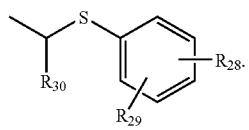

23. A compound of claim 13 where Y is selected from the group consisting of

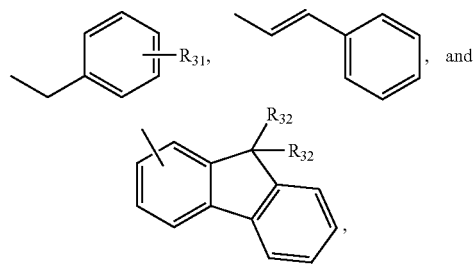

wherein $R_{31}$ is chlorine or phenyl and $R_{32}$ is each independently H.

24. A compound of claim 13 where Y is selected from the group consisting of 3,3-dimethylbutane, cyclohexyl, isobutane, 1-naphthyl, or 2-naphthyl.

25. A compound that is:
 a. 10-{[2'-(1-Hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 b. 10-{[2'-(Hydroxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 c. 10-{[2'-(Methoxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 d. Methyl(4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetate;
 e. (−)-10-({2'-[1-Hydroxyethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 f. 10-{[2'-(2-Amino-2-oxoethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide; or g. 10-({2'-[2-Amino-2-(hydroxyimino)ethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide; or a pharmaceutically acceptable salt thereof.

26. A compound of claim 1 that is:
 a) N-{[3-Hydroxy-5-(hydroxymethyl)-2-methylpyridin-4-yl]methyl}-10-[(2-methoxy-2'-methyl-1,1'-biphenyl-4-yl)carbonyl]-10,11-dihydro-5H-pyrrolo[2,1-c][1,4]benzodiazepine-3-carboxamide;
 b) 10-[(2,2'-Dimethyl-1,1'-biphenyl-4-yl)carbonyl]-N-[(1-oxidopyridin-3-yl)methyl]-10,11-dihydro-5H-pyrrolo[2,1-c][1,4]benzodiazepine-3-carboxamide;
 d) 10-[(2'-Methoxy-1,1'-biphenyl-4-yl)carbonyl]-N-[(2-phenoxypyridin-3-yl)methyl]-10,11-dihydro-5H-pyrrolo[2,1-c][1,4]benzodiazepine-3-carboxamide;
 e) 10-[(2'-Methoxy-1,1'-biphenyl-4-yl)carbonyl]-N-(2-pyridin-3-yl-2-pyrrolidin-1-ylethyl)-10,11-dihydro-5H-pyrrolo[2,1-c][1,4]benzodiazepine-3-carboxamide;
 f) N-(Pyridin-3-ylmethyl)-10-[(2,2',6'-trimethyl-1,1'-biphenyl-4-yl)carbonyl]-10,11-dihydro-5H-pyrrolo[2,1-c][1,4]benzodiazepine-3-carboxamide;
 h) 10-[(2',6'-Dimethyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 i) 10-(1,1'-Biphenyl-4-ylcarbonyl)-N-(pyridin-3-ylmethyl)-10,11-dihydro-5H-pyrrolo[2,1-c][1,4]benzodiazepine-3-carboxamide;
 j) 10-{[2'-(Methylthio)-1,1'-biphenyl-4-yl]carbonyl}-N-(pyridin-3-ylmethyl)-10,11-dihydro-5H-pyrrolo[2,1-c][1,4]benzodiazepine-3-carboxamide 0.67 hydrate;
 k) 10-{[2'-(Methylsulfonyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 l) 10-{[2'-(Aminosulfonyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 m) 10-{[2'-(Cyanomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 n) 10-({2'-[2-Amino-2-(hydroxyimino)ethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 o) N-(Pyridin-3-ylmethyl)-10-{[2'-(1H-tetrazol-5-ylmethyl)-1,1'-biphenyl-4-yl]carbonyl}-10,11-dihydro-5H-pyrrolo[2,1-c][1,4]benzodiazepine-3-carboxamide;
 p) 10-[(2'-Fluoro-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 q) 10-[(2'-Chloro-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 r) 10-[(2,4'-Dimethyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 s) 10-[(3'-Chloro-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 t) 10-[(4'-Chloro-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 u) 10-[(3',4'-Dichloro-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 v) 10-[(4'-Acetyl-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 w) 10-[(2'-Acetyl-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 x) 10-[(2'-Cyano-1,1'-biphenyl-4-yl)carbonyl]-N-(pyridin-3-ylmethyl)-10,11-dihydro-5H-pyrrolo[2,1-c][1,4]benzodiazepine-3-carboxamide;
 y) 10-[(2'-Isopropyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 z) Methyl(4'-{[3-{[(pyridin-3-ylmethyl)amino]carbonyl}-5H-pyrrolo[2,1-c][1,4]benzodiazepin-10(11H)-yl]carbonyl}-1,1'-biphenyl-2-yl)acetate;
 aa) 10-[(2'-Ethoxy-1,1'-biphenyl-4-yl)carbonyl]-N-(pyridin-3-ylmethyl)-10,11-dihydro-5H-pyrrolo[2,1-c][1,4]benzodiazepine-3-carboxamide;
 bb) 10-[(2'-Hydroxy-1,1'-biphenyl-4-yl)carbonyl]-N-(pyridin-3-ylmethyl)-10,11-dihydro-5H-pyrrolo[2,1-c][1,4]benzodiazepine-3-carboxamide;
 cc) (4'-{[3-{[(Pyridin-3-ylmethyl)amino]carbonyl}-5H-pyrrolo[2,1-c][1,4]benzodiazepin-10(11H)-yl]carbonyl}-1,1'-biphenyl-2-yl)acetic acid;
 dd) 10-[(2'-Isobutyryl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 ee) 10-{[2'-(1-Hydroxy-2-methylpropyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 ff) 10-{[2'-(2-Amino-2-oxoethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 gg) 10-({2'-[2-(Methylamino)-2-oxoethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 hh) 10-({2'-[2-(Dimethylamino)-2-oxoethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 ii) N-(Pyridin-3-ylmethyl)-10-{[2'-(pyrrolidin-1-ylmethyl)-1,1'-biphenyl-4-yl]carbonyl}-10,11-dihydro-5H-pyrrolo[2,1-c][1,4]benzodiazepine-3-carboxamide;
 jj) 10-({2'-[(Methylamino)methyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 kk) 10-{[2'-(Morpholin-4-ylmethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 ll) 10-{[2'-(Piperidin-1-ylmethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 mm) 10-({2'-[(Dimethylamino)methyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;
 nn) 10-{[2'-(Aminomethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;
 oo) 10-[(2'-Ethoxy-2-methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;
 pp) 10-{[2'-(Methoxymethyl)-2-methyl-1,1'-biphenyl-4-yl]carbonyl}-N-(pyridin-3-ylmethyl)-10,11-dihydro-5H-pyrrolo[2,1-c][1,4]benzodiazepine-3-carboxamide;

qq) 10-{[2'-(1-Hydroxyethyl)-2-methyl-1,1'-biphenyl-4-yl]carbonyl}-N-(pyridin--3-ylmethyl)-10,11-dihydro-5H-pyrrolo[2,1-c][1,4]benzodiazepine-3-carboxamide;

rr) 10-[(2'-Acetyl-1,1'-biphenyl-4-yl)carbonyl]-N-(pyridin-3-ylmethyl)-10,11-dihydro-5H-pyrrolo[2,1-c][1,4]benzodiazepine-3-carboxamide;

ss) 10-{[2'-(1-Hydroxyethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;

tt) (−)-10-({2'-[1-Hydroxyethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

uu) (+)-10-({2'-[1-Hydroxyethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

vv) 10-{[2'-(1-Hydroxyethyl)-1,1'-biphenyl-4-yl]carbonyl}-N-[(1-oxidopyridin-3-yl)methyl]-10,11-dihydro-5H-pyrrolo[2,1-c][1,4]benzodiazepine-3-carboxamide;

ww) 10-[(2'-Formyl-1,1'-biphenyl-4-yl)carbonyl]-N-(pyridin-3-ylmethyl)-10,11-dihydro-5H-pyrrolo[2,1-c][1,4]benzodiazepine-3-carboxamide;

xx) 10-[(2-Methyl-1,1'-biphenyl-4-yl)carbonyl]-N-(pyridin-3-ylmethyl)-10,11-dihydro-5H-pyrrolo[2,1-c][1,4]benzodiazepine-3-carboxamide;

yy) 10-{[2'-(1-Hydroxypropyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;

zz) 10-{[2'-(Hydroxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;

aaa) 10-[(2'-Benzoyl-1,1'-biphenyl-4-yl)carbonyl]-N-(pyridin-3-ylmethyl)-10,11-dihydro-5H-pyrrolo[2,1-c][1,4]benzodiazepine-3-carboxamide;

bbb) 10-{[2'-(Methoxymethyl)-1,1'-biphenyl-4-yl]carbonyl}-N-(pyridin-3-ylmethyl)-10,11-dihydro-5H-pyrrolo[2,1-c][1,4]benzodiazepine-3-carboxamide;

ccc) 10-({2'-[(E)-(Hydroxyimino)methyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

ddd) Methyl-4'-{[3-{[(Pyridin-3-ylmethyl)amino]carbonyl}-5H-pyrrolo[2,1-c][1,4]benzodiazepin-10(11H)-yl]carbonyl}-1,1'-biphenyl-2-carboxylate;

eee) tert-Butyl-4'-{[3-{[(Pyridin-3-ylmethyl)amino]carbonyl}-5H-pyrrolo[2,1-c][1,4]benzodiazepin-10(11H)-yl]carbonyl}-1,1'-biphenyl-2-carboxylate;

fff) 4'-{[3-{[(Pyridin-3-ylmethyl)amino]carbonyl}-5H-pyrrolo[2,1-c][1,4]benzodiazepin-10(11H)-yl]carbonyl}-1,1'-biphenyl-2-carboxylic acid;

ggg) 10-({2'-[2-(Ethylamino)-2-oxoethyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

hhh) 10-({2'-[2-(Diethylamino)-2-oxoethyl]-1,1'-biphenyl-4-yl}carbonyl) -N-(pyridin-3-ylmethyl)-10,11-dihydro-5H-pyrrolo[2,1-c][1,4]benzodiazepine-3-carboxamide;

iii) 10-({2'-[(Dimethylamino)carbonyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

jjj) 10-({2'-[(Methylamino)carbonyl]-1,1'-biphenyl-4-yl}carbonyl)-N-(pyridin-3-ylmethyl)-10,11-dihydro-5H-pyrrolo[2,1-c][1,4]benzodiazepine-3-carboxamide;

kkk) 10-[(2'-Methoxy-1,1'-biphenyl-4-yl)sulfonyl]-N-(pyridin-3-ylmethyl)-10,11-dihydro-5H-pyrrolo[2,1-c][1,4]benzodiazepine-3-carboxamide;

lll) 10-[(2'-Chloro-1,1'-biphenyl-4-yl)sulfonyl]-N-(pyridin-3-ylmethyl)-10,11-dihydro-5H-pyrrolo[2,1-c][1,4]benzodiazepine-3-carboxamide;

mmm) 10-(1,1'-Biphenyl-4-ylmethyl)-N-(pyridin-3-ylmethyl)-10,11-dihydro-5H- pyrrolo[2,1-c][1,4]benzodiazepine-3-carboxamide;

or a pharmaceutically acceptable salt thereof.

27. A compound that is:

a) 10-(4-Iodo-3-methylbenzoyl)-N-(pyridin-3-ylmethyl)-10,11-dihydro-5H-pyrrolo[2,1-c][1,4]benzodiazepine-3-carboxamide;

b) 10-(4-Benzoylbenzoyl)-N-(pyridin-3-ylmethyl)-10,11-dihydro-5H-pyrrolo[2,1-c][1,4]benzodiazepine-3-carboxamide;

c) 10-Benzoyl-N-(pyridin-3-ylmethyl)-10,11-dihydro-5H-pyrrolo[2,1-c][1,4]benzodiazepine-3-carboxamide;

d) 10-(4-Methylbenzoyl)-N-(pyridin-3-ylmethyl)-10,11-dihydro-5H-pyrrolo[2,1-c][1,4]benzodiazepine-3-carboxamide;

e) 10-(3-Fluorobenzoyl)-N-(pyridin-3-ylmethyl)-10,11-dihydro-5H-pyrrolo[2,1-c][1,4]benzodiazepine-3-carboxamide;

f) N-(Pyridin-3-ylmethyl)-10-[4-(trifluoromethyl)benzoyl]-10,11-dihydro-5H-pyrrolo[2,1-c][1,4]benzodiazepine-3-carboxamide;

g) 10-(4-tert-Butylbenzoyl)-N-(pyridin-3-ylmethyl)-10,11-dihydro-5H-pyrrolo[2,1-c][1,4]benzodiazepine-3-carboxamide;

h) 10-(3,4-Dichlorobenzoyl)-N-(pyridin-3-ylmethyl)-10,11-dihydro-5H-pyrrolo[2,1-c][1,4]benzodiazepine-3-carboxamide;

i) N-(Pyridin-3-ylmethyl)-10-[2-(trifluoromethyl)benzoyl]-10,11-dihydro-5H-pyrrolo[2,1-c][1,4]benzodiazepine-3-carboxamide;

j) 10-(3-Methylbenzoyl)-N-(pyridin-3-ylmethyl)-10,11-dihydro-5H-pyrrolo[2,1-c][1,4]benzodiazepine-3-carboxamide;

k) 10-[4-(Dimethylamino)benzoyl]-N-(pyridin-3-ylmethyl)-10,11-dihydro-5H-pyrrolo[2,1-c][1,4]benzodiazepine-3-carboxamide;

l) N-(Pyridin-3-ylmethyl)-10-[4-(trifluoromethoxy)benzoyl]-10,11-dihydro-5H-pyrrolo[2,1-c][1,4]benzodiazepine-3-carboxamide;

m) 10-(2,6-Difluorobenzoyl)-N-(pyridin-3-ylmethyl)-10,11-dihydro-5H-pyrrolo[2,1-c][1,4]benzodiazepine-3-carboxamide;

n) Methyl 4-{[3-{[(pyridin-3-ylmethyl)amino]carbonyl}-5H-pyrrolo[2,1-c][1,4]benzodiazepin-10(11H)-yl]carbonyl}benzoate;

o) 4-{[3-{[(Pyridin-3-ylmethyl)amino]carbonyl}-5H-pyrrolo[2,1-c][1,4]benzodiazepin-10(11H)-yl]carbonyl}benzoic acid;

p) 10-(4-Methoxybenzoyl)-N-(pyridin-3-ylmethyl)-10,11-dihydro-5H-pyrrolo[2,1-c](1,4]benzodiazepine-3-carboxamide;

q) 10-(4-Cyanobenzoyl)-N-(pyridin-3-ylmethyl)-10,11-dihydro-5H-pyrrolo[2,1-c][1,4]benzodiazepine-3-carboxamide;

r) 10-(4-Chlorobenzoyl)-N-(pyridin-3-ylmethyl)-10,11-dihydro-5H-pyrrolo[2,1-c][1,4]benzodiazepine-3-carboxamide;

s) N-(Pyridin-3-ylmethyl)-10-[3-(trifluoromethyl)benzoyl]-10,11-dihydro-5H-pyrrolo[2,1-c][1,4]benzodiazepine-3-carboxamide;

t) 10-(4-Fluorobenzoyl)-N-(pyridin-3-ylmethyl)-10,11-dihydro-5H-pyrrolo[2,1-c][1,4]benzodiazepine-3-carboxamide;

u) 10-(2-Methylbenzoyl)-N-(pyridin-3-ylmethyl)-10,11-dihydro-5H-pyrrolo[2,1-c][1,4]benzodiazepine-3-carboxamide;

v) 10-(3,5-Difluorobenzoyl)-N-(pyridin-3-ylmethyl)-10,11-dihydro-5H-pyrrolo[2,1-c][1,4]benzodiazepine-3-carboxamide;

w) 10-(1,3-Benzodioxol-5-ylcarbonyl)-N-(pyridin-3-ylmethyl)-10,11-dihydro-5H-pyrrolo[2,1-c][1,4]benzodiazepine-3-carboxamide;

x) 10-(2-Fluorobenzoyl)-N-(pyridin-3-ylmethyl)-10,11-dihydro-5H-pyrrolo[2,1-c][1,4]benzodiazepine-3-carboxamide;

y) 10-(4-Propylbenzoyl)-N-(pyridin-3-ylmethyl)-10,11-dihydro-5H-pyrrolo[2,1-c][1,4]benzodiazepine-3-carboxamide;

z) 10-(4-Nitrobenzoyl)-N-(pyridin-3-ylmethyl)-10,11-dihydro-5H-pyrrolo[2,1-c][1,4]benzodiazepine-3-carboxamide;

aa) 10-(3,4-Difluorobenzoyl)-N-(pyridin-3-ylmethyl)-10,11-dihydro-5H-pyrrolo[2,1-c][1,4]benzodiazepine-3-carboxamide;

bb) 10-(4-Phenoxybenzoyl)-N-(pyridin-3-ylmethyl)-10,11-dihydro-5H-pyrrolo[2,1-c][1,4]benzodiazepine-3-carboxamide;

cc) 10-[4-(Diethylamino)benzoyl]-N-(pyridin-3-ylmethyl)-10,11-dihydro-5H-pyrrolo[2,1-c][1,4]benzodiazepine-3-carboxamide;

dd) tert-Butyl(4-{[3-{[(pyridin-3-ylmethyl)amino]carbonyl}-5H-pyrrolo[2,1-c][1,4]benzodiazepin-10(11H)-yl]carbonyl}benzyl)carbamate;

ee) 10-(3-Methyl-4-thien-2-ylbenzoyl)-N-(pyridin-3-ylmethyl)-10,11-dihydro-5H-pyrrolo[2,1-c][1,4]benzodiazepine-3-carboxamide;

ff) N-(Pyridin-3-ylmethyl)-10-(4-pyrimidin-2-ylbenzoyl)-10,11-dihydro-5H-pyrrolo[2,1-c][1,4]benzodiazepine-3-carboxamide;

gg) N-(Pyridin-3-ylmethyl)-10-(4-pyrimidin-5-ylbenzoyl)-10,11-dihydro-5H-pyrrolo[2,1-c][1,4]benzodiazepine-3-carboxamide;

hh) 10-(4-Pyridin-2-ylbenzoyl)-N-(pyridin-3-ylmethyl)-10,11-dihydro-5H-pyrrolo[2,1-c][1,4]benzodiazepine-3-carboxamide;

ii) 10-(4-Pyridin-3-ylbenzoyl)-N-(pyridin-3-ylmethyl)-10,11-dihydro-5H-pyrrolo[2,1-c][1,4]benzodiazepine-3-carboxamide;

jj) 10-[4-(3-Methylpyridin-2-yl)benzoyl]-N-(pyridin-3-ylmethyl)-10,11-dihydro-5H-pyrrolo[2,1-c][1,4]benzodiazepine-3-carboxamide;

kk) 10-(4-Pyridin-4-ylbenzoyl)-N-(pyridin-3-ylmethyl)-10,11-dihydro-5H-pyrrolo[2,1-c][1,4]benzodiazepine-3-carboxamide;

ll) N-(Pyridin-3-ylmethyl)-10-[4-(1,3-thiazol-2-yl)benzoyl]-10,11-dihydro-5H-pyrrolo[2,1-c][1,4]benzodiazepine-3-carboxamide;

mm) 10-[4-(1H-Pyrazol-1-yl)benzoyl]-N-(pyridin-3-ylmethyl)-10,11-dihydro-5H-pyrrolo[2,1-c][1,4]benzodiazepine-3-carboxamide;

nn) 10-(4-Piperidin-1-ylbenzoyl)-N-(pyridin-3-ylmethyl)-10,11-dihydro-5H-pyrrolo[2,1-c][1,4]benzodiazepine-3-carboxamide;

oo) 10-[3-(Aminosulfonyl)-4-morpholin-4-ylbenzoyl]-N-(pyridin-3-ylmethyl)-10,11-dihydro-5H-pyrrolo[2,1-c][1,4]benzodiazepine-3-carboxamide hemihydrate;

pp) N-(Pyridin-3-ylmethyl)-10-(thien-2-ylcarbonyl)-10,11-dihydro-5H-pyrrolo[2,1-c][1,4]benzodiazepine-3-carboxamide;

qq) 10-(Pyridin-2-ylcarbonyl)-N-(pyridin-3-ylmethyl)-10,11-dihydro-5H-pyrrolo[2,1-c][1,4]benzodiazepine-3-carboxamide;

rr) 10-[(6-Chloropyridin-3-yl)carbonyl]-N-(pyridin-3-ylmethyl)-10,11-dihydro-5H-pyrrolo[2,1-c][1,4]benzodiazepine-3-carboxamide;

ss) 10-[(2,5-Dichlorothien-3-yl)carbonyl]-N-(pyridin-3-ylmethyl)-10,11-dihydro-5H-pyrrolo[2,1-c][1,4]benzodiazepine-3-carboxamide;

tt) 10-{[6-(Benzylamino)pyridin-3-yl]carbonyl}-N-(pyridin-3-ylmethyl)-10,11-dihydro-5H-pyrrolo[2,1-c][1,4]benzodiazepine-3-carboxamide;

uu) 10-({6-[(2-Methoxybenzyl)amino]pyridin-3-yl}carbonyl)-N-(pyridin-3-ylmethyl)-10,11-dihydro-5H-pyrrolo[2,1-c][1,4]benzodiazepine-3-carboxamide;

vv) 10-Isonicotinoyl-N-(pyridin-3-ylmethyl)-10,11-dihydro-5H-pyrrolo[2,1-c][1,4]benzodiazepine-3-carboxamide;

ww) 10-({6-[(4-Methoxybenzyl)amino]pyridin-3-yl}carbonyl)-N-(pyridin-3-ylmethyl)-10,11-dihydro-5H-pyrrolo[2,1-c][1,4]benzodiazepine-3-carboxamide;

xx) 10-(Pyrazin-2-ylcarbonyl)-N-(pyridin-3-ylmethyl)-10,11-dihydro-5H-pyrrolo[2,1-c][1,4]benzodiazepine-3-carboxamide;

yy) 10-(Pyridin-3-ylcarbonyl)-N-(pyridin-3-ylmethyl)-10,11-dihydro-5H-pyrrolo[2,1-c][1,4]benzodiazepine-3-carboxamide;

zz) 10-[(6-Piperidin-1-ylpyridin-3-yl)carbonyl]-N-(pyridin-3-ylmethyl)-10,11-dihydro-5H-pyrrolo[2,1-c][1,4]benzodiazepine-3-carboxamide;

aaa) 10-({6-[(2-Phenylethyl)amino]pyridin-3-yl}carbonyl)-N-(pyridin-3-ylmethyl)-10,11-dihydro-5H-pyrrolo[2,1-c][1,4]benzodiazepine-3-carboxamide;

bbb) 10-({6-[(3-Phenylpropyl)amino]pyridin-3-yl}carbonyl)-N-(pyridin-3-ylmethyl)-10,11-dihydro-5H-pyrrolo[2,1-c][1,4]benzodiazepine-3-carboxamide;

ccc) 10-{[6-(4-Methylpiperazin-1-yl)pyridin-3-yl]carbonyl}-N-(pyridin-3-ylmethyl)-10,11-dihydro-5H-pyrrolo[2,1-c][1,4]benzodiazepine-3-carboxamide;

ddd) 10-({6-[(3-Methoxybenzyl)amino]pyridin-3-yl}carbonyl)-N-(pyridin-3-ylmethyl)-10,11-dihydro-5H-pyrrolo[2,1-c][1,4]benzodiazepine-3-carboxamide;

eee) 10-({6-[Benzyl(methyl)amino]pyridin-3-yl}carbonyl)-N-(pyridin-3-ylmethyl)-10,11-dihydro-5H-pyrrolo[2,1-c][1,4]benzodiazepine-3-carboxamide;

fff) N-(Pyridin-3-ylmethyl)-10-({6-[(pyridin-3-ylmethyl)amino]pyridin-3-yl}carbonyl)-10,11-dihydro-5H-pyrrolo[2,1-c][1,4]benzodiazepine-3-carboxamide;

ggg) 10-({6-[(2-Hydroxyethyl)amino]pyridin-3-yl}carbonyl)-N-(pyridin-3-ylmethyl)-10,11-dihydro-5H-pyrrolo[2,1-c][1,4]benzodiazepine-3-carboxamide;

hhh) 10-{[6-(Butylamino)pyridin-3-yl]carbonyl}-N-(pyridin-3-ylmethyl)-10,11-dihydro-5H-pyrrolo[2,1-c][1,4]benzodiazepine-3-carboxamide;

iii) 10-{[6-(Benzyloxy)pyridin-3-yl]carbonyl}-N-(pyridin-3-ylmethyl)-10,11-dihydro-5H-pyrrolo[2,1-c][1,4]benzodiazepine-3-carboxamide;

jjj) 10-[(4-tert-Butylphenoxy)acetyl]-N-(pyridin-3-ylmethyl)-10,11-dihydro-5H-pyrrolo[2,1-c][1,4]benzodiazepine-3-carboxamide;

kkk) 10-(Phenoxyacetyl)-N-(pyridin-3-ylmethyl)-10,11-dihydro-5H-pyrrolo[2,1-c][1,4]benzodiazepine-3-carboxamide;

lll) 10-(2-Phenoxypropanoyl)-N-(pyridin-3-ylmethyl)-10,11-dihydro-5H-pyrrolo[2,1-c][1,4]benzodiazepine-3-carboxamide;

mmm) 10-[(4-Chlorophenoxy)acetyl]-N-(pyridin-3-ylmethyl)-10,11-dihydro-5H-pyrrolo[2,1-c][1,4]benzodiazepine-3-carboxamide;

nnn) 10-[(4-Chloro-2-methylphenoxy)acetyl]-N-(pyridin-3-ylmethyl)-10,11-dihydro-5H-pyrrolo[2,1-c][1,4]benzodiazepine-3-carboxamide;

ooo) 10-{[(4-Bromophenyl)thio]acetyl}-N-{[5-hydroxy-4-(hydroxymethyl)-6-methylpyridin-3-yl]methyl}-10,11-dihydro-5H-pyrrolo[2,1-c][1,4]benzodiazepine-3-carboxamide;

ppp) 10-{[(4-Bromophenyl)thio]acetyl}-N-(pyridin-3-ylmethyl)-10,11-dihydro-5H-pyrrolo[2,1-c][1,4]benzodiazepine-3-carboxamide;

qqq) 10-[(4-Chlorophenyl)acetyl]-N-(pyridin-3-ylmethyl)-10,11-dihydro-5H-pyrrolo[2,1-c][1,4]benzodiazepine-3-carboxamide;

rrr) 10-(1,1'-Biphenyl-4-ylacetyl)-N-(pyridin-3-ylmethyl)-10,11-dihydro-5H-pyrrolo[2,1-c][1,4]benzodiazepine-3-carboxamide;

sss) 10-[(2E)-3-Phenylprop-2-enoyl]-N-(pyridin-3-ylmethyl)-10,11-dihydro-5H-pyrrolo[2,1-c][1,4]benzodiazepine-3-carboxamide;

ttt) 10-(1-Naphthoyl)-N-(pyridin-3-ylmethyl)-10,11-dihydro-5H-pyrrolo[2,1-c][1,4]benzodiazepine-3-carboxamide;

uuu) 10-(2-Naphthoyl)-N-(pyridin-3-ylmethyl)-10,11-dihydro-5H-pyrrolo[2,1-c][1,4]benzodiazepine-3-carboxamide;

vvv) 10-(9H-Fluoren-2-ylcarbonyl)-N-(pyridin-3-ylmethyl)-10,11-dihydro-5H-pyrrolo[2,1-c][1,4]benzodiazepine-3-carboxamide;

www) 10-(3,3-Dimethylbutanoyl)-N-(pyridin-3-ylmethyl)-10,11-dihydro-5H-pyrrolo[2,1-c][1,4]benzodiazepine-3-carboxamide;

xxx) 10-(Cyclohexylcarbonyl)-N-(pyridin-3-ylmethyl)-10,11-dihydro-5H-pyrrolo[2,1-c][1,4]benzodiazepine-3-carboxamide; or yyy) 10-Isobutyryl-N-(pyridin-3-ylmethyl)-10,11-dihydro-5H-pyrrolo[2,1-c][1,4]benzodiazepine-3-carboxamide; or a pharmaceutically acceptable salt thereof.

28. A composition comprising at least one compound of claim 1 or a pharmaceutically acceptable salt thereof.

29. A method of inhibiting fertility in a mammal, said method comprising administering an effective amount of at least one compound of claim 1 to said mammal.

30. A method of inhibiting fertility in a mammal, said method comprising administering an effective amount of at least one compound of Formula III:

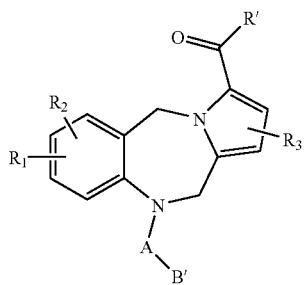

III wherein $R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —$CONH[(C_1$-$C_6)$ alkyl], or —$CON[(C_1$-$C_6)$ alkyl$]_2$, amino, ($C_1$-$C_6$) alkylamino, —$NHCO[(C_1$-$C_6)$ alkyl];

$R_3$ is selected from the group consisting of hydrogen, ($C_1$-$C_6$) alkyl, ($C_1$-$C_6$) alkoxy, hydroxyl, amino, ($C_{1-C6}$) alkylamino, $C(O)$—($C_1$-$C_6$) alkyl, and halogen;

A is selected from the group consisting of C=O, $CH_2$, and $SO_2$;

R' is a group consisting of

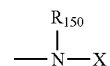

wherein $R_{150}$ is hydrogen or alkyl;

X is selected independently from the group consisting of

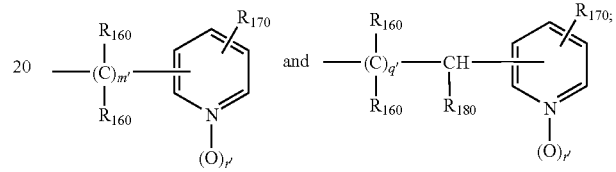

wherein $R_{160}$ is hydrogen or alkyl;

$R_{170}$ is one to three substituents selected from the group consisting of hydrogen, alkyl, halogen, hydroxy, aryloxy, and hydroxyalkyl;

$R_{180}$ is 5 or 6-membered saturated cycloalkylamine;

m' is an integer from 1 to 4;

q' is an integer from 1 to 2;

r' is 0 or 1;

B' is selected independently from the group consisting of

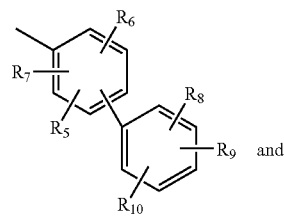

(a)

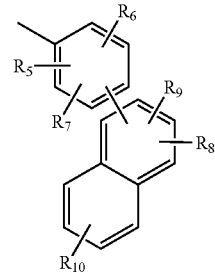

(b)

wherein $R_5$, $R_6$, $R_7$, $R_8$, $R_9$, and $R_{10}$, are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, $_{13(CH2)}pCONR_{13}R_{14}$, —CH=NOH, —CH=NO-alkyl,

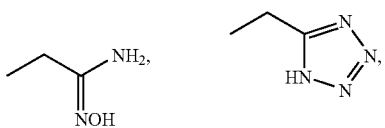

and —C(O)aryl optionally substituted by alkyl;

$R_{11}$ and $R_{12}$ are each indedendently hydrogen or alkyl;

$R_{13}$ and $R_{14}$ are each indedendently hydrogen or alkyl; or can be taken together with the nitrogen to which they are attached to form a 4-6 membered saturated ring optionally containing one or more additional O, S or N atoms;

p is 0 or 1.

31. A method of preventing conception in a mammal, said method comprising administering an effective amount of at least one compound of claim 1 to said mammal.

32. A method of preventing conception in a mammal, said method comprising administering an effective amount of at least one compound of Formula III:

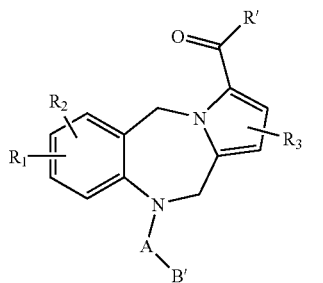

III wherein $R_1$ and $R_2$ are selected independently from hydrogen, ($C_1$-$C_6$) alkyl, halogen, trifluoromethyl, hydroxyl, ($C_1$-$C_6$) alkoxy, $OCF_3$, carboxy, —CONH[($C_1$-$C_6$) alkyl], or —CON[($C_1$—$C_6$) alkyl]$_2$, amino, ($C_1$-$C_6$) alkylamino, —NHCO[($C_1$—$C_6$) alkyl];

$R_3$ is selected from the group consisting of hydrogen, ($C_1$-$C_6$) alkyl, ($C_1$-$C_6$) alkoxy, hydroxyl, amino, ($C_1$-$C_6$) alkylamino, C(O)—($C_1$-$C_6$) alkyl, and halogen;

A is selected from the group consisting of C=O, $CH_2$, and $SO_2$;

R' is a group consisting of

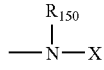

wherein $R_{150}$ is hydrogen or alkyl;

X is selected independently from the group consisting of

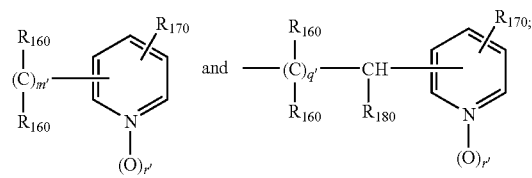

wherein $R_{160}$ is hydrogen or alkyl;

$R_{170}$ is one to three substituents selected from the group consisting of hydrogen, alkyl, halogen, hydroxy, aryloxy, and hydroxyalkyl;

$R_{180}$ is 5 or 6-membered saturated cycloalkylamine;

m' is an integer from 1 to 4;

q' is an integer from 1 to 2;

r' is 0 or 1;

B' is selected independently from the group consisting of

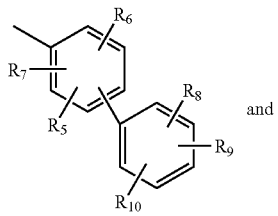

(a)

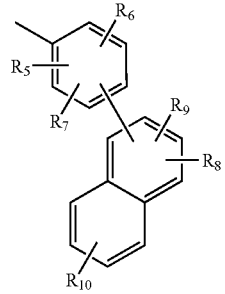

(b)

wherein $R_5$, $R_6$, $R_7$, $R_8$, $R_9$, and $R_{10}$, are selected independently from the group consisting of hydrogen, alkyl, alkoxy, trihalomethyl, halogen, —C(O) alkyl, hydroxy, hydroxyalkyl, alkyloxyalkyl, —CH(OH)alkyl, —CH(alkoxy)alkyl, formyl, nitro, thioalkyl, —$SO_2$alkyl, —$SO_2NHR_{11}$, —$SO_2N(R_{11})_2$, —$(CH_2)_pCN$, —$(CH_2)_pCOOR_{12}$, —$(CH_2)_pNR_{13}R_{14}$, —$(CH_2)_pCONR_{13}R_{14}$, —CH=NOH, —CH=NO-alkyl,

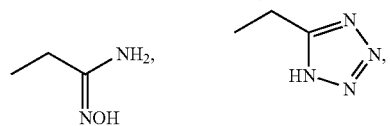

and —C(O)aryl optionally substituted by alkyl;

$R_{11}$ and $R_{12}$ are each independently hydrogen or alkyl;

$R_{13}$ and $R_{14}$ are each independently hydrogen or alkyl; or can be taken together with the nitrogen to which they are attached to form a 4-6 membered saturated ring optionally containing one or more additional O, S or N atoms;

p is 0 or 1.

* * * * *